(12) United States Patent
Nakasuji et al.

(10) Patent No.: US 7,135,676 B2
(45) Date of Patent: Nov. 14, 2006

(54) INSPECTION SYSTEM BY CHARGED PARTICLE BEAM AND METHOD OF MANUFACTURING DEVICES USING THE SYSTEM

(75) Inventors: Mamoru Nakasuji, Kanagawa (JP); Nobuharu Noji, Kanagawa (JP); Tohru Satake, Kanagawa (JP); Toshifumi Kimba, Kanagawa (JP); Hirosi Sobukawa, Kanagawa (JP); Shoji Yoshikawa, Tokyo (JP); Tsutomu Karimata, Kanagawa (JP); Shin Oowada, Kanagawa (JP); Mutsumi Saito, Kanagawa (JP); Muneki Hamashima, Chiba (JP); Toru Takagi, Kanagawa (JP)

(73) Assignee: Ebara Corporation, Tokyo (JP)

( * ) Notice: Subject to any disclaimer, the term of this patent is extended or adjusted under 35 U.S.C. 154(b) by 145 days.

(21) Appl. No.: 09/891,611

(22) Filed: Jun. 27, 2001

(65) Prior Publication Data

US 2002/0033449 A1    Mar. 21, 2002

(30) Foreign Application Priority Data

| Jun. 27, 2000 | (JP) | 2000-192918 |
|---|---|---|
| Nov. 2, 2000 | (JP) | 2000-335751 |
| Nov. 2, 2000 | (JP) | 2000-335752 |
| Nov. 2, 2000 | (JP) | 2000-336091 |
| Nov. 2, 2000 | (JP) | 2000-336156 |
| Nov. 6, 2000 | (JP) | 2000-337058 |
| Dec. 12, 2000 | (JP) | 2000-377285 |
| Feb. 8, 2001 | (JP) | 2001-031901 |
| Feb. 8, 2001 | (JP) | 2001-031906 |
| Feb. 9, 2001 | (JP) | 2001-033599 |
| Apr. 11, 2001 | (JP) | 2001-112745 |
| Apr. 13, 2001 | (JP) | 2001-115060 |
| May 14, 2001 | (JP) | 2001-143084 |
| May 28, 2001 | (JP) | 2001-158571 |

(51) Int. Cl.
   *H01J 37/28* (2006.01)
(52) U.S. Cl. .................... 250/310; 250/307
(58) Field of Classification Search ............... 250/310, 250/396 R, 398
   See application file for complete search history.

(56) References Cited

U.S. PATENT DOCUMENTS

| 4,911,103 A * | 3/1990 | Davis et al. ........... 250/441.11 |
|---|---|---|
| 4,912,052 A | 3/1990 | Miyoshi et al. |
| 4,944,645 A | 7/1990 | Suzuki |
| 4,954,705 A * | 9/1990 | Brunner et al. ............. 250/310 |
| 5,359,197 A | 10/1994 | Komatsu et al. |
| 5,362,968 A | 11/1994 | Miyoshi et al. |
| 5,422,486 A * | 6/1995 | Herrmann et al. .......... 250/310 |
| 5,430,292 A * | 7/1995 | Honjo et al. ................ 250/310 |
| 5,578,821 A | 11/1996 | Meisberger et al. ........ 250/310 |
| 5,747,819 A | 5/1998 | Nakasuji et al. |
| 5,751,538 A | 5/1998 | Nakasuji |
| 5,763,893 A | 6/1998 | Nakasuji |
| 5,770,863 A | 6/1998 | Nakasuji |
| 5,892,224 A * | 4/1999 | Nakasuji ..................... 250/310 |
| 5,981,947 A | 11/1999 | Nakasuji et al. |
| 5,994,704 A | 11/1999 | Nakasuji |
| 6,087,667 A | 7/2000 | Nakasuji et al. |
| 6,125,522 A | 10/2000 | Nakasuji |
| 6,344,750 B1 * | 2/2002 | Lo et al. ...................... 250/310 |
| 6,509,569 B1 * | 1/2003 | Frosien .................. 250/396 R |
| 6,614,026 B1 * | 9/2003 | Adamec ..................... 250/398 |

FOREIGN PATENT DOCUMENTS

| JP | 52-115161 | 9/1977 |
|---|---|---|
| JP | 52-117567 | 10/1977 |
| JP | 57-072326 | 5/1982 |
| JP | 57-125871 | 8/1982 |
| JP | 60-000741 | 1/1985 |
| JP | 61-239624 A | 10/1986 |
| JP | 62-100936 | 5/1987 |
| JP | 62-195838 | 8/1987 |
| JP | 03-022339 | 1/1991 |
| JP | 03-053439 | 3/1991 |
| JP | 03-102814 | 4/1991 |

| | | |
|---|---|---|
| JP | 03-266350 | 11/1991 |
| JP | 03-276548 | 12/1991 |
| JP | 04-266350 | 9/1992 |
| JP | 05-063261 | 3/1993 |
| JP | 05-251316 | 9/1993 |
| JP | 07-065766 | 3/1995 |
| JP | 08-138611 | 5/1996 |
| JP | 09-073872 | 3/1997 |
| JP | 09-311112 | 12/1997 |
| JP | 10-062503 | 3/1998 |
| JP | 10-073424 A | 3/1998 |
| JP | 10-125271 | 5/1998 |
| JP | 10-177952 | 6/1998 |
| JP | 11-132975 | 5/1999 |
| JP | 11-233062 | 8/1999 |
| JP | 2000-003692 | 1/2000 |
| JP | 2000-67798 | 3/2000 |
| JP | 2000-090868 | 3/2000 |
| JP | 2000-100369 | 4/2000 |
| JP | 2000-133565 | 5/2000 |
| JP | 2000-149843 | 5/2000 |

OTHER PUBLICATIONS

*Low Voltage and high speed operating electrostatic wafer chuck using sputtered tantalum oxide membrane,* Mamoru Nakasuji et al., J. Vac. Sci. Technol. A 12(5), Sep./Oct. 1994, American Vacuum Society pp. 2834-2839.

*High-Emittance and Low-Brightness Electron Gun for Reducing-Image Projection System: Computer Simulation,* Mamoru Nakasuji et al.,Jpn. J. Appl. Phys. vol. 36 (1997) pp. 2404-2408.

H. Hayashi, et al., *LSI Testing Symposium 1998, Minutes of the meeting,* P160 (1998) (partial translation).

*Multi-Beam Concepts for Nanometer Devices,* B. Lischke et al., Japanese Journal of Applied Physics, vol. 28, No. 10, Oct. 1989, pp. 2058-2064.

*An electron-beam inspecting system for x-ray mask production,* P. Sandland et al., J. Vac. Sci. Technol. B9 (6), Nov./Dec. 1991, American Vacuum Society, pp. 3005-3009.

*Requirements and performance of an electron-beam column designed for x-ray mask inspection,* W.D. Meisburger et al., J. Vac. Sci. Technol. B9 (6), Nov./Dec. 1991, American Vacuum Society, pp. 3010-3014.

*Table 5-1 Work Function in Metals* p. 116.

* cited by examiner

*Primary Examiner*—Jack I. Berman
(74) *Attorney, Agent, or Firm*—Westerman, Hattori, Daniels & Adrian, LLP.

(57)      ABSTRACT

An inspection apparatus and a semiconductor device manufacturing method using the same. The inspection apparatus is used for defect inspection, line width measurement, surface potential measurement or the like of a sample such as a wafer. In the inspection apparatus, a plurality of charged particles is delivered from a primary optical system to the sample, and secondary charged particles emitted from the sample are separated from the primary optical system and introduced through a secondary optical system to a detector. Irradiation of the charged particles is conducted while moving the sample. Irradiation spots of the charged particles are arranged by N rows along a moving direction of the sample and by M columns along a direction perpendicular thereto. Every row of the irradiation spots of the charged particles is shifted successively by a predetermined amount in a direction perpendicular to the moving direction of the sample.

12 Claims, 60 Drawing Sheets

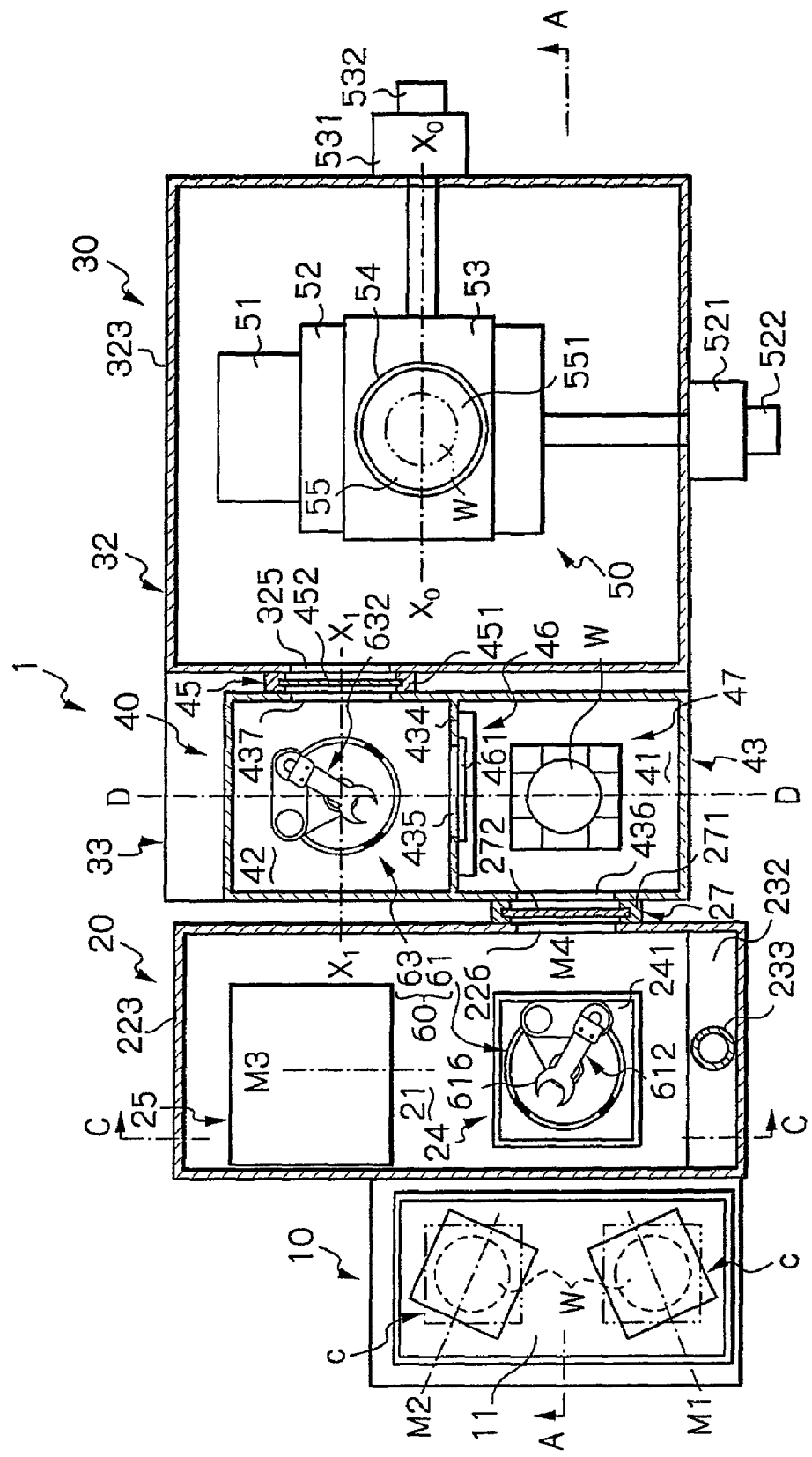

Fig. 6
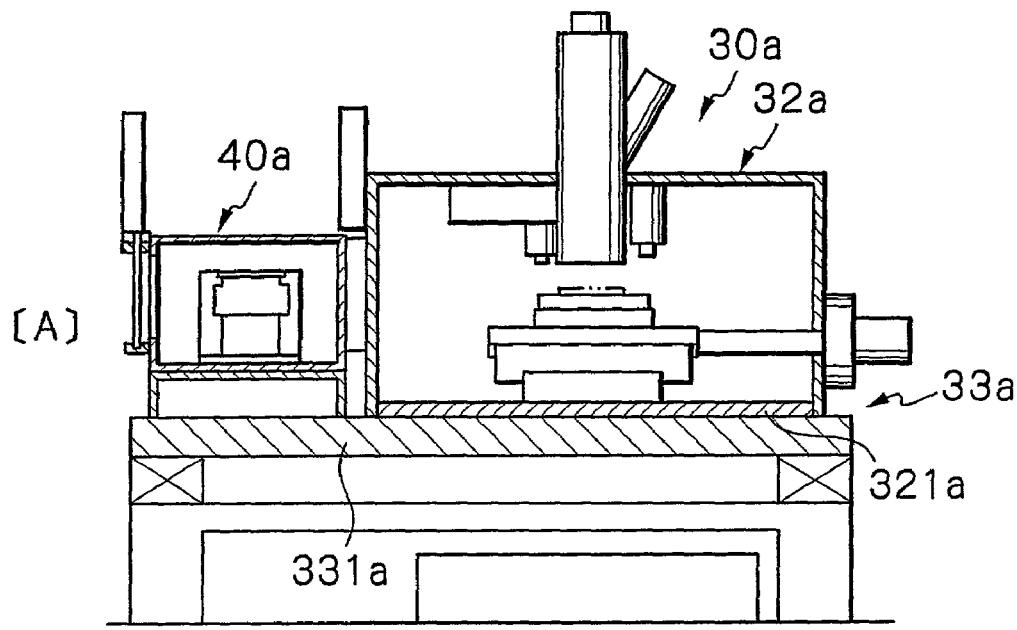
[A]
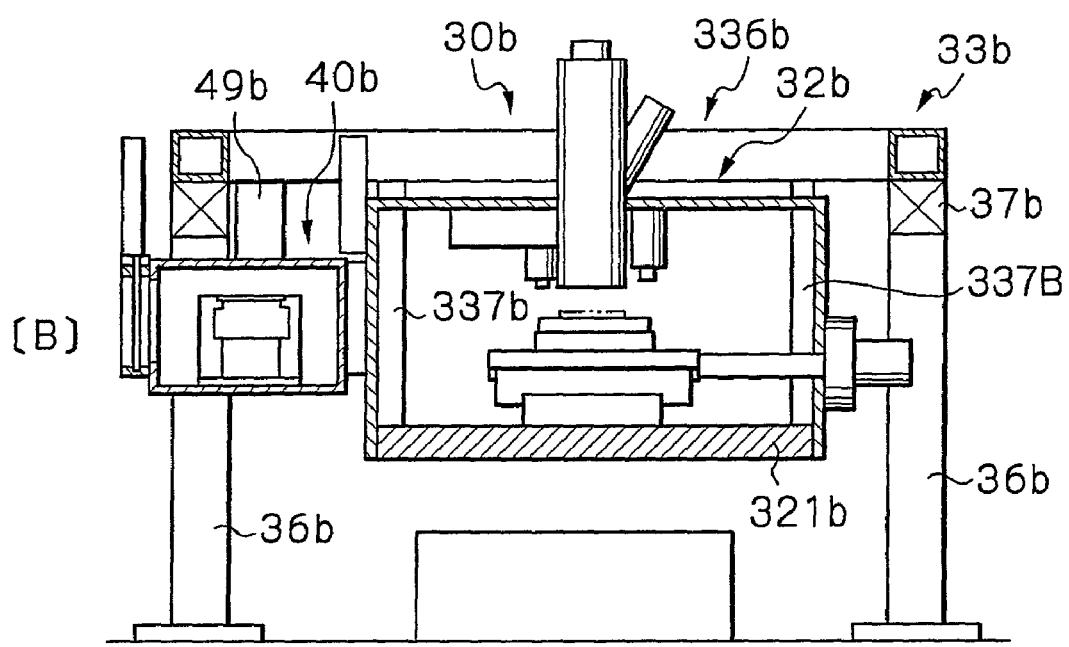
[B]

Fig. 17
(A)
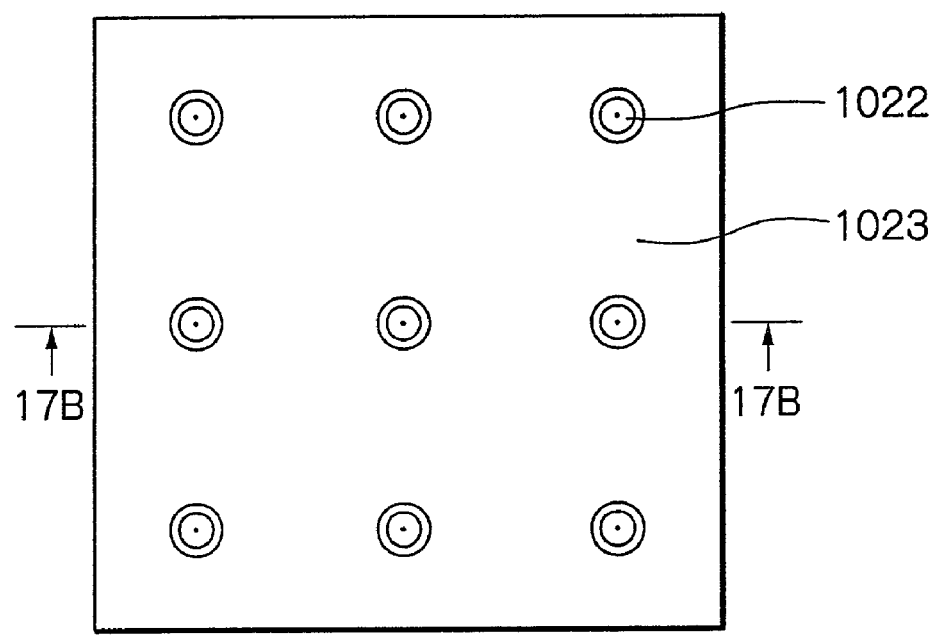
(B)
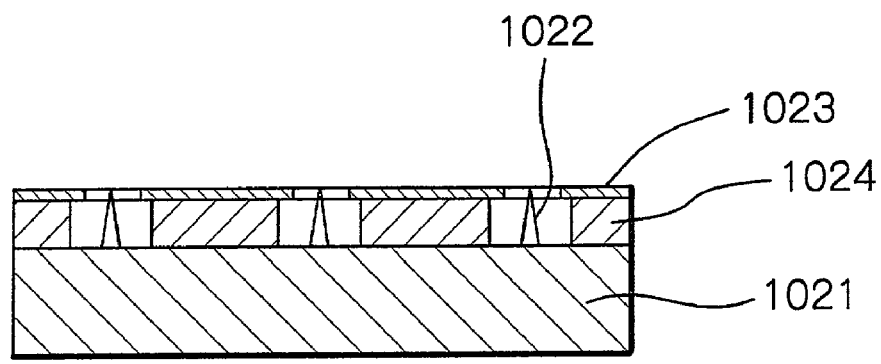

Fig. 27
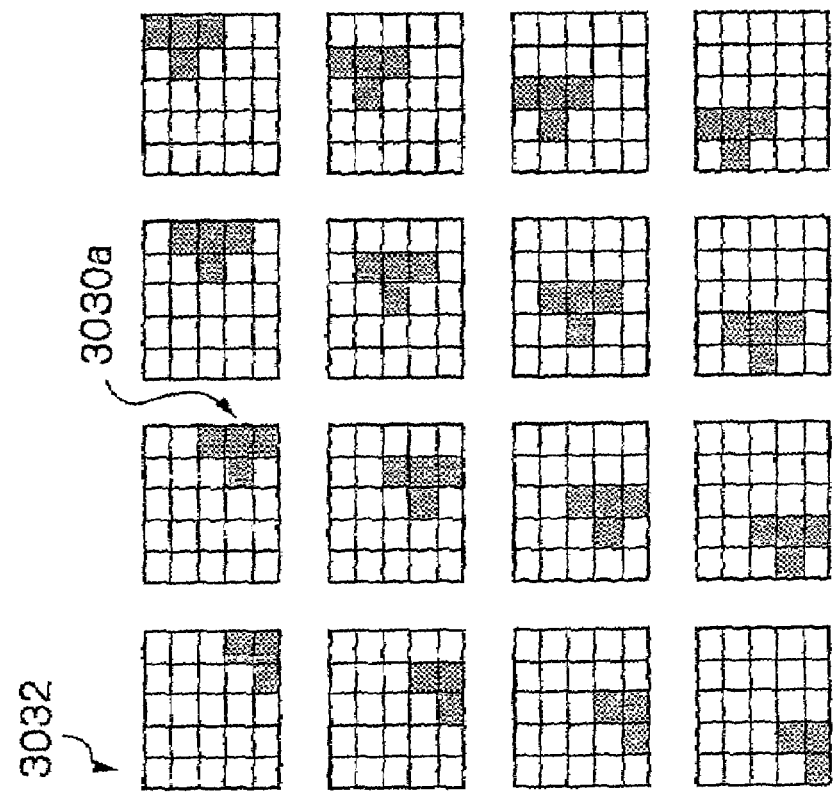
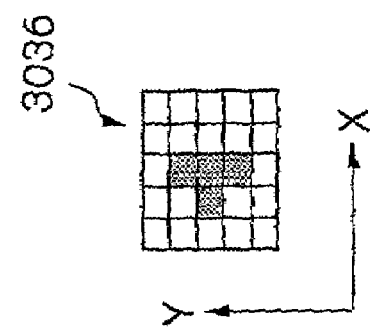

Fig. 41
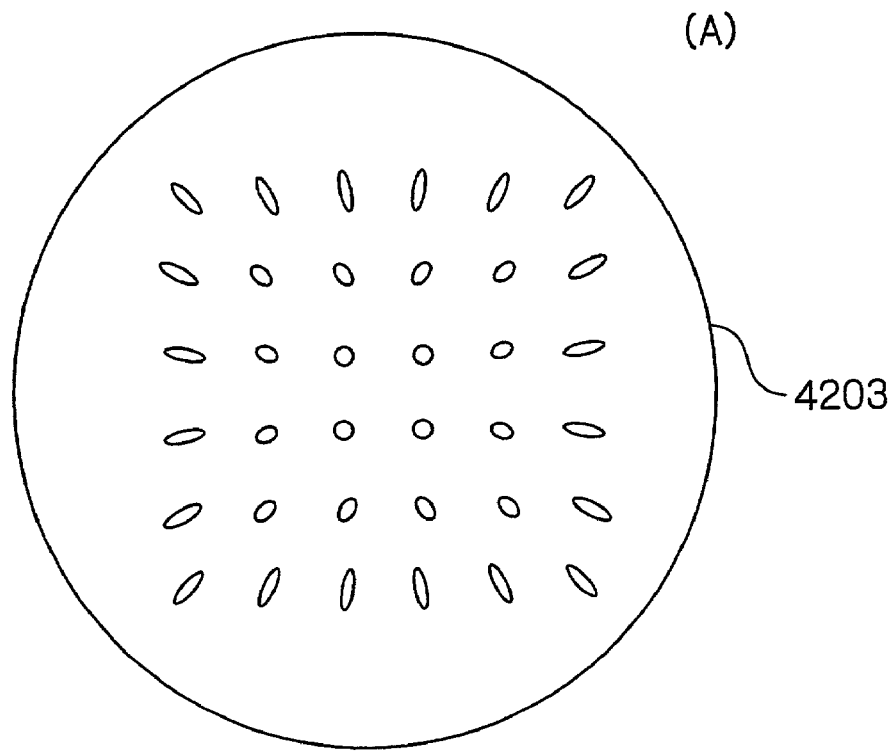
(A)
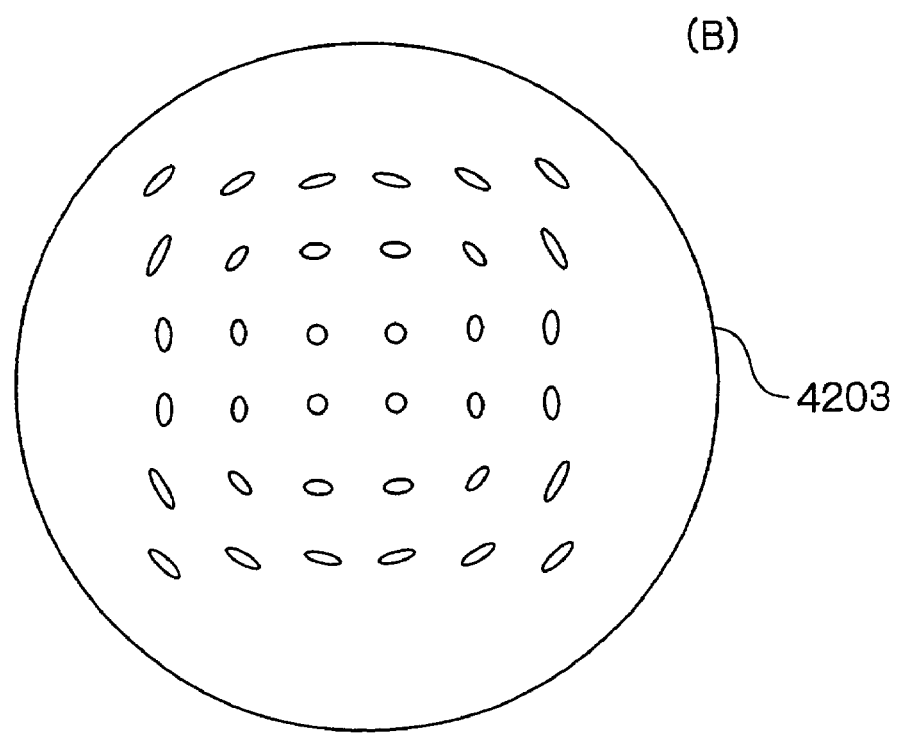
(B)

Fig. 45
(A)
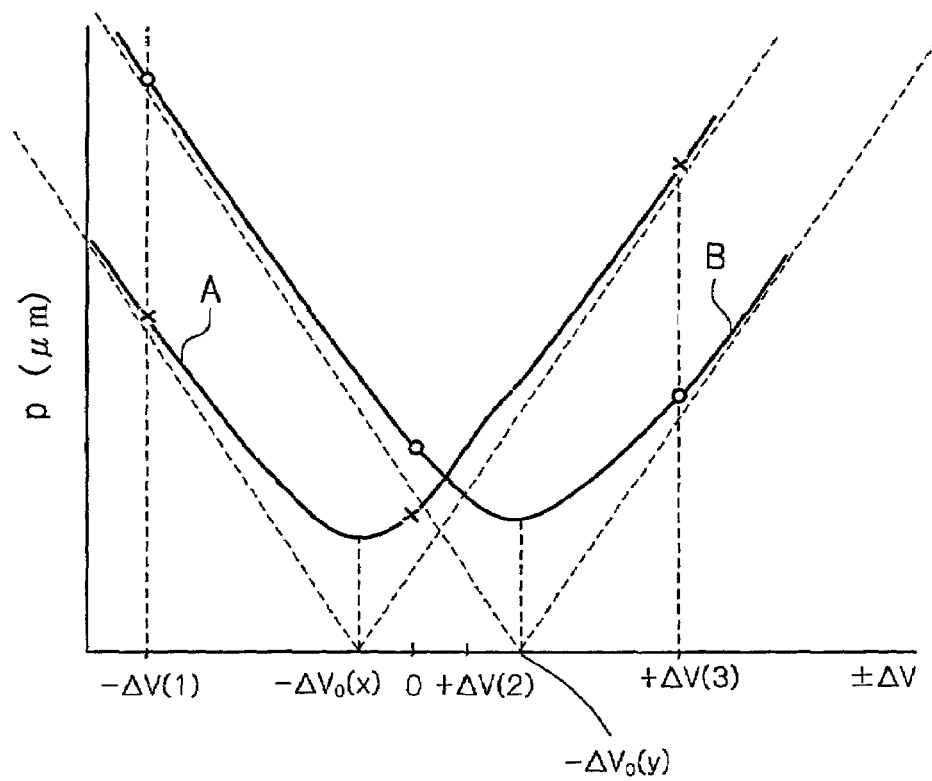
(B)
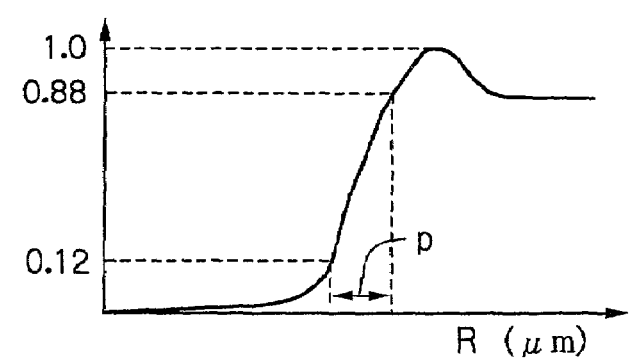

Fig. 50
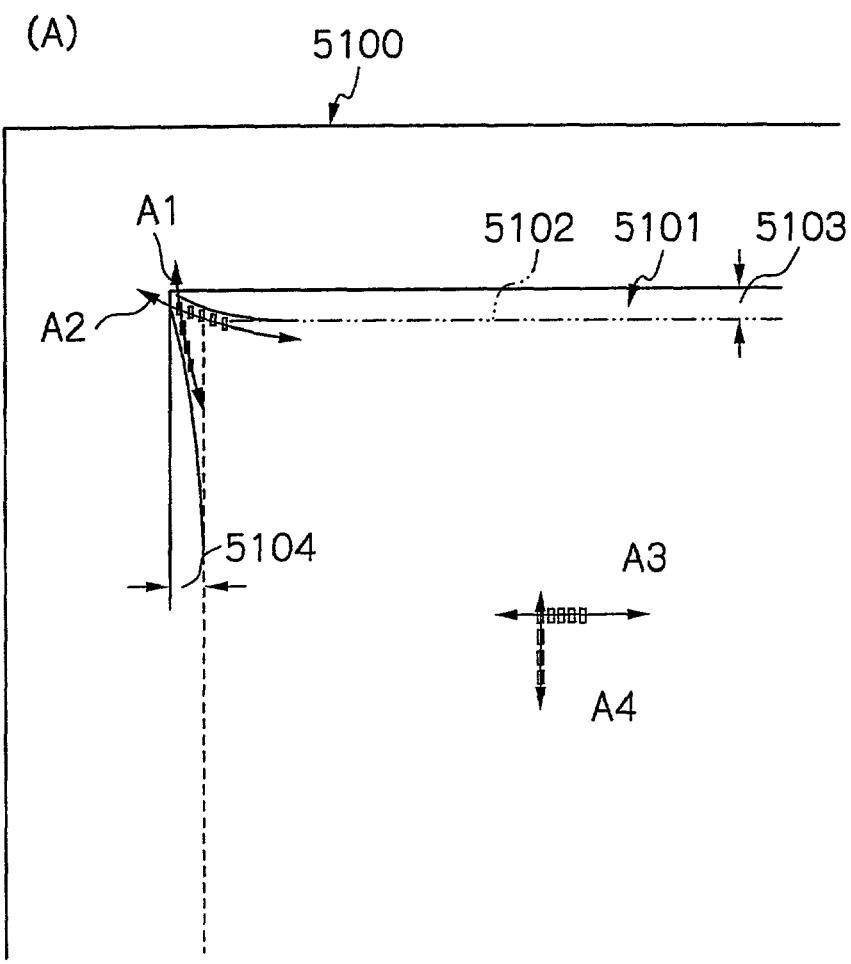
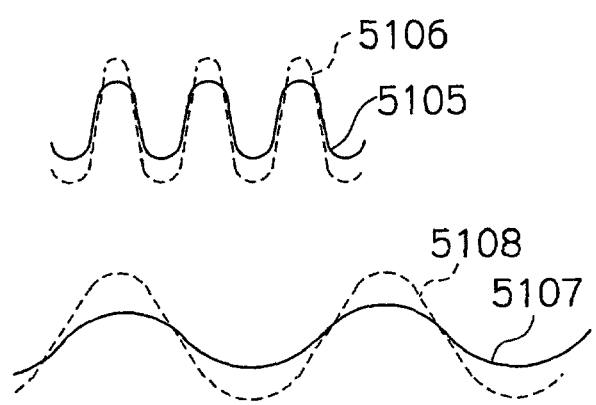

INSPECTION SYSTEM BY CHARGED PARTICLE BEAM AND METHOD OF MANUFACTURING DEVICES USING THE SYSTEM

TECHNICAL FIELD

The present invention relates to an inspection apparatus for the inspection of a defect, etc. of a pattern formed on a surface of an object of inspection by using a plurality of electron beams. More particularly, the present invention relates to an inspecting apparatus for inspecting a pattern or the like with high throughput, which is formed on the surface of an object of inspection on the basis of an image data that in turn is formed by irradiating the object of inspection with electrons and trapping secondary electrons varying in accordance with characteristics and shapes of the surface thereof, as in the case where a defect of a wafer is to be detected in the semiconductor manufacturing process. In addition, the present invention relates to a method for manufacturing devices with a high yield by using the inspection apparatus according to the present invention.

The present invention is concerned with a charged particle beam apparatus for detecting secondary charged particles generating from the point of irradiation of a sample by irradiating the sample with the charged particle beams and to a method for the preparation of a device for inspecting a defect of the device by means of the charged particle beam apparatus.

The present invention relates to an apparatus for irradiating a sample disposed on an XY stage with a charged particle beam and to a defect inspection apparatus or an exposure apparatus by utilizing the apparatus. Moreover, the present invention relates to a method for the preparation of semiconductors by using this apparatus.

The present invention relates to a defect inspection apparatus and a defect inspection method for inspecting a defect of a sample such as a semiconductor wafer or the like by comparing an image of the sample with a reference image prepared in advance, and also relates to a method for the manufacturing semiconductor devices by using the defect inspection apparatus or method.

The present invention is concerned with an electron beam apparatus for performing various inspections on a sample by irradiating the sample with electron beams and measuring the secondary electron beam generated from the point of irradiation. More particularly, the present invention relates to an electron beam apparatus for performing various operations including the inspection of a defect of a pattern of an integrated circuit having a minimum line width of 0.1 micron or less with high throughput, formed on a semiconductor wafer, measurement for CD (critical dimension), measurement for accuracy in alignment, measurement for voltage, etc.

The present invention relates to an electron beam apparatus for projecting an image onto the plane of a detecting device, which comprises irradiating an aperture plate having a plurality of apertures with an electron beam generated from an electron gun, delivering secondary electron beams generated from the sample into a secondary optical system after separation from a primary optical system, and enlarging the secondary electron with the secondary optical system. Further, the present invention relates to a method for the preparation of a device, which comprises evaluating a wafer during the process for manufacturing the wafer by using the electron beam apparatus according to the present invention.

The present invention is concerned with an electron beam apparatus that performs various operations including inspections of a defect of a pattern having a minimal line width of 0.1 micron or less, measurements for line widths, alignment accuracy measurements, voltage measurements, analysis of operations at high speed during the device operations, and so on. Moreover, the present invention relates to a method for the preparation of a device in which the yield is improved by evaluating a wafer during the manufacturing process by using the electron beam apparatus according to the present invention.

The present invention relates to an electron beam apparatus and a method for the preparation of a device by using the electron beam apparatus. More particularly, the present invention relates to an electron beam apparatus that can perform various operations including inspections of a defect of a sample with a device pattern having a minimal line width of 0.1 micron or smaller, line width measurements, alignment accuracy measurements, measurements of voltage on the surface of the sample, or measurements of high precision time resolution with a high throughput and reliability. Moreover, the present invention relates to a method for the preparation of a device, which can improve yield by evaluating a wafer during the manufacturing process by using the electron beam apparatus.

An object of the present invention is to provide an electron beam apparatus capable of performing a focusing an electronic optical system thereof in an electronic optical manner as well as in a short time, and a semiconductor device manufacturing method using the same apparatus.

The present invention relates to an electron beam apparatus and a method for the preparation of a device by using the electron beam apparatus. More particularly, the present invention relates to an electron beam apparatus which can carry out inspections of a defect of a sample having a device pattern with a minimal line width of 0.1 micron or smaller with high throughput and reliability and to the method for the preparation of a device, which can improve a yield by evaluating a wafer during the manufacturing process by using the electron beam apparatus according to the present invention.

The present invention is concerned with an electron beam apparatus for evaluating a pattern or the like formed on the surface of a sample and to a method for the preparation of a device by evaluating the sample during or after the manufacturing process by using the electron beam apparatus according to the present invention. More particularly, the present invention is concerned with an electron beam apparatus that can perform various operations with high throughput and with reliability, the various operations including inspections of a defect of a pattern of a device or the like having a minimal line width of 0.1 micron or smaller on a sample, CD measurements, voltage contrast measurements, high time resolution voltage measurements, and so on. Moreover, the present invention is concerned with a method for the preparation of a device by evaluating the sample during or after the manufacturing process by using the electron beam apparatus according to the present invention.

The present invention relates to an E×B separator and an inspection apparatus for inspecting a semiconductor wafer by using the E×B separator. More particularly, the present invention relates to an E×B separator adapted to enlarge a region around the optical axis where a uniform magnitude of the magnetic field or the electric field can be obtained and to an inspection apparatus that can perform various operations with high throughput and reliability by using the E×B separator, the various operations including inspections of a defect of a semiconductor wafer, measurements of pattern line widths, measurements of accuracy of overlapping patterns or voltage measurements at a high time resolution.

The present invention also relates to an apparatus for irradiating a charged beam against a sample loaded on an XY stage, and in more detail, to a charged beam apparatus provided with a differential exhausting mechanism not in the XY stage but around a lens barrel and to a defect inspection apparatus or an exposing apparatus utilizing the same charged beam apparatus, and further, to a semiconductor manufacturing method using those apparatuses described above.

The present invention also relates to an apparatus for evaluating a wafer or the like having a pattern of minimum line width not greater than 0.1 µm with high throughput as well as with high reliability, and to a method for manufacturing a device by using the same apparatus with an improved yield.

In semiconductor processes, design rules are reaching 100 nm and production is on a transition from mass production with a few models representative of DRAM into small-lot production with a variety of models, such as a SOC (System on Chip). This will result in the increase of the number of processes, and an improvement in yield for each process is essential; which makes it more important to inspect for defects occurring in each process. Accordingly, the present invention relates to an apparatus to be used in the inspection of a wafer after particular steps in the semiconductor formation process, and to an inspection method and apparatus using an electronic beam and further to a device manufacturing method using the same.

BACKGROUND ART

As prior art inspection apparatuses in connection with the present invention, an apparatus using a scanning electron microscope (SEM) has already been launched on the market. This apparatus is designed in such a way that an electron beam converged slenderly is subjected to raster scanning at a raster width having an extremely small interval, forming a SEM image by detecting the secondary electron emitted from the object of inspection upon scanning, and extracting a defect by comparing the SEM image at the same position of different dice.

Further, many proposals have been made so far that a throughput can be improved by using plural electron beams, that is, multi-beams. The proposals disclosed are directed primarily to the way of forming the multi-beams and to the way of detecting the multi-beams. No proposal, however, have been yet made as to an apparatus that has completed a whole system for a defect inspection apparatus.

In order to detect a defect of a mask pattern for use in manufacturing semiconductor devices or a pattern formed on a semiconductor wafer, a scanning electron microscope has been used. The scanning electron microscope requires a long time for inspection of a whole sample because the surface of the sample is scanned with one electron beam converged slenderly and the secondary electrons emitted from the sample are to be detected. In order to solve these problems, it has been proposed that the electrons from a plurality of electron sources are focused on the plane of a sample through a decelerating electron field lens and scanned to deflect the secondary electrons emitted from the surface of the sample by means of a Wien's filter, thereby guiding the deflected secondary electrons to a plurality of detectors (Japanese Journal of Applied Physics, Vol. 28, No. 10, October, 1989, pp. 2058–2064).

For an apparatus for exposing a pattern of a semiconductor circuit or the like to the surface of a sample such as a semiconductor wafer or the like or for inspecting a pattern formed on the surface of such a sample by irradiating the surface of the sample with charged particle beams, such as electron beams or the like, or for an apparatus for subjecting the sample to very high precision processing by irradiating it with the charged particle beams, a stage is used that can align the sample in vacuum with high degree of precision.

When such a stage requires alignment at a very high level of precision, the stage uses a structure that it is supported in a non-contact way by means of a hydrostatic bearing. In this configuration, the vacuum level in a vacuum chamber can be sustained by forming a differential exhaust mechanism for discharging high pressure gases within the range of the hydrostatic bearing so as to prevent the high pressure gases to be supplied from the hydrostatic bearing from being emitted directly into the vacuum chamber.

An example of such a conventional stage is shown in FIGS. 18A and 18B. In the configuration as shown in FIGS. 18A and 18B, a top end portion of a lens barrel 2001 of a charged beam apparatus for irradiating a sample with charged beams, that is, a charged beam irradiation portion 2002, is mounted on a housing 2008 constituting a vacuum chamber C. The inside of the lens barrel is made in a vacuum state by discharging the air with a vacuum line 2010, and the vacuum chamber C is made in a vacuum state by discharging the air with a vacuum line 2011. Charged beams are irradiated from the top end portion 2002 of the lens barrel 2001 onto the sample S such as a wafer, etc. disposed thereunder.

The sample S is detachably held on a sample table 2004 by conventional means. The sample table 2004 is mounted on top surface of a Y-directionally movable portion 2005 of an XY stage (hereinafter referred to as "the stage") 2003. The Y-directionally movable portion 2005 is slidably mounted on an X-directionally movable portion 2006, and the X-directionally movable portion 2006 is slidably mounted on a stage table 2007.

The Y-directionally movable portion 2005 is installed with a plurality of hydrostatic bearings 2009a on the surface (the left- and right-hand surfaces and the bottom surface in FIG. 18A) opposite to a guide surface 6a of an X-directionally movable portion 2006, and the Y-directionally movable portion is disposed so as to be movable in the Y-direction (in the left- and right-hand directions in FIG. 18B) while maintaining a fine clearance from the guide surface by means of the action of the hydrostatic bearing 2009a. Similarly, the X-directionally movable portion 2006 is installed with a plurality of hydrostatic bearings 2009b and is movable in the X-direction (in the left- and right-hand directions in FIG. 18A) while maintaining a fine clearance between the hydrostatic bearings 2009b and the guide surface 2007a.

A differential exhaust mechanism system is further mounted around the hydrostatic bearings so that no high pressure gases fed to the hydrostatic bearings leak into the inside of the vacuum chamber C. This configuration is shown in FIG. 19. Grooves 2017 and 2018 are disposed doubly around the hydrostatic bearings 2009 and subjected to vacuum discharging always by means of a vacuum line and a vacuum pump (not shown). This configuration allows the Y-directionally movable portion 2005 held in vacuum in a non-contact state to be movable in the Y-direction. The grooves 2017 and 2018 of a double structure are formed on the surface with the hydrostatic bearings 2009 of the movable part 2005 disposed thereon so as to encircle the hydrostatic bearings. The configuration of the hydrostatic bearings is a known one so that a detailed description will be omitted from the explanation that follows.

As is apparent from FIGS. 18A and 18B, the X-directionally movable portion 2006 with the Y-directionally movable portion 2005 loaded thereon is a concave with the top face upwardly open. The X-directionally movable portion 2006 is provided with the hydrostatic bearings and the grooves in substantially the same configuration, and it is held in a non-contact state on a stage table 2007 so as to be movable in the X direction. By combining the movement of the Y-directionally movable portion 2005 with the movement of the X-directionally movable portion 2006, the sample S is transferred horizontally to an optional position with respect to the top end portion of the lens barrel, that is, the charged beam irradiation portion 2002, and it is irradiated at the desired position with charged beams.

Hitherto, a defect inspection apparatus for inspecting a defect of a sample such as a semiconductor wafer or the like has been used in a process for manufacturing semiconductors, the defect inspection apparatus being of a structure so as to inspect the defect of the sample by detecting a secondary electron generated by the irradiation of the sample with a primary electron.

This defect inspection apparatus uses technology designed to automate and render the inspection of defects of a sample more efficient by application of an image recognition technique. This technique is designed to subject pattern image data in a region of inspection on the surface of the sample, obtained by the detection of the secondary electrons, and pre-stored reference image data on the surface of the sample, to a matching operation with a computer and to automatically determine the presence or absence of defects on the sample on the basis of the result of the matching operation.

Nowadays, there is a great demand in the field of manufacturing semiconductors to detect fine defects, as patterns are rendered finer. Under such circumstances, further improvements in precision of recognition are demanded for a defect inspection apparatus utilizing the image recognition technique as described above.

Hitherto, the process for scanning electron beams in the direction parallel to the direction of movement of a sample table and perpendicular thereto while continuously transferring the sample table (JP-A-10-134757, Japanese Patent Application Laid-Open) has been known. Another scanning process is known which involves irradiating the surface of a sample with a primary electron beam diagonally in two-dimensions while projecting in a one-axial direction at equal intervals. It has further been known to perform inspections and so on by dividing electrons from each electron gun into a plurality of electrons and scanning each beam in one direction while continuously moving the sample table in the direction perpendicular to the scanning direction.

As an electron beam apparatus for use in inspecting a defect of a mask pattern for use in manufacturing semiconductor devices or a pattern formed on a semiconductor wafer, there is known an electron beam apparatus of the type that inspects defects of a pattern on the sample, which comprises irradiating an aperture plate having a plurality of apertures with an electron beam emitted from a single electron gun to produce a plurality of images of the apertures, delivering the resulting plural images of the apertures onto a sample, and projecting the secondary electrons emitted from the sample onto the surface of a detector as an image by using a secondary optical system.

The conventional electron beam apparatus of that type, however, fails to take into account the dependency on the angle of the electron beam emitted from the electron gun, and it treats the magnitude of the electron beam as being uniform regardless of the angles of irradiation of the electron beam. In other words, the problem has not been taken into consideration that, in the electron beams emitted from the electron gun, an electron beam having a high magnitude of illuminance is emitted in the direction of the optical axis, however, the illuminance (magnitude) of the electron beam is gradually decreased as the electron beam becomes apart from the optical axis.

Further, there is the problem that the rate of detection of the secondary electron emitted from the sample is high for the secondary electron emitted in the vicinity of the optical axis and that the rate of detection of the secondary electrons drops as the secondary electrons separate from the optical axis. The conventional electron beam apparatus, however, fails to take this problem into consideration.

An electron beam apparatus using a plurality of electron beams is also known, which is used for inspecting a defect in a circuit having a fine circuit pattern, such as a super LSI circuit, or measuring a line width of such a circuit pattern. Such an electron beam apparatus using multi-beams was proposed in order to solve the problem of a conventional electron beam apparatus of the type using one electron beam for forming or inspecting such a fine circuit pattern because such a conventional electron beam apparatus requires a long period of time for processing and fails to gain a sufficient degree of throughput.

In connection with such an electron beam apparatus of the type using multi-beams, there is also known an electron beam apparatus, for example, of the type having a large number of electron emitters arranged in a matrix configuration, which is provided with an open mask between the surface of a sample and the surface of inspection in order to solve the problem that a level of precision in inspection could not be increased because intervals of a detector for detecting reflected electrons or a secondary electrons is extremely narrow so that the reflected electrons or the secondary electrons are likely to invade the detecting region from the adjacent irradiating region.

Moreover, there is known an electron beam apparatus of the type which forms a plurality of electron beams by irradiating a mask with plural apertures with an electron beam emitted from a single electron gun, in order to solve the problem that throughput is decreased due to the fact that scanning requires a long period of time if a defect of a pattern having a line width of approximately 0.1 micron is to be inspected by scanning the pattern on the sample with one electron beam.

In order to perform defect inspection, etc. on a sample having a device pattern having a minimal line width of 0.1 micron or smaller, the ability of a light system is in a limit of inspection from the viewpoint of resolution on the diffraction of light and, therefore it has been proposed that an inspection-evaluation apparatus that utilizes an electron beam. The use of the electron beam, however, has the problem from the viewpoint of productivity because a drastic decrease in throughput is caused, although resolution can be improved. An electron beam apparatus that is modified so as to use multi-beams to improve productivity is also known. More specifically, this known electron beam apparatus is configured in such a manner that the electron beams emitted from a single electron gun are irradiated onto a plurality of apertures and the electron beams passed through the apertures are subjected to scanning of the surface of a sample (hereinafter referred to sometimes as "sample surface"), thereby allowing the secondary electron to be emitted from each image and guiding the secondary electron to each of a plurality of detectors for inspecting the sample.

When a pattern formed on a sample surface such as a semiconductor wafer is to be evaluated with high accuracy by using result of a scanning operation of the electron beam, it is necessary to consider variation in the height of the sample. This is because differences in the height of the sample vary distances between a pattern on the surface of the sample and an objective lens by which the electron beam is to be focused on said pattern, and thereby focusing condition was not satisfied, resulting in deterioration of resolution, which make it impossible to perform an accurate evaluation.

In order to overcome this problem, an electron beam apparatus has been suggested that performs a focusing operation of the electronic optical apparatus in a manner whereby the light is irradiated against the sample surface at a certain angle, the reflected light thereof is utilized to measure the height of the sample, a measurement is fed back to the electronic optical system by which the electron beam is to be focused on the sample, and thereby the current and the voltage applied to the components of the electronic optical system are controlled.

However, in a method for irradiating the light against the sample at a certain angle, an optical component for reflecting the incident light, which is mainly composed of insulating material, should be disposed in a space between the sample surface and a lower surface of the electronic optical system. Thereby, the space between the sample surface and the lower surface of the electronic optical system has to be made wider than is required, while on the other hand, the wider spacing makes such problems as an aberration of the electronic optical system non-negligible. Accordingly, although it is required to perform focusing of the electronic optical system and simultaneously to solve such problems of aberration of the electronic optical system, such method by which both requirements are accomplish has not been suggested.

In addition, since the focusing of the electronic optical system should be performed taking into account not only the distance between the sample surface and the lower surface of the electronic optical system but also a charging condition on the sample surface and a space-charge effect of the electron beam, if parameters relating to the focusing of the electronic optical system are not measured in an electronic optical manner, errors might possibly occur.

Further, there is another problem that, in a case that exciting current of a magnetic lens included in the electronic optical system is regulated to perform the focusing operation, a period from when the exciting current being set to a predetermined value until when a focal length of the electronic optical system is stabilized, namely settling time, must be taken rather longer, and consequently it is difficult to perform the focusing quickly. In another case where exciting voltage of an electrostatic lens is regulated to perform the focusing operation, a high voltage applied to the electrostatic lens shall be varied, which results in the same problem of longer settling time. Furthermore, there is another problem that evaluation by the electron beam results in low throughput.

The present invention has been made with a view solving the various problems described above, and an object of the present invention is to provide an electron beam apparatus capable of performing a focusing operation in an electronic optical system thereof in an electronic optical manner as well as in a short time, and a semiconductor device manufacturing method using the same apparatus.

In a case that defects are to be inspected on a sample having a minimal line width of 0.1 micron or smaller, the inspection by means of a optical light system has a limit due to the resolution due to diffraction of light. Therefore, an inspection-evaluation apparatus using an electron beam has been proposed. The use of the electron beam has improved resolution, however, since it has an extremely decreased throughput, there is a problem from the point of view of productivity. A patent application has been made for an invention relating to an electron beam apparatus for inspecting a sample by using multi-beams with the object to improve productivity, which comprises irradiating a plurality of apertures with electron beams emitted from a single electron gun and scanning the sample with the electron beams passed through the plural apertures, thereby guiding the secondary electron beam generated from each image reciprocally to a detector without causing crosstalk.

A variety of technologies have been reported on apparatuses for observing and evaluating a sample including an insulating material. Among apparatuses installed with such technology, there are known apparatuses installed with a scanning electron microscope, which has a charging detection function for evaluating charging state by measuring beam current of a primary beam, a current absorbed into a sample, amount of electrons reflected from an irradiating apparatus, an amount of secondary electrons emitted, and the like.

Hitherto, there has been known an E×B energy filter for use in conducting an analysis of energy in a field where the electric field is orthogonal to the magnetic field, which allows charged particles to move straight in the direction intersecting with both the electric field and the magnetic field at right angles. This filter allows only the charged particles having a particular degree of energy in the electron beams to travel straight by means that deflection of the electron beams by the electric field is canceled by the deflection of the electron beams by the magnetic field.

As the energy filter of the E×B type, one having the configuration as shown in FIG. 4 is proposed. In FIG. 4, reference numerals 1 and 1' each denotes a magnetic pole piece held at earth voltage; and reference numerals 2 and 2' each denote an electrode. A voltage +V is applied to the electrode 2 and a voltage −V is applied to the electrode 2'. These voltages are equal to each other as an absolute value and variable. A charged electron can travel straight in the direction intersecting both the electric field and the magnetic field, that is, in the direction perpendicular to the plane of the drawing.

A stage for accurately positioning a sample in a vacuum atmosphere has been used in an apparatus in which a charged beam such as an electron beam is irradiated onto a surface of a sample such as a semiconductor wafer so as to expose the surface of the sample to a pattern of a semiconductor circuit or the like or so as to inspect a pattern formed on the surface of the sample; it has also been used in another apparatus in which the charged beam is irradiated onto the sample so as to apply an ultra-precise processing thereto.

When said stage is required to be positioned highly accurately, there has been employed a structure in which the stage is supported by a hydrostatic bearing in a non-contact manner. In this case, a vacuum level in a vacuum chamber is maintained by forming a differential exhausting mechanism for exhausting a high pressure gas in an extent of the hydrostatic bearing so that the high pressure gas supplied from the hydrostatic bearing is not directly exhausted into the vacuum chamber.

FIGS. 18A and 18B show one of the examples of such stage according to the prior art. In the stage shown in FIGS. 18A and 18B, a tip portion of a lens barrel 2001 or a charged beam irradiating section 2002 of a charged beam apparatus for generating and irradiating a charged beam against a sample is attached to a housing 8 which makes up a vacuum chamber C. A sample S is detachably held on a sample table 2004. Other structures of the stage of FIGS. 18A and 18B will be described later.

A differential exhausting mechanism is provided surrounding the hydrostatic bearing 2009b so that a high-pressure gas supplied to the hydrostatic bearing does not leak into the vacuum chamber C. This is shown in FIG. 19. Doubled grooves 2017 and 2018 are formed surrounding the hydrostatic bearing 2009b, and are regularly exhausted to vacuum through a vacuum pipe by a vacuum pump, though not shown. Owing to such structure, a Y directionally movable unit 2005 is allowed to move freely in the Y direction in the vacuum atmosphere while supported in non-contact manner.

Those doubled grooves 2017 and 2018 are formed in a plane of the movable unit 2005 in which the hydrostatic bearing 2009b is arranged, so as to circumscribe said hydrostatic bearing. Combining the Y directionally movable unit 5 with an X directionally movable unit 2006 allows the sample S to be moved to any desired position in the horizontal direction relative to the tip portion of the lens barrel or the charged beam irradiating section 2002, so that the charged beam can be irradiated onto a desired location of the sample.

However, the stage including a combination of the hydrostatic bearing and the differential exhausting mechanism as described above has a problem that the overall structure thereof becomes more complex and rather larger in comparison with a stage of hydrostatic bearing type used in the atmospheric air due to the differential exhausting mechanism included therein, resulting in lower reliability as a stage and also in higher cost.

As for methods for compensating for magnification chromatic aberration and rotation chromatic aberration in the electronic optical system, a method using a symmetric magnetic doublet lens is well known. Since no rotation chromatic aberration is generated in the electro static lens system, the magnification chromatic aberration is compensated for by using a doublet lens.

As high integration of semiconductor devices and microfabrication of patterns thereof advance, an inspection apparatus with higher resolution and throughput has been desired. In order to inspect a wafer substrate of 100 nm design rules for defects, a resolution corresponding to 100 nm or finer is required, and the increased number of processes resulting from high integration of the device causes an increase in an amount of inspection, which consequently requires higher throughput. In addition, as multi-layer fabrication of the devices has progressed, the inspection apparatus has been further required to have a function for detecting a contact malfunction in a via for interconnecting wiring between layers (i.e., an electrical defect). In the current trend, a defect inspection apparatus of optical method has been typically used, but it is expected that inspection apparatuses using an electron beam may soon be mainstream, substituting for optional inspection apparatuses from the viewpoint of resolution and of inspection performance for contact malfunction. Defect inspection apparatuses using electron beam methods, however, has a weak point that it is inferior to that of optical method in throughput.

Accordingly, an apparatus having higher resolution and throughput and being capable of detecting the electrical defects is desired. It is known that the resolution in the optical inspection apparatus is limited to ½ of the wavelength of the light to be used, and it is about 0.2 micrometer for an exemplary case of a visible light in practice.

On the other hand, in the method using an electron beam, typically a scanning electron beam method (SEM method) has been used, wherein the resolution thereof is 0.1 µm and the inspection time is 8 hours per wafer (20 cm wafer). The electron beam method has the distinctive feature that it can inspect for electrical defects (breaking of wire in the wirings, bad continuity, bad continuity of via); however, the inspection speed (sometime also referred to as the inspection rate) thereof is very low, and so the development of an inspection apparatus with higher inspection speed is desirable.

Generally, since inspection apparatus is expensive and the throughput thereof is rather lower as compared to other processing apparatuses, therefore the inspection apparatus has been used after an important process, for example, after the process of etching, film deposition, CMP (Chemical-mechanical polishing) flattening or the like.

A inspection apparatus of scanning electron beam (SEM) will now be described. In the inspection apparatus of SEM, the electron beam is contracted to be narrower (the diameter of this beam corresponds to the resolution thereof) and this narrowed beam is used to scan a sample so as to irradiate it linearly. On the one hand, moving a stage in the direction normal to the scanning direction allows an observation region to be irradiated by the electron beam as a plane area. The scanning width of the electron beam is typically some 100 µm. Secondary electrons emanating from the sample by the irradiation of said contracted and narrowed electron beam (referred to as the primary electron beam) are detected by a detector (a scintillator plus photo-multiplier (i.e., photoelectron multiplier tube) or a detector of semiconductor type (i.e., a PIN diode type) or the like).

The coordinates for an irradiated location and an amount of the secondary electrons (signal intensity) are combined and formed into an image, which is stored in a storage or displayed on a CRT (a cathode ray tube). The above description demonstrates the principles of the SEM (scanning electron microscope), and defects in a semiconductor wafer (typically made of Si) being processed may be detected from the image obtained in this method. The inspection rate (corresponding to the throughput) depends on the amount of the primary electron beam (the current value), the beam diameter thereof and the speed of response of the detector. The beam diameter of 0.1 µm (which may be considered to be equivalent to the resolution), a current value of 100 nA, and the speed of response of the detector of 100 MHz are currently the highest values, and in the case using those values the inspection rate has been evaluated to be about 8 hours for one wafer having a diameter of 20 cm. This inspection rate, which is much lower compared with the case using light (not greater than 1/20), has been a serious drawback.

On one hand, as a method for improving the inspection rate, which is a drawback of the SEM method, a multi beam SEM using a plurality of electron beams is well known. Although this method can improve the inspection rate by an amount of number of plurality of electron beams, there are other problems associated with this method that since the plurality of electron beams is irradiated from an oblique direction and a plurality of secondary electron beams from the sample is taken out in an oblique direction, only the secondary electrons emanated from the sample at the oblique direction could be captured by the detector, that a shadow is generated on an image, and that since it is difficult to separate respective secondary electrons generated by respective plural electron beams, secondary electron signals are mixed with each other.

SUMMARY OF THE INVENTION

It can be noted herein that the conventional defect inspection apparatuses with SEM applied thereto have a small beam dimension so that the dimension of the resulting image and raster width become small. Therefore, the conventional apparatuses have the problem that a long period of time is required for inspection of a defect of a sample. Moreover, they may present the problem that a quality SEM image cannot be obtained because a wafer with an insulating material disposed on the surface thereof is charged with electricity when the beam current is made larger in order to accomplish high throughput.

Further, apparatuses using multi-beams present various problems: the overall configuration of the entire apparatus as well as the electronic-optical system are not clear; the mutual interaction between the electronic-optical system and the sub-systems is not at all clear so far; moreover, as wafers as objects of inspection become larger, sub-systems of the apparatus must be compatible with larger-sized wafers.

The present invention has been accomplished with the above problems taken into account, and one object of the present invention is to provide an inspection apparatus in which an electronic-optical system with multi-beams can be used, and throughput can be improved, by harmonizing the electronic-optical system with the other parts constituting the inspection apparatus.

Another object of the present invention is to provide an inspection apparatus that can inspect an object of inspection with high precision by solving the problem relating to the SEM which arises from the charging with electricity.

A further object of the present invention is to provide a method for the preparation of a device at high yield by inspecting an object of inspection such as a wafer and so on by means of the inspection apparatus as described above.

The present invention provides an inspection apparatus for inspecting a pattern formed on an object of inspection by irradiating the pattern with an electron beam. The inspection apparatus comprises an electronic-optical system having sources of electrons, an objective lens, an E×B separator and an enlarging lens of at least one stage, the electronic-optical system being adapted to shape a plurality of primary electron beams, irradiate the object of inspection with the plurality of primary electron beams, accelerate secondary electrons emitted by the irradiation with the primary electron beams by means of the objective lens, separate the secondary electrons from the primary electron beams with the E×B separator, and project an image of the secondary electrons with an enlarging lens of at least one stage after separation of the secondary electrons from a primary optical system by the E×B separator.

The inspection apparatus further comprises a plurality of detectors for detecting the image of the secondary electrons projected by the electronic-optical system, a stage device disposed for holding the object of inspection and transferring it relative to the electronic-optical system, a working chamber arranged for accommodating the stage device and controlled so as to become in a vacuum atmosphere, a loader disposed for loading the object of inspection onto the stage device inside the working chamber, a voltage application mechanism system disposed in the working chamber for applying voltage to the object of inspection, and an alignment control device for controlling the alignment of the object of inspection relative to the electronic-optical system by observing the surface of the object of inspection for the alignment of the object of inspection relative to the electronic-optical system. The vacuum chamber is supported by the aid of a vibration isolator so as to block vibration from the floor on which said inspection apparatus is disposed.

The loader of the above inspection apparatus includes a first loading chamber and a second loading chamber, each being adapted to be capable of discretely controlling its atmosphere, a first transferring unit for transferring the object of inspection between the first loading chamber and the outside thereof, and a second transferring unit disposed in the second loading chamber for transferring the object of inspection between the inside of the first loading chamber and the stage device; wherein the inspection apparatus is further provided with a mini-environment space partitioned to feed the object of inspection to the loader.

Further, the inspection apparatus of this invention is provided with a laser gauge interferometer for detecting coordinates of the object of inspection on the stage device, wherein the coordinates of the object of inspection are determined with the alignment control device by utilizing a pattern existing on the object of inspection. In this case, the alignment of the object of inspection may include the rough alignment to be effected within the mini-environment space and the alignments of the positions in the X- and Y-directions and in the rotating direction to be effected on the stage device.

A further invention according to this application is directed to a method for manufacturing a device, which comprises detecting a defect on a wafer on the way or subsequent to the manufacturing process by means of the inspection apparatus.

The prior art apparatuses, however, cannot efficiently prevent crosstalk between plural electron beams and detect secondary electrons from the sample surface. On the other hand, the present invention has an object to provide a charged particle beam apparatus that can prevent the occurrence of crosstalk and guide emitted secondary electrons efficiently to the detector.

The charged particle beam apparatus 1000 according to the present invention may comprise at least one primary optical system for irradiating a sample with a plurality of primary charged particle beams and at least one secondary optical system for leading the secondary charged particles to at least one detector, wherein the plurality of the primary charged particle beams are irradiated at positions apart from one another by the distance resolution of the secondary optical system.

Further, the primary optical system is provided with a function of scanning the primary charged particle beams at an interval wider than the interval of irradiation of the primary charged particle beams.

A stage device with a combination of the hydrostatic bearings and the differential exhaust mechanism system shown in FIGS. 18A and 18B is arranged so as for the guide faces 2006a and 2007a opposite to the hydrostatic bearings 2009 to reciprocally move between the high pressure gas atmosphere of the hydrostatic bearing portion and the vacuum environment within the chamber, upon transferring the stage device. At this time, gases are adsorbed onto the guide faces while being exposed to the high-pressure gas atmosphere, and the gases adsorbed thereon are allowed to be dischargingon exposure to the vacuum environment. These actions are repeated. Therefore, whenever the stage device is transferred, a phenomenon occurs, in which the vacuum level within the chamber C is degraded, thereby rendering it difficult to conduct various operations, including exposure, inspection, processing, etc., by the charged beams and contaminating the sample with foreign materials.

Another object to be achieved by the present invention is to provide a charged beam apparatus that can perform various operations, including inspection, processing, and so on by means of charged beams while preventing a decrease in the vacuum level.

A further object to be accomplished by the present invention is to provide a charged beam apparatus disposed so as to produce a pressure differential between the region of irradiation of the charged beams and a support portion of the hydrostatic bearing, the charged beam apparatus having a non-contact support mechanism by means of a hydrostatic bearing and a vacuum sealing mechanism system by means of the differential exhaust.

A still further object of the present invention is to provide a charged beam apparatus adapted so as to reduce gases emitted from the surface of a part opposite to the hydrostatic bearing.

A still further object of the present invention is to provide a defect inspection apparatus for inspecting the surface of a sample with the charged beam apparatus as described above or an exposure apparatus for delineating a pattern on the surface of the sample.

A still further object of the present invention is to provide a method for manufacturing a semiconductor device by using the charged beam apparatus as described above.

The invention of this application is directed to an apparatus 2000 adapted to irradiate the surface of a sample with a charged beam by loading the sample on the XY-stage and moving the sample to a chosen position within a vacuum atmosphere. In this apparatus, the XY-stage is provided with a non-contact support mechanism by means of the hydrostatic bearing and with a vacuum sealing mechanism by means of differential exhaust; the XY-stage is further provided with a partition for rendering conductance smaller between a portion where the sample is irradiated with the charged beams and a support portion of the XY-stage for supporting the hydrostatic bearings, and a pressure differential occurs between the region of irradiation with the charged beam and the support portion for the hydrostatic bearing.

In accordance with the present invention, the stage device can achieve alignment performance with high precision within a vacuum atmosphere by applying the non-contact support mechanism by means of the hydrostatic bearings to the support mechanism of the XY-stage with the sample loaded thereon and arranging the vacuum sealing mechanism by means of the operating exhaust around the hydrostatic bearings to prevent the high pressure gas fed to the hydrostatic bearings from leaking into the vacuum chamber.

Moreover, the pressure at the position of irradiation with the charged beams is unlikely to rise because the gases are arranged unlikely to reach the position of irradiation of the charged beams by means of the partition apart from the position of irradiation with the charged beams, by which conductance can be made smaller, even if the gases adsorbed on the surface of a sliding portion of the stage are emitted whenever the sliding portion of the stage is transferred from the high pressure gas portion into the vacuum environment. In other words, the above configuration can accomplish processing of the sample by means of the charged beams with high precision without causing any contamination on the surface of the sample because the degree of vacuum at the position of irradiation with the charged beams on the sample surface can be stabilized and the stage can be driven with high precision.

The present invention is directed to the charged beam apparatus 2200 in which the differential exhaust structure is installed in the partition. In accordance with this invention, the partition is interposed between the hydrostatic bearing support portion and the region irradiated y charged beam, and the inside of the partition is installed with a vacuum exhaust passage to provide the differential exhaust mechanism. The differential exhaust structure can prevent gases emitted from the hydrostatic bearing support portion from passing through the partition and entering the region of irradiation with the charged beams. Therefore, the degree of vacuum at the position of irradiation with the charged beams can be made further stable.

The invention is directed to the charged beam apparatus 2300 in which the partition is provided with a cold trap function. Generally, in the pressure region having 10–7 Pa or higher, the major components of the residue gases in the vacuum atmosphere and the gases emitted from the surface of a material is water molecules. Therefore, if water molecules can be emitted in an efficient manner, a high degree of stability of vacuum can be sustained. On the basis of the concept as described immediately above, this invention is configured such that a cold trap, which is chilled at approximately −100° C. to −200° C., is disposed at the partition in order to allow the cold trap to freeze the gases emitted at the side of the hydrostatic bearing and trap them. The use of the cold trap makes it impossible or difficult for the emitted gases to enter the side of the region of irradiation with charged beam so that it becomes possible to sustain the degree of vacuum in the region of irradiation therewith in a stable manner. It is also to be noted herein as a matter of course that the cold trap is effective for the elimination of gaseous organic molecules such as oils, which are a major factor for impairing clean vacuum, as well as for the removal of the water molecule.

The invention of this application is directed to the charged beam apparatus 2400 which is provided with partitions at two locations in the vicinity of both positions of the region of irradiation with charged beam and the hydrostatic bearings. In accordance with this invention, partition that can reduce conductance is disposed at two locations nearby the position of the region of irradiation with charged beam and the hydrostatic bearings so that the vacuum chamber is eventually divided into three smaller chambers consisting of a charged beam irradiation chamber, a hydrostatic bearing chamber and an intermediate chamber, each having a smaller conductance. The pressure in each of the chambers is set such that the pressure in the charged particle beam irradiation chamber is the lowest and the pressure in the hydrostatic bearing chamber is the highest, while the pressure in the intermediate chamber is in between.

The three chambers constitute a vacuum exhaust system. The arrangement of the partition enables the control the rate of variation in pressure at a low level even if a rise in pressure would occur in the hydrostatic bearing chamber by the emitted gases, because the pressure in the hydrostatic bearing chamber is set to be higher. Therefore, a variation in pressure in the intermediate chamber can be controlled to a lower level by means of the partition, so that a variation of the pressure in the irradiation chamber can further be lowered to a lower level by means of the additional partition. This arrangement of the partition can reduce any variation in pressure to a level that does not substantially cause any problems.

The present invention is directed to a charged beam apparatus in which the gases to be fed to the hydrostatic bearings of the XY-stage are dry nitrogen gas or an inert gas of high purity. The invention is directed to the charged beam apparatus in which the XY-stage is subjected to surface processing at least on the surface facing the hydrostatic bearing in order to reduce the emitted gases.

As described above, the gas molecules contained in the high pressure gases are adsorbed on the surface of the sliding portion of the stage when exposed to the high pressure gas atmosphere at the hydrostatic bearing portion, and they are caused to be released from the surface of the sliding portion thereof and emitted as emitted gases, when the sliding portion thereof is exposed to the vacuum environment, thereby worsening the vacuum level. In order to control the lowering of the degree of vacuum, it is required to reduce an amount of the gas molecules to be adsorbed on the sliding portion of the stage and to discharge the adsorbed gas molecules as quickly as possible.

In order to achieve this, it is effective to remove gaseous components (such as organic materials, moisture, etc.), which are likely to be adsorbed on the surface of the part yet unlikely to be eliminated therefrom, from the high pressure gas to be fed to the hydrostatic bearings by removing a sufficient amount of moisture from the high pressure gas to give dry nitrogen gas or an inert gas of high purity (e.g. highly pure nitrogen gas, etc.). The inert gas such as nitrogen is low in the rate of adsorption on the surface of the part compared with moisture and organic materials and comparatively great in the speed at which it is eliminated from the surface thereof.

Therefore, when an inert gas of high purity from which moisture and organic materials are eliminated to the highest possible extent is used as the high pressure gas, the amount of gases to be emitted can be controlled to a lower level and the emitted gases can be emitted quickly, upon transferal of the sliding portion from the hydrostatic bearing portion to the vacuum environment, thereby reducing the extent to which the degree of vacuum is degraded. Accordingly, it is possible to reduce the rise in pressure when the stage is transferred.

Further, it is also effective to subject the structuring parts of the stage, particularly the part being transferred reciprocally between the high pressure gas atmosphere and the vacuum environment, to surface processing thereby reducing an energy of adsorption with the gas molecules. When a metal is used as a base material, the surface processing may be carried out, for example, by means of processing with TiC (titanium carbide) or TiN (titanium nitride), nickel plating, passivation treatment, electrolytic polishing, composite electrolytic polishing, glass bead shot, and so on. When SiC ceramics is used as a base material, the surface processing may be carried out, for example, by means of coating with a fine SiC layer by means of CVD. Accordingly, it is further possible to reduce the rise in pressure when the stage is transferred.

The present invention is directed to a wafer defect inspection apparatus for inspecting a defect on the surface of a semiconductor wafer by using the apparatus as described above. This invention provides an inspection apparatus that is high in inspection precision and causes no contamination of a sample, because the invention can realize an inspection apparatus that is highly accurate in the alignment performance of the stage and stable in the degree of vacuum within the region onto which the charged beam is irradiated.

The present invention is directed to an exposure apparatus for delineating a circuit pattern of a semiconductor device on the surface of a semiconductor wafer or a reticle by using the apparatus as described above.

The present invention can provide an exposure apparatus that is high in exposure performance and causes no contamination of a sample, because this invention can realize an inspection apparatus that is highly accurate in the alignment performance of the stage and stable in the degree of vacuum within the region on which the charged beam is irradiated.

The present invention is also directed to a method for manufacturing a semiconductor by using the apparatus as described in the above. This invention can provide a high quality fine semiconductor circuit by manufacturing the semiconductor with the apparatus that has high accuracy stage alignment performance and a stable degree of vacuum in the region of irradiation with charged beam.

Conventional technology has the problem a deviation in the position may be caused between an image of a secondary electron beam obtained by irradiation of an inspecting region on the surface of a sample with a primary electron beam and a reference image prepared in advance, so that precision of the inspection of the defect is lowered. This positional deviation may cause a big problem where part of an inspecting pattern is deleted from the inspecting image of the secondary electron beam due to a deviation of the irradiation region of the primary electron beam with respect to the wafer. This problem cannot be overcome alone by technology that optimizes the matching region within the inspecting image. It is further to be noted that this problem can become a critical defect in the inspection of a highly fine pattern.

The present invention is completed on the basis of the above findings and it has an object to provide a defect inspection apparatus that can prevent a decrease in precision of the inspection of a defect caused by the deviation in the position between the inspecting image and the reference image.

Moreover, the present invention has another object to provide a method for manufacturing a semiconductor device, which can improve a yield of device products as well as prevent the loading of defective products by conducting inspections of a defect of samples by means of the defect inspection apparatus having the above configuration.

In order to achieve the above objects, the defect inspection apparatus 3000 according to the present invention is concerned with a defect inspection apparatus for inspecting a defect of a sample, which is composed of an image acquisition means for acquiring an image of each of a plurality of inspecting regions which deviate from one another while overlapping partially with one another on the sample, a means for storing a reference image, and a defect determination means for determining a defect of the sample by comparing the image of each of the plurality of the inspecting regions acquired by the image acquisition means with the reference image pre-stored by the meaning means. As the sample as an object of inspection, there may be selected any sample on which a defect is to be inspected. For the present invention, a semiconductor wafer is particularly preferred because it can demonstrate excellent effects.

The present invention comprises an image acquisition means that is adapted to acquire the image of each of the plural inspecting regions which are deviated from one another while overlapping partially with one another on the sample, and the defect determination means for determining the defect of the sample by comparing the acquired image of each of the plural inspecting regions a stored reference image. As described above, the present invention can selectively utilize the reference image and the inspecting images less in the positional deviation in the subsequent step and consequently control a decrease in precision of detecting a defect due to the positional deviation because the images of the inspecting regions at different locations can be acquired.

Moreover, even if the sample and the image acquisition means are located in a relationship in which part of an inspecting pattern may usually be deleted from the inspecting image region, there is the extremely high probability that the entire inspecting pattern may be located in any one region in which the images of the plural inspecting regions that are deviated in their positions from one another are covered. Therefore, errors in detecting a defect which may be caused to occur due to a partial deletion of the pattern can be prevented.

The comparing means may be arranged so as to determine if the sample is free from defects, for example, when the sample is subjected to a so-called matching operation between each of the acquired images of the inspecting regions and the reference image and at least one image of the plural inspecting regions has no substantial difference from the reference image. Conversely, if the image of the entire inspecting region is substantially different from the reference image, it is determined that the sample involved has a defect. This permits defect inspection with high precision.

In a preferred embodiment of the present invention, the defect inspection apparatus further comprises a charged particle irradiation means in which each of the plural inspecting regions is irradiated with a primary charged particle beam to generate a secondary charged particle beam from the sample, wherein the image acquisition means is so arranged as to acquire the image of each of the plural inspecting regions one after another by detecting the secondary charged particle beam emitted from each of the plural inspecting regions. As the charged particle beam, an electron beam is preferred.

In a more preferred embodiment, the charged particle irradiation means comprises a source of the primary charged particles and a deflecting means for deflecting the primary charged particles and a deflecting means for deflecting the primary charged particles. The plural inspecting regions are irradiated one after another with the primary charged particles emitted by deflecting the primary charged particles emitted from the source of the particles with the deflecting means. In this embodiment, the position of the input image can be altered with ease by the deflecting means, so that a plurality of the inspecting images at different positions can be acquired at high speed. In a further embodiment of the present invention, there are provided a primary optical system for irradiating the sample with the primary charged particle beam and a secondary optical system leading a secondary charged particles to a detector.

The method for manufacturing the semiconductor according to another embodiment of the present invention includes a step of inspecting a defect of a wafer during the manufacturing process or as a finished product by using the defect inspection apparatus in each of the embodiments as described above. The other embodiments as well as the action and features of the present invention will become further apparent in the following description.

In the conventional technology as described above, electrons as many as three can be generated from one electron gun so that the disposition of a number of lens barrels is required. Further, for the above apparatuses, the electronic-optical system requires a partially semispherical inspection electrode. Moreover, the conventional technology adopts a system of the type that inspects minute inspecting regions one after another, so that the inspecting regions on which the electron beams are irradiated have to be changed frequently. Therefore, the inspecting surface (the sample) has to be transferred at an intermittent interval so that the time required for transferal of the sample is ineffective and consequently the time required for the inspection of the entire sample is considerably long.

Therefore, the present invention has the object to provide an electron beam apparatus that can solve the problems prevailing in the conventional technology as described above and can conduct inspections efficient.

The electron beam apparatus 4000 according to the present invention is directed to an electron beam apparatus for detecting a secondary electron beam from a predetermined region on the surface of the sample while transferring the sample, which includes a primary electron beam irradiation device for irradiating the surface of the sample with a plurality of primary electron beams and a secondary electron detector for detecting a secondary electron beam from the point of irradiation of each of the primary electron beams formed on the surface of the sample. The primary electron beam irradiation apparatus is configured in such a manner that the points of irradiation of the plurality of the primary electron beams formed on the surface of the sample are disposed in rows N in the direction of movement of the sample and in columns M in the direction perpendicular to the direction of movement of the sample and that each row of from row 1 to row N of the points of irradiation of the primary electron beams deviates one from another by a constant amount in both of the direction of movement of the sample and in the direction perpendicular thereto.

More specifically, the primary electron beam irradiation apparatus has an electron gun and an aperture plate having a plurality of apertures forming a plurality of electron beams which form the points of irradiation of the primary electron beams in rows N and in columns M upon receipt of the electrons emitted from the electron gun. The apertures are disposed in such a manner that the electrons emitted from the electron gun are located within the range of a predetermined electron density. Further specifically, each of the points of irradiation of the primary electron beams is arranged so as to scan the sample by (the distance between the adjacent rows)/(the number of the columns N)+α in the direction perpendicular to the direction of movement of the sample (in which α is the width of scanning in an overlapped manner together with the point of irradiation of the primary electron beam in the adjacent row, it could be from −1% to +20% of the scanning width, and it is usually approximately 10% or smaller of the scanning width).

This arrangement can widen a width for irradiation with an electron beam in the direction perpendicular to the direction of movement of the sample and conduct a continual inspection of the sample by means of such a wide width therefor. Each of M and N is an independent integral number which is greater than or equal to one.

The secondary electron beams to be detected by the secondary electron beam detector may be used for various measurements including, for example, measurements for a defect on the surface of a sample, measurements of a wire width of an integrated circuit to be formed on the surface of a sample, voltage contrast measurements, alignment precision measurements, and so on.

Further, for the electron beam apparatus as described above, the primary electron beam irradiation device is provided with a plurality of the electron guns, a plurality of aperture plates corresponding to the plural electron guns, and a plurality of primary electron beam irradiation systems in which the aperture plate corresponding to each electron gun can form the primary electron beam to be irradiated to the surface of the sample. The primary electron beam of each of the primary electron beam irradiation systems is arranged so as to avoid interference with the primary electron beams of the other primary electron beam irradiation systems. Further, it is possible to provide a plurality of the secondary electron beam detectors for each of the primary electron beam irradiation systems. This apparatus allows an inspection of the sample with a wider scanning width while transferring the sample, so that efficiency of inspection can be further increased.

The present invention has the object to provide an electron beam apparatus for detecting secondary electrons from a sample by means of multi-detectors by irradiating the sample with multi-beams, which can solve the problem that the strength of the beam on the optical axis of the primary electron is different from that of the beam outside the optical axis thereof and which can make the efficiency of detecting the secondary electrons from the sample substantially uniform.

Further, the present invention has the object to provide an electron beam apparatus for inspecting a secondary electron from a sample with multi-detectors by irradiating the sample with multi-beams, wherein the electron beam apparatus can solve the problems that the efficiency of detection of the secondary electron emitted in the vicinity of the optical axis on the sample is higher than that of detection of the secondary electron emitted in the position apart from the optical axis thereof and that it can make efficiency of detection of the secondary electrons from the sample substantially uniform.

Further, the present invention has the object to provide a method for evaluating a device during the manufacturing process by using the apparatuses as described above.

In order to solve the problems as described above, the invention is directed to an electron beam apparatus which irradiates an aperture plate having plural apertures with electron beams emitted from a source of the electron beams to create a plurality of images of the apertures; delivers the plural images of the apertures to a sample; separate the secondary electrons emitted from the sample from a primary optical system; to deliver the secondary electrons to a secondary optical system; to enlarge the secondary electrons with the secondary optical system; and projects the secondary electrons to the surface of a detector. In this electron beam apparatus, a single aperture plate is disposed at a position deviated toward the side of the electron beam source from the position of the image of the electron beam source formed by the lens of the primary optical system, so that the position of the aperture plate in the direction of the optical axis is disposed so as to minimize a difference of the beam strength from each aperture through which the beam is delivered to the surface of the sample.

By minimizing the difference in beam strength between each of the beams in the multi-beams to be delivered onto the surface of the sample in the manner as described above, the difference in beam strength between the beam nearby the optical axis and the beam apart from the optical axis can be made smaller so that the beams can be delivered onto the surface of the sample in a uniform way. Therefore, the electron beam apparatus can improve precision in inspection and measurement.

Further, by reducing the difference in beam strength between the beams in the multi-beams to be delivered onto the surface of the sample, the number of beams can be increased, and the multi-beams can be irradiated in a wider range. Therefore, the electron beam apparatus can further improve efficiency in inspection and measurement.

Moreover, the present invention is directed to the electron beam apparatus for projecting the secondary electron onto the surface of the detector by irradiating the aperture plate having the plural apertures with the electron beam emitted from the source of the electron beam to create the plural images of the apertures, delivering the plural images of the apertures to the sample, separating the secondary electrons emitted from the sample from the primary optical system, delivering the secondary electrons to the secondary optical system, and enlarging the secondary electrons with the secondary optical system.

In this electron beam apparatus, a single aperture plate is disposed at the position deviated toward the side of the electron beam source from the position of the image of the electron beam source formed by the lens of the primary optical system, and the amount of deviation of the position of the single aperture plate is set so as to minimize the difference in the amount of inspection of the secondary electron between the plural apertures becomes rendered minimal when a sample having no pattern is disposed on the surface of the sample.

By minimizing the amount of detection of the secondary electrons between the apertures by the detector of the secondary optical system in the manner as described above, this apparatus can control a variation in the ratio of detection of the electron beams in the secondary optical system, so that this invention can achieve high precision inspection and measurement, in addition to the features as described in the above.

Further, the present invention is directed to the electron beam apparatus, wherein a wafer during the manufacturing process is to be evaluated by means of the electron beam apparatus. The electron beam apparatus according to the present invention can evaluate the wafer at a high degree of precision and efficiency by evaluating the wafer during the manufacturing process.

In an apparatus of the type producing a plurality of electron beams by irradiating an aperture plate having a plurality of apertures with electron beams emitted from a single electron gun, reducing the electron beam from each of the apertures with a primary optical system, and projecting and scanning the reduced electron beam onto the surface of the sample, there may be found the problem that each of the electron beams cannot be projected on the desired position due to the distortion of the primary optical system. In addition, there is another problem in this apparatus that visual field astigmatism is present in the primary optical system for projecting the reduced electron beam on the surface of the sample, so that the dimensions and the shapes of the electron beams differ between the positions of the electron beams close to and outside the optical axis of the primary optical system.

Furthermore, the apparatus has the problem that the secondary electron beam cannot be projected on the desired position of a group of the detectors due to the presence of aberration in the secondary optical system for projecting the secondary electron beam emitted from the sample to the group of the detectors.

The present invention is proposed with the objects to solve the problems inherent in the conventional electron beam apparatuses. One of the objects of the present invention is to provide an electron beam apparatus that can reduce astigmatism of the primary optical system by correcting the distortion of the primary optical system and the aberration of the secondary optical system. The other object of the present invention is to provide a method for the preparation of a device that can improve a yield of the devices by conducting a variety of evaluations of the wafer during the manufacturing process by using the electron beam apparatus according to the present invention.

In order to achieve the objects as described above, the present invention is directed to an apparatus for irradiating an aperture plate having a plurality of apertures with an electron beam emitted from an electron gun, projecting and scanning a reduced image of each of the primary electron beams passed through the plurality of the apertures on the sample by means of the primary optical system, and projecting the secondary electron beam emitted from the sample onto the detector by enlarging the secondary electron beam with the secondary optical system, wherein the positions of the plurality of the apertures of the aperture plate are set so as to correct the distortion of the primary optical system.

The present invention is directed to an electron beam apparatus for the detection of the secondary electron beam emitted from a sample with a detector composed of a plurality of detection elements by irradiating a first multi-aperture plate having a plurality of apertures with the electron beams emitted from the electron gun, projecting and scanning the reduced image of the primary electron beam passed through each of the plural apertures on the sample by means of the primary optical system, and enlarging the secondary electron beams with the secondary optical system, the electron beam apparatus being disposed with a second multi-aperture plate having a plurality of apertures located in the front of the detector, wherein the positions of the apertures formed in the second multi-aperture plate are set so as to correct the distortion of the secondary optical system.

The present invention as is directed to an electron beam apparatus for irradiating the aperture plate having a plurality of apertures with the electron beam emitted from the electron gun, projecting and scanning the reduced image of the primary electron beam passed through the plurality of the apertures thereof on the sample, and projecting an image of the secondary electron beam emitted from the sample onto the detector by means of the secondary optical system, wherein the shape of each of the apertures is set so as to correct visual field astigmatism of the primary optical system.

The present invention provides an electron beam apparatus for acquiring an image data with a multi-channel by irradiating an aperture plate having a plurality of apertures with the electron beams emitted from the electron gun, projecting and scanning the reduced image of the primary electron beam passed through each of the plural apertures thereof on the sample by means of the primary optical system containing an ExB separator, and projecting the image of the secondary electron beam emitted from the sample on the detector by means of an imaging optical system, wherein the image of the secondary electron beam is formed on the deflecting main plane of the ExB separator at the sample side and the image of the primary electron beam from each of the plurality of the apertures thereof is formed on the deflecting main plane of the ExB separator.

The present invention is directed to an electron beam apparatus, which is selected from a group consisting of a defect inspection apparatus, a line width measurement apparatus, an alignment precision measurement apparatus, a voltage contrast measurement apparatus, a defect review apparatus and a stroboscopic SEM apparatus.

The electron beam apparatus of the present invention is directed to the electron beam apparatus that is so arranged as to irradiate the sample with the electron beams from the plurality of electron guns and to detect the secondary electron beams emitted from the sample by means of a plurality of the detectors disposed so as to correspond to the plural electron guns. Further, the electron beam apparatus of the present invention can be used for conducting evaluations of the wafer during the manufacturing process.

In the known technology, it is not clear as to how the secondary electron can be detected specifically by a plurality of detectors and whether a sample can be inspected and evaluated at high resolution. Further, the known technology has the problems that an electron beam cannot be converged slenderly because the electron beam is irradiated diagonally onto the surface of a sample in the primary optical system and an electrostatic objective lens and the sample are not arranged in a relationship of an axial symmetry.

Further, there is also known the technology of separating the secondary electron beam from the sample by means of the ExB separator and leading it to the detector. This known technology has the problem that chromatic aberration is caused to occur because the amount and the direction of deflection of the electron beam deflected by the electric field of the ExB separator is different between the electron beam having a low energy and the electron beam having a high energy. Moreover, it also has the problem that it is difficult to ensure a space for a deflector in the vicinity of the sample in the case where the ExB separator is disposed.

One of the objects to be achieved by the present invention is to provide an electron beam apparatus of a specific configuration, in which an electron beam apparatus of an optical system of an imaging projection type is provided with an ExB separator and can conduct various operations including inspections and evaluations of a sample with high throughput and with high reliability by using a plurality of electron beams.

Another object of the present invention is to provide an electron beam apparatus that can converge an electron beam in a slender form.

A further object of the present invention is to provide an electron beam apparatus that can correct a chromatic aberration to be caused by the use of the ExB separator.

A still further object of the present invention is to provide an electron beam apparatus in which the optical systems are disposed in two rows and in plural columns and which can conduct inspections, evaluations, etc. of the sample with high throughput and with high reliability.

A still further object of the present invention is to provide an electron beam apparatus in which the ExB separator and the deflector can be disposed at optimal positions by allowing the ExB separator to be also used as the deflector.

A still further object of the present invention is to provide a method for the preparation of a device, which can evaluate a sample during the manufacturing process by using the electron beam apparatus as described above.

The above objects can be achieved by the following aspects of the present invention. One of the inventions of this application is directed to an electron beam apparatus which comprises a primary optical system having a single electron gun for discharging an electron beam, an aperture plate having a plurality of apertures, a plurality of lenses, and at least two ExB separators disposed in a spaced arrangement, the primary optical system being disposed to irradiate the surface of the sample with the electron beam emitted from the electron gun, and a secondary optical system for separating a secondary electron beam emitted from the sample from the primary optical system by means one of the ExB separators, delivering it to a secondary electron beam detection device, and detecting it with the secondary electron beam detection device.

This electron beam apparatus is configured in such a manner that the electron beam from the electron gun is irradiated onto the aperture plate to form a plurality of images of the apertures of the aperture plate, the positions of the plurality of the images of the apertures thereof are allowed to coincide with the respective positions of the E×B separators, and the directions of the electron beams to be deflected in the electric field of the respective E×B separators are opposite to each other, when looked on the plane of the sample. This configuration of the electron beam apparatus allows the operations including inspections, evaluations, etc. of the sample with high throughput and with high reliability by using the plural electron beams. Moreover, this apparatus can correct a chromatic aberration caused to be produced by the E×B separator. In addition, the electron beam can be converged in a slender form. Therefore, the electron beam apparatus according to the present invention can ensure a high precision of inspection.

In another aspect of the invention relating to the electron beam, the amount of deflection of the electron beam to be deflected by means of the electric field of each of the E×B separators may be opposite to each other, when looked on the plane of the sample, although their absolute values are equal to each other.

For the electron beam apparatus having the above configuration, paths of the secondary electron beams deflected by the E×B separators may be disposed in two rows and in plural columns so as to cause no interference with one another. This arrangement can perform inspections, evaluations, etc. of the sample with high throughput and with high reliability.

In another aspect of the invention according to this application, there is provided an electron beam apparatus comprising a primary optical system having a single electron gun for generating an electron beam, an aperture plate having a plurality of apertures, a plurality of lenses, and an E×B separator, the primary optical system being arranged such that the electron beam generated from the single electron gun is irradiated onto the surface of a sample; and a secondary optical system disposed such that the secondary electron beam emitted from the sample is separated from the primary optical system by means of the E×B separator and delivered to a secondary electron detection device for inspection, wherein the electron beam generated from the electron gun is irradiated on the aperture plate to form images of the plural apertures of the aperture plate, the positions of the images of the apertures thereof are allowed to agree with the position of the E×B separator, and a scanning voltage is superimposed on the electric field of the E×B separator so as to deflect the electron beam. This configuration permits an optimal arrangement of the E×B separator and the deflector by using the E×B separator in common as the deflector.

In the one aspect and another aspect of the present invention, the electron beam apparatus may comprise a defect inspection apparatus, a line width measurement apparatus, a defect review apparatus, an EB tester apparatus and a voltage contrast measurement apparatus.

Another aspect of the invention of this application is to manufacture a device by evaluating a wafer during the manufacturing process by using the electron beam apparatus as described above.

An object of the present invention is to provide an electron beam apparatus capable of performing a focusing operation of an electronic optical system thereof in an electronic optical manner as well as in short time, and a semiconductor device manufacturing method using the same apparatus. In order to accomplish this object, the present invention has provided an electron beam apparatus in which a plurality of primary electron beams is irradiated against a sample by a primary optical system; a plurality of secondary electron beams emanated from the sample is, after having passed through an objective lens, introduced into a secondary optical system by an E×B separator; and, after introduction, spacing between respective secondary electron beams is expanded by at least a single stage of lens and then respective secondary electron beams are detected by a plurality of detectors, said apparatus characterized in that the objective lens is supplied with at least three different exciting voltage, and at least three data are measured, which represent build up width of an electric signal corresponding to an intensity of the secondary electron beam, which electric signal is obtained when a pattern edge parallel with a first direction is scanned in a second direction. This allows the focusing operation of the electronic optical system to be performed in short time.

The electron beam apparatus described above may be arranged as a lens barrel so as to face to a plurality of samples so that a primary optical system of each lens barrel may irradiate a plurality of primary electron beams onto the sample in a location different from those for other lens barrels. This allows to improve the throughput.

Preferably, the electron beam apparatus may be configured such that an exciting condition of the objective lens may be determined while a pattern on the wafer is in its charged condition.

The present invention also provides an electron beam apparatus characterized in that a plurality of primary electron beams is irradiated against a sample by a primary optical system; a plurality of secondary electron beams emanated from the sample is, after having passed through an objective lens, introduced into a secondary optical system by an E×B separator; and, after introduction, spacing between respective secondary electron beams is expanded by at least a single stage of lens and then respective secondary electron beams are detected by a plurality of detectors.

In this electron beam apparatus, the objective lens comprises a first electrode to which a first voltage near to that of an earth is applied, and a second electrode to which a second voltage higher than the first voltage is applied, and is configured such that a focal length of the objective lens may be varied by controlling the first voltage applied to the first electrode, and an exciting means for exciting the objective lens comprises a means for changing a voltage to be applied to the second electrode in order to greatly vary the focal length of the objective lens, and another means for changing a voltage to be applied to the first electrode in order to vary the focal length thereof in short time. The present invention further provides a semiconductor device manufacturing method for evaluating a wafer in the course of or after finishing the process by using the electron beam apparatus described above.

It is not necessarily apparent as to whether an electron beam apparatus can be commercially available, which can actually detect secondary electron beams with a plurality of detectors and inspect and evaluate a sample at a high degree of resolution. Further, in this case, it is required to use two different modes in one electron beam apparatus, one mode being arranged so as to detect only a relatively large defect with high throughput yet with a relatively low degree of resolution (hereinafter referred to sometimes as "standard mode") and the other mode being arranged so as to detect a very small defect at a small throughput yet at a high degree of resolution (hereinafter referred to sometimes as "high resolution mode"). It is to be noted herein, however, that a practically usable apparatus having such a function has not been yet developed.

In addition, when the two modes are used in one apparatus, it is further required to alter a scanning width of multi-beams, a rate of magnification of an electrostatic lens of the secondary optical system, and so on. However, this may cause another problems that a gap of scanning may be caused to be formed between the beams of the multi-beams when the scanning width is made narrower than the scanning width as set in the standard mode or the beam dimension of the beam in the secondary optical system does not agree with the dimension of a pixel of the detector. The present invention has the object to solve these problems.

In order to solve the problems as described above, one of the invention according to this application is directed to an apparatus comprising a primary optical system and a secondary primary optical system, the primary optical system being configured in such a manner that an electron beam emitted from a single electron gun is formed in multi-beams by means of an aperture plate with a plurality of apertures and a sample as an object of inspection is scanned with the multi-beams by reducing it with an electrostatic lens having at least two stages, and the secondary optical system being configured in such a manner that the secondary electron beam emitted from the sample is separated from the primary optical system with an E×B separator after passing through an electrostatic objective lens and delivered to a plurality of detectors by enlarging it with an electrostatic lens having at least one stage, wherein the sample is evaluated on the basis of dimensions of at least two kinds of pixels so as to allow an evaluation of the sample by the mode having a high throughput yet a relatively low resolution and the mode having a small throughput yet a high resolution. This arrangement can accomplish inspections and evaluations, etc. of the sample with high throughput and with high reliability by using the plural electron beams. Further, this allows the use of the two modes, that is, the standard mode and the high-resolution mode, in one apparatus.

In another aspect of the electron beam apparatus according to the present invention, a rate of reduction of the multi-beams in the primary optical system is associated with a rate of enlargement with the electrostatic lens of the secondary optical system.

In a further aspect of the electron beam apparatus according to the present invention, a crossover image in the primary optical system is adapted to be formed on the main plane of the electrostatic objective lens in the mode having a high throughput yet a relatively low resolution.

In a still further aspect of the electron beam apparatus according to the present invention, the rate of enlargement of the secondary optical system is adjusted with the electrostatic lens disposed at the side of the detector from an aperture disposed in the secondary optical system.

Another invention according to this application is directed to the manufacturing of a device by evaluating the wafer during the manufacturing process by using the electron beam apparatus having the configuration as described above.

The conventional scanning microscopes suffer from the problem that a great decrease in throughput is caused particularly when a sample having a wide area is to be evaluated because the surface of the sample has to be scanned with fine electron beams. In addition, a charging detection function cannot always detect a charging state in a correct way because each kind of currents has to be measured at a high time resolution.

The present invention has been completed on the basis of the problems as described above and has the object to provide an electron beam apparatus adapted to evaluate a sample at an improved throughput and with high reliability.

Another object of the present invention is to provide an electron beam apparatus with an improved charging detection function and at an improved reliability of evaluation as well as with an improved throughput by irradiating the sample with a plurality of the electron beams concurrently.

A further object of the present invention is to provide a method for manufacturing a device in which the sample during or after the manufacturing process is evaluated at a high manufacturing yield by using the electron beam apparatus having the configuration as described above.

One of the inventions according to this application is concerned with an electron beam apparatus having a primary optical system arranged so as to generate a primary electron beam, converge it and scan a sample with it, a secondary optical system having a lens of at least one stage adapted so as to deliver the secondary electron beam emitted from an electron beam irradiation portion of the sample, and a detector for detecting the secondary electron, wherein the secondary electron emitted from the electron beam irradiation portion of the sample is accelerated and separated from the primary optical system with an E×B separator, it is delivered onto the secondary optical system, and it is then detected by enlarging an image of the secondary electron with the lens;

wherein the primary optical system generates a plurality of the primary electron beams and irradiates the sample concurrently with the plural primary electron beams, and a plurality of the detectors are disposed so as to correspond to the number of the primary electron beams;

wherein a retarding voltage application device is disposed for applying a retarding voltage to the sample; and wherein a charging investigation unit is disposed for investigating a charging state of the sample.

The electron beam apparatus according to the present invention is further provided with a function for determining an optimal retarding voltage on the basis of information relating to the charging state from the charging investigation unit and applying the optimal retarding voltage to the sample or a function for varying an amount of irradiation of the primary electron beam.

Another invention according to the present invention is concerned with an electron beam apparatus which has an optical system for irradiating a sample with a plurality of electron beams and a charging state investigation unit that can evaluate a distortion of a pattern or a faded pattern on a particular portion of the sample, when an image is formed by detecting the secondary electron beams generated upon irradiation of the sample with the primary electron beams by means of the plural detectors and a charging state is evaluated as large when the extent of distortion of the distorted pattern or the fading extent of the faded pattern is determined to be large.

In the electron beam apparatus in each of the aspects of the present invention, in which the charging investigation function is arranged so as to apply a retarding voltage having a variable value to the sample, there may be further provided with a device for displaying the image in such a manner that the operator can evaluate the distorted pattern or the faded pattern by forming the image in the vicinity of a boundary at which a pattern density of the sample varies to a great extent in such a state that at least two retarding voltages are applied.

A still further invention of this application provides the method for the preparation of a device, wherein a defect of a wafer during or after the manufacturing process is detected by means of the electron beam apparatus having the configuration as described above.

It is to be noted herein, however, that even if a conventional example of an E×B energy filter having the configuration as shown in FIG. 54 would be used as an E×B separator of an inspection apparatus adapted to evaluate a semiconductor wafer by obtaining an image data by means of electron reams, a region around the optical axis where the primary electron beams travel straight without causing any substantial aberration cannot be rendered so wide.

One of the reasons is because a conventional E×B energy filter has a complicated structure so that symmetry is not so good. In other words, no good symmetry makes it complicated in computing an aberration because a three-dimensional analysis of the electric field or the magnetic field is required for computing the aberration. Therefore, a long period of time is required for designing the optimal aberration.

Another reason resides in the fact that a region is narrow, where the electric field and the magnetic field are crossing the optical axis at right angles and the magnitudes of the electric field and the magnetic field are substantially uniform.

The present invention has been completed on the basis of the problems prevailing in the conventional examples of the electron beam apparatuses and has one of the objects to provide an E×B separator that has a simple configuration and permits a simple calculation of aberration as well as a region around the optical axis where the magnitudes of the electric field and the magnetic field are uniform.

The second object of the present invention is to provide an electron beam apparatus containing the E×B separator that can achieve the first object of the present invention and a method for the preparation of a device by evaluating the semiconductor wafer by using the electron beam apparatus as described above.

In order to achieve the first object of the present invention, there is provided the E×B separator adapted to form an electric field and a magnetic field, each of which is crossing the optical axis at right angles and separates at least two electron beams which travel in different directions; which comprises:

an electrostatic deflector having a pair of electrodes for generating the electric field, each being in the form of a plate, which are disposed so as for the distance between the electrodes to become shorter than the length of an electrode crossing the electric field; and an electromagnetic deflector of a toroidal type or a saddle type, which can deflect the electron beams in the direction opposite to the electrostatic deflector.

Further, the E×B separator may be configured in such a manner that the electrostatic deflector is provided with six electrodes for generating the rotatable electric fields.

Moreover, the E×B separator may preferably be configured in such a manner that the electromagnetic deflector of the toroidal type or the saddle type has two sets of electromagnetic coils capable of generating the electric field and the magnetic field in both directions and that the direction of deflection caused by the electromagnetic deflector can be adjusted to become opposite to the direction of deflection caused by the electrostatic deflector by adjusting a current ratio of the two sets of the electromagnetic coils.

In addition, the E×B separator is preferably configured in such a manner that the electrostatic deflector is disposed inside the electromagnetic deflector of the toroidal type or the saddle type, thereby forming the electromagnetic deflector in two divisions. The two divisions of the electromagnetic deflector may be readily combined integrally outside the outer periphery of the electrostatic deflector. Therefore, the E×B separator can be manufactured with ease.

Furthermore, the present invention provides an inspection apparatus with the E×B separator installed therein for use in separation of the secondary electron beams from the primary electron beams, which is configured so as to irradiate the semiconductor wafer with the plural primary electron beams and detect the secondary electron beams from the semiconductor wafer with the plural detectors to give an image data and to evaluate the processed state of the semiconductor wafer on the basis of the image data.

An object of the present invention is to provide a charged beam apparatus having a simple structure capable of being made compact without employing a differential exhausting mechanism for an XY stage. Another object of the present invention is to provide a charged beam apparatus provided with a differential exhausting mechanism for exhausting a region on a surface of a sample to which a charged beam is to be irradiated, as well as for exhausting an inside of a housing containing an XY stage to vacuum. Still another object of the present invention is to provide a defect inspection apparatus for inspecting a surface of a sample for defects or an exposing apparatus for printing a pattern on the surface of the sample by using either of the charged beam apparatuses described above. Yet another object of the present invention is to provide a semiconductor manufacturing method for manufacturing a semiconductor device by using either of the charged beam apparatuses described above.

In an apparatus of the present invention for irradiating a charged beam against a sample loaded on an XY stage, said XY stage is accommodated in a housing and supported by a hydrostatic bearing in a non-contact manner with respect to said housing; said housing in which said stage is accommodated is exhausted to vacuum; and a differential exhausting mechanism is arranged surrounding a portion in said charged beam apparatus, where the charged beam is to be irradiated against a surface of said sample, so that a region on said sample to which said charged beam is to be irradiated may be exhausted to vacuum.

According to the charged beam apparatus of this invention, a high-pressure gas supplied for the hydrostatic bearing and leaked-out into the vacuum chamber is primarily evacuated by a vacuum exhausting pipe connected to the vacuum chamber.

Further, arranging the differential exhausting mechanism, which functions to exhaust the region to which the charged beam is to be irradiated, so as to surround the portion to which the charged beam is to be irradiated, allows the pressure in the irradiation region of the charged beam to be decreased to significantly lower level than that in the vacuum chamber, thus achieving stably a vacuum level where the processing to the sample by the charged beam can be performed without any troubles. That is to say, the stage with a structure similar to that of a stage of hydrostatic bearing type commonly used in the atmospheric pressure (a stage supported by the hydrostatic bearing having no differential exhausting mechanism) may be used to stably apply the processing by the charged beam to the sample on the stage.

In a charged beam apparatus of the present invention, a gas to be supplied to said hydrostatic bearing of the XY stage is dry nitrogen or a high-purity inert gas, and said dry nitrogen or high-purity inert gas is pressurized after having being exhausted from said housing containing said stage so as to be supplied again to said hydrostatic bearing.

According to the present invention, since the residual gas components in the vacuum housing are the high-purity inert gas, there should be no fear that the surface of the sample or any surfaces of the structures within the vacuum chamber defined by the housing would be contaminated by water contents or oil and fat contents, and in addition, even if inert gas molecular is adsorbed onto the sample surface, once being exposed to the differential exhausting mechanism or the high vacuum section of the irradiation region of the charged beam, said inert gas molecular would be released immediately from the sample surface, so that the effect on the vacuum level in the irradiation region of the charged beam can be minimized and the processing applied by the charged beam to the sample can be stabilized.

The present invention also provides a wafer defect inspection apparatus for inspecting a surface of a semiconductor wafer for defects by using either of the apparatuses described above. This allows to provide an inspection apparatus which accomplishes positioning performance of the stage with high precision and also provides a stable vacuum level in the irradiation region of the charged beam with low cost. The present invention also provides an exposing apparatus for printing a circuit pattern of a semiconductor device on a surface of a semiconductor wafer or a reticle by using either of the charged beam apparatuses described above. This allows to provide an exposing apparatus which accomplishes positioning performance of the stage with high precision and also provides a stable vacuum level in the irradiation region of the charged beam with low cost.

The present invention also provides a semiconductor manufacturing method for manufacturing a semiconductor by using either of the apparatuses described above, which allows a micro semiconductor circuit to be formed by of manufacturing a semiconductor with the apparatus which accomplishes positioning performance of the stage with high precision and also provides a stable vacuum level in the irradiation region of the charged beam.

In a symmetric doublet lens, for example, when a reduction lens system is to be fabricated, two stages of lens are required and a size ratio of respective lenses should be equal to a reduction ratio thereof. For example, when the system with a reduction ratio of 1/10 is to be fabricated, there has occurred such problems that, since a size of a lens of a smaller size cannot be made smaller than that defined by a possible processing accuracy, for example, a bore diameter thereof is determined to be 5 mmφ and a lens gap to be about 5 mm, and accordingly, a lens of a larger side has to be of rather larger size with a bore diameter of 50 mmφ and a lens gap of 50 mm, and that, when a magnification ratio is to be varied in the practical apparatus, a symmetric condition would get out of order.

In the light of the problems described above, an object of the present invention is to provide an electronic optical system capable of controlling the magnification by using a lens system with two or more stages and also capable of compensating for a magnification chromatic aberration by using a single lens. Another object of the present invention is to provide a method for evaluating a wafer in order to find a possible cause of deterioration of yield in the device manufacturing as soon as possible by using the apparatus described above.

The present invention provides an electron beam apparatus in which a plurality of electron beams is focused by a lens system including a condenser lens and then is formed into an image on a sample by an objective lens, said apparatus characterized in that a crossover position of said electron beam defined by a lens of a front stage of said objective lens is set to be in a proximal position of said lens system side of said objective lens. In the concrete, said crossover position is located in said lens system side with respect to a principal plane of the objective lens. Setting the crossover position as described above allows to reduce the aberration, in particular the chromatic aberration otherwise appearing in the electron beam formed into an image on the sample.

The above-described plurality of electron beams may be a plurality of electron beams which has been emitted from a single electron gun as a single beam and passed through a plurality of apertures to be formed into said plurality of electron beams, a plurality of electron beams emitted from a plurality of electron guns, or a plurality of electron beams emitted from a plurality of emitters formed in a single electron gun. The present invention also provides a device manufacturing method in which a wafer in the course of manufacturing process is evaluated by using the electron beam apparatus described above.

The present invention employs a plurality of primary electron beams, in which said plurality of electron beams is made to pass through an ExB filter (Wien filter) to enter a surface of a sample at right angles while making a scanning operation in one-dimensional direction (x-direction), and secondary electrons emanated from the sample are separated from the primary electron beams by the ExB filter to be introduced at an oblique direction with respect to an axis of the primary electron beam and are formed into an image or focused on a detecting system by a lens system. A stage is moved along an orthogonal direction (y-direction) with respect to a scanning direction (x-direction) of the primary electron beam and thereby a serial image can be obtained.

When the primary electron beam passes through the ExB filter, a certain condition where a force applied to the electron beam by the electric field and that by the magnetic field are equal in intensity and opposite in direction (Wien condition) is established, so that the primary electron beam can go straight ahead.

On the other hand, since the secondary electron beam has a direction opposite to that of the primary electron beam, the force applied to the secondary electron beam by the electric field and that by the magnetic field have the same direction, so that the secondary electron beam is deflected from the axial direction of the primary electron beam. As a result, the primary electron beam and the secondary electron beam are separated from each other.

When the electron beam passes through the ExB filter, the aberration of the electron beam becomes greater in the case of being deflected in comparison with the case of straight advance, and therefore, a plurality of detectors each corresponding to each of the primary electron beams required to be of high accuracy is provided, and the secondary electrons generated by one electron beam are introduced into a corresponding detector by said image forming system without exception.

This make it possible to prevent a mixing of signals. A scintillator plus photo-multiplier is used as a detector. A PIN diode (semiconductor detector) may also be used as a detector. The present invention employs sixteen primary electron beams each having a beam diameter of 0.1 µm and a beam current of 20 nA, and a current value three times as much as that of the apparatus available on the market could be obtained.

Electron Gun (Electron Beam Source)

In the present invention, a thermal electron beam source is employed as an electron beam source. An electron emitting (emitter) member is made of $LaB_6$. Other material may be used for the emitter member so far as it has a high melting point (low vapor pressure at high temperature) and a small work function. Two kinds of methods are employed to obtain a plurality of electron beams. One is a method where a single electron beam is derived from a single emitter (with one projection) and then is passed through a thin plate with a plurality of apertures formed therein (aperture plate) to obtain a plurality of electron beams, and the other is a method where a plurality of projections is formed in one emitter and a plurality of electron beams is derived therefrom. Either case takes advantage of the property that the projection facilitates the emission of electron beam from the tip thereof. Other types of electron beam source, for example, a thermal electric field emission type of electron beam source may be used to emit the electron beam.

It is to be appreciated that the thermal electron beam source method is such that the electron emitting member is heated to emit electrons, while the thermal electric field emission electron beam source is such method in which a high electric field is applied to the electron emitting member to emit electrons and further the electron emitting section is heated so as to stabilize the electron emission.

Vacuum Exhausting System

In the present invention, a vacuum exhausting system is composed of a vacuum pump, a vacuum valve, a vacuum gauge, a vacuum pipe and the like, and exhausts to vacuum an electronic optical system, a detector section, a sample chamber, a load-lock chamber and the like according to a predetermined sequence. In each of those sections, the vacuum valve is controlled so as to accomplish a required vacuum level. The vacuum level is regularly monitored, and in the case of irregularity, an interlock mechanism executes an emergency control of an isolation valve or the like to secure the vacuum level. As for the vacuum pump, a turbo molecular pump may be used for main exhaust, and a dry pump of the Roots type may be used as a roughing vacuum pump. The pressure at an inspection spot (an electron beam irradiating section) is practically in the range of $10^{-3}$ to $10^{-5}$ Pa, more preferably, in a range of $10^{-4}$ to $10^{-6}$ Pa as shifted by one digit down.

Control System

In the present invention, a control system is mainly composed of a main controller, a controlling controller, and a stage controller. The main controller is equipped with a man-machine interface, through which an operator manipulates the controller (a variety of instructions/commands, entry of a recipe, instructions to start an inspection, switching between an automatic inspection mode and a manual inspection mode, an input of all of the commands required in the manual inspection mode and so forth). In addition, the main controller further executes communication with a host computer in a factory, a control of a vacuum exhausting system, control of carrying and positioning operations of a sample such as a wafer, an operation for sending commands and receiving information to/from the other controlling controllers and/or stage controller and so fourth.

Further, the main controller has a function to obtain an image signal from an optical microscope, and also has a stage vibration compensating function for compensating a deterioration in the image by feeding back a fluctuation signal of the stage to an electronic optical system, and an automatic focal point compensating function for detecting a displacement of the sample observation point in the Z direction (in the axial direction of the secondary optical system) and feeding back the detected displacement to the electronic optical system so as to automatically compensate the focal point. Sending and receiving operations of the feedback signal to/from the electronic optical system and sending and receiving operations of the signal to/from the stage are performed via the controlling controller and the stage controller respectively.

The controlling controller is mainly responsible for the control of the electronic optical system (an electron gun, a lens, an aligner, a control of a high-precision power supply for a Wien filter or the like). In specific, the controlling controller performs a control operation, for example, an automatic voltage setting for each of the lens systems and the aligners in response to each operation mode (gang control), so that a constant electron current may be regularly irradiated against the irradiation region even if the magnification is changed, and voltages to be applied to each of the lens systems and the aligners may be automatically set in response to each magnification and so forth.

The stage controller is mainly responsible for control regarding the movement of the stage so that precise movement in the X and the Y directions may be on the order of µm (with tolerance of about ±0.5 µm). Further, in the present stage, control at the rotational direction (θ control) is also performed with a tolerance equal to or less than about ±0.3 seconds.

Inspection Procedure

In the present invention, an inspection procedure is conducted as described below (see FIG. 63). Generally, since an inspection apparatus using an electron beam is expensive and the throughput thereof is rather lower than that provided by other processing apparatuses, this type of inspection apparatus is currently applied to a wafer after an important process (for example, etching, film deposition, or CMP (chemical and mechanical polishing) flattening process) which is considered that the inspection is required most.

A wafer to be inspected is, after having been positioned on an ultra-precise X-Y stage through an atmosphere transfer system and a vacuum transfer system, secured by an electrostatic chucking mechanism or the like, and then a defect inspection is conducted according to a flow chart shown in FIG. 63. At first, if required, a position of each of dies is checked and/or a height of each location is sensed, and those values are stored. In addtion, an optical microscope is used to obtain an optical microscope image in an area of interest possibly including defects or the like, which may also be used in, for example, the comparison with an electron beam image.

Then, recipe information corresponding to the kind of the wafer (for example, after which process the inspection should be applied; what the wafer size is, 20 cm or 30 cm, and so on) is entered into the apparatus, and subsequently, after a designation of an inspection place, a setting of an electronic optical system and a setting of an inspection condition being established, a defect inspection is conducted typically at real time while simultaneously obtaining the image. A fast data processing system with an algorithm installed therein executes an inspection, such as the comparisons between cells, between dies or the like, and any results would be output to a CRT or the like and stored in a memory, if desired. Those defects include a particle defect, an irregular shape (a pattern defect) and an electric defect (a broken wire or via, a bad continuity or the like), and the fast data processing system also can automatically and at realtime distinguish and categorize them according to a defect size, or whether their being a killer defect (a critical defect or the like which disables a chip).

The detection of the electric defect may be accomplished by detecting an irregular contrast. For example, since a location having bad continuity would generally be charged positive by electron beam irradiation (about 500 eV) and thereby its contrast would be decreased, the location of bad continuity can be distinguished from normal locations. The electron beam irradiation means in that case designates an electron beam generation means (means for generating thermal electron, UV/photoelectron) with lower energy arranged in order to emphasize the contrast by a potential difference, in addition to the electron beam irradiation means used for a regular inspection. Before the electron beam for inspection is irradiated against the objective region for inspection, the electron beam having that lower energy is generated and irradiated.

In the case of a map-projecting method in which the object can be positively charged by the irradiation of the electron beam for inspection, the electron beam generation means with lower potential is not necessarily arranged separately, depending on the specification of the system for the method. Further, the defect may be detected based on the difference in contrast (which is caused by the difference in flow ability of elements depending on the forward or backward direction) created by, for example, applying a positive or negative potential relative to reference potential to a wafer or the like. This electron beam generation means may be applicable to a line-width measuring apparatus and also to an aligning accuracy measurement.

Cleaning of Electrode

Since, while an electron beam apparatus according to the present invention is operated, a target substance is extricated by a proximity interaction (charging of particles in the proximity of a surface) and attracted to a high-voltage region, an organic substance would be deposited on a variety of electrodes used for forming or deflecting an electron beam. Since the insulating material gradually depositing on the surface of the electrodes by the electric charge affects adversely on the forming or deflecting mechanism for the electron beam, accordingly those deposited insulating material must be removed periodically. To remove the insulating material periodically, an electrode adjacent to the region where the insulating material has been deposited is used to generate the plasma of hydrogen, oxygen, fluorine or compounds including them, such as HF, $O_2$, $H_2O$, $C_MF_N$ or the like, in the vacuum and to control the plasma potential in the space to be a potential level (several kV, for example, 20V–5 kV) where the spatter would be generated on the electrode surface, thereby allowing only the organic substance to be oxidized, hydrogenated or fluorinated and removed.

BRIEF DESCRIPTION OF THE DRAWINGS

FIG. 2 is a plan view illustrating those main components of the inspection apparatus illustrated in FIG. 1 taken along the line B—B of FIG. 1.

FIGS. 5A and 5B are enlarged views of a wafer rack, wherein FIG. 5A is a side elevational view and FIG. 5B is a cross sectional view taken along the line E—E of FIG. 5A.

FIGS. 6A and 6B illustrate respectively first and second alternatives of the supporting method of the main housing.

FIGS. 10A and 10B illustrate an electron beam calibration mechanism, wherein FIG. 10A is a side elevational view and FIG. 10B is a plan view.

FIG. 17A is a plan view of a multi-emitter, and

FIG. 17B is a cross sectional view taken along the line 17B—17B of FIG. 17A.

FIGS. 18A and 18B are cross sectional views of a vacuum chamber and an XY stage of a charged beam apparatus according to the prior art, wherein FIG. 18A is a front elevational view and FIG. 18B is a side elevational view.

FIGS. 20A and 20B are cross sectional views of a vacuum chamber and an XY stage of a charged beam apparatus of a fourth embodiment according to the present invention, wherein FIG. 20A is a front elevational view and FIG. 20B is a side elevational view.

FIG. 27 illustrates some examples of a plurality of images to be inspected which is obtained by the defect inspection apparatus of FIG. 26, and an example of a reference image.

FIGS. 41A and 41B illustrate respectively a multi-aperture plate of another example to be used in the electron beam apparatus of FIG. 38.

FIG. 45 is composed of FIGS. 45A and 45B, wherein FIG. 45A is a graph illustrating a relation between a voltage applied to an objective lens and a build-up width of an electric signal, and FIG. 45B is a graph for explaining the build-up width of the electric signal.

FIG. 50A is a diagram for explaining an evaluation location and an evaluation method of charging, and FIG. 50B is a diagram for comparing contrasts of signal intensity.

EMBODIMENTS OF THE INVENTION

Figure 1:
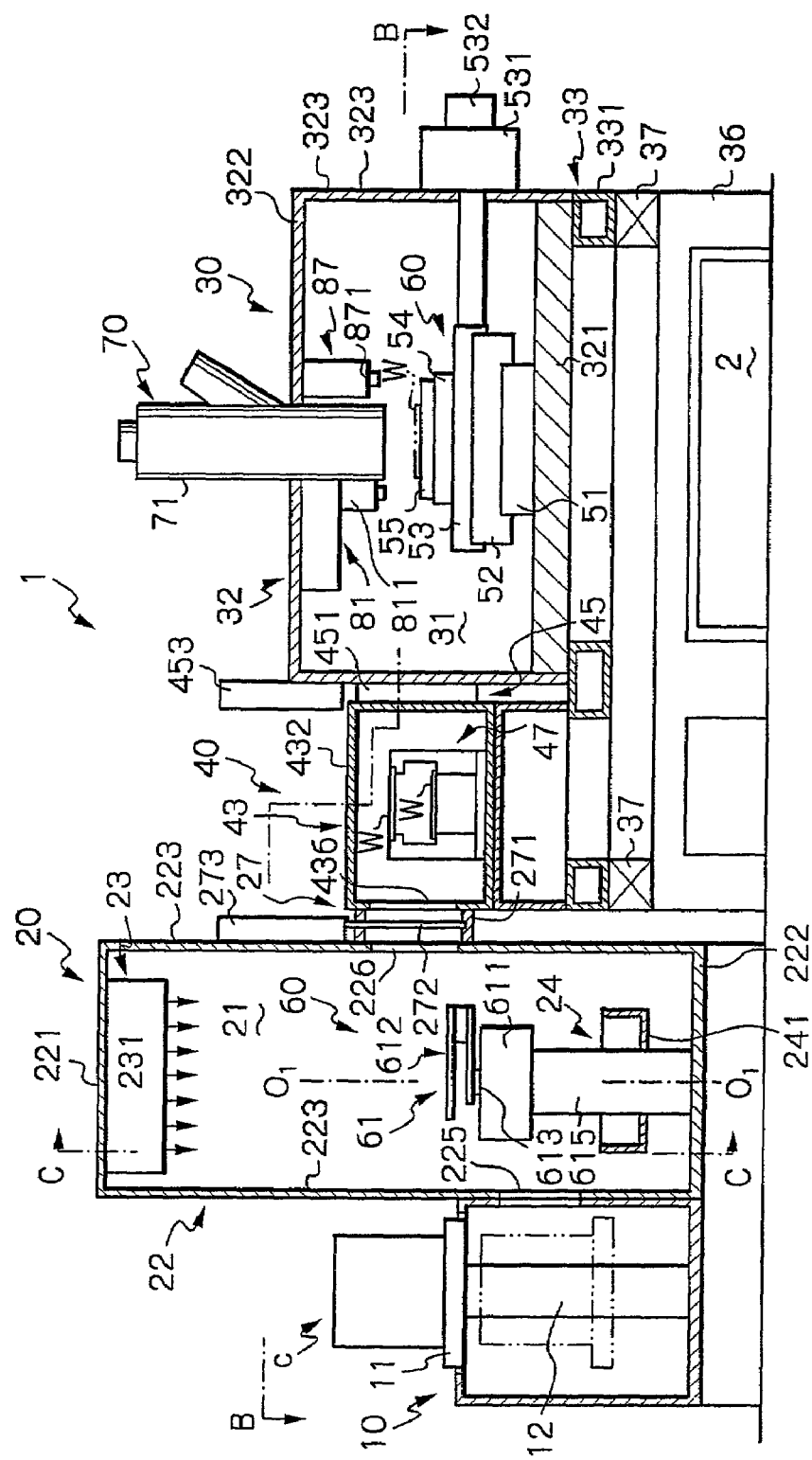
FIG. 1 is a partially cross sectional elevation view illustrating main components of an inspection apparatus of a first embodiment according to the present invention taken along the line A—A of FIG. 2.

With reference to FIGS. 1 and 2, a first embodiment of the present invention will be explained in the form of a semiconductor testing apparatus for testing, as an object under testing, a substrate, i.e., a wafer which has patterns formed on the surface thereof. FIGS. 1 and 2 illustrate main components of a semiconductor testing apparatus 1 according to this embodiment in elevation and a plan view, respectively.

The semiconductor testing apparatus 1 of this embodiment comprises a cassette holder 10 for holding cassettes which stores a plurality of wafers; a mini-environment device 20; a main housing 30 which defines a working chamber; a loader housing 40 disposed between the mini-environment device 20 and the main housing 30 to define two loading chambers; a loader 60 for loading a wafer from the cassette holder 10 onto a stage device 50 disposed in the main housing 30; and an electro-optical device 70 installed in the vacuum main housing 30. These components are arranged in a positional relationship as illustrated in FIGS. 1 and 2. The semiconductor testing apparatus 1 further comprises a pre-charge unit 81 disposed in the vacuum main housing 30; a potential applying mechanism 83 (see in FIG. 8) for applying a to a wafer; an electron beam calibration mechanism 85 (see in FIG. 10); and an optical microscope 871 which forms part of an alignment controller 87 for aligning the wafer on the stage device 50.

The cassette holder 10 is configured to hold a plurality (two in this embodiment) of cassettes c (for example, closed cassettes such as SMIF,FOUP manufactured by Assist Co.) in which a plurality (for example, 25) of wafers are placed side by side in parallel, oriented in the vertical direction. The cassette holder 10 can be arbitrarily selected for installation adapted to a particular loading mechanism. Specifically, when a cassette, carried to the cassette holder 10, is automatically loaded into the cassette holder 10 by a robot or the like, the cassette holder 10 having a structure adapted to the automatic loading can be installed. When a cassette is manually loaded into the cassette holder 10, the cassette holder 10 having an open cassette structure can be installed.

In this embodiment, the cassette holder 10 is the type adapted to the automatic cassette loading, and comprises, for example, an up/down table 11, and an elevation mechanism 12 for moving the up/down table 11 up and down. The cassette c can be automatically set onto the up/down table 11 in the position indicated by chain lines in FIG. 2. After the setting, the cassette c is automatically rotated to the position indicated by solid lines in FIG. 2 so that it is directed to the axis of pivotal movement of a first carrier unit within the mini-environment device 20. In addition, the up/down table 11 is moved down to the position indicated by chain lines in FIG. 1. In this way, the cassette holder 10 for use in automatic loading, or the cassette holder 10 for use in manual loading may be both implemented by those in known structures, so that detailed description on their structures and functions are omitted.

Figure 3A:
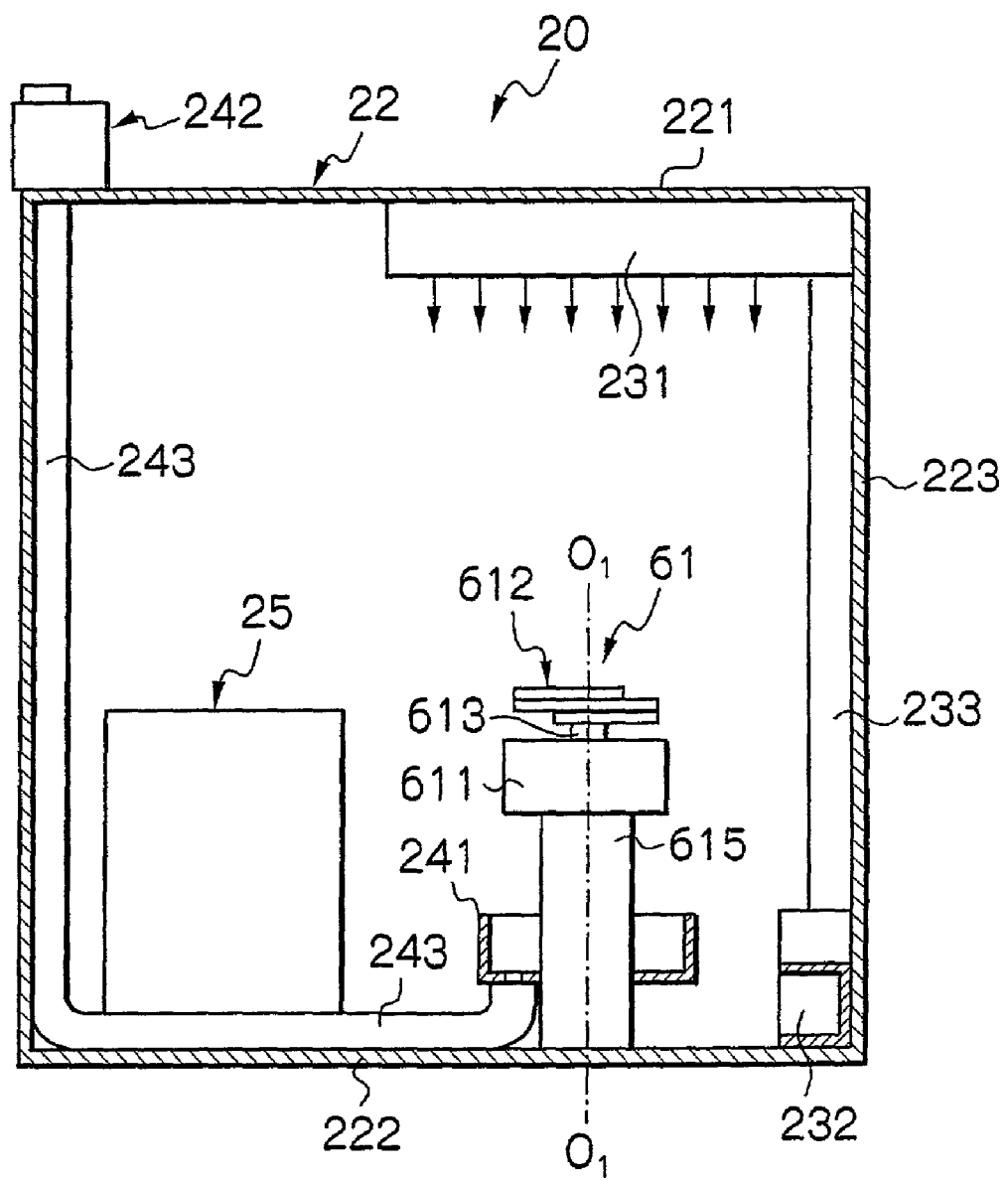
FIG. 3A is a cross sectional view of a mini-environmental unit of FIG. 1 taken along the line C—C of FIG. 1.
Figure 3B:
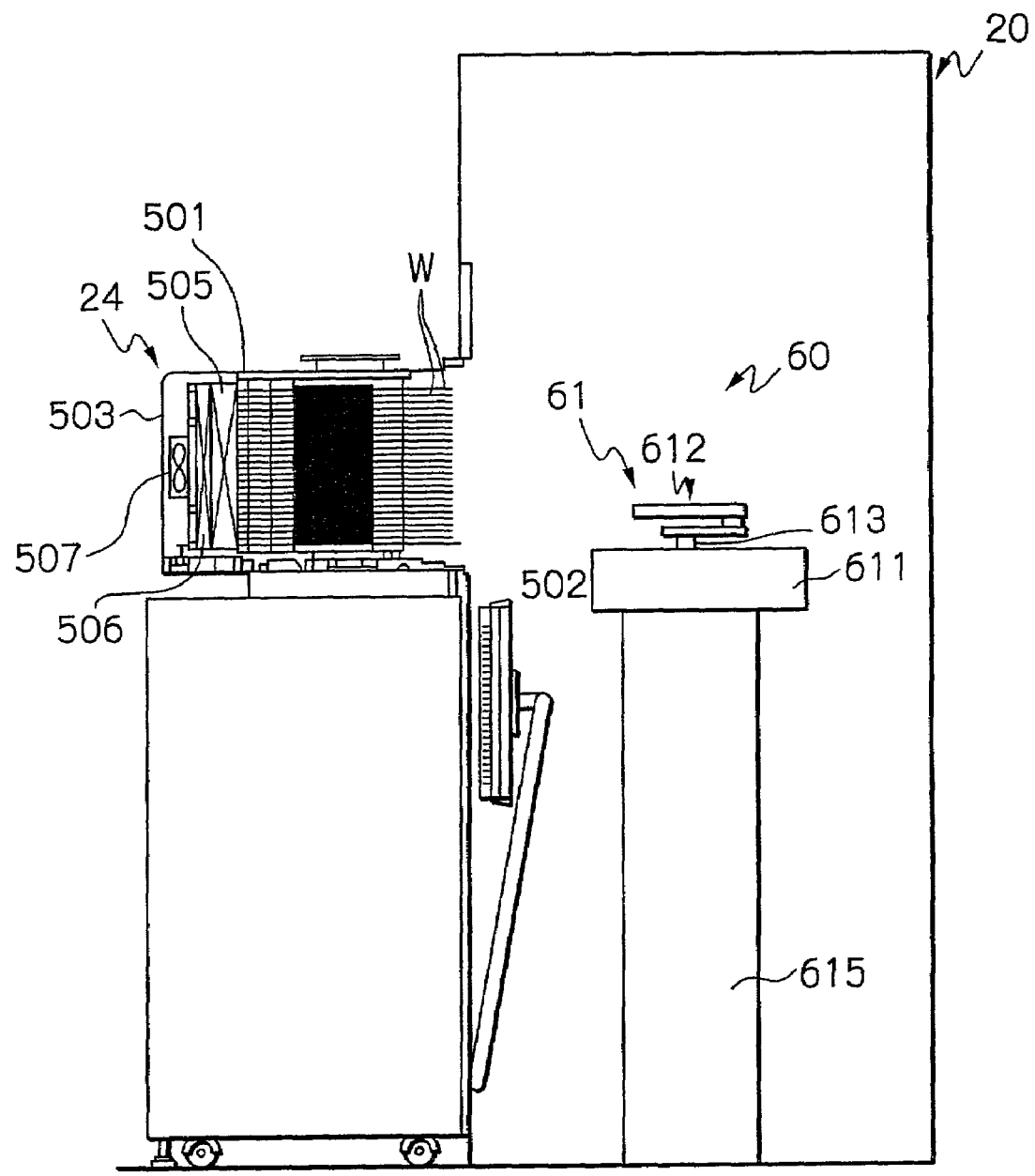
FIG. 3B is a sectional view of another mini-environmental unit.

In another embodiment shown in FIG. 3B, a plurality of 300 mmφ substrates W is accommodated in a slot-like pocket (not shown) fixedly mounted in a box main body 501 so as to be transferred and stored. This substrate carrier box 24 is composed of a box main body 501 of cylinder with angular section, a door 502 for carrying in/out the substrate, which is coupled with an automatic aperture/closing unit of the door for carrying in/out the substrate so as to be capable of mechanically aperture/closing an aperture in a side face of the box main body 501, a lid body 503 disposed in an opposite side of said aperture, for covering another aperture through which filters and a fun motor are to be attached or detached, a slot-like pocket (not shown) for holding a substrate W, a ULPA filter 505, a chemical filter 506, and a fun motor 507. In this embodiment, the substrate W is carried in or out by a first carrier unit 612 of robot type in a loader 60.

It should be noted that substrates, i.e., wafers accommodated in the cassette c are wafers subjected to testing which is generally performed after a process for processing the wafers or in the middle of the process within semiconductor manufacturing processes. Specifically, accommodated in the cassette are substrates or wafers which have undergone a deposition process, CMP, ion implantation and so on; wafers each formed with circuit patterns on the surface thereof; or wafers which have not been formed with wiring patterns. Since a large number of wafers accommodated in the cassette c are spaced from each other in the vertical direction and arranged side by side in parallel, the first carrier unit has an arm which is vertically movable such that a wafer at an arbitrary position can be held by the first carrier unit, as described later in detail.

In FIGS. 1 through 3, the mini-environment device 20 comprises a housing 22 which defines a mini-environment space 21 that is controlled for the atmosphere; a gas circulator 23 for circulating a gas such as clean air within the mini-environment space 21 for the atmosphere control; a discharger 24 for recovering a portion of air supplied into the mini-environment space 21 for discharging; and a pre-aligner 25 for roughly aligning a substrate, i.e., a wafer under testing, which is placed in the mini-environment space 21.

The housing 22 has a top wall 221, a bottom wall 222, and peripheral wall 223 which surrounds four sides of the housing 22 to provide a structure for isolating the mini-environment space 21 from the outside. For controlling the atmosphere in the mini-environment space 21, the gas circulator 23 comprises a gas supply unit 231 attached to the top wall 221 within the mini-environment space 21 as illustrated in FIG. 3 for cleaning a gas (air in this embodiment) and delivering the cleaned gas downward through one or more gas nozzles (not shown) in laminar flow; a recovery duct 232 disposed on the bottom wall 222 within the mini-environment space for recovering air which has flown down to the bottom; and a conduit 233 for connecting the recovery duct 232 to the gas supply unit 231 for returning recovered air to the gas supply unit 231.

In this embodiment, the gas supply unit 231 takes about 20% of air to be supplied, from the outside of the housing 22 for cleaning. However, the percentage of gas taken from the outside may be arbitrarily selected. The gas supply unit 231 comprises an HEPA or ULPA filter in a known structure for creating cleaned air. The laminar downflow of cleaned air is mainly supplied such that the air passes a carrying surface formed by the first carrier unit, later described, disposed within the mini-environment space 21 to prevent dust particles, which could be produced by the carrier unit, from attaching to the wafer.

Therefore, the downflow nozzles need not be positioned near the top wall as illustrated, but is only required to be above the carrying surface formed by the carrier unit. In addition, the air need not either be supplied over the entire mini-environment space 21.

It should be noted that an ion wind may be used as cleaned air to ensure the cleanliness as the case may be. Also, a sensor may be provided within the mini-environment space 21 for observing the cleanliness such that the apparatus is shut down when the cleanliness is degraded. An access port 225 is formed in a portion of the peripheral wall 223 of the housing 22 that is adjacent to the cassette holder 10. A shutter device in a known structure may be provided near the access port 225 to shut the access port 225 from the mini-environment device 20. The laminar downflow near the wafer may be, for example, at a rate of 0.3 to 0.4 m/sec. The gas supply unit 231 may be disposed outside the mini-environment space 21 instead of within the mini-environment space 21.

The discharger 24 comprises a suction duct 241 disposed at a position below the wafer carrying surface of the carrier unit and below the carrier unit; a blower 242 disposed outside the housing 22; and a conduit 243 for connecting the suction duct 241 to the blower 242. The discharger 24 aspires a gas flowing down around the carrier unit and including dust, which could be produced by the carrier unit, through the suction duct 241, and discharges the gas outside the housing 22 through the conduits 243, 244 and the blower 242. In this event, the gas may be emitted into an exhaust pipe (not shown) which is laid to the vicinity of the housing 22.

The aligner 25 disposed within the mini-environment space 21 optically or mechanically detects an orientation flat (which refers to a flat portion formed along the outer periphery of a circular wafer) formed on the wafer, or one or more V-shaped notches formed on the outer peripheral edge of the wafer to previously align the position of the wafer in a rotating direction about the axis $O_1$-$O_1$ at an accuracy of approximately ±one degree. The pre-aligner forms part of a mechanism for determining the coordinates of an object under testing, which is a feature of the claimed invention, and is responsible for rough alignment of an object under testing. Since the pre-aligner itself may be of a known structure, description on its structure and operation is omitted.

Although not shown, a recovery duct for the discharger 24 may also be provided below the pre-aligner such that air including dust, emitted from the pre-aligner, is emitted to the outside.

In FIGS. 1 and 2, the main housing 30, which defines the working chamber 31, comprises a housing body 32 that is supported by a housing supporting device 33 fixed on a vibration isolator 37 disposed on a base frame 36. The housing supporting device 33 comprises a frame structure 331 assembled into a rectangular form. The housing body 32 comprises a bottom wall 321 securely fixed on the frame structure 331; a top wall 322; and a peripheral wall 323 which is connected to the bottom wall 321 and the top wall 322 and surrounds four sides of the housing body 32, and isolates the working chamber 31 from the outside. In this embodiment, the bottom wall 321 is made of a relatively thick steel plate to prevent distortion due to the weight of equipment carried thereon such as the stage device 50. Alternatively, another structure may be employed.

In this embodiment, the housing body 32 and the housing supporting device 33 are assembled into a rigid construction, and the vibration isolator 37 prevents vibrations from the floor, on which the base frame 36 is placed, from being transmitted to the rigid structure. A portion of the peripheral wall 323 of the housing body 32 that adjoins the loader housing 40, later described, is formed with an access port 325 for introducing and removing a wafer.

The vibration isolator 37 may be either of an active type which has an air spring, a magnetic bearing and so on, or a passive type likewise having these components. Since any known structure may be employed for the vibration isolator 37, description on the structure and functions of the vibration isolator itself is omitted. The working chamber 31 is held in a vacuum atmosphere by a vacuum system (not shown) in a known structure. A controller 2 for controlling the operation of the overall apparatus is disposed below the base frame 36.

Figure 4:
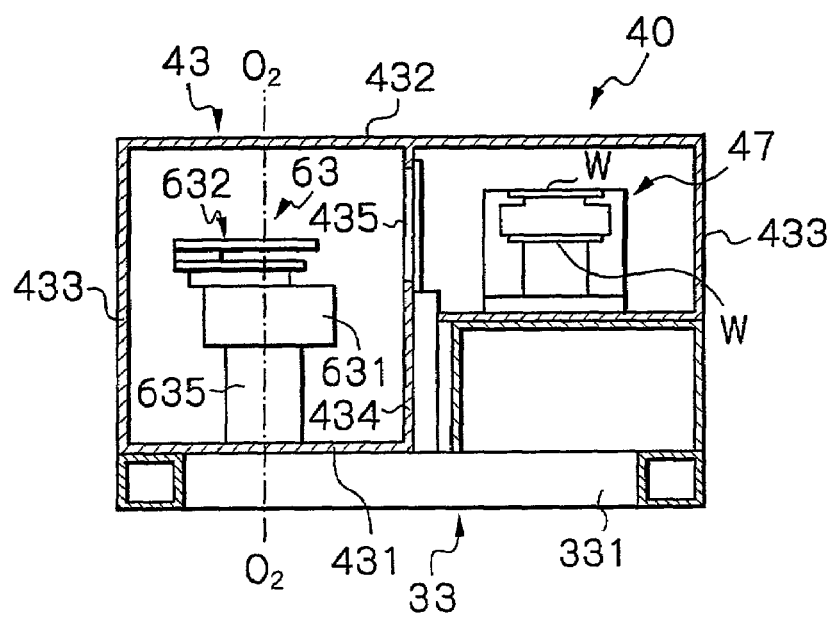
FIG. 4 is a cross sectional view of a loader housing taken along the line D—D of FIG. 1.

In FIGS. 1, 2 and 4, the loader housing 40 comprises a housing body 43 which defines a first loading chamber 41 and a second loading chamber 42. The housing body 43 comprises a bottom wall 431; a top wall 432; a peripheral wall 433 which surrounds four sides of the housing body 43; and a partition wall 434 for partitioning the first loading chamber 41 and the second loading chamber 42 such that both the loading chambers can be isolated from the outside. The partition wall 434 is formed with an aperture, i.e., an access port 435 for passing a wafer between both the loading chambers. Also, a portion of the peripheral wall 433 that adjoins the mini-environment device 20 and the main housing 30 is formed with access ports 436, 437.

The housing body 43 of the loader housing 40 is carried on and supported by the frame structure 331 of the housing supporting device 33. This prevents the vibrations of the floor from being transmitted to the loader housing 40 as well. The access port 436 of the loader housing 40 is in alignment with the access port 226 of the housing 22 of the mini-environment device 20, and a shutter device 27 is provided for selectively isolating a interaction between the mini-environment space 21 and the first loading chamber 41. The gate valve 27 has a sealing material 271 which surrounds the peripheries of the access ports 226, 436 and is fixed to the side wall 433 in close contact therewith; a door 272 for isolating air from flowing through the access ports in cooperation with the sealing material 271; and a driver 273 for moving the door 272.

Likewise, the access port 437 of the loader housing 40 is in alignment with the access port 325 of the housing body 32, and a shutter 45 is provided for selectively isolating a intraction between the second loading chamber 42 and the working chamber 31 in a hermetic manner. The shutter 45 comprises a sealing material 451 which surrounds the peripheries of the access ports 437, 325 and is fixed to side walls 433, 323 in close contact therewith; a door 452 for isolating air from flowing through the access ports in cooperation with the sealing material 451; and a driver 453 for moving the door 452.

Further, the aperture formed through the partition wall 434 is provided with a shutter 46 for closing the aperture with the door 461 to selectively isolating a interaction between the first and second loading chambers in a hermetic manner. These gate valve 27, 45, 46 are configured to provide air-tight sealing for the respective chambers when they are in a closed state. Since these gate valve may be implemented by known ones, detailed description on their structures and operations is omitted. It should be noted that a method of supporting the housing 22 of the mini-environment device 20 is different from a method of supporting the loader housing 40. Therefore, for preventing vibrations from being transmitted from the floor through the mini-environment device 20 to the loader housing 40 and the main housing 30, a vibration-absorption cushion material may be disposed between the housing 22 and the loader housing 40 to provide air-tight sealing for the peripheries of the access ports.

Figure 5:
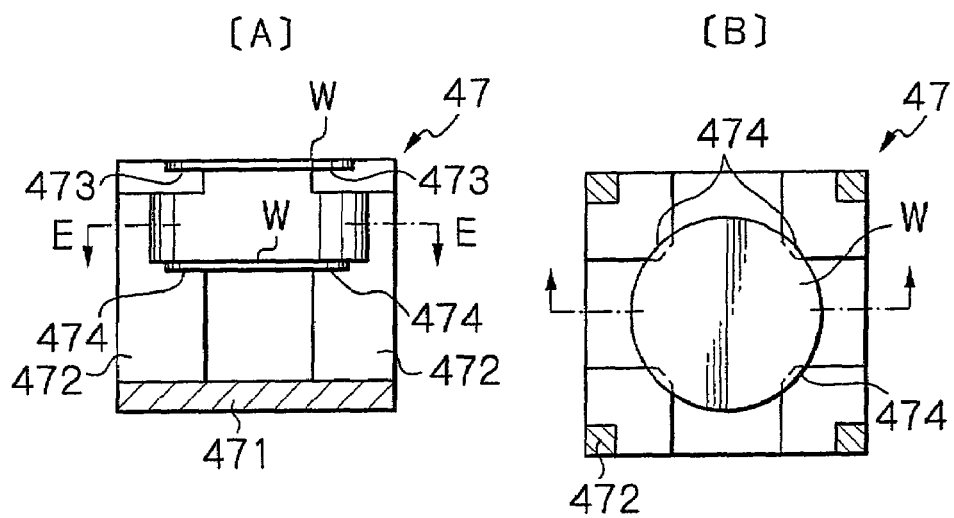

Within the first loading chamber 41, a wafer rack 47 is disposed for supporting a plurality (two in this embodiment)

of wafers spaced in the vertical direction and maintained in a horizontal position. As illustrated in FIG. 5, the wafer rack 47 comprises posts 472 fixed at four corners of a rectangular substrate 471, spaced from one another, in an upright position. Each of the posts 472 is formed with supporting devices 473, 474 in two stages, such that peripheral edges of wafers W are carried on and held by these supporting devices. Then, leading ends of arms of the first and second carrier units, later described, are brought closer to wafers from adjacent posts and grab the wafers.

The loading chambers 41, 42 can be controlled for the atmosphere to be maintained in a high vacuum condition (at a pressure of $10^{-5}$ to $10^{-6}$ Pa) by a pumping system (not shown) in a known structure including a vacuum pump, not shown. In this event, the first loading chamber 41 may be held in a low vacuum condition as a low vacuum chamber, while the second loading chamber 42 may be held in a high vacuum condition as a high vacuum chamber, to effectively prevent contamination of wafers. The employment of such a structure allows a wafer, which is accommodated in the loading chamber and is next subjected to the defect testing, to be carried into the working chamber without delay. The employment of such a loading chambers provides for an improved throughput for the defect testing, and the highest possible vacuum condition around the electron source which is required to be kept in a high vacuum condition, together with the principle of a multi-beam type electron system, later described.

The first and second loading chambers 41, 42 are connected to a vacuum exhaust pipe and a vent pipe for an inert gas (for example, dried pure nitrogen) (neither of which are shown), respectively. In this way, the atmospheric state within each loading chamber is attained by an inert gas vent (which injects an inert gas to prevent an oxygen gas and so on other than the inert gas from attaching on the surface). Since an apparatus itself for implementing the inert gas vent is known in structure, detailed description thereon is omitted.

In the testing apparatus according to the present invention which uses an electron beam, when representative lanthanum hexaboride (LaB$_6$) used as an electron source for an electro-optical system, later described, is once heated to such a high temperature that causes emission of thermal electrons, it should not be exposed to oxygen within the limits of possibility so as not to shorten the lifetime. The exposure to oxygen can be prevented without fail by carrying out the atmosphere control as mentioned above at a stage before introducing a wafer into the working chamber in which the electron-optical system is disposed.

The stage device 50 comprises a fixed table 51 disposed on the bottom wall 301 of the main housing 30; a Y-table 52 movable in a Y-direction on the fixed table 51 (the direction vertical to the drawing sheet in FIG. 1); an X-table 53 movable in an X-direction on the Y-table 52 (in the left-to-right direction in FIG. 1); a turntable 54 rotatable on the X-table; and a holder 55 disposed on the turntable 54. A wafer is releasably held on a wafer carrying surface 551 of the holder 55. The holder 55 may be of a known structure which is capable of releasably grabbing a wafer by means of a mechanical or electrostatic chuck feature.

The stage device 50 uses servo motors, encoders and a variety of sensors (not shown) to operate a plurality of tables as mentioned above to permit highly accurate alignment of a wafer held on the carrying surface 551 by the holder 55 in the X-direction, Y-direction and Z-direction (in the up-down direction in FIG. 1) with respect to an electron beam irradiated from the electro-optical device, and in a direction about the axis normal to the wafer supporting surface (θ direction). The alignment in the Z-direction may be made such that the position on the carrying surface 551 of the holder 55, for example, can be finely adjusted in the Z-direction. In this event, a reference position on the carrying surface 551 is sensed by a position measuring device using a laser of an extremely small diameter (a laser interference range finder using the principles of interferometer) to control the position by a feedback circuit, not shown. Additionally or alternatively, the position of a notch or an orientation flat of a wafer is measured to sense a plane position or a rotational position of the wafer relative to the electron beam to control the position of the wafer by rotating the turntable 54 by a stepping motor which can be controlled in extremely small angular increments.

In order to maximally prevent dust produced within the working chamber, servo motors 531, 531 and encoders 522, 532 for the stage device 50 are disposed outside the main housing 30. Since the stage device 50 may be of a known structure used, for example, in steppers and so on, detailed description on its structure and operation is omitted. Likewise, since the laser interference range finder may also be of a known structure, detailed description on its structure and operation is omitted.

It is also possible to establish a basis for signals which are generated by previously inputting a rotational position, and X-, Y-positions of a wafer relative to the electron beam in a signal detecting system or an image processing system, later described. The wafer chucking mechanism provided in the holder 55 is configured to apply a voltage for chucking a wafer to an electrode of an electrostatic chuck, and the alignment is made by pinning three points on the outer periphery of the wafer (preferably spaced equally in the circumferential direction). The wafer chucking mechanism comprises two fixed aligning pins and a push-type clamp pin. The clamp pin can implement automatic chucking and automatic releasing, and constitutes a conducting spot for applying the voltage.

While in this embodiment, the X-table is defined as a table which is movable in the left-to-right direction in FIG. 2; and the Y-table as a table which is movable in the up-down direction, a table movable in the left-to-right direction in FIG. 2 may be defined as the Y-table; and a table movable in the up-down direction as the X-table.

The loader 60 comprises a robot-type first carrier unit 61 disposed within the housing 22 of the mini-environment device 20; and a robot-type second carrier unit 63 disposed within the second loading chamber 42. The first carrier unit 61 comprises a multi-node arm 612 rotatable about an axis $O_1$-$O_1$ with respect to a driver 611. While an arbitrary structure may be used for the multi-node arm, the multi-node arm in this embodiment has three parts which are pivotably attached to each other. One part of the arm 612 of the first carrier unit 61, i.e., the first part closest to the driver 611 is attached to a rotatable shaft 613 by a driving mechanism (not shown) of a known structure, disposed within the driver 611.

The arm 612 is pivotable about the axis $O_1$-$O_1$ by means of the shaft 613, and radially telescopic as a whole with respect to the axis $O_1$-$O_1$ through relative rotations among the parts. At a leading end of the third part of the arm 612 furthest away from the shaft 613, a grabber 616 in a known structure for grabbing a wafer, such as a mechanical chuck or an electrostatic chuck, is disposed. The driver 611 is movable in the vertical direction by an elevating mechanism 615 in a known structure.

The first carrier unit 61 extends the arm 612 in either a direction M1 or a direction M2 within two cassettes c held in the cassette holder 10, and removes a wafer accommodated in a cassette c by carrying the wafer on the arm or by grabbing the wafer with the chuck (not shown) attached at the leading end of the arm.

Subsequently, the arm is retracted (in a position as illustrated in FIG. 2), and then rotated to a position at which the arm can extend in a direction M3 toward the prealigner 25, and stopped at this position. Then, the arm is again extended to transfer the wafer held on the arm to the prealigner 25. After receiving a wafer from the prealigner 25, contrary to the foregoing, the arm is further rotated and stopped at a position at which it can extend to the second loading chamber 41 (in the direction M3), and transfers the wafer to a wafer receiver 47 within the second loading chamber 41.

For mechanically grabbing a wafer, the wafer should be grabbed on a peripheral region (in a range of approximately 5 mm from the peripheral edge). This is because the wafer is formed with device construction (circuit patterns) over the entire surface except for the peripheral region, and grabbing the inner region would result in failed or defective devices.

The second carrier unit 63 is basically identical to the first carrier unit 61 in structure except that the second carrier unit 63 carries a wafer between the wafer rack 47 and the carrying surface of the stage device 50, so that detailed description thereon is omitted.

In the loader 60, the first and second carrier units 61, 63 each carry a wafer from a cassette held in the cassette holder 10 to the stage device 50 disposed in the working chamber 31 and vice versa, while remaining substantially in a horizontal position. The arms of the carrier units are moved in the vertical direction only when a wafer is removed from and inserted into a cassette, when a wafer is carried on and removed from the wafer rack, and when a wafer is carried on and removed from the stage device 50. It is therefore possible to smoothly carry a larger wafer, for example, a wafer having a diameter of 30 cm. Next, how a wafer is carried will be described in sequence from the cassette c held by the cassette holder 10 to the stage device 50 disposed in the working chamber 31.

As described above, when the cassette is manually set, the cassette holder 10 having a structure adapted to the manual setting is used, and when the cassette is automatically set, the cassette holder 10 having a structure adapted to the automatic setting is used. In this embodiment, as the cassette c is set on the up/down table 11 of the cassette holder 10, the up/down table 11 is moved down by the elevating mechanism 12 to align the cassette c with the access port 225.

As the cassette is aligned with the access port 225, a cover (not shown) provided for the cassette is opened, and a cylindrical cover is applied between the cassette c and the access port 225 of the mini-environment to block the cassette and the mini-environment space 21 from the outside. Since these structures are known, detailed description on their structures and operations is omitted. When the mini-environment device 20 is provided with a shutter for aperture and closing the access port 225, the shutter is operated to open the access port 225.

On the other hand, the arm 612 of the first carrier unit 61 remains oriented in either the direction M1 or M2 (in the direction M1 in this description). As the access port 225 is opened, the arm 612 extends to receive one of wafers accommodated in the cassette at the leading end. While the arm and a wafer to be removed from the cassette are adjusted in the vertical position by moving up or down the driver 611 of the first carrier unit 61 and the arm 612 in this embodiment, the adjustment may be made by moving up and down the up/down table 11 of the cassette holder 10, or made by both.

As the arm 612 has received the wafer, the arm 621 is retracted, and the shutter is operated to close the access port (when the shutter is provided). Next, the arm 612 is pivoted about the axis $O_1$-$O_1$ such that it can extend in the direction M3. Then, the arm 612 is extended and transfers the wafer carried at the leading end or grabbed by the chuck onto the prealigner 25 which aligns the orientation of the rotating direction of the wafer (the direction about the central axis vertical to the wafer plane) within a predetermined range. Upon completion of the alignment, the carrier unit 61 retracts the arm 612 after a wafer has been received from the prealigner 25 to the leading end of the arm 612, and takes a posture in which the arm 612 can be extended in a direction M4. Then, the door 272 of the gate valve 27 is moved to open the access ports 223, 236, and the arm 612 is extended to place the wafer on the upper stage or the lower stage of the wafer rack 47 within the first loading chamber 41. It should be noted that before the shutter device 27 opens the access ports to transfer the wafer to the wafer rack 47, the aperture 435 formed through the partition wall 434 is closed by the door 461 of the shutter 46 in an air-tight state.

In the process of carrying a wafer by the first carrier unit, clean air flows (as downflow) in laminar flow from the gas supply unit 231 disposed on the housing of the mini-environment device to prevent dust from attaching on the upper surface of the wafer during the carriage. A portion of the air near the carrier unit (in this embodiment, about 20% of the air supplied from the supply unit 231, mainly contaminated air) is aspired from the suction duct 241 of the discharger 24 and emitted outside the housing. The remaining air is recovered through the recovery duct 232 disposed on the bottom of the housing and returned again to the gas supply unit 231.

As the wafer is placed into the wafer rack 47 within the first loading chamber 41 of the loader housing 40 by the first carrier unit 61, the shutter device 27 is closed to seal the loading chamber 41. Then, the first loading chamber 41 is filled with an inert gas to expel air. Subsequently, the inert gas is also evacuated so that a vacuum atmosphere dominates within the loading chamber 41.

The vacuum atmosphere within the loading chamber 41 may be at a low vacuum degree. When a certain degree of vacuum is provided within the loading chamber 41, the shutter 46 is operated to open the access port 434 which has been sealed by the door 461, and the arm 632 of the second carrier unit 63 is extended to receive one wafer from the wafer receiver 47 with the grabber at the leading end (the wafer is carried on the leading end or grabbed by the chuck attached to the leading end). Upon completion of the receipt of the wafer, the arm 632 is retracted, followed by the shutter 46 again operated to close the access port 435 by the door 461. It should be noted that the arm 632 has previously taken a posture in which it can extend in the direction N1 of the wafer rack 47 before the shutter 46 is operated to open the access port 435.

Also, as described above, the access ports 437, 325 have been closed by the door 452 of the shutter 45 before the shutter 46 is operated to block the interaction between the second loading chamber 42 and the working chamber 31 in an air-tight condition, so that the second loading chamber 42 is evacuated.

As the shutter 46 is operated to close the access port 435, the second loading chamber 42 is again evacuated at a higher degree of vacuum than the first loading chamber 41. Meanwhile, the arm 632 of the second carrier unit 63 is rotated to a position at which it can extend toward the stage device 50 within the working chamber 31. On the other hand, in the stage device 50 within the working chamber 31, the Y-table 52 is moved upward, as viewed in FIG. 2, to a position at which the center line $O_0$-$O_0$ of the X-table 53 substantially matches an X-axis $X_1$-$X_1$ which passes a pivotal axis $O_2$-$O_2$ of the second carrier unit 63. The X-table 53 in turn is moved to the position closest to the leftmost position in FIG. 2, and remains awaiting at this position.

When the second loading chamber 42 is evacuated to substantially the same degree of vacuum as the working chamber 31, the door 452 of the gate valve 45 is moved to open the access ports 437, 325, allowing the arm 632 to extend so that the leading end of the arm 632, which holds a wafer, approaches the stage device 50 within the working chamber 31. Then, the wafer is placed on the carrying surface 551 of the stage device 50. As the wafer has been placed on the carrying surface 551, the arm 632 is retracted, followed by the shutter 45 operated to close the access ports 437, 325.

The foregoing description has been made on the operation until a wafer in the cassette c is carried and placed on the stage device 50. For returning a wafer, which has been carried on the stage device 50 and processed, from the stage device 50 to the cassette c, the operation reverse to the foregoing is performed. Since a plurality of wafers are stored in the wafer rack 47, the first carrier unit 61 can carry a wafer between the cassette and the wafer rack 47 while the second carrier unit 63 is carrying a wafer between the wafer rack 47 and the stage device 50, so that the testing operation can be efficiently carried out.

In specific, when there are a wafer A, which has been already processed, and a wafer B, which has not yet been processed, in a wafer rack 47 of a second carrier unit, at first, the wafer B which has not yet been processed is transferred to the stage 50 and the processing is started. During this processing, the wafer A which has already been processed is transferred from the stage 50 to the wafer rack 47 by an arm, a wafer C which has not yet been processed is picked up from the wafer rack 47 again by the arm, which after having been positioned by a pre-aligner, is further transferred to the wafer rack 47 of a loading chamber 41.

This procedure may allow, in the wafer rack 47, the wafer A which has already been processed to be substituted by the wafer C which has not yet been processed, during the wafer B being processed.

Alternatively, depending on the way how to use such an apparatus for executing an inspection and/or an evaluation, a plurality of stage units 50 may be arranged in parallel, so that the wafers may be transferred from one wafer rack 47 to each of the stage units 50 thereby applying a similar processing to a plurality of wafers.

FIGS. 6A, 6B illustrate exemplary modifications to the method of supporting the main housing 30. In an exemplary modification illustrated in FIG. 6A, a housing supporting device 33a is made of a thick rectangular steel plate 331a, and a housing body 32a is placed on the steel plate. Therefore, the bottom wall 321a of the housing body 32a is thinner than the bottom wall 222 of the housing body 32 in the foregoing embodiment. In an exemplary modification illustrated in FIG. 6B, a housing body 32b and a loader housing 40b are suspended by a frame structure 336b of a housing supporting device 33b. Lower ends of a plurality of vertical frames 337b fixed to the frame structure 336b are fixed to four corners of a bottom wall 321b of the housing body 32b, such that the peripheral wall and the top wall are supported by the bottom wall. Then, a vibration isolator 37b is disposed between the frame structure 336b and a base frame 36b.

Likewise, the loader housing 40 is suspended by a suspending member 49b fixed to the frame structure 336. In the exemplary modification of the housing body 32b illustrated in FIG. 6B, the housing body 32b is supported in suspension, the general center of gravity of the main housing and a variety of devices disposed therein can be brought downward. The methods of supporting the main housing and the loader housing, including the exemplary modifications described above, are configured to prevent vibrations from being transmitted from the floor to the main housing and the loader housing.

In another exemplary modification, not shown, the housing body of the main housing is only supported by the housing supporting device from below, while the loader housing may be placed on the floor in the same way as the adjacent mini-environment device. Alternatively, in a further exemplary modification, not shown, the housing body of the main housing is only supported by the frame structure in suspension, while the loader housing may be placed on the floor in the same way as the adjacent mini-environment device.

Figure 7:
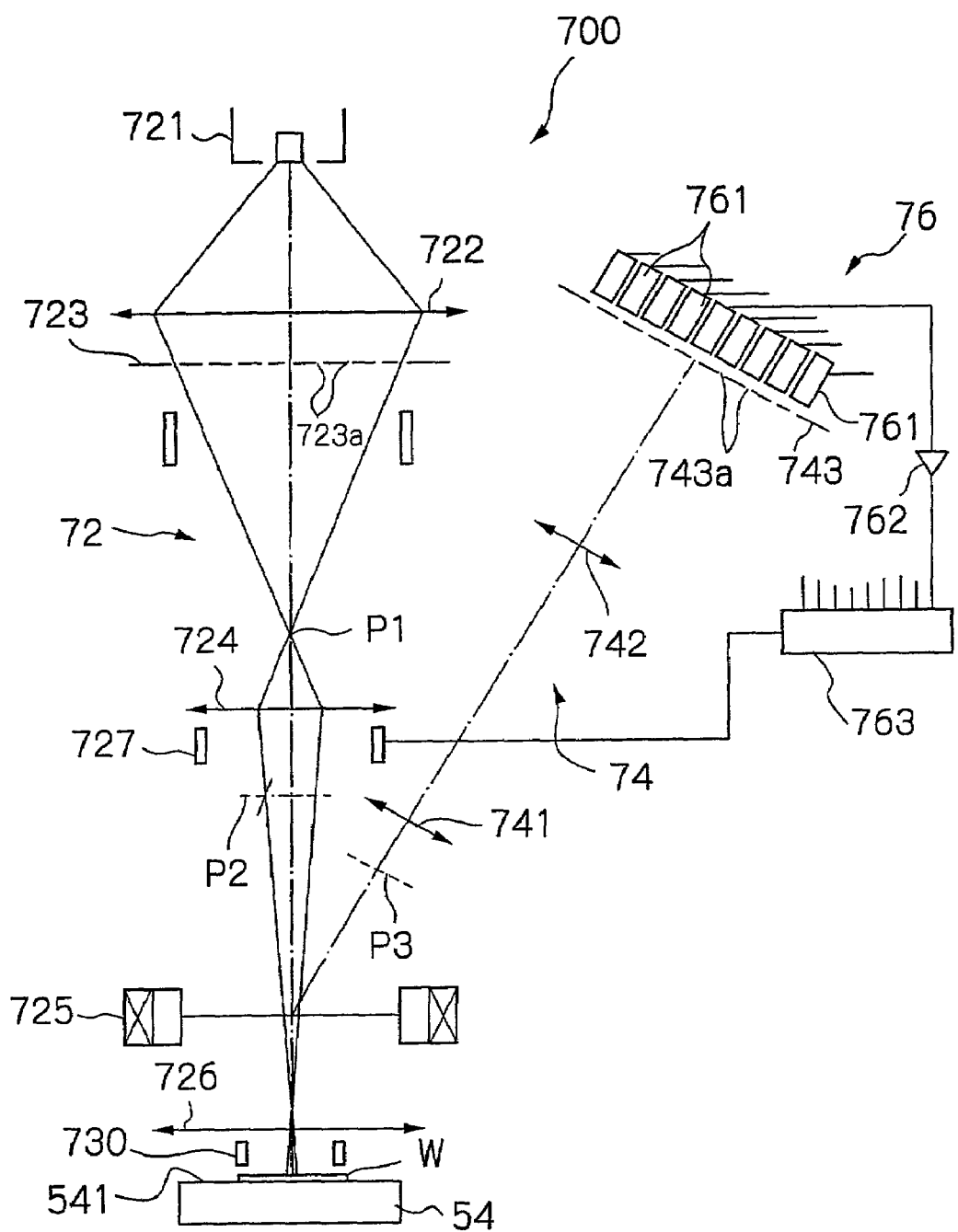
FIG. 7 is a schematic view illustrating a general configuration of an electronic optical apparatus of a second embodiment according to the present invention to be used in the inspection apparatus of FIG. 1.
Figure 8:
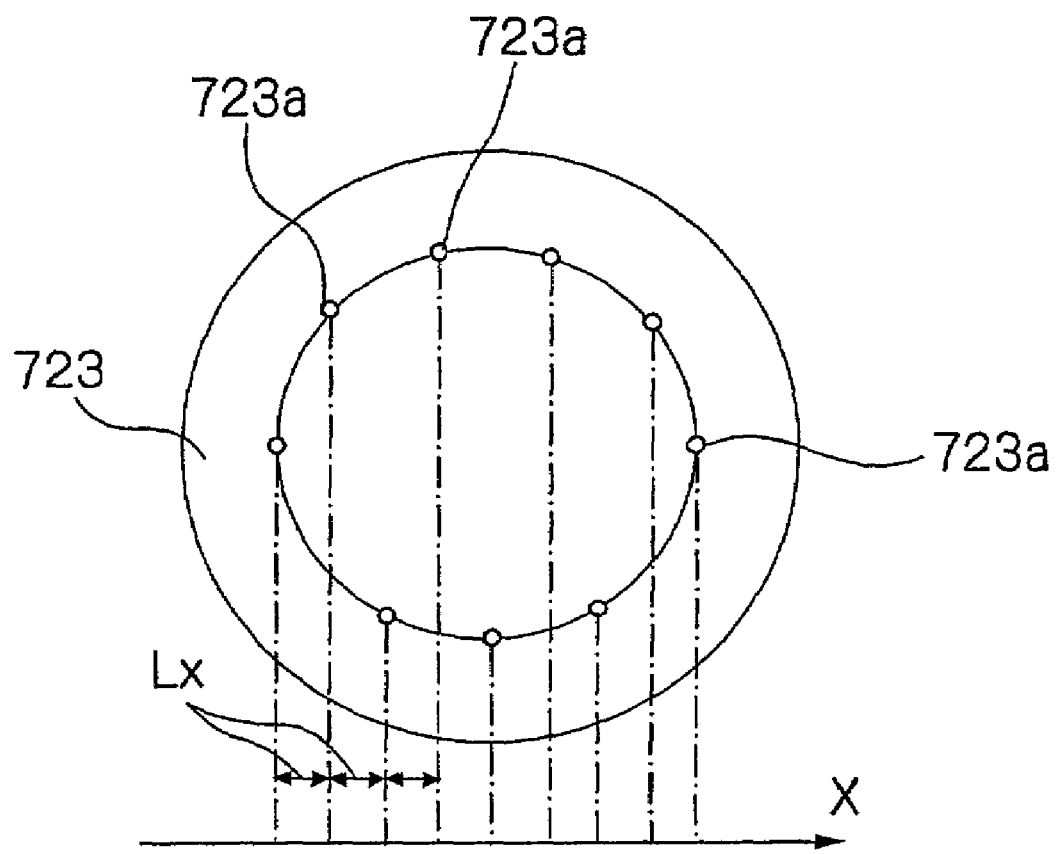
FIG. 8 illustrates a physical relationship defining a location of each aperture of a multi-aperture plate used in a primary optical system of the electronic optical apparatus of FIG. 7.

An electron optical apparatus 70 (first embodiment in FIG. 1) comprises a lens column 71 fixedly mounted to a housing 32, said lens column containing an electron optical system therein comprising a primary electron optical system 72 (hereafter referred to as a primary optical system for simplicity) and a secondary electron optical system 74 (hereafter referred to as a secondary optical system for simplicity), and a detecting system 76, as schematically illustrated in FIGS. 7 and 8.

The primary optical system 72 is such an optical system that irradiates an electron beam against a top surface of a wafer W being inspected, and comprises an electron gun 721 for emitting an electron beam, an electrostatic lens or a condenser lens 722 for converging the primary electron beam emitted from the electron gun 721, a multi-aperture plate 723 disposed beneath the condenser lens 722 and having a plurality of apertures formed therethrough for forming the primary electron beam into a plurality of electron beams or a multi-beam, an electrostatic lens or a demagnifying lens 724 for demagnifying the primary electron beams, a Wien filter or an E×B separator 725, and an objective lens 726, which are sequentially arranged with the electron gun 721 in the topmost level as shown in FIG. 7 so that an optical axis of the primary electron beam emitted from the electron gun should be normal with respect to the surface of an object S to be inspected.

In order to remove a negative effect of field curvature aberration by the demagnifying lens 724 and the objective lens 726, a plurality of small apertures 723a (nine apertures in this embodiment) is arranged on the multi-aperture plate 723 so as to be located in a concentric circular configuration with the optical axis, as shown in FIG. 8, such that a space Lx between the projections of the apertures in the X direction is equal to one another.

The secondary optical system 74 comprises magnifying lenses 741 and 742 forming a unit of two-stage electrostatic lenses which allows secondary electrons separated from the primary optical system by the E×B type deflecting system (E×B filter) 724 to pass therethrough, and also comprises a multi-aperture detection plate 743. A plurality of apertures 743a formed through the multi-aperture detection plate 743 corresponds to the plurality of apertures 723a formed through the multi-aperture plate 723 in the primary optical system on one to one basis.

The detecting system 76 comprises a plurality of detectors 761 (nine detectors in this embodiment) disposed adjacently to the multi-aperture detection plate 743 in the secondary optical system 74 so as for each of them to correspond respectively to each of the apertures 743a, and also an image processing section 763 electrically connected to each of the detectors 761 via an A/D converter 762.

An operation of the electro optical apparatus (second embodiment in FIG. 7) with an above configuration will now be described. The primary electron beam emitted from the electron gun 721 is converged by the condenser lens 722 in the primary optical system 72 to form a crossover at a point P1. On the other hand, the primary electron beam converged by the condenser lens 722 passes through the plurality of apertures 723a of the multi-aperture plate to form into a plurality of primary electron beams, which are contracted by the minifying lens 724 so as to be projected onto a point P2. After being focused onto the point P2, the beams are further focused onto a surface of a wafer W by the objective lens 726. On the other hand, the deflecting system 727 disposed between the minifying lens 724 and the objective lens 726 deflects the primary electron beams so as to scan the surface of the wafer W.

The plurality of focused primary electron beams (nine beams in this embodiment) is irradiated onto the sample S at a plurality of points thereon, and secondary electrons are emanated from said plurality of points. Those secondary electrons are attracted by an electric field of the objective lens 726 to be converged narrower, and then deflected by the E×B separator 725 so as to be introduced into the secondary optical system 74. The secondary electron image is focused on a point P3 which is much closer to the deflector 725 than the point P2. This is because the primary electron beam has the energy of 500 eV on the surface of the wafer, while the secondary electron beam only has the energy of a few eV.

Each of the images of the secondary electrons focused at the point P3 is focused by the two-stage magnifying lenses 741 and 742 onto each of the corresponding apertures 743a of the multi-aperture detection plate 743 to be formed into an image, so that each of the detectors 761 disposed correspondingly to each of the apertures 743a detects the image. Each of the detectors 761 thus detects the electron beam and converts it into an electric signal representative of its intensity. The generated electric signals are output from respective detectors 761, and after being converted respectively into digital signals by the A/D converter 762, they are input to the image processing section 763.

The image processing section 763 converts the input digital signals into image data. Since the image processing section 763 is further supplied with a scanning signal for deflecting the primary electron beam, the image processing section 763 can display an image representing the surface of the wafer. Comparing this image with a reference pattern that has been pre-set in a setting device (not shown) allows to determine whether or not the pattern on the wafer W being inspected (evaluated) is acceptable. Further, the line width of the pattern formed on the surface of the wafer W can be measured in such a way that the pattern to be measured on the wafer W is moved by a registration to the proximity of the optical axis of the primary optical system, and the pattern is then line-scanned to extract the line width evaluation signal, which in turn is appropriately calibrated.

In this regard, it is required to make special arrangements in order to minimize the affection by the three aberrations, i.e., the distortion caused by the primary optical system, the axial chromatic aberration, and the filed astigmatism, when the primary electron beams passed through the apertures of the multi-aperture plate 723 in the primary optical system are focused onto the surface of the wafer W and then the secondary electrons emanated from the wafer W are formed into an image on the detector 761.

It is to be noticed that, with respect to the relationship between the spacing of a plurality of primary electron beams and the secondary optical system, any space between the primary electron beams made longer than the aberration by the secondary optical system may eliminate the cross talks among the plurality of beams.

As shown in FIG. 1, a pre-charge unit 81 is disposed in a working chamber 31, adjacent to a lens column 71 of an electronic optical apparatus 70. Since this inspection apparatus is of a type in which an electron beam is used to scan and irradiate a substrate to be inspected or a wafer, and thereby a device pattern or the like formed on a surface of the wafer is inspected, information such as secondary electrons emitted by the irradiation of the electron beam is utilized as an information of the wafer surface, and sometimes, depending on a condition including a material of the wafer, an energy level of the irradiated electron or the like, the wafer surface may be charged-up.

Further, depending on the locations on the wafer, some locations might be more strongly charged-up than other locations. If there are non-uniform distribution in a charging amount on the wafer, the information of the secondary electron beam is made to be non-uniform, which makes it impossible to obtain an accurate information.

Accordingly, in the present embodiment, there is provided a pre-charge unit 81 having a charged particle irradiating section 811 in order to prevent this non-uniform distribution. In order to prevent a non-uniform distribution in charging, before the electrons for inspection being irradiated onto a predetermined location of the wafer to be inspected, the charged particles are irradiated from the charged particle irradiating section 811 of the pre-charge unit thereto, thus preventing the non-uniform charging. The charging on the wafer surface is detected by forming and evaluating an image of the wafer surface in advance, and based on a result of the detection, the pre-charge unit 81 is operated. Further, in this pre-charge unit, the primary electron beam may be irradiated with some gradation.

Figure 9:
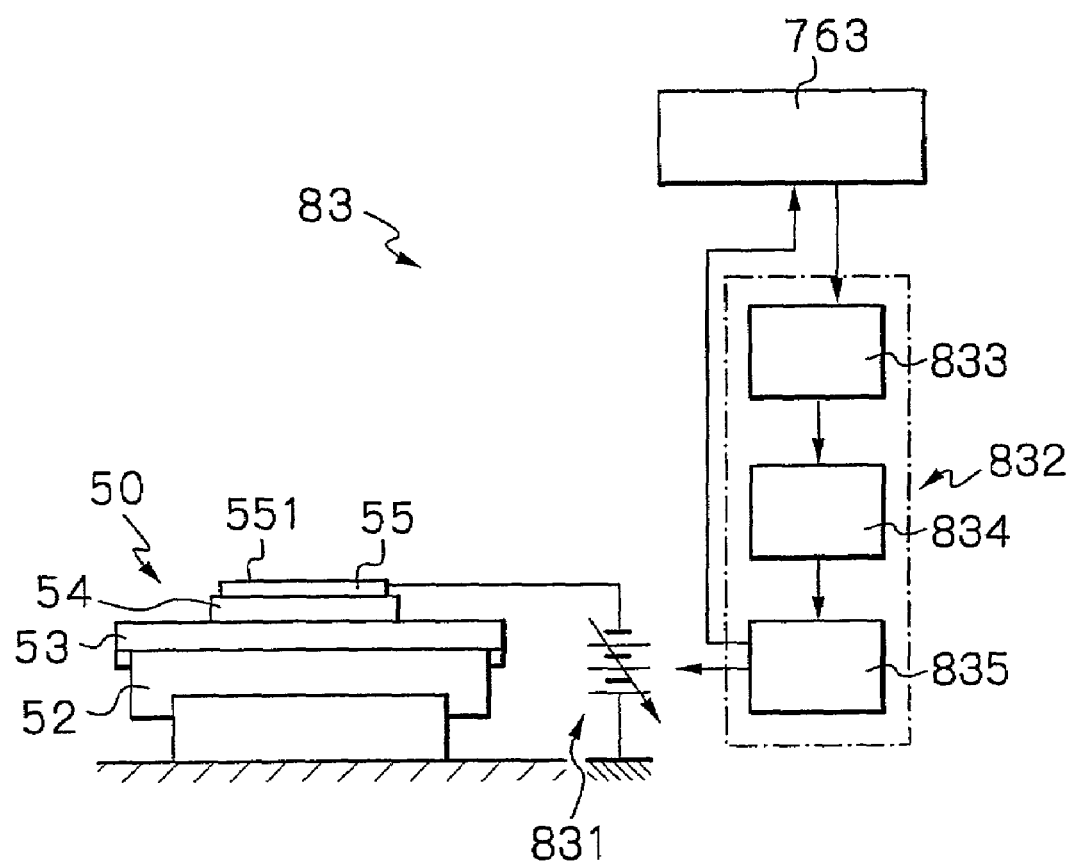
FIG. 9 illustrates a potential applying mechanism.

Referring next to FIG. 9, the potential applying mechanism 83 applies a potential of several kilo volts to a carrier of a stage, on which the wafer is placed, to control the generation of secondary electrons based on the fact that the information on the secondary electrons emitted from the wafer (secondary electron yield) depend on the potential on the wafer. The potential applying mechanism 83 also serves to decelerate the energy originally possessed by irradiated electrons to provide the wafer with irradiated electron energy of approximately 100 to 500 eV.

As illustrated in FIG. 9, the potential applying mechanism 83 comprises a voltage applying device 831 electrically connected to the carrying surface 541 of the stage device 50; and a charging detection/voltage determining system (hereinafter detection/determining system) 832. The detection/determining system 832 comprises a monitor 833 electrically connected to an image forming unit 763 of the detecting system 76 in the electro-optical device 70; an operator 834 connected to the monitor 833; and a CPU 835 connected to the operator 834. The CPU 835 supplies a signal to the voltage applying device 831. The potential applying mechanism 83 is designed to find a potential at which the wafer under testing is hardly charged, and to apply such potential to the carrying surface 541.

As for a method for inspecting for an electric defect on a sample to be inspected, the defect on the portion which is designed to be electrically insulated can be detected based on the fact that there is a voltage difference therein between the normal case where the portion being insulated and the defective case where the portion being under conductive condition. In this method, at first the electric charges is applied to the sample in advance, so that the voltage difference is generated between the voltage in the portion essentially insulated electrically and the voltage in another portion which is designed to be electrically insulated but is under conductive condition because of any defective reason, then the beam of the present invention is applied thereto to obtain a data with voltage difference, which is then analyzed to detect the conductive condition.

Figure 10:
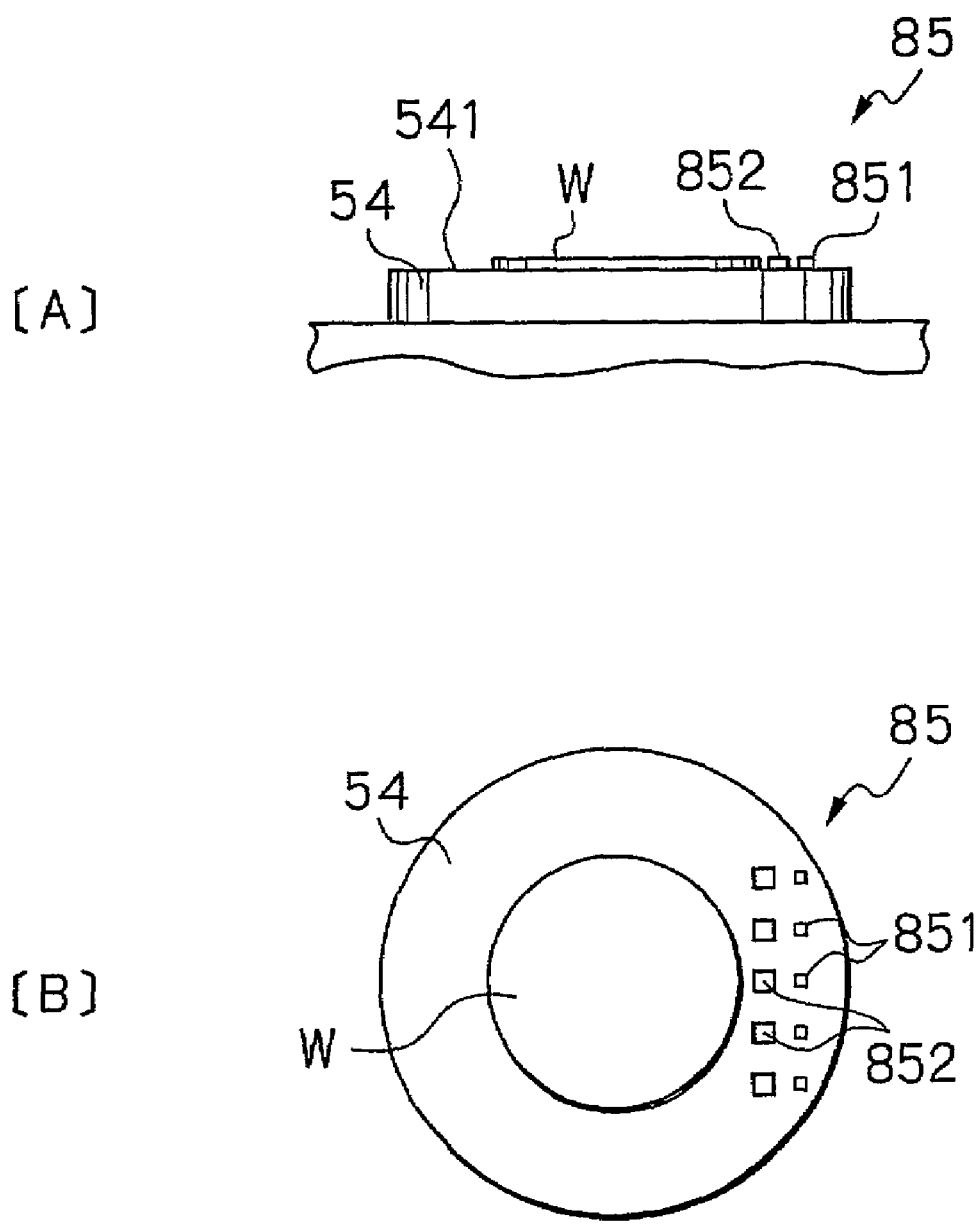
Figure 11:
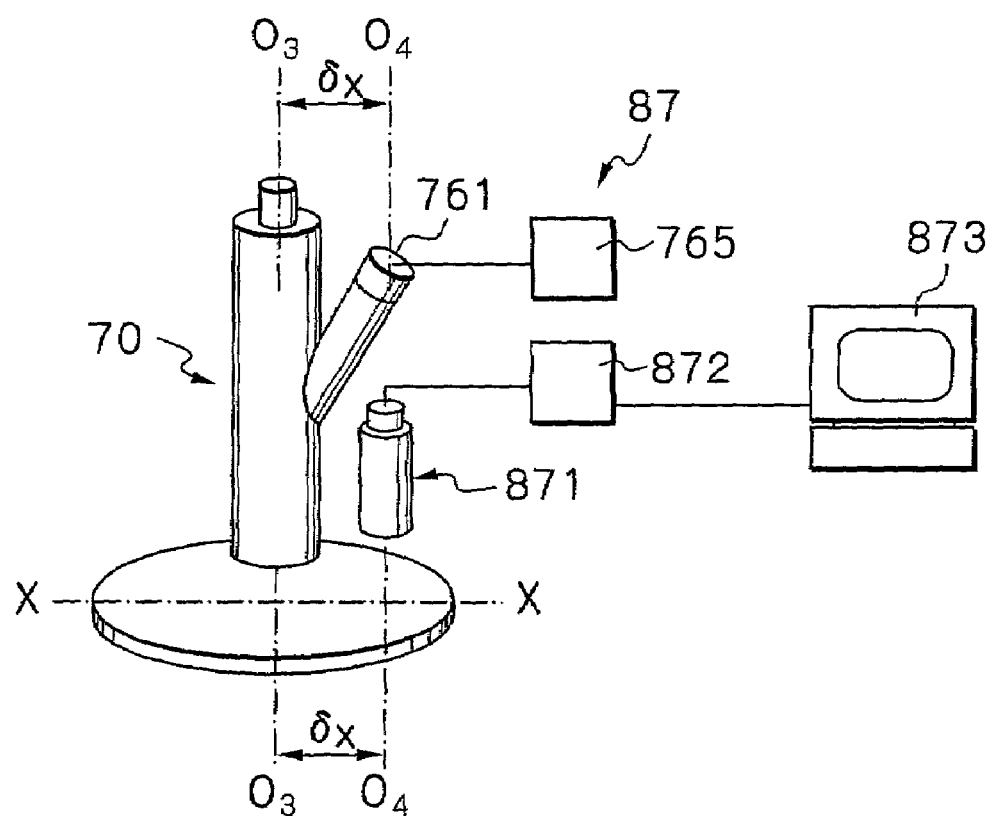
FIG. 11 is a schematic diagram illustrating an alignment controller for a wafer.

Referring next to FIG. 10, the electron beam calibration mechanism 85 comprises a plurality of Faraday cups 851, 852 for measuring a beam current, disposed at a plurality of positions in a lateral region of the wafer carrying surface 541 on the turntable 54. The Faraday cuts 851 is used for a fine beam (approximately $\phi$ 2 µm), while the Faraday cups 852 is used for total beams (approximately $\phi$ 30 µm). The Faraday cups 851 for a fine beam measures a beam profile by driving the turntable, while the Faraday cups 852 for a wide beam measure a total amount of currents. The Faraday cups 851, 852 are mounted on the wafer carrying surface 541 such that their top surfaces are coplanar with the upper surface of the wafer W carried on the carrying surface 541. In this way, the primary electron beam emitted from the electron gun 721 is monitored at all times. This is because the electron gun 721 cannot emit a constant electron beam at all times but varies in the emitting amount as it is used over time.

The alignment controller 87, which aligns the wafer W with the electron-optical system 70 using the stage system 50, performs the control for rough alignment through wide field observation using the optical microscope 871 (a measurement with a lower magnification than a measurement made by the electron-optical system); high magnification alignment using the electron-optical system of the electron-optical system 70; focus adjustment; testing region setting; pattern alignment; and so on. The wafer is tested at a low magnification using the optical system in this way because an alignment mark must be readily detected by an electron beam when the wafer is aligned by observing patterns on the wafer in a narrow field using the electron beam for automatically testing the wafer for patterns thereon.

The optical microscope 871 is disposed on the housing 30 (alternatively, may be movably disposed within the housing 30), with a light source, not shown, being additionally disposed within the housing 30 for operating the optical microscope. The electron-optical system for observing the wafer at a high magnification shares the electron-optical systems (primary optical system 72 and secondary optical system 74) of the electron-optical system 70. The configuration may be generally illustrated in FIG. 10. For observing a point of interest on a wafer at a low magnification, the X-stage 53 of the stage device 50 is moved in the X-direction to move the point of interest on the wafer into a view field of the optical microscope 871. The wafer is viewed in a wide field by the optical microscope 871, and the point of interest on the wafer to be observed is displayed on a monitor 873 through a CCD 872 to roughly determine a position to be observed. In this event, the magnification of the optical microscope may be changed from a low magnification to a high magnification.

Next, the stage device 50 is moved by a distance corresponding to a spacing $\delta x$ between the optical axis of the electron-optical system 70 and the optical axis of the optical microscope 871 to move the point on the wafer under observation, previously determined by the optical microscope 871, to a point in the view field of the electron-optical device 70.

The distance $\delta x$ between the axis $O_3$-$O_3$ of the electron-optical device and the axis $O_4$-$O_4$ of the optical microscope 871 is previously known (while it is assumed that the electron-optical system 70 is deviated from the optical microscope 871 in the direction along the X-axis in this embodiment, they may be deviated in the Y-axis direction as well as in the X-axis direction), such that the point under observation can be moved to the viewing position by moving the stage device 50 by the distance $\delta x$. The point under observation has been moved to the viewing position of the electron-optical device 70, the point under observation is imaged by the electron-optical system at a high magnification for storing a resulting image or displaying the image on the monitor 765 through the CCD 761.

After the point under observation on the wafer imaged by the electron-optical system at a high magnification is displayed on the monitor 765, misalignment of the stage device 50 with respect to the center of rotation of the turntable 54 in the wafer rotating direction, and misalignment $\delta\theta$ of the stage device 50 with respect to the optical axis $O_3$-$O_3$ of the electron-optical system in the wafer rotating direction are detected in a known method, and misalignment of a predetermined pattern with respect to the electron-optical device in the X-axis and Y-axis is also detected. Then, the operation of the stage device 50 is controlled to align the wafer based on the detected values and data on a testing mark attached on the wafer or data on the shape of the patterns on the wafer which have been acquired in separation.

Next, an embodiment of a method of manufacturing a semiconductor device according to the present invention will be described with reference to FIGS. 12 and 13.

Figure 12:
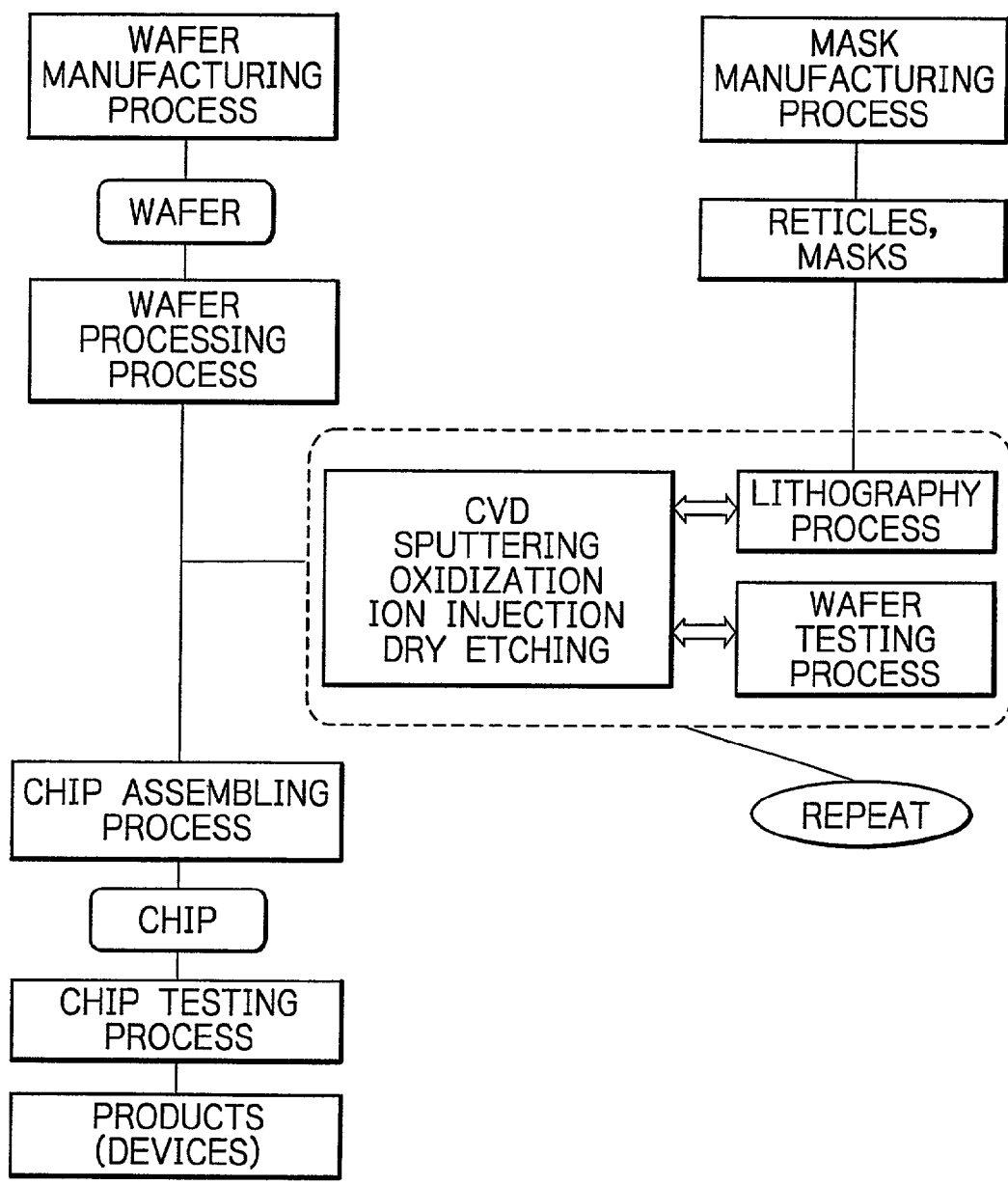
FIG. 12 is a flow chart for a semiconductor device manufacturing method of one embodiment according to the present invention.

FIG. 12 is a flow chart illustrating an embodiment of a method of manufacturing a semiconductor device according to the present invention. Manufacturing processes of this embodiment include the following main processes:

(1) a wafer manufacturing process for manufacturing a wafer (or a wafer preparing process for preparing a wafer);

(2) a mask manufacturing process for manufacturing masks for use in exposure (or mask preparing process for preparing masks);

(3) a wafer processing process for performing processing required to the wafer;

(4) a chip assembling process for dicing one by one chips formed on the wafer and making them operable; and (5) a chip testing process for testing complete chips.

The respective main processes are further comprised of several sub-processes.

Among these main processes, the wafer fabricating process set forth in (3) exerts critical affections to the performance of resulting semiconductor devices. This process involves sequentially laminating designed circuit patterns on the wafer to form a large number of chips which operate as memories, MPUs and so on. The wafer fabricating process includes the following sub-processes:

(A) a thin film forming sub-process for forming dielectric thin films serving as insulating layers, metal thin films for forming wirings or electrodes, and so on (using CVD, sputtering and so on);

(B) an oxidation sub-process for oxidizing the thin film layers and the wafer substrate;

(C) a lithography sub-process for forming a resist pattern using masks (reticles) for selectively fabricating the thin film layers and the wafer substrate;

(D) an etching sub-process for fabricating the thin film layers and the substrate in conformity to the resist pattern (using, for example, dry etching techniques);

(E) an ion/impurity inplantation/diffusion sub-process;

(F) a resist striping sub-process; and (G) a sub-process for testing the fabricated wafer;

As appreciated, the wafer fabrication process is repeated a number of times equal to the number of required layers to manufacture semiconductor devices which operate as designed.

Figure 13:
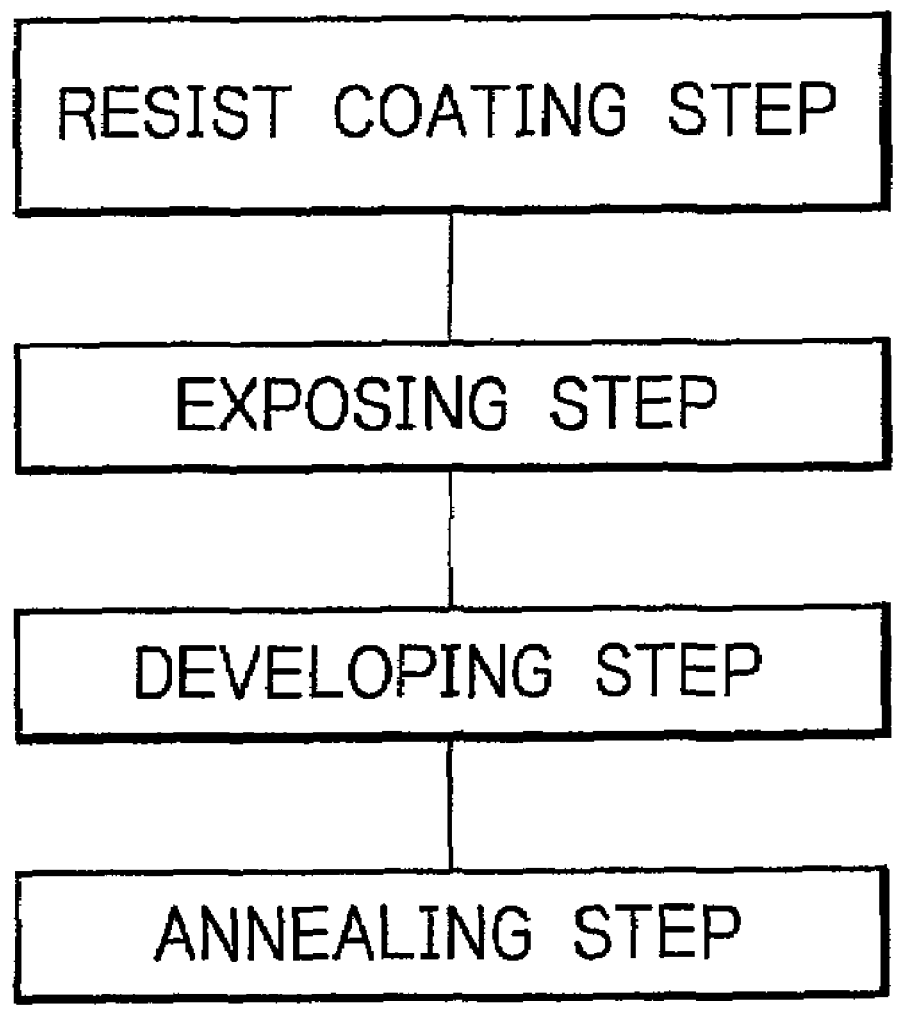
FIG. 13 is a flow chart for a lithography process, a core process in a wafer processing process of FIG. 12.

FIG. 13 is a flow chart illustrating the lithography sub-process which forms the core of the wafer processing process in FIG. 12. The lithography sub-process includes the following steps:

(a) a resist coating step for coating a resist on the wafer on which circuit patterns have been formed in the previous process;

(b) a resist exposing step;

(c) a developing step for developing the exposed resist to produce a resist pattern; and (d) an annealing step for stabilizing the developed resist pattern.

Since the aforementioned semiconductor device manufacturing process, wafer fabrication process and lithography process are well known, and therefore no further description will be required.

When the defect testing method and defect testing apparatus according to the present invention are used in the testing sub-process set forth in (G), any semiconductor devices even having submicron (sized) patterns can be tested at a high throughput, so that a total inspection can also be conducted, thereby making it possible to improve the yield rate of products and prevent defective products from being shipped.

The present invention provides the following effects:

(a) Since the present invention has allowed the functional combination of the respective components of the inspection apparatus using a plurality of electron beams or a multi-beam, the apparatus may handle any objects to be inspected with high throughput;

(b) Arranging a sensor in the environmental space for observing the cleanness level allows to inspect the object to be inspected under monitoring dirt (or particle) within the space; and (c) Since a pre-charge unit has been arranged, even those wafers made of insulating materials are hardly affected by the electric discharge.

FIG. 14A is a schematic diagram of an optical system in an electron beam apparatus 1000 of a third embodiment according to the present invention. Primary electron beams emitted from multiple emitters 1001, 1002 and 1003 are converged by a condenser lens 1004 to be projected onto an image field 1005, which are further converged by a lens 1006 and an objective lens 1008 to be contracted and projected onto a sample surface 1010. Although FIG. 14A has illustrated only one row of multiple emitters, plural rows of emitters may be arranged as shown in FIG. 17A.

FIG. 17A shows emitters in the array of 3×3, and FIG. 17B is a cross sectional view taken along the line 17B-17B of FIG. 17A. In FIGS. 17A and 17B, reference numeral 1021 designates a Si substrate, 1022 is a Mo emitter, 1023 is an Au leading electrode, and 1024 is a $Si_3N_4$ insulating film. The number of emitters may be chosen appropriately. A lens unit has been constructed with a few numbers of planar electrodes each having an aperture with a diameter of 2 to 10 μm and having been aligned in the optical axial direction with the interval of 2 to 10 μm therebetween and have different voltages applied thereto, so that it may operates as a convex lens.

Secondary electrons emanated from the sample surface 1010 which has been irradiated with the primary electron beam delivered from the multiple emitters 1001, 1002 and 1003 are accelerated by an accelerating electric field applied between the sample surface 1010 and the objective lens 1008, and even the secondary electrons emitted at a great emission angle may be converged narrower by the time when they enter into the objective lens 1008, which further pass through an aperture diaphragm 1007 to be formed into an image by the lens 1006 on the same image field 1005 as of the primary beams.

An E×B separator 1009 is arranged at the location of the image field 1005 so as to separate the secondary electrons passed through the lens 1006 from the primary optical system. The E×B separator 1009 has such a configuration in which an electric field and a magnetic field are crossed at a right angle within a plane orthogonal to the normal of the sample surface 1010 (the upper direction on paper), and the relationship between the electric field, the magnetic field and the primary electron energy has been established to allow the primary electrons to be advanced straight forward.

The separated secondary electrons are optically magnified with lenses 1011 and 1012 so as to be formed into a plurality of images on a detection system 1013. The detection system 1013 is provided with detectors 1014, 1015 and 1016 corresponding respectively to the primary electron beams from the multiple emitters 1001, 1002 and 1003, each of which detects the secondary electrons emanated from the surface of the sample which has been irradiated with each of those electron beams. It is to be noted that the multiple emitters 1001, 1002 and 1003 are arranged such that they are slightly offset to one another in the Z-axis direction in order to compensate for the image field curvature of the primary optical system. That is, the emitter 1001 on the optical axis is arranged at the farthest location from the sample, the emitter 1002 distant from the optical axis is displaced to be closer to the sample in comparison with the location of the emitter 1001 by the value corresponding to the field curvature, and the emitter 1003 more distant from the optical axis is displaced to be much closer to the sample.

To irradiate overall surface of the sample, the primary electron beams from the multiple emitters are controlled to make a scanning motion by an electrostatic deflecting system 1017. Further, in synchronism with the scanning motion of the primary electron beams, another electrostatic deflecting system 1018 arranged in the secondary optical system also controls the motion of the secondary electrons so as to enter always into the specified detectors 1014, 1015 and 1016 regardless of their scanning position.

That is, the secondary electrons emanated by the primary electron beams from the emitters 1001, 1002 and 1003 are controlled to enter respectively into the detectors 1014, 1015 and 1016. The detectors take the form of electrodes arranged on a curved surface having the same number of apertures as that of the detectors formed in front of a PIN diode with the voltage of about 20 kV applied thereto, and the voltage of about 1 kV is applied to this electrode. The convex lens effect of the electric field produced by the voltage of 20 kV leaking from those apertures affects all of the secondary electrons approaching to the vicinity of those apertures so as to go through the apertures into the detectors. The curved surface has such a shape that can compensate for the field curvature of the secondary optical system.

Figure 15:
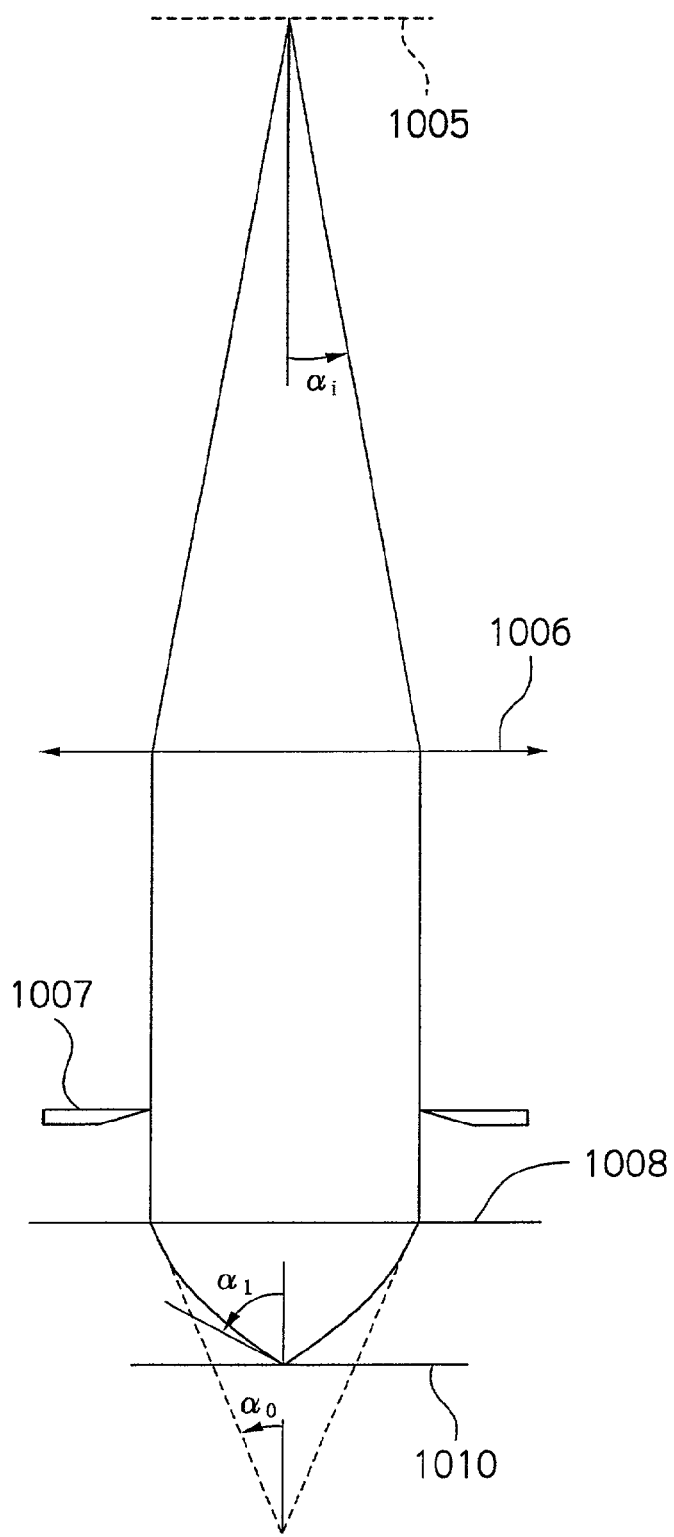
FIG. 15 illustrates a secondary optical system and an angular aperture in the third embodiment of the present invention.

Now, a relationship between the spacing of the irradiating positions of the plurality of primary electron beams and the secondary optical system will be described. FIG. 15 shows the secondary optical system and an angular aperture. As shown in FIG. 15, it is assumed that the secondary electrons within the acceptance angle al go through the objective lens 1008, the diaphragm 1007 and the lens 1006 to be imaged on the image field 1005. At that time, a half-angular aperture at the image field 1005 is $\alpha i$, and apparent angles $\alpha 0$ and $\alpha i$ viewed from the objective lens 1008 will be defined as $\alpha i/\alpha 0=1/M$, where the magnification for the secondary optical system is M. Further, the angles $\alpha 0$ and $\alpha i$ will be also defined as $(\alpha 1/\alpha 0)2=V8/Vini$, where the beam potential at the objective lens 1008 is V8 and the initial energy of the secondary electron is Vini.

Figure 16:
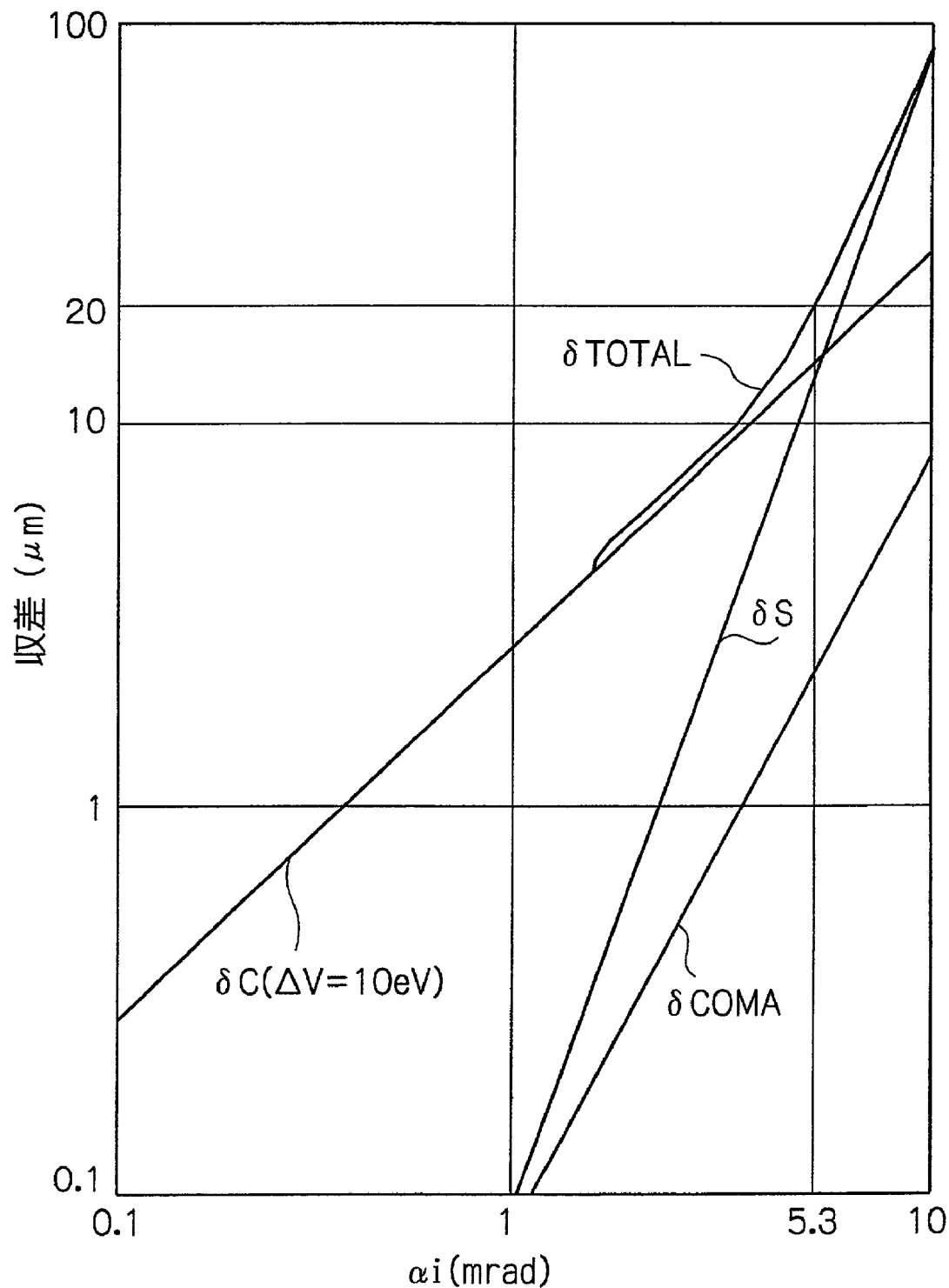
FIG. 16 illustrates a relationship between an aberration and an angular aperture "αi" on a surface 10 of a sample.

FIG. 16 shows the relationship between the aberration at the surface of the sample 1010 and the half-angular aperture $\alpha i$. In FIG. 16, $\delta S$ is defined as a spherical aberration, $\delta coma$ as a coma aberration, $\delta C$ as a chromatic aberration and $\delta total$ as the total of them.

Now, for the acceptance of 20 µm of aberration, the half-angular aperture $\alpha i$ should be equal to or smaller than 5.3 mrad. Further, the initial energy Vini of the secondary electron to be inspected is sufficient to be considered as much as 0.1 eV to 10 eV, so that when the magnification M is assumed to be 5 and the beam potential V8 at the objective lens 1008 to be 20 kV, the relationship will be denoted as $\alpha 1=1185$ mrad=67.9°.

Since it has been found that less than 90% of the secondary electrons can be taken in for the acceptance angle of 0° to 60° (see, for example, FIG. 6 in the specification of the U.S. Pat. No. 5,412,210), therefore for the half-angular aperture $\alpha i$ or the resolution of the secondary optical system of around 5.3 mrad and the size of the detector being about four times of 20 µm in the conversion for the sample surface, not less than 90% of the secondary electrons can be collected without any cross talks. Further, the spacing between the multiple emitters being around 100 µm can reduce the cross talks among the emitters to be negligible lam level.

If there is no need to collect not less than 90% of the secondary electrons but the collection of 50% of the secondary electrons guarantees the sufficient S/N ratio to be obtained, then the secondary electrons emanated within an angle smaller than 45° may be sufficient to be collected into the detectors. This is because an collecting efficiency of the secondary electrons, $\eta$, is denoted by [equation 1] as follows:

$$\eta = \int_0^{45°} \sin\theta \cos\theta d\theta / \int_0^{90°} \sin\theta \cos\theta d\theta = 0.5$$

Thus, respective primary electron beams are irradiated on respective locations such that a distance between any locations may be apart more than that for the resolution of the secondary optical system. FIG. 14B is an enlarged top plan view of an electron beam irradiation plane, wherein a distance N represents the resolution converted to the distance on the sample after having passed through lenses 1008, 1011 and 1012. In FIG. 14B, the distance N being equal to or longer than a distance between distinguishable two points allows to obtain a multi-beam without cross-talk and also allows to accomplish high throughput. The electron beam apparatus configured as described above can be used for defect inspection of semiconductor and for measurement of micro-distance.

If the electron beam apparatus of FIG. 14A is used in the chip inspection process according to the flow chart illustrative of an exemplary method for manufacturing a semiconductor device as shown in FIGS. 12 and 13, the inspection with higher throughput or even a hundred percent inspection may be attained while allowing the yield of the products to be improved and preventing any faulty products from being delivered.

Figure 14:
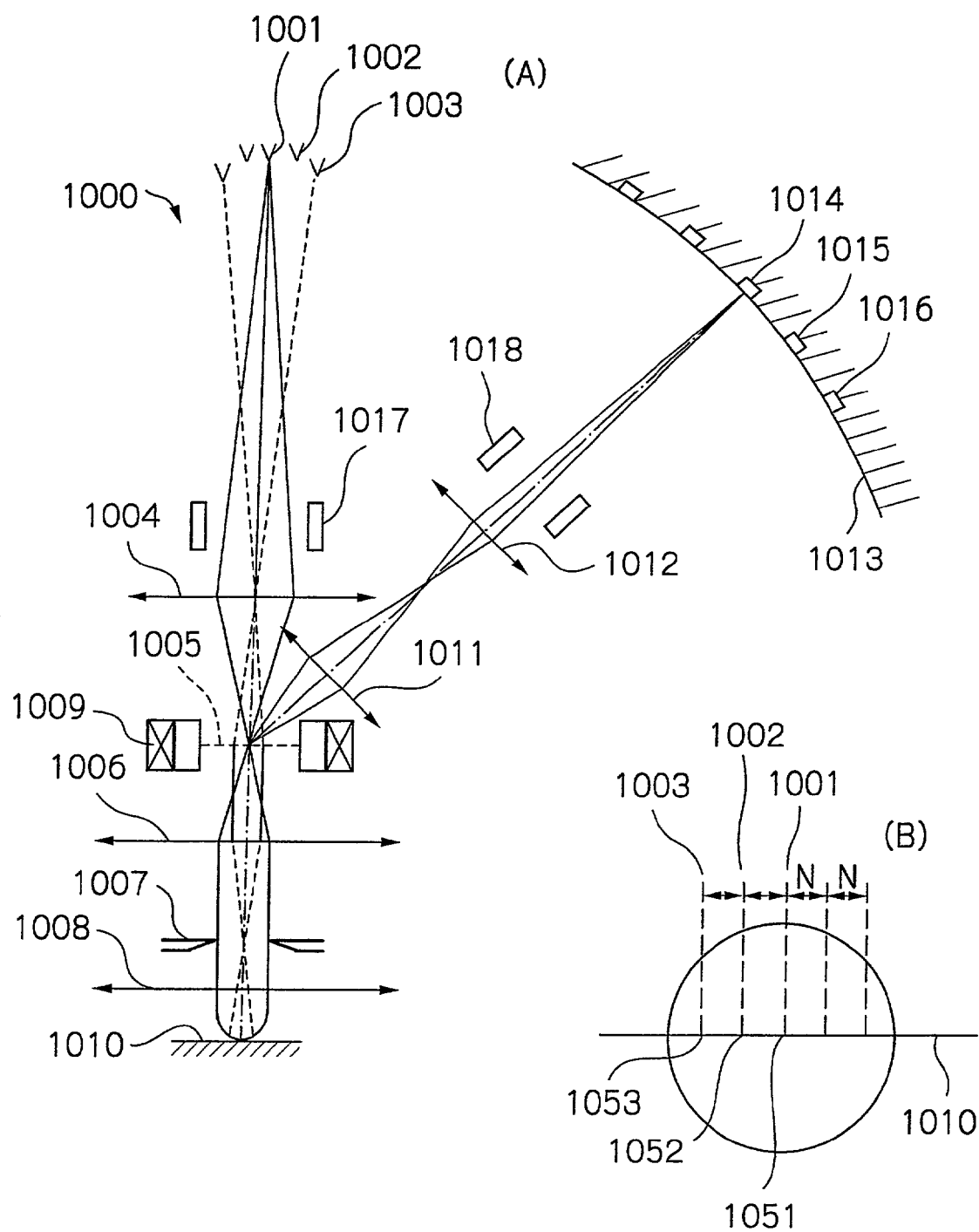
FIG. 14A is a schematic diagram of an optical system in an electron beam apparatus of a third embodiment according to the present invention.
FIG. 14B is an enlarged view of an image on a sample by a multi-beam.

As apparent from the above description, according to the electron beam apparatus of FIG. 14, since almost all of the secondary charged particles emanated from the sample can be detected without generating any cross talks, the defect inspection or the pattern line width measurement with higher S/N ratio can be attained successfully.

Further, since the aberration of the secondary optical system of about 20 µm on the sample surface also provides a satisfied detection result, the secondary optical system may not necessarily be of high precision, while the primary optical system orthogonal to the sample requires the formation of a plurality of charged particle beams to be of high precision.

Still further, since between the sample surface and the first stage of lens in the secondary optical system, there has been applied a decelerating electric field with respect to the primary optical system or an accelerating electric field with respect to the secondary optical system, the primary charged particle beams are more easily converged and also the secondary charged particles emanated over the wide angle range are more easily formed into a narrower bundle of particles at the position of the first stage of lens so as to be detected efficiently, so that a signal with better S/N ratio can be obtained and also the accuracy in measurement can be improved.

Figure 18A:
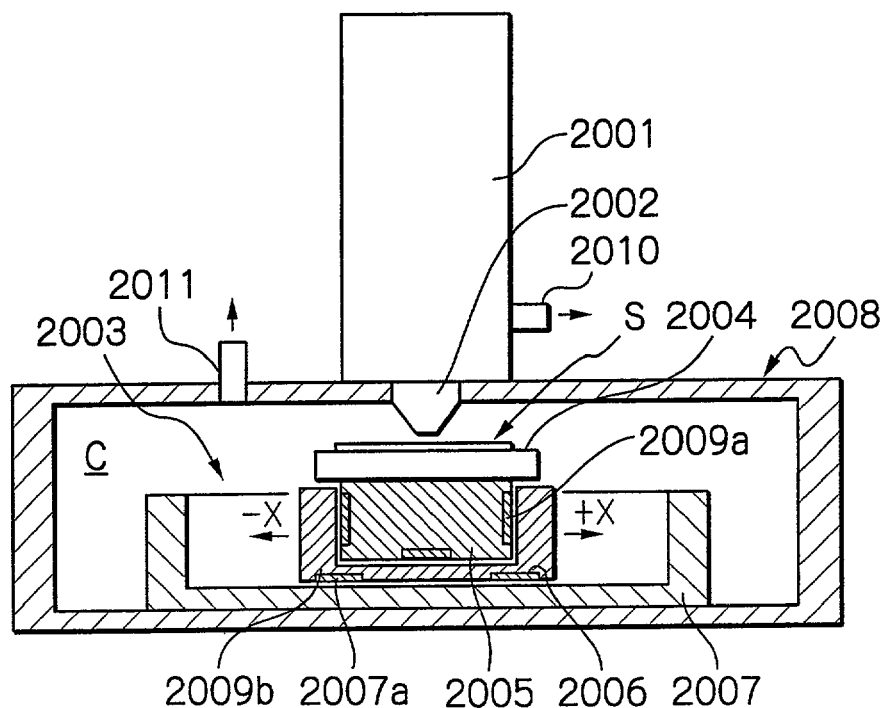
Figure 18B:
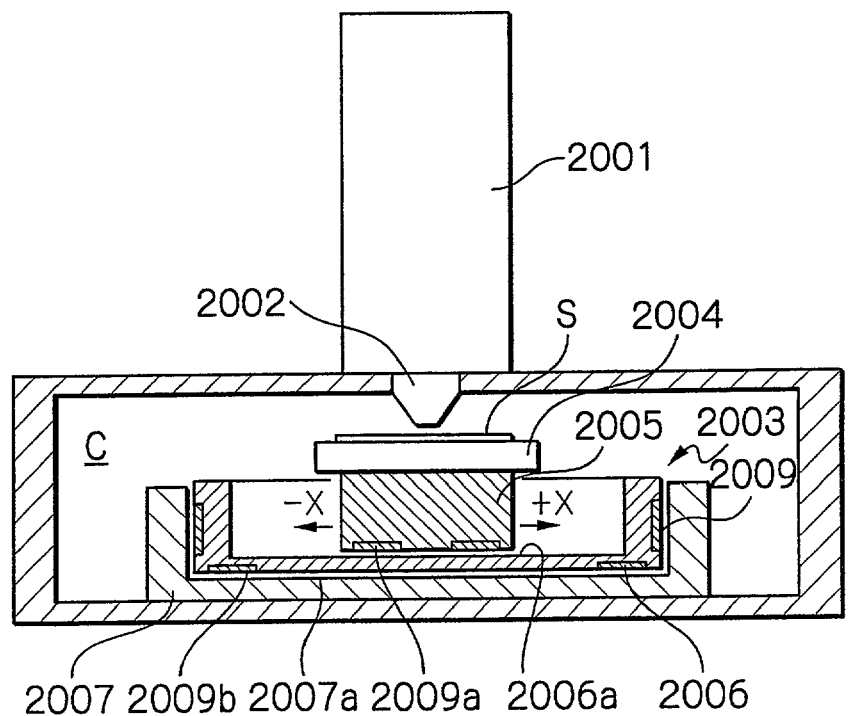
Figure 19:
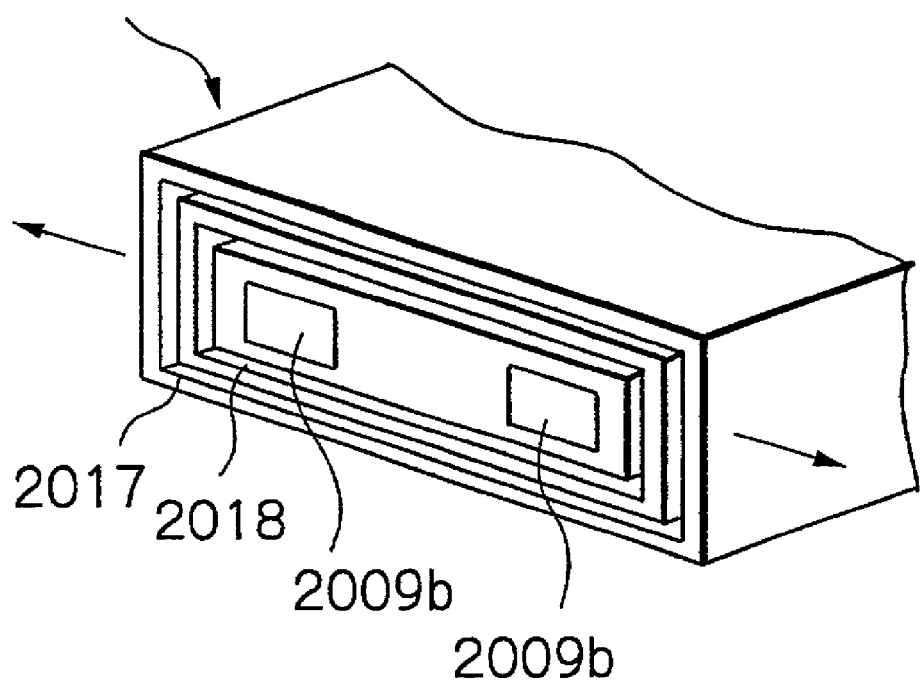
FIG. 19 is a perspective view of an exhaust gas discharging mechanism used in for the XY stage of FIGS. 18A and 18B.
Figure 20A:
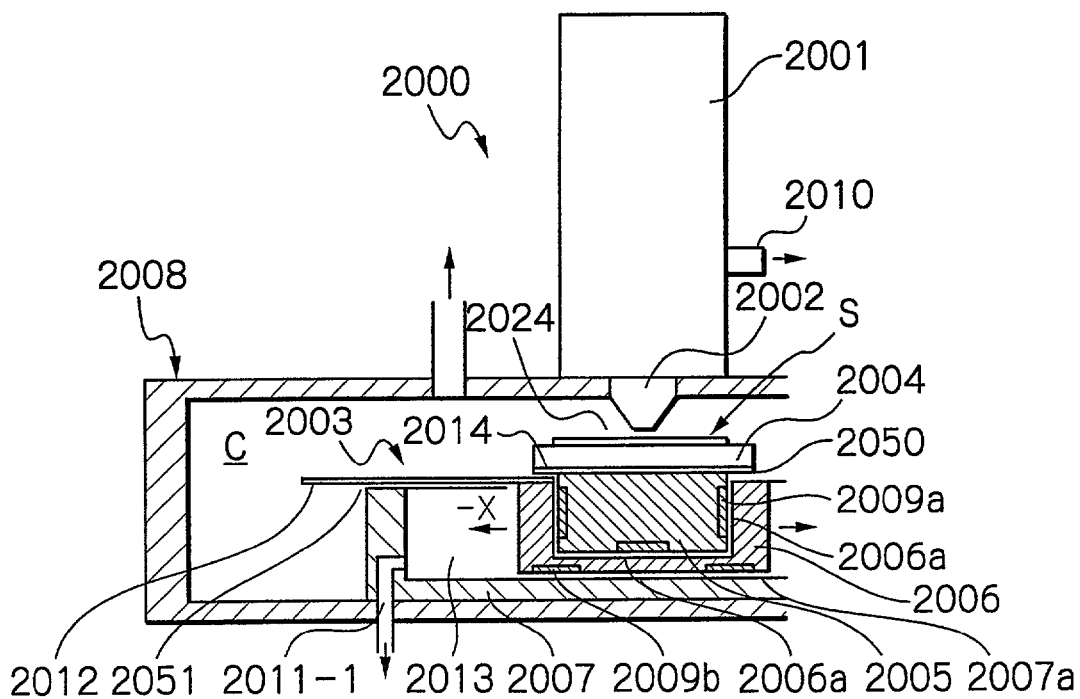
Figure 20B:
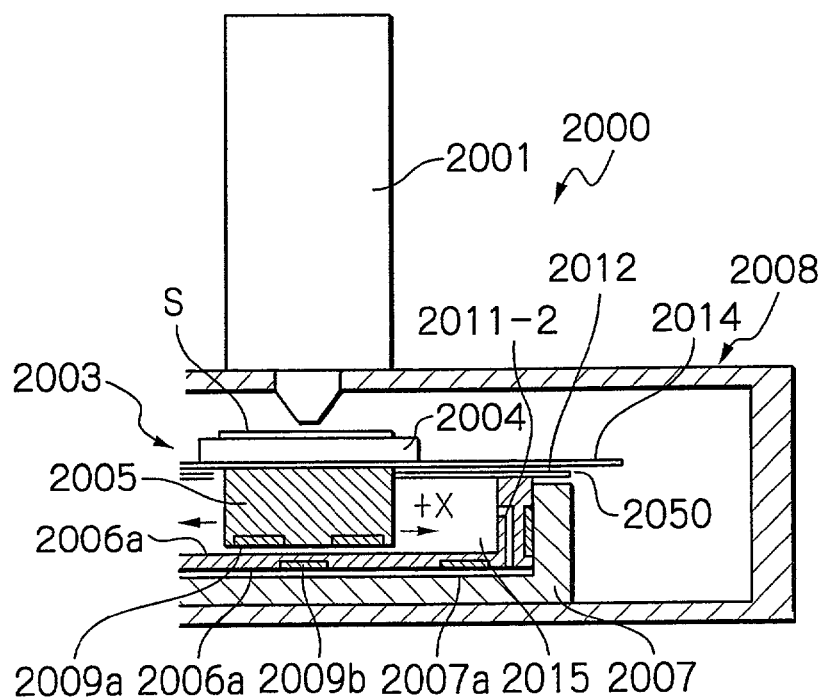
Figure 21:
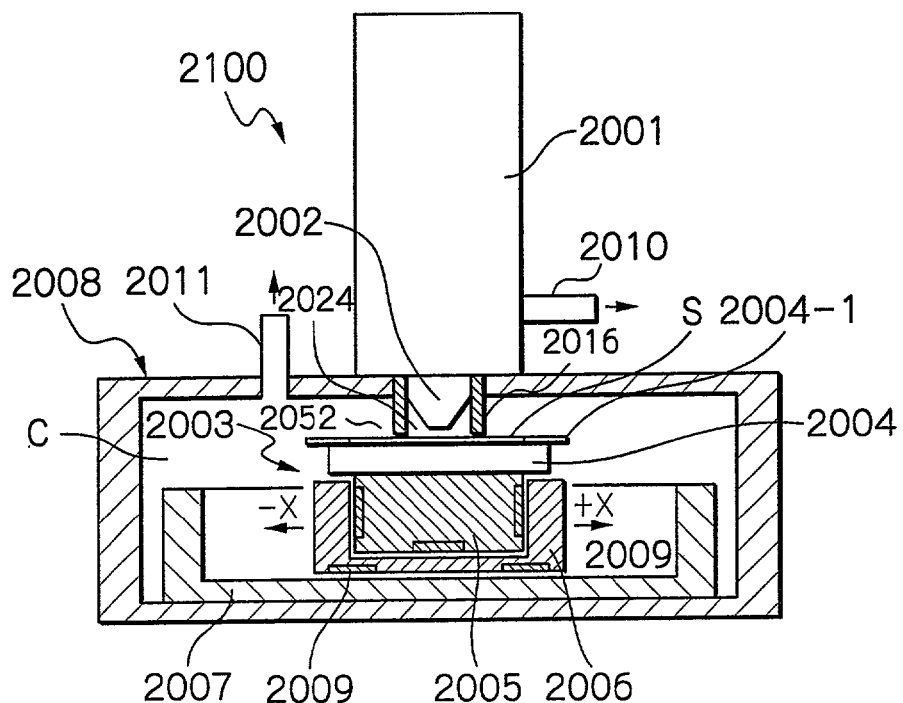
FIG. 21 is a cross sectional view of a vacuum chamber and an XY stage of a charged beam apparatus of a fifth embodiment according to the present invention.

FIGS. 18A and 18B are cross sectional views of a vacuum chamber and an XY stage of a charged beam apparatus according to the prior art, FIG. 19 is a perspective view of a conventional exhaust gas discharging mechanism used for the XY stage of FIGS. 18A and 18B, FIGS. 20A and 20B are cross sectional views of a vacuum chamber and an XY stage of a charged beam apparatus (stages etc.) 2000 of a fourth embodiment according to the present invention, FIG. 21 is a cross sectional view of a vacuum chamber and an XY stage of a charged beam apparatus (stages etc.) 2100 of a fifth embodiment according to the present invention.

Figure 22:
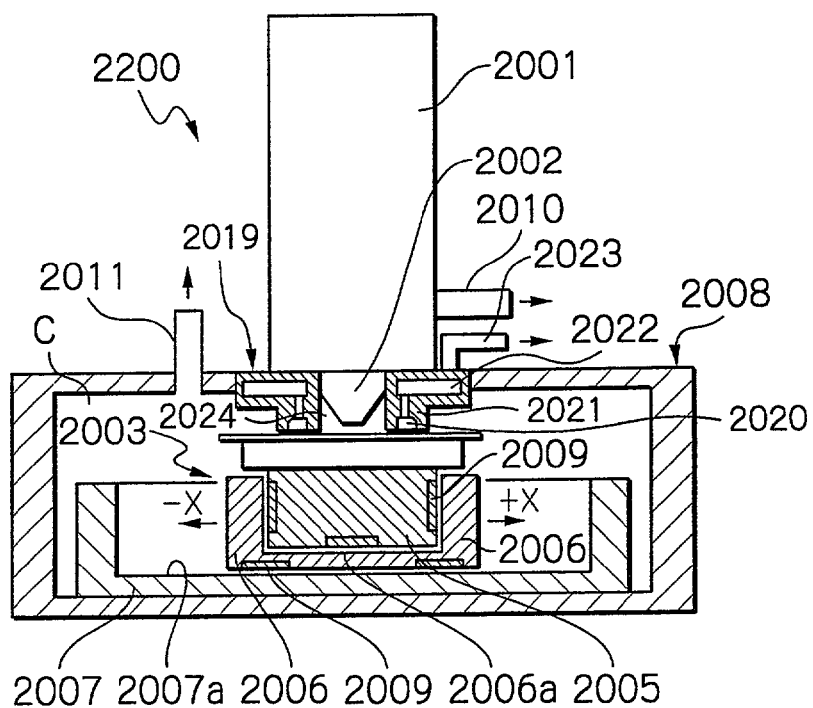
FIG. 22 is a cross sectional view of a vacuum chamber and an XY stage of a charged beam apparatus of a sixth embodiment according to the present invention.
Figure 23:
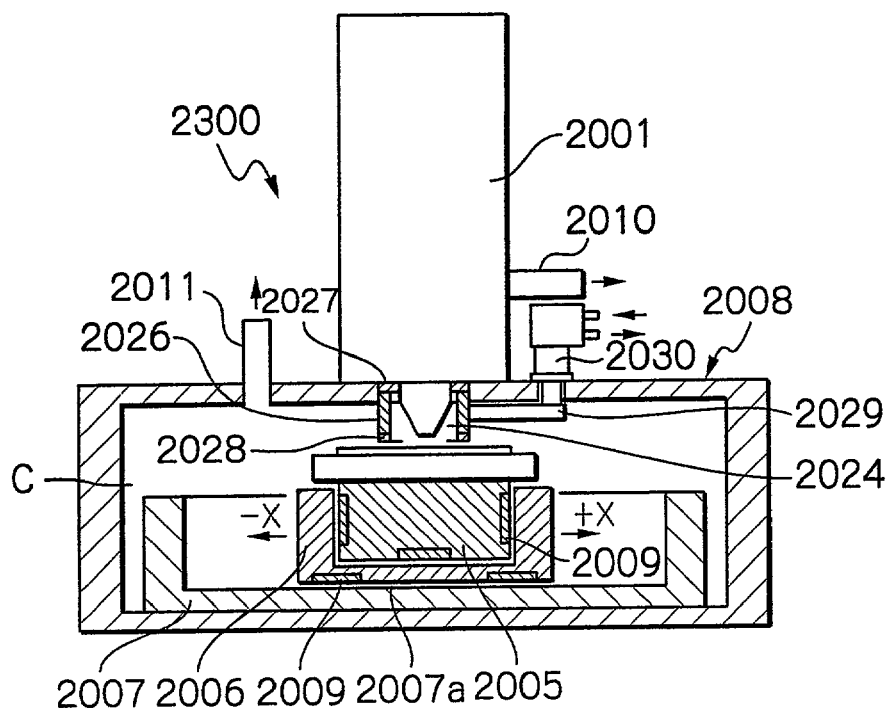
FIG. 23 is a cross sectional view of a vacuum chamber and an XY stage of a charged beam apparatus of a seventh embodiment according to the present invention.
Figure 24:
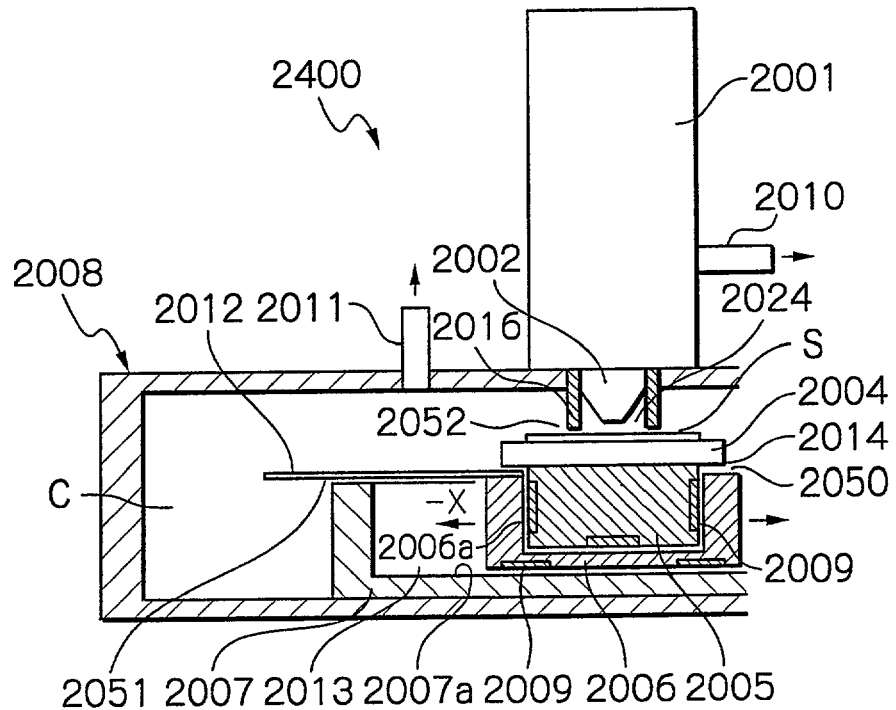
FIG. 24 is a cross sectional view of a vacuum chamber and an XY stage of a charged beam apparatus of an eighth embodiment according to the present invention.

FIG. 22 is a cross sectional view of a vacuum chamber and an XY stage of a charged beam apparatus (stages etc.) 2200 of a sixth embodiment according to the present invention, FIG. 23 is a cross sectional view of a vacuum chamber and an XY stage of a charged beam apparatus (stages etc.) 2300 of a seventh embodiment according to the present invention, FIG. 24 is a cross sectional view of a vacuum chamber and an XY stage of a charged beam apparatus (stages etc.) 2400 of an eighth embodiment according to the present invention. In FIGS. 18-24, the similar reference numerals are used to designate the components in common.

FIGS. 20A and 20B show a charged beam apparatus of a fourth embodiment of the present invention. A division plate 2014 is attached onto an upper face of a Y directionally movable unit 2005 of a stage 2003, wherein said division plate 2014 overhangs to a great degree approximately horizontally in the +Y direction and the −Y direction (the lateral direction in FIG. 20B), so that between an upper face of an X directionally movable unit 2006 and said division plate 2014 may be always provided a narrow gap 2050 with small conductance therebetween. Also, a similar division plate 2012 is attached onto the upper face of the X directionally movable unit 2006 so as to overhang in the ± X direction (the lateral direction in FIG. 20A), so that a narrow gap 2051 may be constantly formed between an upper face of a stage table 2007 and said division plate 2012. The stage table 2007 is fixedly secured onto a bottom wall within a housing 2008 with a known method.

In this way, since the narrow gaps 2050 and 2051 are constantly formed wherever the sample table 2004 may move to, and the gaps 2050 and 2051 can prevent the movement of a desorbed gas even if a gas is desorbed or leaked along the guiding plane 2006*a* or 2007*a* upon movement of the movable unit 2005 or 2006, a pressure increase can be significantly controlled to low level in a space 2024 adjacent to the sample to which the charged beam is irradiated.

Since in a side face and an under face of the movable unit 2005 and also in an under face of the movable unit 2006 of the stage 2003, there are provided grooves for differential pumping formed surrounding hydrostatic bearings 2009, as shown in FIG. 19, which work for vacuum-pumping, therefore in a case where narrow gaps 2050 and 2051 have been formed, the emitted gas from the guiding planes is mainly evacuated by those differential pumping sections. Owing to this, the pressure in those spaces 2013 and 2015 within the stage are kept to be higher level than the pressure within a chamber C.

Accordingly, if there are more portions provided for vacuum-pumping the spaces 2013 and 2015 in addition to the differential pumping grooves 2017 and 2018, the pressure within the spaces 2013 and 2015 can be decreased, and the pressure rise of the space 2024 in the vicinity of the sample can be controlled to be further low. For this purpose, vacuum pumping channels 2011-1 and 2011-2 are provided. The vacuum pumping channel 2011-1 extends through the stage table 2007 and the housing 2008 to interact with an outside of the housing 2008. On the other hand, the pumping channel 2011-2 is formed in the X directionally movable unit 2006 and opened in an under face thereof.

It is to be noted that though arranging the division plates 2012 and 2014 might cause a problem requiring the chamber C to be extended so as not to interfere with the division plates, this can be improved by employing those division plates of stretchable material or structure. There may be suggested one embodiment in this regard, which employs the division plates made of rubber or in a form of bellows, and the ends portions thereof in the direction of movement are fixedly secured respectively, so that each end of the division plate 2014 is secured to the X directionally movable unit 2006 and that of the division plate 2012 to the inner wall of the housing 2008.

FIG. 21 shows a charged beam apparatus of a fifth embodiment of the present invention. In the fifth embodiment, a cylindrical divider 2016 is disposed surrounding the tip portion of the lens column or the charged beam irradiating section 2002, so that a narrow gap may be produced between an upper face of a sample S and the tip portion of the lens column. In such configuration, even if the gas is emitted from the XY stage to increase the pressure within the chamber C, since a space within the divider 2024 has been isolated by the divider 2016 and exhausted with a vacuum pipe 2010, there could be generated a pressure deference between the pressure in the chamber C and that in the space within the divider 2024, thus to control the pressure rise in the space within the divider 2024 to be low. Preferably, the gap between the divider 2016 and the sample surface should be approximately some ten μm to some mm, depending on the pressure level to be maintained within the chamber C and in the surrounding of the irradiating section 2002. It is to be understood that the interior of the divider 2016 is made to communicate with the vacuum pipe by the known method.

On the other hand, the charged beam irradiation apparatus may sometimes apply a high voltage of about some kV to the sample S, and so it is feared that any conductive materials located adjacent to the sample could cause an electric discharge. In this case, the divider 2016 made of insulating material such as ceramic may be used in order to prevent any discharge between the sample S and the divider 2016.

It is to be noted that a ring member 2004-1 arranged so as to surround the sample S (a wafer) is a plate-like adjusting part fixedly mounted on the sample table 2004 and set to have the same height with the wafer so that a micro gap 2052 may be formed throughout a full circle of the tip portion of the divider 2016 even in a case of the charged particles beam being irradiated against an edge portion of the sample such as the wafer. Thereby, whichever location on the sample S may be irradiated by the charged beam, the constant micro gap 2052 can be always formed in the tip portion of the divider 2016 so as to maintain the pressure stable in the space 2024 surrounding the lens column tip portion.

FIG. 22 shows a charged beam apparatus 2200 of a sixth embodiment of the present invention. A divider 2019 having a differential pumping structure integrated therein is arranged so as to surround the charged particles beam irradiating section 2002 of a lens column 2001. The divider 2019 is cylindrical in shape and has a circular channel 2020 formed inside thereof and an exhausting path 2021 extending upwardly from said circular channel 2020. Said exhausting path 2021 is connected to a vacuum pipe 2023 via an inner space 2022. A micro space as narrow as a few some tens μm to a few some mm is formed between the lower end of the divider 2019 and the upper face of the sample S.

With such configuration, even if the gas is emitted from the stage in association with the movement of the stage resulting in an increase of the pressure within the chamber C, and eventually is to possibly flow into the space of tip portion or the charged beam irradiating section 2002, the gas is blocked to flow in by the divider 2019, which has reduced the gap between the sample S and itself so as to make the conductance very low, thus to reduce the flow-in rate. Further, since any gas that has flown into is allowed to be evacuated through the circular channel 2020 to the vacuum pipe 2023, there will be almost no gas remained to flow into the space 2024 surrounding the charged particles beam irradiating section 2002, and accordingly the pressure of the space surrounding the charged particles beam irradiating section 2002 can be maintained to be a desired high vacuum level.

FIG. 23 shows a charged particles beam apparatus 2300 of a seventh embodiment of the present invention. A divider 2026 is arranged so as to surround the charged beam irradiating section 2002 in the chamber C and accordingly to isolate the charged beam irradiating section 2002 from the chamber C. This divider 2026 is coupled to a refrigeration system 2030 via a support member 2029 made of material of high thermal conductivity such as copper or aluminum, and is kept as cool as −100° C. to −200° C. A member 2027 is provided for isolating a thermal conduction between the cooled divider 2026 and the lens column and is made of material of low thermal conductivity such as ceramic, resin or the like. Further, a member 2028 is made of insulating material such as ceramic or the like and is attached to the lower end of the divider 2026 so as to prevent any electric discharge between the sample S and the divider 2026.

With such configuration, any gas molecules attempting to flow into the space surrounding the charged particles beam irradiating section from the chamber C are blocked by the divider 2026, and even if there are any molecules successfully flown into the section, they are frozen to be captured on the surface of the divider 2026, thus allowing the pressure in the space 2024 surrounding the charged beam irradiating section to be kept low. It is to be noted that a variety type of refrigeration system may be used for the refrigerating machine in this embodiment, for example, a cooling machine using liquid nitrogen, a He refrigerating machine, a pulse-tube type refrigerating machine or the like.

FIG. 24 shows a charged particles beam apparatus 2400 of an eighth embodiment of the present invention. The division plates 2012 and 2014 are arranged on both of the movable units of the stage 2003 similarly to those illustrated in FIG. 20, and thereby, if the sample table 2004 is moved to any locations, the space 2013 within the stage is separated from the inner space of the chamber C by those division plates communicating therewith through the narrow gaps 2050 and 2051.

Further, another divider 2016 similar to that as illustrated in FIG. 21 is formed surrounding the charged beam irradiating section 2002 so as to separate a space 2024 accommodating the charged beam irradiating section 2002 therein from the interior of the chamber C with a narrow gap 2052 disposed therebetween. Owing to this, upon movement of the stage, even if the gas absorbed on the stage is desorbed into the space 2013 to increase the pressure in this space, the pressure increase in the chamber C is kept to be low, and the pressure increase in the space 2024 is also kept to be much lower. This allows the pressure in the space 2024 for irradiating the charged beam to be maintained at low pressure level.

Alternatively, employing the divider 2019 having the differential pumping mechanism integrated therein as explained with reference to the divider 2016, or the divider 2026 cooled with the refrigerating system as shown in FIG. 22 allows the space 2024 to be maintained stably with further lowered pressure.

Figure 25:
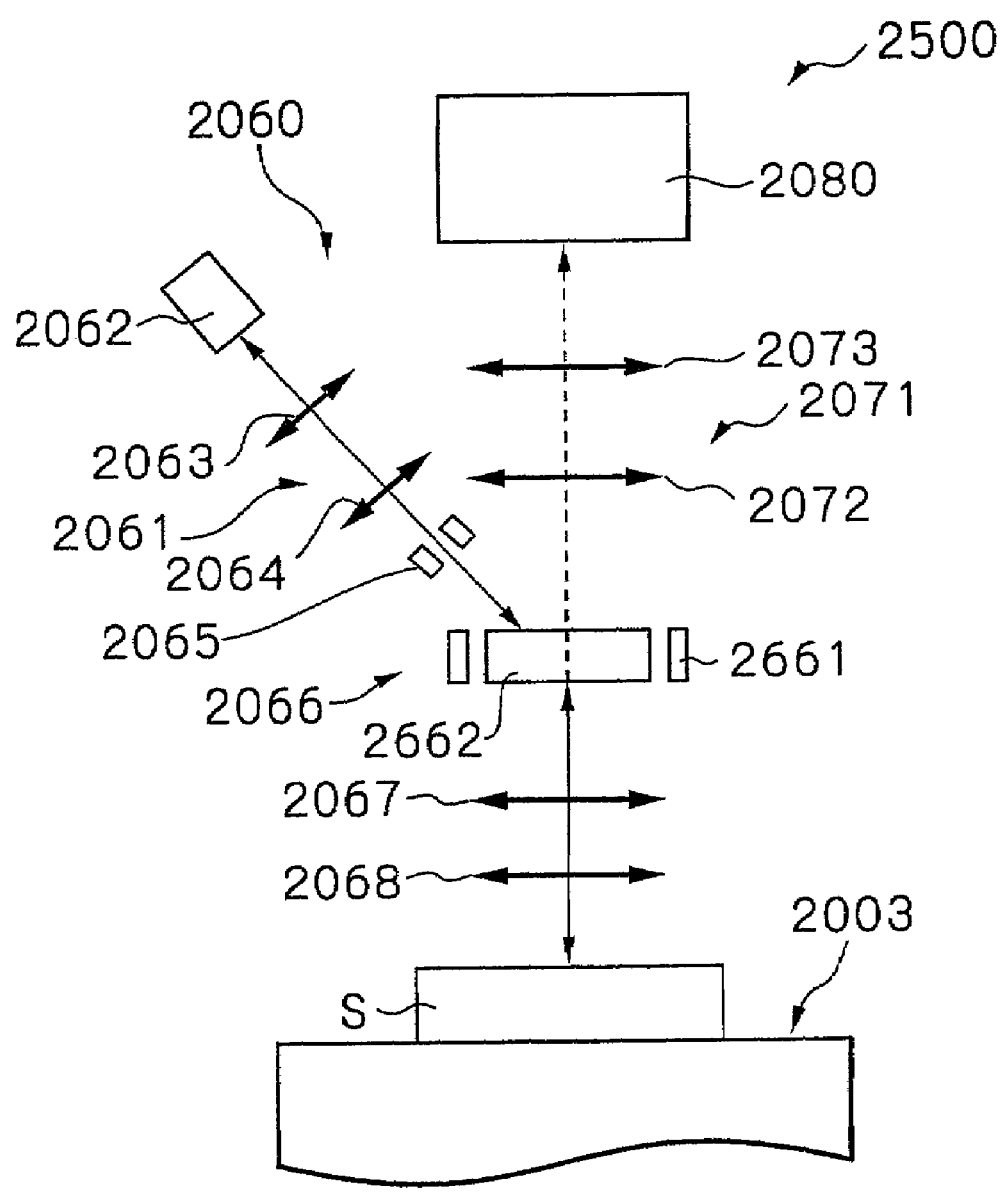
FIG. 25 is a schematic diagram illustrating an optical system and a detection system of a ninth embodiment according to the present invention, which are to be arranged in a lens barrel shown in either of FIGS. 18 to 24.

FIG. 25 schematically shows an exemplary optical system and detection system of the charged beam apparatus 2500 of a ninth embodiment according to the present invention. The optical system is arranged within the lens column, and said optical system and a detector are illustrative only, but the other optical systems and detectors may be used when required. The optical system 2060 of the charged particles beam apparatus comprises a primary optical system 2061 for irradiating a charged particles beam against the sample S loaded on the stage 2003, and a secondary optical system 2071 to which secondary electrons emanated from the sample are introduced.

The primary optical system 2061 comprises; an electron gun 2062 for emitting the charged beam; lens systems 2063 and 2064 composed of two stages of electrostatic lenses for converging the charged beam emitted from the electron gun 2011; a deflector 2065; a Wien filter or an E×B separator 2066 for deflecting the charged beam so as for an optical axis thereof to be directed to perpendicular to the objective face; and lens systems 2067 and 2068 composed of two stages of electrostatic lenses, wherein said components of the primary optical system 2061 are disposed in order from the electron gun 2062 placed in the top so that the optical axis of the charged beam is inclined to the line orthogonal to the surface of the sample S (the sample plane), as shown in FIG. 25. The E×B deflecting system 2066 comprises an electrode 2661 and a magnet 2662.

The secondary optical system 2071 is an optical system to which the secondary electrons emanated from the sample S are introduced, and comprises lens systems 2072 and 2073 composed of two stages of electrostatic lenses arranged in an upper side of the E×B deflecting system 2066 of the primary optical system. The detector 2080 detects the secondary electrons sent through the secondary optical system 2071. Since respective components and structures of the above optical systems 2060 and the detector 2080 are the same as those according to the prior art, the detailed descriptions thereof should be omitted.

The charged particles beam emitted from the electron gun 2062 is formed with a square aperture of the electron gun and contracted with the two-stage lens systems 2063 and 2064, and after the optical axis thereof having been adjusted by the deflector 2065, the beam is formed into a square with respective edges of 1.25 mm on the deflecting center plane of the E×B deflecting system 2066. The E×B deflecting system 2066 is designed so that an electric field and a magnetic field are crossed within a plane orthogonal to a normal line of the sample, wherein when the relation among the electric field, the magnetic field and the energy of electrons satisfies a certain condition, the electrons are advanced straight forward, and for the case other than the above, the electrons are deflected into a predetermined direction depending on said mutual relation among the electric field, the magnetic field and the energy of electrons.

In FIG. 25, the charged particles beam from the electron gun is directed to enter onto the sample S at a right angle, and further the secondary electrons emanated from the sample is advanced straight toward the detector 2080. The formed beam deflected by the E×B deflecting system is contracted to $\frac{1}{5}$ in size with the lens systems 2067 and 2068 to be projected onto the sample S. The secondary electrons emanated from the sample S with the data for a pattern image contained therein is magnified with the lens systems 2067, 2068 and 2072, 2073, so as to form a secondary electron image on the detector 2080. These four stages of magnifying lenses, which are composed of the lens systems 2067 and 2068 forming a symmetrical tablet lens and the lens systems 2072 and 2073 forming another symmetrical tablet lens, make up the lenses of no. distortion.

When the defect inspection apparatus and method or the exposing apparatus and method according to either of the third to the eighth embodiments of the present invention is applied to the inspection process (G) or the exposing process (c) in the flow chart illustrating an exemplary method for manufacturing a semiconductor device of FIGS. 12 and 13, any fine patterns are allowed to be inspected or exposed stably with higher accuracy, so that the yield of the products can be improved and any faulty products can be prevented from being delivered. According to the third to the ninth embodiments of the present invention, the following effects may be expected to obtain.

(a) According to the fourth and the fifth embodiments (FIGS. 20A, 20B and 21), the stage device can bring out a good performance of accurate positioning within vacuum atmosphere, and further the pressure in the space surrounding the charged particles beam irradiating location is hardly increased. That is, it allows the charged particles beam processing to be applied to the sample with high accuracy.

(b) According to the sixth embodiment (FIG. 22), it is almost impossible for the gas emitted or leaked from the hydrostatic bearing support section to go though the divider and reach to the space for the charged beam irradiating system. Thereby, the vacuum level in the space surrounding the charged beam irradiating location can be further stabilized.

(c) According to the seventh embodiment (FIG. 23), it is harder for the desorbed gas to go through to the space for the charged particles beam irradiating system, and it is facilitated to maintain the vacuum level in the space surrounding the charged beam irradiating location stable.

(d) According to the eighth embodiment (FIG. 24), the interior of the vacuum chamber is partitioned into three chambers, i.e., a charged particles beam irradiation chamber, a hydrostatic bearing chamber and an intermediate chamber which communicate with each other via a small conductance. Further, the vacuum pumping system is constructed to control the pressures in the respective chambers sequentially, such that the pressure in the charged particles beam irradiation chamber is the lowest, the intermediate chamber medium, and the hydrostatic bearing chamber the highest. The pressure fluctuation in the intermediate chamber can be reduced by the divider, and the pressure fluctuation in the charged beam irradiation chamber can be further reduced by another step of divider, so that the pressure fluctuation therein can be reduced substantially to a non-problematic level.

(e) According to the fifth to seventh embodiments of the present invention, the pressure increase upon movement of the stage can be controlled to be low.

(f) According to the eighth embodiment (FIG. 24) of the present invention, the pressure increase upon movement of the stage can be further controlled to be lower.

(g) According to the fifth to eighth embodiments of the present invention, since the defect inspection apparatus with highly accurate stage positioning performance and with a stable vacuum level in the charged beam irradiating region can be accomplished, the inspection apparatus with high inspection performance and without any fear of contamination of the sample can be provided.

(h) According to the fifth to eighth embodiments of the present invention, since the defect inspection apparatus with highly accurate stage positioning performance and with a stable vacuum level in the charged particles beam irradiating region can be accomplished, the exposing apparatus with high exposing accuracy and without any fear of contamination of the sample can be provided.

(i) According to the fifth to eighth embodiments of the present invention, manufacturing the semiconductor by using the apparatus with highly accurate stage positioning performance and with a stable vacuum level in the charged beam irradiating region allows to form a fine semiconductor circuit.

Figure 26:
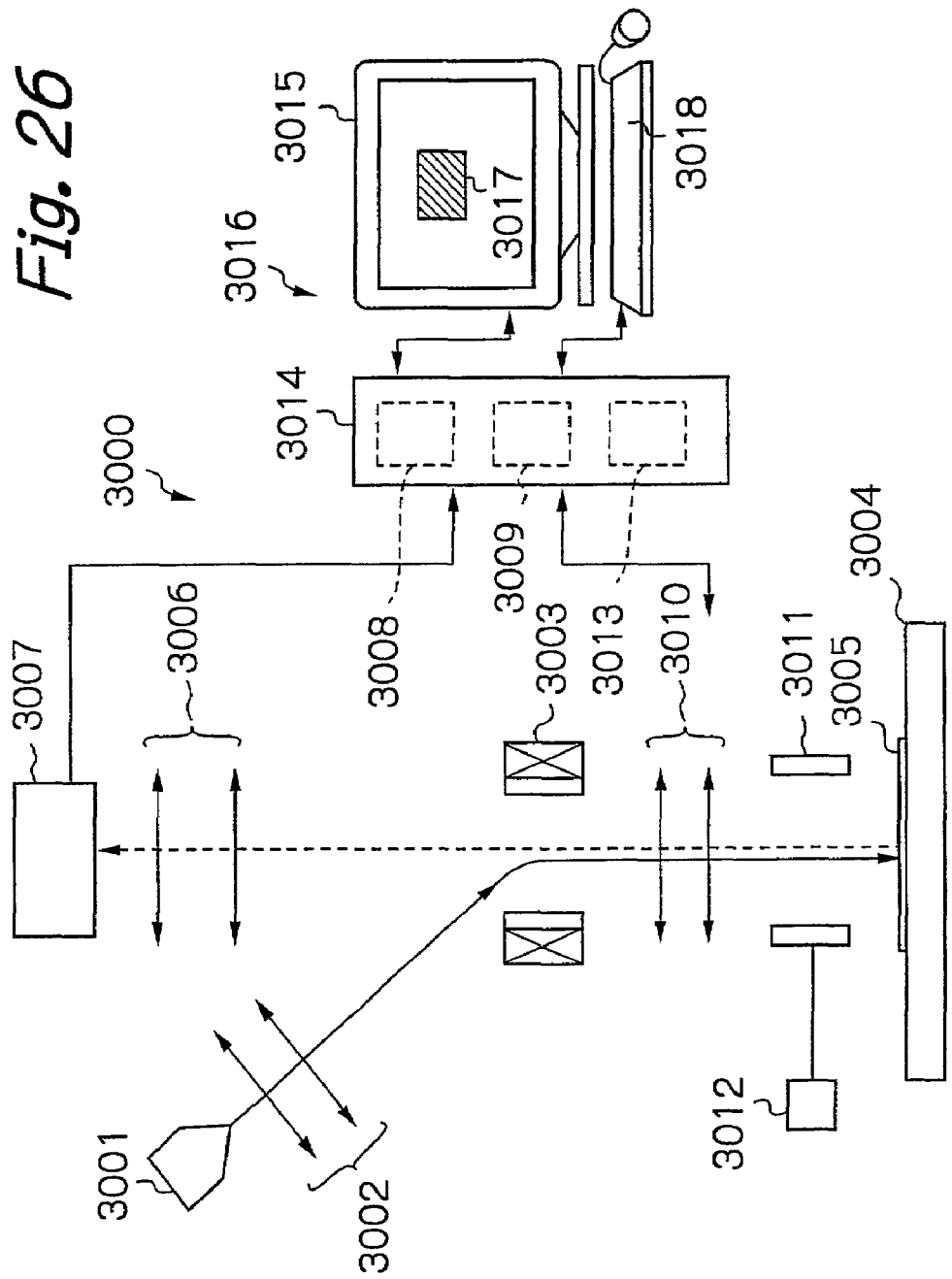
FIG. 26 is a schematic diagram illustrating an exemplary configuration of a defect inspection apparatus according to a tenth embodiment of the present invention.

A tenth and an eleventh embodiments of the present invention will now be described below with reference to FIGS. 26 to 33. FIG. 26 shows a schematic configuration of a defect inspection apparatus 3000 according to the tenth embodiment of the present invention.

This defect inspection apparatus is, what is called, an image projection type inspection apparatus, which comprises: an electron gun 3001 for emitting a primary electron beam; an electrostatic lens 3002 for forming the emitted primary electron beam; an E×B deflecting system 3003 for deflecting the accordingly formed primary electron beam at a field where an electric field "E" and a magnetic field "B" are crossed at a right angle, so that the beam impinges against a semiconductor wafer 3005 at an approximately right angle; an objective lens 3010 for forming the deflected primary electron beam into an image on the wafer 3005; a stage 3004 arranged in a sample chamber(not shown) allowed to be evacuated to vacuum and capable of moving within a horizontal plane with the wafer 3005 loaded thereon; an electrostatic lens 3006 in a map projection system for map-projecting at a predetermined magnification a secondary electron beam and/or a reflected electron beam emanated from the wafer 3005 upon the irradiation of the primary electron beam to be formed into an image; a detector 3007 for detecting the formed image as a secondary electron image of the wafer; and a control section 3016 for controlling the whole unit of the apparatus and for performing the process for detecting a defect in the wafer 3005 based on the secondary electron image detected by the detector 3007, as well.

It is to be noted that the present specification has designated said image as the secondary electron image, although said secondary electron image actually affected by not only the secondary electrons but also the contribution of the scattered electrons and the reflected electrons.

Further, between the objective lens 3010 and the wafer 3005, there is arranged a deflecting electrode 3011 for deflecting an incident angle of the primary electron beam onto the wafer 3005 by the electric field or the like. This deflecting electrode 3011 is connected with a deflection controller 3012 for controlling the electric field of said deflecting electrode. This deflection controller 3012 is connected to the control section 3016 to control the deflecting electrode 3011 so that the electric field may be generated by said deflecting electrode 3011 in response to a command from the control section 3016. It is to be noted that the deflection controller 3012 may be a voltage controller for controlling a voltage applied to the deflecting electrode 3011.

The detector 3007 may have any arbitrary configuration so far as it can convert the secondary electron image formed by the electrostatic lens 3006 into a signal capable of being processed later. For example, as shown in detail in FIG. 31, the detector 3007 may comprise a multi-channel plate 3050, a fluorescent screen 3052, a relay optical system 3054, and an image sensor 3056 composed of a plurality of CCD elements. The multi-channel plate 3050 comprises a plurality of channels within the plate so as to generate more electrons during the secondary electrons formed into the image by the electrostatic lens 3006 passing through those channels. That is, the multi-channel plate 3050 amplifies the secondary electrons.

The fluorescent screen 3052 emits fluorescence by the amplified secondary electrons to convert the secondary electrons into light (fluorescence). The relay lens 3054 guides said fluorescence to the CCD image sensor 3056, and then said CCD image sensor 3056 converts the intensity distribution of the secondary electrons on the surface of the wafer 3005 to an electric signal, i.e., a digital image data for each element, which in turn is output to the control section 3016.

The control section 3016, as shown in FIG. 26, may be composed of a general-purpose computer or the like. This computer may comprise a control section main unit 3014 for executing various controls and operations according to a predetermined program, a CRT 3015 for displaying processed results from the main unit 3014, and an input section 3018 such as a mouse or a keyboard used by an operator for inputting an command, and, of course, said control section 3016 may be composed of a hardware working exclusively for a defect inspection apparatus, a work station, or the like.

The control section main unit 3014 may comprises various control substrates such as a CPU, a RAM, a ROM, a hard disk, and a video substrate, which are not illustrated. A secondary electron image storage region 3008 is allocated onto the memory such as the RAM or the hard disk, for storing the electric signal received from the detector 3007, i.e., the digital image data for the secondary electron image of the wafer 3005. Further, on the hard disk, there is a reference image storage section 3013 for storing beforehand a reference image data of the wafer having no defect. Still further, on the hard disk, in addition to the control program for controlling the whole unit of the defect inspection apparatus, a defect detection program 3009 is stored for reading the secondary electron image data from the storage region 3008 and automatically detecting a defect in the wafer 3005 based on said image data according to the predetermined algorithm.

This defect detection program 3009, as will be described in more detail later, has such a function that it performs a matching of reference image read out from the reference image storage section 3013 to an actually detected secondary electron image in order to automatically detect any defective parts, so that it may indicate a warning to the operator when it determines there is the defect existing. In this regard, the CRT 3015 may be designed to also display the secondary electron image 3017 on the display section thereof.

Then, an operation in the defect inspection apparatus 3000 according to the tenth embodiment will be described referring to those flow charts of FIGS. 28 to 30.

Figure 28:
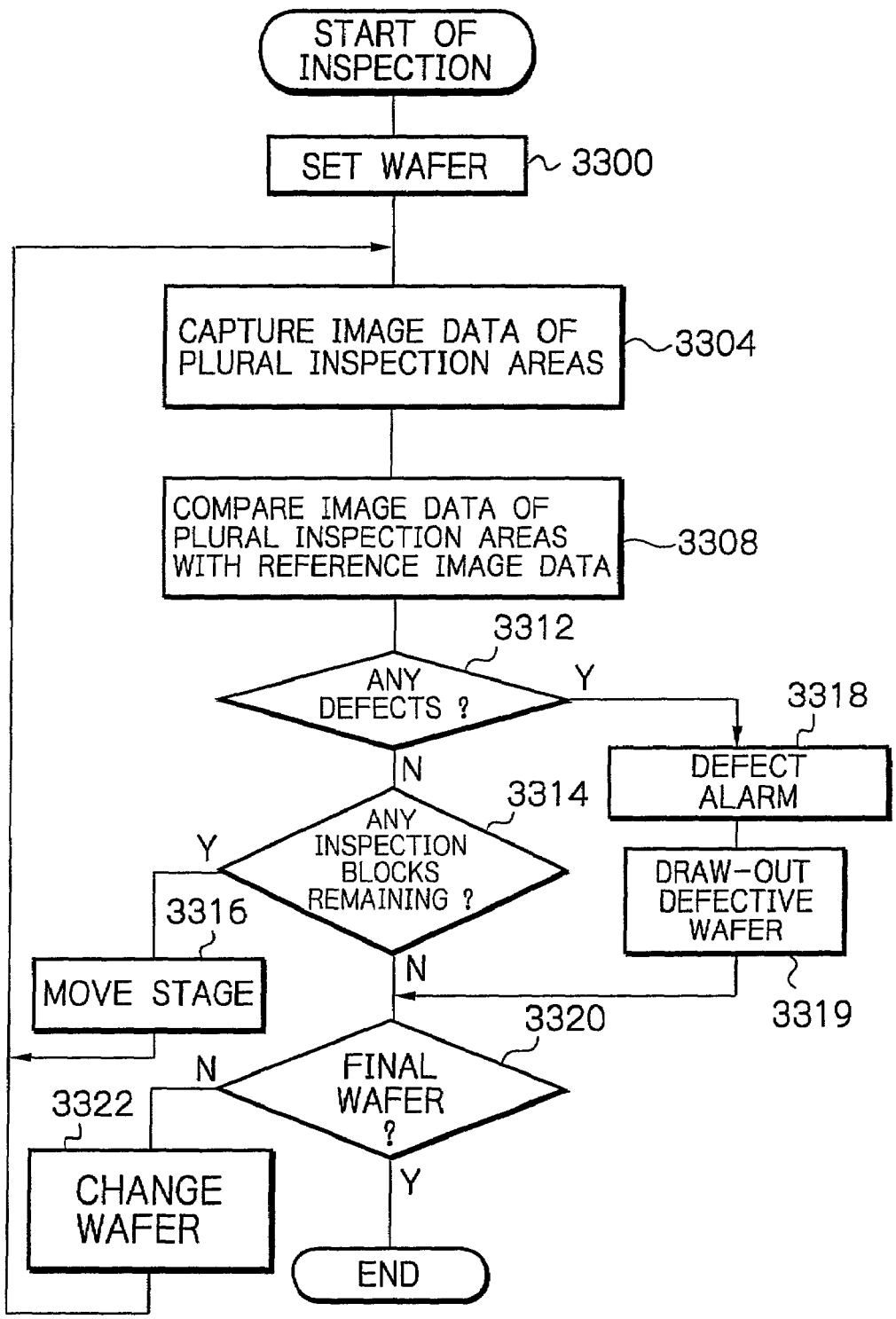
FIG. 28 is a flow chart illustrating a flow of a main routine for wafer inspection in the defect inspection apparatus of FIG. 26.

First of all, as shown in the flow of the main routine of FIG. 28, the wafer 3005 to be inspected is placed on the stage 3004 (step 3300). In this regard, the way of setting the wafer 3005 may take such a form that each of a plurality of wafers 3005 contained in a loader, though not shown, is set on the stage 3004 automatically one by one.

Then, images for a plurality of regions to be inspected are respectively obtained, which are displaces one from another while being superimposed partially one on another on the XY plane of the surface of the wafer 3005 (Step 3304). Each of said plurality of regions to be inspected, from which the image is to be obtained, is a rectangular region as designated by reference numeral 3032*a*, 3032*b* . . . 3032*k* . . . each of which is observed to be displaced relative to one another while being partially superimposed one on another around the inspection pattern 3030 of the wafer. For example, 16 pieces of images for the regions to be inspected 3032 (the images to be inspected) may be obtained as shown in FIG. 27. Herein, for the image as shown in FIG. 27, each square contained in the rectangle region corresponds to one pixel (or a block, whose unit is greater than the unit of pixel), and among those squares, shaded ones correspond to the imaged area of the pattern on the wafer 3005. This step 3304 will be described in more detail later with reference to the flow chart of FIG. 29.

Then the process compares the image data for the plurality of regions to be inspected, which have been obtained at Step 3304, respectively with the reference image stored in the storage section 3013 to look for any matching (Step 3308 in FIG. 3), and determines whether or not there is a defect existing in the wafer inspection plane encompassed by said plurality of regions to be inspected. This process performs, what is called, the matching operation between image data, which will be explained later in detail with reference to the flow chart shown in FIG. 30.

If the result from the comparing process at Step 3308 indicates that there is a defect in the wafer inspection plane encompassed by said plurality of regions to be inspected (Step 3312, affirmative determination), the process gives a warning to the operator indicating the existence of the defect (Step 3318). As for the way of warning, for example, the display section of the CRT 3015 may display a message noticing the operator that there is a defect, or at the same time may additionally display a magnified image 3017 of the pattern determined to have the defect. Such defective wafers may be immediately taken out of a sample chamber 3 and stored in another storage separately from those wafers having no defect (Step 3319).

If the result from the comparing process at Step 3308 indicates that there is no defect in the wafer 3005 (Step 3312, negative determination), the process determines whether or not there are remained more regions to be inspected for the wafer 3005 currently treated as the inspection object (Step 3314). If there are more regions remained for inspection (Step 3314, affirmative determination), the stage 3004 is driven to move the wafer 3005 so that other regions to be further inspected are positioned within the irradiative region of the primary electron beam (Step 3316). Subsequently, the process goes back to Step 3302 to repeat the similar operations for said other regions to be inspected.

If there is no more regions remained to be further inspected (Step 3314, negative determination), or after a drawing out processing of the defective wafer (Step 3319), the process determines whether or not the current wafer treated as the inspection object is the last wafer to be inspected, that is, whether or not there are any wafers remaining for the inspection in the loader, though not shown (Step 3320). If the current wafer is not the last one (Step 3320, negative determination), the wafers having been inspected already are stored in a predetermined storing location, and a new wafer which has not been inspected yet is set instead on the stage 3004 (Step 3322). Then, the process goes back to Step 3302 to repeat the similar operations for said wafer. In contrast, the current wafer is the last one (Step 3320, affirmative determination), the wafer having been inspected is stored in the predetermined storing location to end the whole process.

Then, the process flow of step 3304 will now be described with reference to the flow chart of FIG. 29. In FIG. 29, first of all, an image number "i" is set to the initial value "1" (Step 3330). This image number is an identification number assigned serially to each of the plurality of images for the regions to be inspected. Secondary, the process determines an image position (Xi,Yi) for the region to be inspected as designated by the set image number i (Step 3332).

Figure 32:
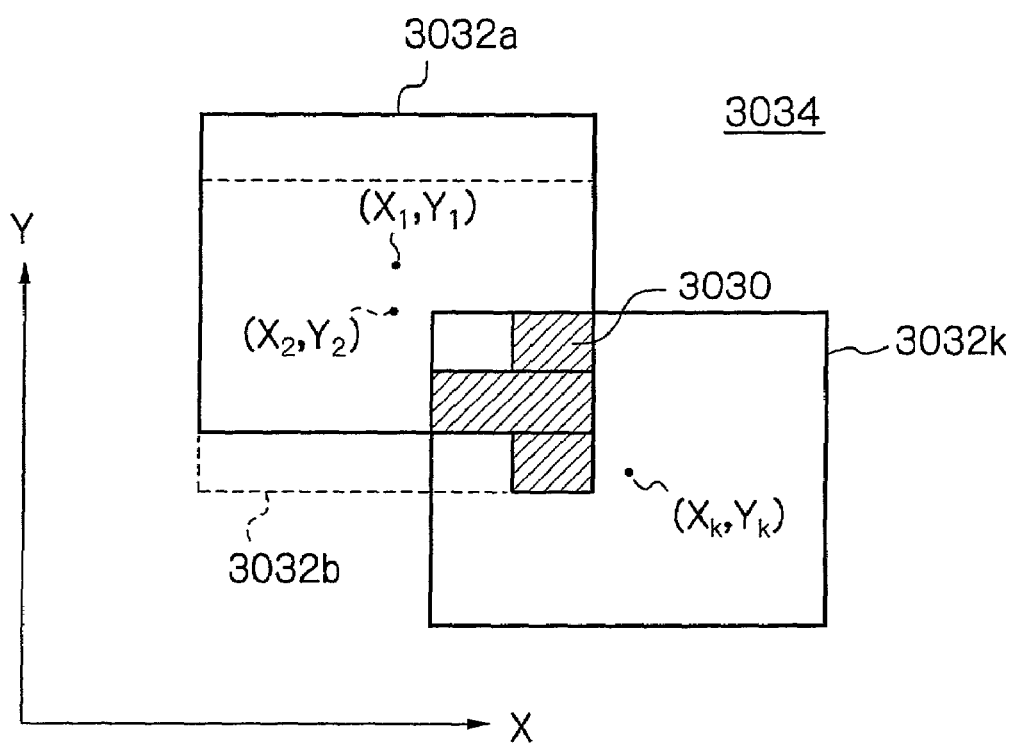
FIG. 32 is a schematic diagram illustrating a plurality of regions to be inspected which are displaced one from another while being partially superimposed one on another on a semiconductor wafer surface.

This image position is defined as a specific location within the region to be inspected for bounding said region, for example, a central location within said region. Currently, i=1 defines the image position as (X1, Y1), which corresponds, for example, to a central location of the region to be inspected 3032*a* as shown in FIG. 32. The image position has been determined previously for every image region to be inspected, and stored, for example, in the hard disk of the control section 3016 to be read out at Step 3332.

Then, the deflection controller 3012 applies a potential to the deflecting electrode 3011 (Step 3334 in FIG. 29) so that the primary electron beam passing through the deflecting electrode 3011 of FIG. 26 may be irradiated against the image region to be inspected in the image position (Xi, Yi) determined at Step 3332.

Then, the electron gun 3001 emits the primary electron beam, which goes through the electrostatic lens 3002, the E×B deflecting system 3003, the objective lens 3010 and the deflecting electrode 3011, and eventually impinges upon a surface of the set wafer 3005 (Step 3336). At that time, the primary electron beam is deflected by an electric field generated by the deflecting electrode 3011 so as to be irradiated onto the wafer inspection surface 3034 covering the whole image region to be inspected at the image position (Xi, Yi). When i=1, the region to be inspected is 3032*a*.

The secondary electrons and/or the reflected electrons (hereafter referred exclusively to as "secondary electrons" for simplification) are emanated from the region to be inspected, to which the primary electron beam has been irradiated. Then, the generated secondary electron beam is formed into an image on the detector 3007 at a predetermined magnification by the electrostatic lens 3006 of a magnifying projection system. The detector 3007 detects the imaged secondary electron beam, and converts it into an electric signal for each detecting element, i.e., a digital image data (Step 3338). Then, the detected digital image data for the image number i is sent to the secondary electron image storage region 3008 (Step 3340).

Subsequently, the image number i is incremented by 1 (Step 3342), and the process determines whether or not the incremented image number (i+1) is greater than a constant value "iMAX" (Step 3344). This iMAX is the number of images to be inspected that are required to obtain, which is "16" for the above example of FIG. 27.

If the image number i is not greater than the constant value iMAX (Step 3344, negative determination), the process goes back to Step 3332 again, and determines again the image position (Xi+1, Yi+1) for the incremented image number (i+1). This image position is a position moved from the image position (Xi, Yi) determined at the previous routine by a specified distance ($\Delta$Xi, $\Delta$Yi) in the X direction and/or Y direction. The region to be inspected in the example of FIG. 32 is at the location (X2, Y2), i.e., the rectangular region 3032*b* indicated with the dotted line, which has been moved from the position (X1, Y1) only in the Y direction. It is to be noted that the value for ($\Delta$Xi, $\Delta$Yi) (i=1,2 ... iMAX) may have been appropriately determined from the data indicating practically and experimentally how much is the displacement of the pattern 3030 on the wafer inspection surface 3034 from the field of view of the detector 3007 and a number and an area of the regions to be inspected.

Then, the operations for Step 3332 to Step 3342 are repeated in order for iMAX regions to be inspected. These regions to be inspected are continuously displaced while being partially superimposed one on another on the wafer inspection surface 3034 so that the image position after k times of movement (Xk,Yk) corresponds to the inspection image region 3032*k*, as shown in FIG. 32. In this way, the 16 pieces of inspection image data exemplarily illustrated in FIG. 27 are obtained in the image storage region 3008. It is observed that a plurality of images obtained for the regions to be inspected 3032(i.e., inspection image) contains partially or fully the image 3030*a* of the pattern 3030 on the wafer inspection surface 3034, as illustrated in FIG. 27.

If the incremented image number i has become greater than iMAX (Step 3344, affirmative determination), the process returns out of this subroutine and goes to the comparing process (Step 3308) of the main routine of FIG. 28.

It is to be noted that the image data that has been transferred to the memory at Step 3340 is composed of intensity values of the secondary electrons for each pixel (so-called, raw data), and these data may be stored in the storage region 3008 after having been processed through various operations in order to use for performing the matching operation relative to the reference image in the subsequent comparing process (Step 3308 of FIG. 28).

Such operations includes, for example, a normalizing process for setting a size and/or a density of the image data to be matched with the size and/or the density of the reference image data, or the process for eliminating as a noise the isolated group of elements having the pixels not greater than the specified number. Further, the image data may be converted by means of data compression into a feature matrix having extracted features of the detected pattern rather than the simple raw data, so far as it does not negatively affect to the accuracy in detection of the highly precise pattern.

Such feature matrix includes, for example, m$\times$n feature matrix, in which a two-dimensional inspection region composed of M$\times$N pixels is divided into m$\times$n (m<M, n<N) blocks, and respective sums of intensity values of the secondary electrons of the pixels contained in each block (or the normalized value defined by dividing said respective sums by a total number of pixels covering all of the regions to be inspected) should be employed as respective components of the matrix. In this case, the reference image data also should have been stored in the same form of representation. The image data in the content used in the tenth embodiment of the present invention includes, of course, a simple raw data but also includes any image data having the feature extracted by any arbitrary algorithms as described above.

The process flow for Step 3308 will now be described with reference to the flow chart of FIG. 30. First of all, the CPU in the control section 3016 (FIG. 26) reads the reference image data out of the reference image storage section 3013 (FIG. 26) onto the working memory such as the RAM or the like (Step 3350). This reference image is identified by reference numeral 3036 in FIG. 27. Then, the image number "i" is reset to 1 (Step 3352), and then the process reads out the inspection image data having the image number i onto the working memory (Step 3354).

Then, the read out reference image data is compared with the data of the image i for any matching to calculate a distance value "Di" between both data (Step 3356). This distance value Di indicates a similarity level between the reference image and the image to be inspected "i", wherein a greater distance value indicates the greater difference between the reference image and the inspection image. Any unit of amount representative of the similarity level may be used for said distance value Di.

For example, if the image data is composed of M$\times$N pixels, the process may consider that the secondary electron intensity (or the amount representative of the feature) for each pixel is each of the position vector components of M$\times$N dimensional space, and then calculate an Euclidean distance or a correlation coefficient between the reference image vector and the image i vector in the M$\times$N dimensional space. It will be easily appreciated that any distance other than the Euclidean distance, for example, the urban area distance may be calculated. Further, if the number of pixels is huge, which increases the amount of the operation significantly, then the process may calculates the distance value between both image data represented by the m$\times$n feature vector as described above.

Subsequently, it is determined if the calculated distance value Di is smaller than a predetermined threshold Th (Step 3358). This threshold Th is determined experimentally as a criteria for judging a sufficient matching between the reference image and the inspection image to be inspected.

If the distance value Di is smaller than the predetermined threshold Th (Step 3358, affirmative determination), the process determines that the inspection plane 3034 of said wafer 3005 has "no defect" (Step 3360) and returns out of this sub routine. That is, if there is found at least one image among those inspection images matching to the reference image, the process determines there is "no defect". Accordingly, since the matching operation shall not necessarily be applied to every inspection image, the high-speed judgment becomes possible. As for the example of FIG. 27, it is observed that the image to be inspected at the column 3 of the row 3 is approximately matching to the reference image without any offset thereto.

When the distance value Di is not smaller than the threshold Th (Step 3358, negative determination), the image number i is incremented by 1 (Step 3362), and then it is determined whether or not the incremented image number (i+1) is greater than the predetermined value iMAX (Step 3364).

If the image number i is not greater than the predetermined value iMAX (Step 3364 negative determination), the process goes back to Step 3354 again, reads out the image data for the incremented image number (i+1), and repeats the similar operations.

If the image number i is greater than the predetermined value iMAX (Step 3364, affirmative determination), then the process determines that said inspection plane 3034 of said wafer 3005 has "a defect existing" (Step 3366), and returns out of the sub routine. That is, if any one of the images to be inspected is not approximately matching to the reference image, the process determined that there is "a defect existing". A defect inspection apparatus 3000 according to the present invention may use not only the electron beam apparatus of the image projective type as described above but also an electron beam apparatus of, what is called, the scanning type. This will now be explained as an eleventh embodiment with reference to FIG. 33.

Figure 33:
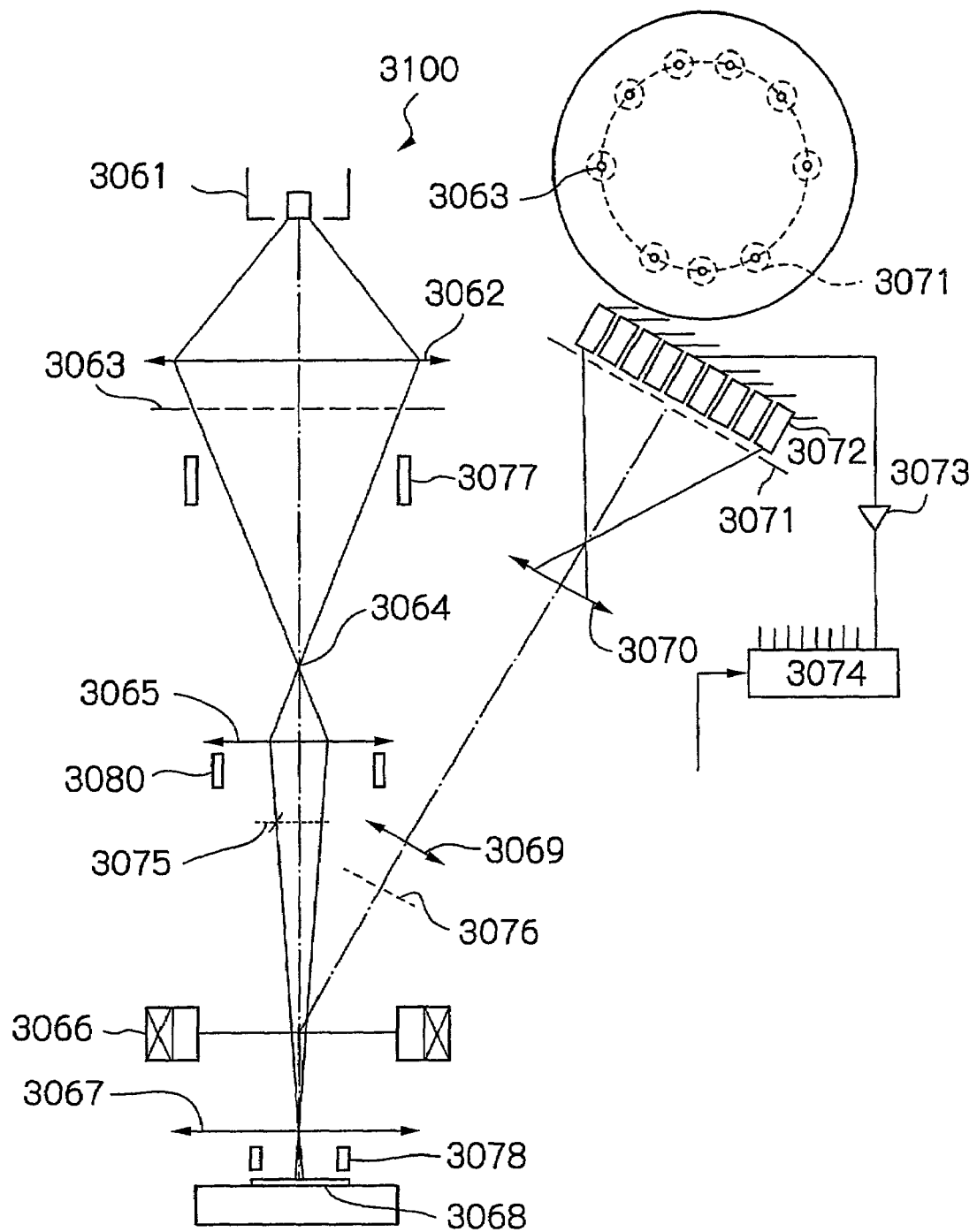
FIG. 33 is a schematic diagram illustrating a configuration of a scanning electron beam apparatus included in a defect inspection apparatus of an 11th embodiment according to the present invention.

FIG. 33 is a schematic diagram of an electron beam apparatus of the eleventh embodiment according to the present invention, in which the electron beam emitted from an electron gun 3061 is converged by a condenser lens 3062 to form a crossover at a point 3064.

Beneath the condenser lens 3062 a first multi-aperture plate 3063 having a plurality of apertures is disposed, thereby to form a plurality of primary electron beams. Each of those primary electron beams formed by the first multi-aperture plate 3063 is contracted by a demagnifying lens 3065 to be projected onto a point 3075. After being focused on the point 3075, the first electron beams are further focused onto a sample 3068 by an objective lens 3067. A plurality of first electron beams exited from the first multi-aperture plate 3063 is deflected all together by a deflecting system 3080 arranged between the demagnifying lens 3065 and the objective lens 3067 so as to scan the surface of the sample 3068.

In order not to produce any field curvature aberration by the demagnifying lens 3065 and the objective lens 3067, as shown in FIG. 33, the multi-aperture plate is provided with a plurality of small apertures located along a circle such that projections thereof in the X direction is equally spaced.

A plurality of focused primary electron beams is irradiated onto the sample 3068 at a plurality of points thereon, and secondary electrons emanated from said plurality of points are attracted by an electric field of the objective lens 3067 to be converged narrower, and then deflected by an E×B separator 3066 so as to be introduced into a secondary optical system. The secondary electron image is focused on the point 3076 which is much closer to the objective lens 3067 than the point 3075. This is because each of the primary electron beams has the energy of 500 eV on the surface of the sample, while the secondary electron beam only has the energy of a few eV.

The secondary optical system has a magnifying lens 3069 and 3070, wherein the secondary electron beam after passing through those magnifying lenses 3069 and 3070 is imaged on a plurality of apertures in a second multi-aperture plate 3071. Then, the second electron beam passes through those apertures to be detected by a plurality of detectors 3072. It is to be noted that the plurality of apertures formed through the second multi-aperture plate 3071 disposed in front of the detectors 3072 corresponds to the plurality of apertures formed through the first multi-aperture plate 3063 on one to one basis.

Each of the detectors 3072 converts the detected secondary electron beam into an electric signal representative of its intensity. Such electric signals output from respective detectors, after being amplified respectively by an amplifier 3073, are received by an image processing section 3074 so as to be converted into image data. Since the image processing section 3074 is further supplied with a scanning signal from the deflecting system 3080 for deflecting the primary electron beam, the image processing section 3074 can display an image representing the surface of the sample 3068. This image corresponds to one of those plural images to be inspected at the different locations (FIG. 27) as described with reference to the tenth embodiment.

Comparing this image with the reference image 3036 allows any defects in the sample 3068 to be detected. Further, the line width of the pattern on the sample 3068 can be measured in such a way that the evaluation pattern on the sample 3068 is moved by a registration to the proximity of an optical axis of the primary optical system, and the evaluation pattern is then line-scanned to extract the line width evaluation signal, which is in turn appropriately calibrated.

In this regard, it is preferred to make arrangements when the primary electrons passed through the apertures of the first multi-aperture plate 3063 is focused onto the surface of the sample 3068, and then the secondary electrons emanated from the sample 3068 are formed into an image on the detector 3072, in order to minimize the affection by the three aberrations, i.e., the distortion caused by the primary electron optical systems, the field curvature, and the astigmatism.

Then, regarding the relation between the spacing in the plurality of primary electron beams and the secondary electron optical system, if the space between respective primary electron beams is determined to be greater than the aberration of the secondary optical system, then the cross talk among a plurality of beams can be eliminated.

Figure 29:
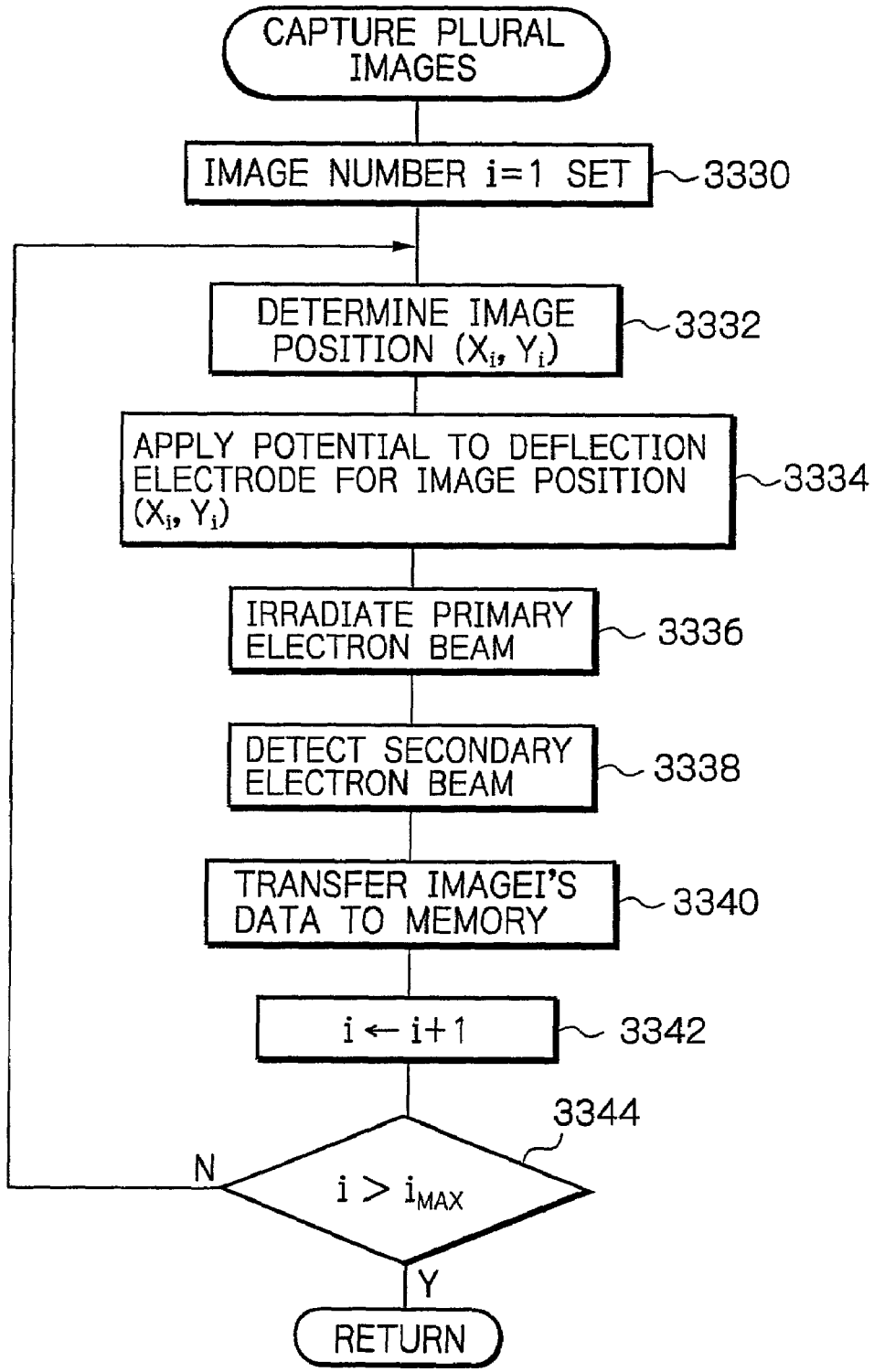
FIG. 29 is a flow chart illustrating a detailed flow of a sub-routine in a process for obtaining image data for a plurality of regions to be inspected (step 3304) in the flow chart of FIG. 28.
Figure 30:
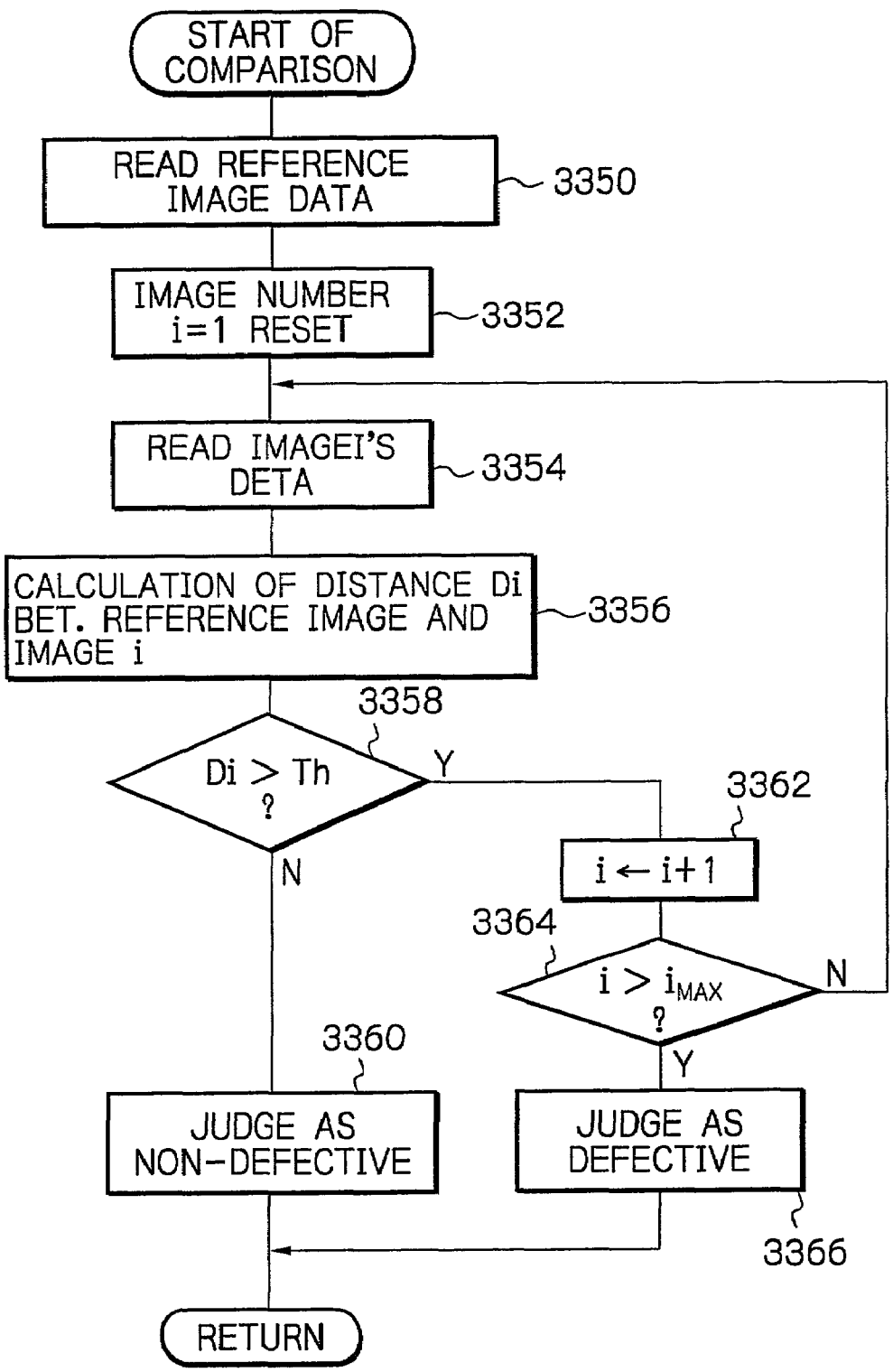
FIG. 30 is a flow chart illustrating a detailed flow of a sub-routine in a comparing process (step 3308) of FIG. 28.
Figure 31:
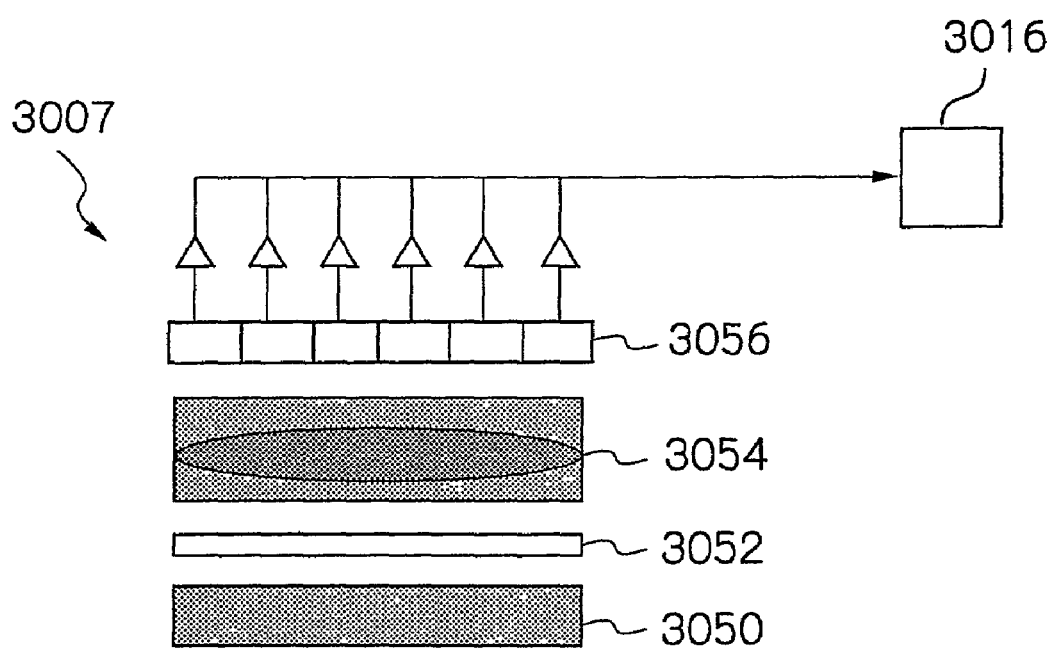
FIG. 31 is a schematic diagram illustrating an exemplary configuration of a detector in the defect inspection apparatus of FIG. 26.

Also in the scanning electron beam apparatus 3100 of FIG. 33, the sample 3068 is inspected according to the flow chart as illustrated in FIGS. 28 and 29. In this case, the image position (Xi, Yi) at Step 3332 of FIG. 29 corresponds to the central location of the two-dimensional image made by combining a plurality of line images obtained through scanning with the multi-beam. This image position (Xi, Yi) could be sequentially modified in the subsequent processes, which may be performed by, for example, changing the offset voltage of the deflecting system 3080. The deflecting system 3080 performs the normal line scanning by changing the voltage around the set offset voltage. It is apparent that a separate deflecting means other than the deflecting system 3080 may be employed to control the image position (Xi, Yi).

A defect inspection apparatus described in either of the tenth or the eleventh embodiment may be applied to the semiconductor device manufacturing processes of FIGS. 12 and 13 for a wafer evaluation. Those flow charts of FIGS. 12 and 13 includes a wafer manufacturing process for manufacturing the wafer (or a wafer preparing process for preparing the wafer), a mask fabrication process for fabricating the mask to be used in the exposing process (or a mask preparing process for preparing the mask), a wafer fabrication process for performing any necessary processes for a wafer, a chip assembling process for cutting out chips formed on the wafer one by one so as to be operative, and a chip inspection process for inspecting those assembled chips.

Among these processes, the main process that decisively affects the performance of the device is the wafer processing process. In this wafer processing process, the designed circuit patterns are printed on the wafer one on another, thus to form many chips which will work as memories or CPUs. This wafer processing process includes the following respective processes:

(1) A thin film deposition process for forming a dielectric thin film to be used as an insulation layer and/or a metallic thin film to form an interconnect section or an electrode section, or the likes (by using the CVD process or the sputtering);

(2) An oxidation process for oxidizing the deposited thin film layer and/or the wafer substrate;

(3) A lithography process for forming a pattern of the resist by using the mask (reticle) in order to selectively process the thin film layer and/or the wafer substrate;

(4) An etching process for processing the thin film layer and/or the wafer substrate in accordance with the resist pattern (e.g., by using the dry etching process);

(5) An ions/impurities implantation and diffusion process;

(6) A resist stripping process; and (7) An inspection process for inspecting the processed wafer.

It should be noted that, the wafer processing process must be performed repeatedly depending on the number of layers required thus to manufacture the semiconductor device that will be operative as designed.

The flow chart of FIG. 13 shows the lithography process which is a core process in the wafer processing processes described above. The lithography process comprises the respective processes as described below:

(1) A resist coating process for coating the wafer having the circuit pattern formed thereon in the previous process, with the resist;

(2) An exposing process for exposing the resist;

(3) A developing process for developing the exposed resist to obtain the pattern of the resist; and (4) An annealing process for stabilizing the developed pattern.

Any known processes may be applied to the semiconductor device manufacturing process, the wafer processing process and the lithography process described above.

When the defect inspection apparatus according to either of the above described embodiments of the present invention is used in the above (7) wafer inspection process, the apparatus can inspect even a semiconductor device having a fine pattern for defect detection with high accuracy under the conditions where there is no resultant faulty image for the secondary electron image, so that a yield of the products can be improved and any defective products can be prevented from being delivered into the market.

The present invention is not limited only to the above embodiments but also may be modified arbitrarily and preferably without departing from the scope and spirit of the present invention. For example, although the description has illustratively employed a semiconductor wafer 3005 as a sample to be inspected, the sample to be inspected in the present invention is not limited to this but anything may be selected as the sample so far as it can be inspected for defects by using the electron beam. For example, the object to be inspected may be a mask with an exposure pattern formed thereon.

Further, the present invention may be applied not only to an apparatus which detects any defects with charged particle beams other than electrons but also to any apparatus which allows any images to be obtained for inspecting the sample for defect detection.

Still further, the deflecting electrode 3011 may be disposed not only between the objective lens 3010 and the wafer 3005 but also at any arbitrary locations so far as the irradiation region of the primary electron beam can be controlled. For example, the deflecting electrode 3011 may be disposed between the E×B deflecting system 3003 and the objective lens 3010, or between the electron gun 3001 and the E×B deflecting system 3003. Further the E×B deflecting system 3003 may control the deflecting direction by controlling the field generated thereby. That is, the E×B deflecting system 3003 may function also as the deflecting electrode 3011.

Further, although in the above tenth and eleventh embodiments, either one of the matching between the pixels and the matching between the feature vectors has been employed for the matching operation between image data, they may be combined together for it. For example, a much faster and more precise matching process can be constructed by two-step matching, in which firstly a high-speed matching is performed with the feature vectors which requires fewer number of operations, and subsequently the more precise matching is performed with more detailed pixel data for the images to be inspected that have been found to be quite similar.

Still further, although in the tenth and the eleventh embodiments according to the present invention, the position mismatch for the image to be inspected has been resolved only by displacing the irradiating region of the primary electron beam, the present invention may be combined with a process for retrieving an optimal matching region on the image data before or during the matching processes (e.g., first detecting the regions having higher correlation coefficient and then performing the matching). This can improve the accuracy in defect detection, because the major position mismatch for the image to be inspected is rectified by displacing the irradiating region of the primary electron beam, while the relatively minor position mismatch can be absorbed subsequently with the digital image processing.

Yet further, although the configurations for an electron beam apparatus for defect detection have been illustratively shown in FIGS. 26 and 33, the electron optical systems or the like may be preferably and arbitrarily modified so far as it functions well. For example, although each of the electron beam irradiation means (3001, 3002, 3003) shown in FIG. 26 has been designed so as to irradiate the primary electron beam onto the surface of the wafer 3005 at a right angle from above, the E×B deflecting system 3003 may be omitted so that the primary electron beam may diagonally impinge upon the wafer 3005.

Still further, the flow in the flow chart of FIG. 28 is also not limited to the illustrated one. For example, although in the embodiment the process does not further perform the defect detection in any other regions of the sample that has been determined to have a defect at Step 3312, the flow may be modified so that the overall area can be inspected for any defects to be detected. Yet further, if the irradiating area of the primary electron beam can be expanded so as to cover almost overall area of the sample with one shot of irradiation, Steps 3314 and 3316 can be omitted.

As described above in detail, according to the defect inspection apparatus of the tenth and the eleventh embodiment of the present invention, since the defect in the sample can be detected by first obtaining respective images of a plurality of regions to be inspected, which are displaced from one another while being partially superimposed one on another on the sample, and comparing those images of the regions to be inspected with the reference image, therefore an advantageous effect can be provided in that the accuracy in the defect detection can be prevented from being deteriorated.

Further, according to the device manufacturing method employing the tenth and the eleventh embodiments of the present invention, since the defect detection is performed by using such a defect inspection apparatus as described above, therefore another advantageous effect can be provided in that the yield of the products can be improved and any faulty products can be prevented from being delivered.

Figure 34:
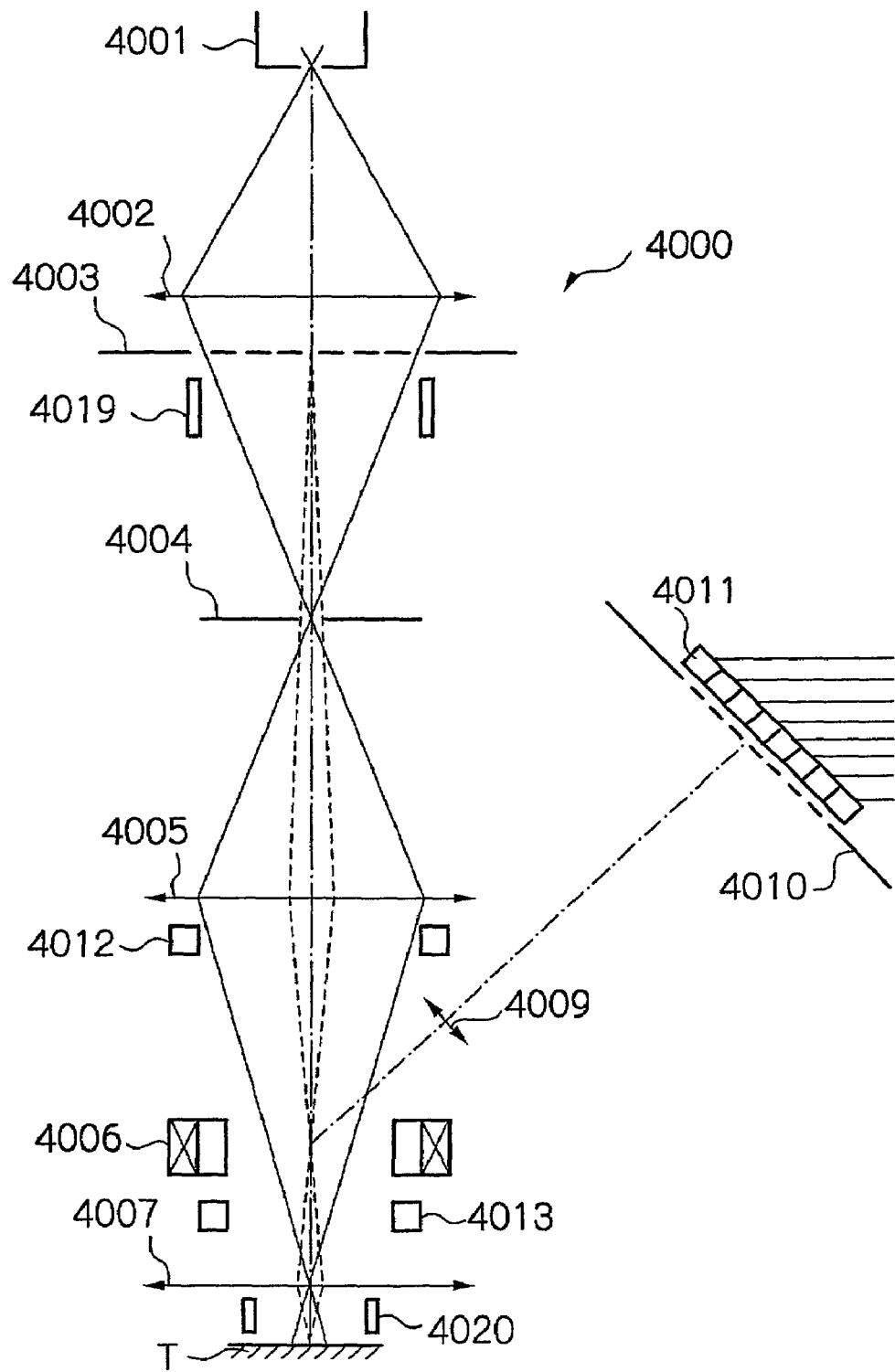
FIG. 34 is a schematic diagram illustrating a configuration of main elements of an electron beam apparatus of a 12th embodiment according to the present invention.

FIG. 34 shows an electron beam apparatus 4000 of a twelfth embodiment according to the present invention.

As can be seen from FIG. 34, this electron beam apparatus comprises an electron gun 4001 for irradiating a primary electron beam against a sample T, and a secondary electron detector 4011 for detecting secondary electron beam from the sample T.

Figure 35:
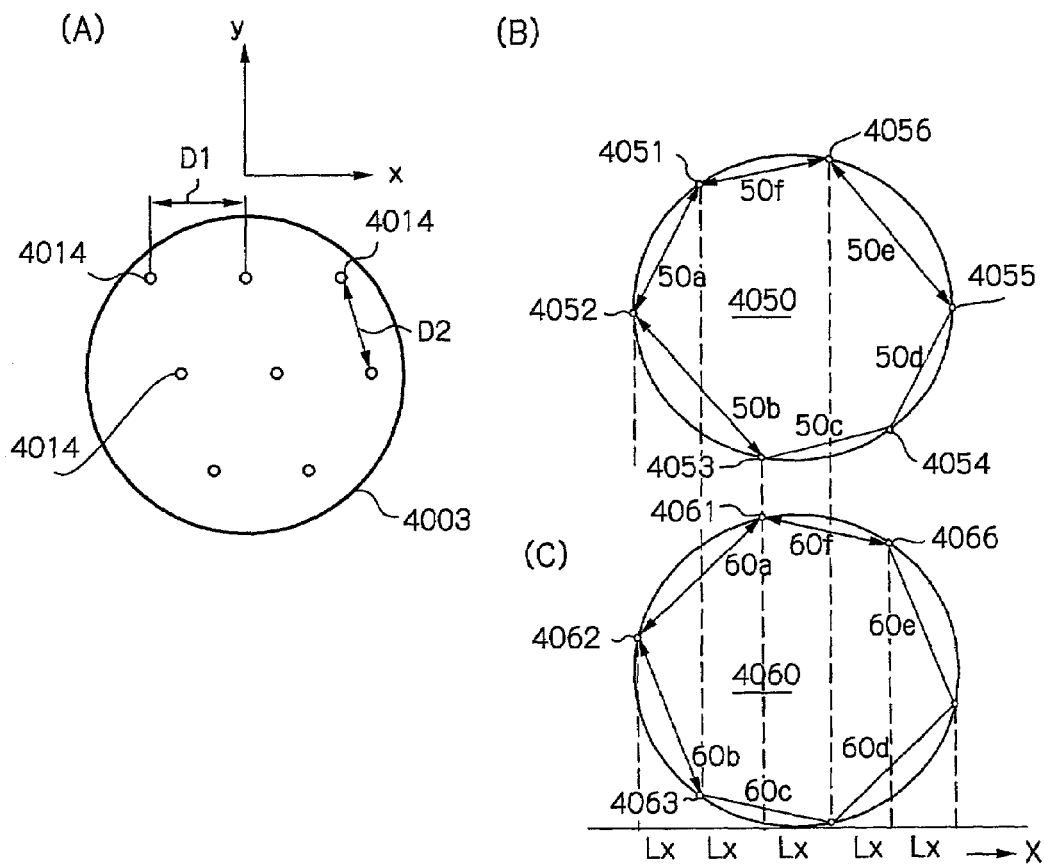
FIG. 35A is a plan view of an aperture plate in the apparatus of FIG. 34, FIGS. 35B and 35C are plan views showing arrangement of the apertures.
Figure 36:
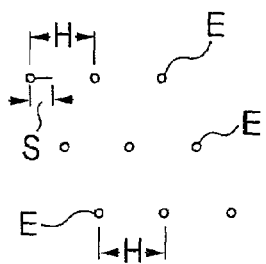
FIG. 36 illustrates an arrangement of primary electron beam irradiation points formed on a surface of a sample by the electron beam apparatus of FIG. 34.

The electron beam emitted from an electron gun 4001 is converged by a condenser lens 4002 to form a crossover on an aperture 4004 which determines NA (numerical aperture). Beneath the condenser lens 4002 is disposed a multi-aperture plate 4003 which is provided with 8 apertures 4014 in total as shown in FIG. 35. Said apertures 4014 are imaged on a deflection principal plane of an E×B deflecting system 4006 by a demagnifying lens 4005, and further contracted by an objective lens 4007 and projected onto the sample T to form resultantly primary electron beam irradiation points E (FIG. 36). Those second electrons emanated from respective primary electron beam irradiation points E are deflected by the E×B deflecting system 4006 to the right hand side on paper and magnified by a secondary optical system 4009 so as to be imaged on a group of apertures of detectors 4010. The sample T is carried on a movable stage (not shown) so as to be moved in the direction normal to paper of FIG. 34 (Y direction).

Although the array of apertures 4014 of the aperture plate 4003 is designed as 3 rows×3 columns, as shown in FIG. 35, preferably the apertures 4014 should be formed within only such a specific diameter that has the intensity of the electrons emitted from the electron gun (electron current density) greater than a certain level, and so in the illustrated example, the aperture on the third row at the third column has not been provided. Further, the apertures at the second and the third rows are offset respectively with respect to the apertures at the first and the second rows toward the right direction viewed in FIG. 35 by the amount of ⅓ of the distance D1 between the columns.

Still further, those distances D1 and D2 between the apertures 4014 are designed so that the spacing between the irradiation points of the primary electron beams on the sample may be sufficient. This arrangement is employed to prevent any possible cross talks of the secondary electron images among respective beams on the group of apertures of the detector 4010 since the secondary optical system has a larger angular aperture to improve the detection efficiency and accordingly has large degree of aberration which could cause the above cross talks.

FIGS. 35B and 35C are plan views of aperture plates 4050 and 4060, each having apertures formed therein along a circle respectively. Projected points onto the x-axis of apertures 4051, 4052, . . . of the aperture plate 4050 shown in FIG. 35B are equally spaced by Lx, and similarly, projected points onto the x-axis of apertures 4061, 4062, . . . of the aperture plate 4060 shown in FIG. 35C are also equally spaced by Lx. In the electron beam apparatus 4000 according to an embodiment of the present invention, each of the primary electron beams is disposed so as to minimize a maximum value of distances between any adjacent primary electron beams to be arranged two-dimensionally on a sample surface.

Distance ratios between adjacent two apertures of the aperture plate 4050 shown in FIG. 35B, which are designated by 50*a*, 50*b*, 50*e* and 50*f*, are 47, 63, 63 and 41 respectively, and distance ratios between adjacent two apertures of the aperture plate 4060 shown in FIG. 35C, which are designated by 60*a*, 60*b* and 60*f*, are 56, 57 and 41 respectively. By comparison between these two aperture plates, it is found that since in the aperture plates 4060, the maximum value of the distance ratios between adjacent primary electron beams is 57, which is smaller than 50*b* (63) of the aperture plate 4050, the aperture plate 4060 of FIG. 35C is superior to the aperture plate 4050 of FIG. 35B in the arrangement of the apertures.

Using the aperture plate with such a condition described above is advantageous in that the distances between actually adjacent primary beams are approximately equal, thus providing good symmetry property, that the astigmatism is not likely to occur, that since being spaced apart from each other, the primary electron beam is not likely to be made blur by the space charge effect, and that since respective primary electron beams are irradiated onto the sample at or near to symmetric positions thereon respectively, an effect of charging on the sample may be alleviated.

The primary electron beam is separated into a plurality of beams by those small apertures 4014, and they are imaged on the deflection principal plane of the E×B deflecting system 4006 by the demanifying lens 4005, further contracted by the objective lens 4007 and projected onto the sample T to resultantly form the primary electron beam irradiation points E as shown in FIG. 36.

Those second electrons emanated from respective primary electron beam irradiation points E are accelerated and converged in an electric field applied between the objective lens 4007 and the sample surface, deflected by the E×B deflecting system 4006 disposed between the objective lens 4007 and another lens on the electron gun side to the right hand side in FIG. 34, magnified by the lens 4009 of the secondary optical system to be imaged on the detective aperture plate 4010 having a plurality of apertures formed therethrough, and finally detected by the secondary electron detector 4011. The sample T is carried on a movable stage (not shown) so as to be moved in the direction normal to paper of FIG. 34 (Y direction).

Further, those distances D1 and D2 between the small apertures 4014 are designed so that the spacing between the irradiation points of the primary electron beams on the sample T may be sufficient. For a case where the spacing between the irradiation points is not constant, the smallest value for the spacing will be a matter of problem and said smallest value for the spacing is accordingly required to be made as large as possible. This is required to prevent any possible cross talks of the secondary electron images among respective secondary electron beams on the detective aperture plate 4010 since the secondary optical system has a larger angular aperture to improve the detection efficiency and accordingly has large degree of aberration which could cause the above cross talks.

The deflecting system 4012 and 4013 for electron beam scanning have been designed so as to cause a scanning motion of the primary electron beam irradiation points E on the sample T in the direction toward the column on the right hand side (X direction) viewed in FIG. 35, and the scanning distance S should be designed so as to be equivalent to the amount of about ⅓ of the spacing H between the columns of the irradiation points E (S=H/3+α).

Then, after the sample T being moved in the Y direction by the distance encompassing the region to be detected, the stage is moved by step in the X direction to move the sample in the X direction by 400 μm, and then as similarly to the above description, the raster scanning (in the X direction by 400 μm+α) will be performed while continuously moving the stage in the −Y direction. Repeating said processes may provide the image data for every region to be inspected.

When the inspection of the sample T is carried out in said electron beam apparatus, the movable stage 4020 is moved so as to move the sample in the Y direction continuously. During this movement, the scanning deflectors 4012 and 4014 causes the scanning motion of each of the primary electron beam irradiation points E in the X direction by ⅓H+α as described above, and in an exemplary case where the spacing H between the respective primary electron beam irradiation points E is 150 μm, each of the primary electron beam irradiation points E accomplishes the scanning with the width of (150 μm×⅓)+α to obtain the image data for the range of (150 μm×⅓)×8 (points) (=400 μm+α) as a whole. When the sample is moved by the distance equivalent to the length of the sample in the Y direction, the movable stage moves the sample in the X direction by 400 μm and the scanning is carried out by the retrace movement in the Y direction as similarly to the above description.

Comparing this image data with the image obtainable from a predetermined pattern data accomplishes a desired inspection. Since in the illustrated example, 8 channels have been employed to receive the signals and also the serial inspection has been carried out during the period other than the time required for the retrace movement, the processing speed will be significantly improved to be higher in comparison with that in the prior art. It is to be noted that, when the inspection region width of the sample (the width in the X direction) being assumed to be 200 mm, the number of retraces is calculated as 200 mm/0.4 mm=500 times, and this value is approximately equivalent to 4 minutes to be necessary for the retrace scanning in the overall inspection of one piece of sample with the rate of 0.5 second for each retrace, which seems to be extremely short. It is also noted that an axis-symmetrical electrode is designated by the reference numeral 4020 in FIG. 34.

In case of the measurement of the line width, preferably each of the scanning deflectors 4012 and 4013 is made in the form of an octupole to also allow the scanning motion in the Y direction, in which the beam is moved to a location of the pattern to be measured by being deflected in the X direction, and then the Y directional scanning motion may be performed. In case of the measurement of the pattern line width in the X direction, the beam should be moved to a location of the pattern to be measured by adjusting the stage position and also by being deflected in the Y direction, and then the X directionally scanning motion and the signal processing similar to that in the prior art may be applied thereto.

In case of an alignment accuracy measurement, the pattern employable for evaluating the alignment accuracy should have been fabricated and then the scanning similar to that for the line width measurement may be performed.

It is to be noted that in the 12th embodiment (FIG. 34), a single electron beam irradiating system with a single electron gun 4001 has been shown for the illustrative purpose, a plurality of electron beam irradiating systems may be employed which comprises a plurality of electron guns, and an aperture plate and a secondary electron detector which work associatively with said plurality of electron guns, wherein, in case of the above embodiment, said plurality of electron guns may be placed side by side in the X direction, so that the inspection for the width of 400 μm×(the number of the irradiating systems) may be performed with a single stroke of movement of the sample in the Y direction.

According to the 12$^{th}$ embodiment (FIG. 34) of the present invention, since the inspection of the sample surface may be performed by moving the sample continuously in the direction orthogonal to the scanning width while covering an extended scanning width (400 μm in the above embodiment) with a plurality of primary electron beams, the scanning time for the overall surface of said sample may be significantly reduced. Further, since the plurality of primary electron beams is employed, the scanning width of each of the electron beams can be made narrower to reduce the chromatic aberration and thus to reduce the irradiation point E for the sample surface to be smaller, and the spacing between the electron beams can be kept sufficient, as well. Accordingly, this may also reduce any cross talks in the secondary optical system.

Further, since the sample is continuously moved, there should be no time to be wasted for moving the sample in comparison with the conventional electron beam apparatus in which the sample must be held stationary for scanning the micro region and then the sample is moved for scanning another micro region. Yet further, employing a plurality of electron guns and constructing a plurality of electron beam irradiating systems may allow the inspection to be carried out more efficiently.

According to the twelfth embodiment of the present invention, since the irradiation points of the plurality of primary electron beams have been arranged two-dimensionally, the distance between the irradiations may be made greater. Also, since the distances between the irradiation points projected onto one axis (the X axis) are all equal, the scanning of the sample may be accomplished leaving no space between. Further, since the E×B has been used to allow the normal-incidence of the primary electron beam, the electron beam may be converged to be narrower.

Figure 37:
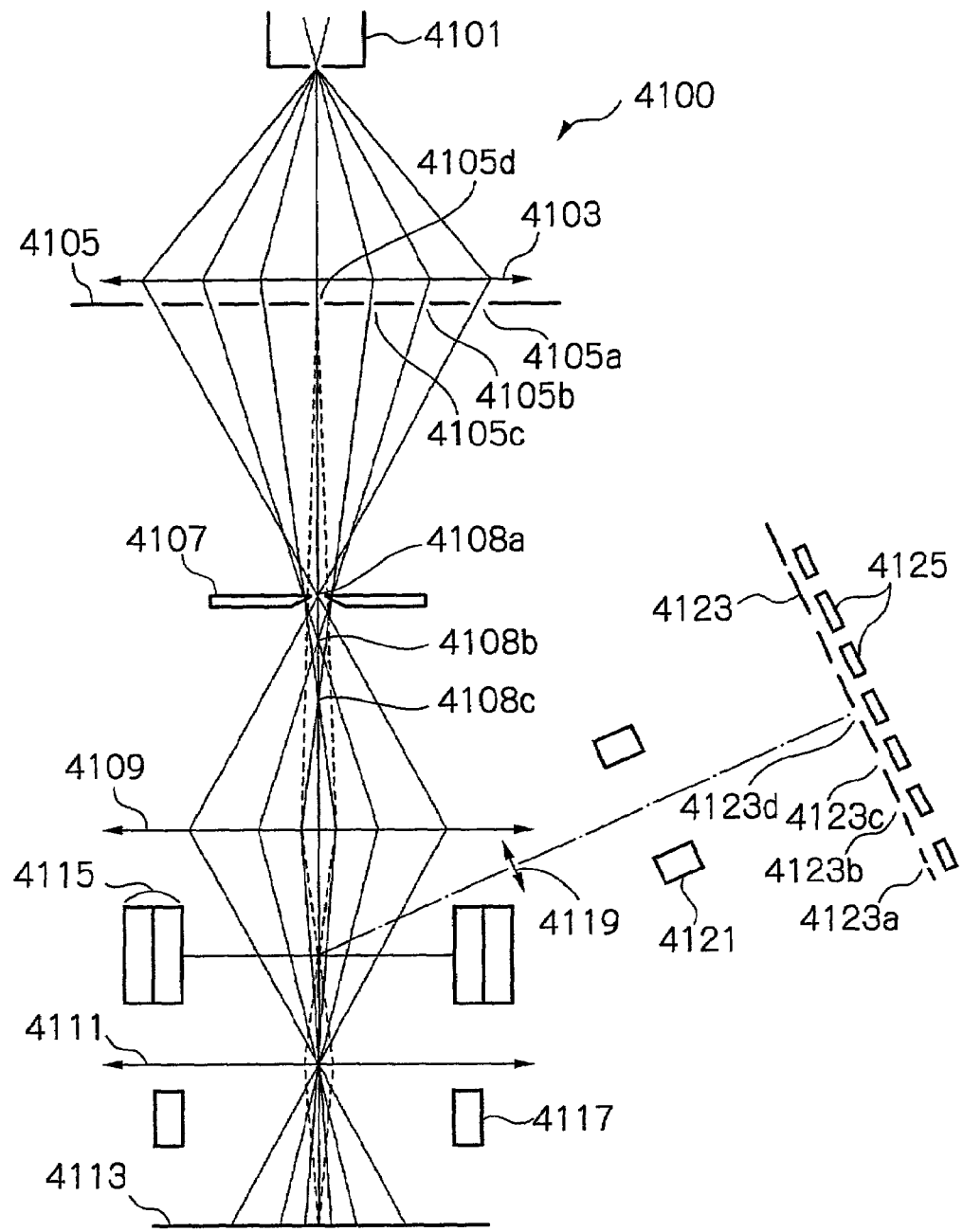
FIG. 37 is a schematic diagram illustrating a configuration of an electron beam apparatus of a 13th embodiment according to the present invention.

FIG. 37 is a schematic diagram illustrating a configuration of an electron beam apparatus 4100 of a thirteenth embodiment according to the present invention.

In FIG. 37, reference numeral 4101 is a single electron gun having an integrated cathode for emitting an electron beam used in inspection, 4103 is a condenser lens, 4105 is a multi-aperture plate for forming a plurality of electron beams from the electron beam exited from the condenser lens, 4107 is a NA aperture plate arranged at a location of an enlarged image of an electron beam source formed by the condenser lens, 4111 is a lens for contracting the plurality of electron beams formed by the multi-aperture plate at a certain reduction ratio to be imaged thereafter on a surface of an object to be inspected or a sample 4113, and 4115 is an E×B separator for separating secondary electrons passed through the lens from the primary electrons.

Herein, the integrated cathode implies the cathode materials such as single-crystal $LaB_6$ or the likes whose tip portions having been processed in various shapes.

Said E×B separator 4115 has such a configuration in which an electric field and a magnetic field are crossed at a right angle within a plane orthogonal to the normal line of the sample (the upper direction on paper), and has been adapted such that the primary electrons are advanced straight forward depending on the relationship among the electric filed, the magnetic field and the primary electron energy. The apparatus further comprises a deflector 4117 for deflecting all together the plurality of electron beams formed by the multi-aperture plate 4105 to scan the inspection region on the sample 4113, a magnifying lens 4119 of a secondary optical system, a deflector 4121 for synchronizing with the deflector 4117 of the primary optical system and for guiding the second electrons from the incident points of respective beams passed through those apertures 4105a, 4105b, 4105c and 4105d of the multi-aperture plate 4105 to enter the corresponding detectors regardless of the scanning of the sample, a multi-aperture plate 4123 of the secondary optical system having a plurality of apertures 4123a, 4123b, 4123c and 4123d respectively corresponding to those apertures of the multi-aperture plate of the primary optical system, and an electron multiplier tube 4125 for generating a detection signal depending on the quantity of the entered electrons in the group of detectors arranged behind said multi-aperture plate.

Referring to the electron beam apparatus 4100 of FIG. 37, the electron beams delivered from the electron gun 4101 are converged by the condenser lens 4103 and are irradiated onto the apertures 4105a–4105d of the multi-aperture plate 4105 for forming a multi-beam. The electron beams passed through each of the apertures 4105a, 4105b, 4105c and 4105d form a crossover at an aperture location of the NA aperture plate 4107 for determining the numerical aperture of the primary optical system. The electron beams after passing through the crossover are made to form a crossover image on the main field of the objective lens 4111 by the condenser lens 4109. Herein, NA is an abbreviation for the Numerical Aperture.

The aperture image for each of the apertures of the multi-aperture plate 4105 is imaged at first on the main field of the E×B separator 4115 by the condenser lens 4109 and then on the surface of the sample 4113 by the objective lens 4111.

On the other hand, the secondary electrons emanated from the sample are separated from the primary electrons by the E×B separator 4115 to be deflected toward the secondary optical system, and magnified by the magnifying lens 4119 of the secondary optical system and then pass through the apertures of the multi-aperture plate 4123 to be detected by the group of detectors arranged behind said multi-aperture plate.

In this regard, since the value representative of the current density of the electron beam emitted from the electron gun 4101 is the greatest for that directed to the central aperture 4105d of the multi aperture plate 4105d and said value sequentially decreases in order of 4105c, 4105b and 4105a as being more distant from the optical axis, therefore there might be difference in beam currents on the surface of the sample 4113 depending on the location thereon.

In order to deal with this phenomenon, in one embodiment, the size of the apertures 4105a–4105d of the multi-aperture plate 4105 may be finely adjusted such that the apertures in the vicinity of the optical axis are made smaller and the apertures are made larger gradually as they are distant from the optical axis, so that the beam currents passed through the respective apertures may be made equal for all of the beams on the surface of the sample 4113. To accomplish this, a group of detectors for detecting each of the beam currents is mounted on the surface of the sample 4113 so as to detect the current for each of the beams.

There is also suggested another method to deal with the above problem, in which the position along the optical axis of the NA aperture plate 4107 for determining the numerical aperture of said primary optical system is set to a position offset toward the electron gun 1 from the Gaussian image field (focal point of the paraxial beam) for the magnified image of the electron beam source formed by the lens of the primary optical system. This attempts to use the fact that the position of the crossover formed by the condenser lens 4103 depends on the spherical aberration of the lens, that is, the crossover position (the position along the optical axial direction) may be different for each of the beams passed through each of the apertures of the multi-aperture plate 4105.

For example, the position of the crossover to be formed by the beam from the aperture 4105a is equivalent to the position 4108a, while the position of the crossover to be formed by the beam from the aperture 4105c is equivalent to the position 4108c. That is, the Gaussian image field for the electron source formed by the lens of the primary optical system is at the farthest location from the NA aperture plate 4107.

Accordingly, if the NA aperture plate 4107 is displaced from the Gaussian image field position toward the electron gun 1 so as to be placed in a position of the crossover formed by the beam passed through the outermost aperture 4105a of the multi-aperture plate 4105, then for the beam having passed through the aperture 4105a, the current density thereof may be greater when passing through the aperture 4107 without the passing thereof being limited, while the current density of the beam having passed through the aperture 4105c adjacent to the optical axis may be lower with the passing rate thereof being limited, so that the ununiformity in the intensities or beam currents on the surface of the sample 4113 could be reduced. It is to be noted that also in this case similarly to the previous embodiment, a group of detectors for detecting each of the beam currents may be disposed in a position for the sample surface in order to detect the current for each beam passed through each of the apertures.

Further, the above problem may be dealt with by combining said adjustment in aperture size of the multi-aperture plate 4105 with said adjustment in position of the NA aperture plate 4107 on the optical axis.

Although the above embodiments have been described in the light of the common goal to uniform the beam currents entering onto the surface of the sample 4113, there is another problem that the detection rate of the secondary electron in the secondary optical system actually varies depending on the location whether it is adjacent to or distant from the optical axis.

Accordingly, in still another embodiment of the present invention, the ununiformity in the detection rate of the secondary electron in the secondary optical system may be corrected by at first placing a sample having no pattern in the sample position, then detecting secondary electrons from said sample with no pattern by the group of detectors 4125, and finally determining the location of the NA aperture plate

4107 on the optical axis so that the differences in outputs from the respective detectors are minimized.

Further, the ununiformity in the detection rate of secondary electrons in the secondary optical system may be corrected by, as similarly to the above description, at first placing a sample having no pattern in the sample position, then detecting secondary electrons from said sample with no pattern by the group of detectors 4125, and finally performing a fine tuning of the aperture size in the multi-aperture plate 4105 of the primary optical system in order to minimize the differences in outputs from the respective detectors, such that the aperture size is made smaller for the locations closer to the optical axis and made sequentially larger for the locations farther from the optical axis.

Still further, the ununiformity in the detection rate of secondary electrons in the secondary optical system may be corrected by, as similarly to the above description, at first placing a sample having no pattern in the sample position, then detecting secondary electrons from said sample with no pattern by the group of detectors 4125, and finally performing a fine tuning of the aperture size of the multi-aperture plate 4123 of the secondary optical system in order to minimize the differences in outputs from the respective detectors, such that the aperture size is made smaller for the locations closer to the optical axis and made sequentially larger for the locations farther from the optical axis Yet further, the above problem may be overcome by the combination of said adjustment of the aperture size in the multi-aperture plate 4105, said adjustment in positioning the NA aperture plate 4107 along the optical axis and said adjustment of the aperture size in the multi-aperture plate 4123 of the secondary optical system. This is accomplished by utilizing the adjusting method in which the differences in the outputs from the respective detectors 4125 is minimized by a certain control and calculation techniques, though not illustrated.

It is to be understood that in the thirteenth embodiment of FIG. 37, the evaluation between respective beams is performed in such a manner that the deflector 4117 deflects all the beams at once to scan the surface of the sample 4133 and the detector concurrently detects the signals. Also upon causing the scanning motion of the beams, the deflector 4121 has synchronized with the deflector 4111 to cause the scanning motion of the secondary electrons so that the secondary electrons from the respective incident points on the sample surface can enter the corresponding apertures of the multi-aperture plate 4123.

Applying an electron beam apparatus 4100 of the thirteenth embodiment according to the present invention to the inspection process for inspecting a wafer in the flow chart of FIG. 12 may accomplish the inspection or measurement of higher throughput and higher accuracy.

The electron beam apparatus 4100 of the thirteenth embodiment according to the present invention is applicable to a variety of inspections or measurements including a defect inspection, a line width measurement, an alignment accuracy measurement, a voltage contrast measurement and the likes for photo mask or reticle and wafer or the likes (sample).

According to the electron beam apparatus 4100 of the thirteenth embodiment of the present invention, since an integrated cathode or a single electron gun has been employed to generate a plurality of beams, the possibility of malfunctions in the electron gun is significantly reduced in comparison with the case of a plurality of emitters being used, so that the reliability of the apparatus can be improved. Further, since the apparatus can accomplish the uniformity in the currents for the respective beams, the inspection and measurement with higher accuracy and higher throughput may be provided.

An electron gun such as the thermal field-emission electron gun that emits electrons toward a limited range may also be used in the electron beam apparatus 4100 of the thirteenth embodiment.

According to the electron beam apparatus 4100 of the thirteenth embodiment, since the currents of the respective beams can be made uniform, the number of beams of the multi-beam can be increased and thus the multi-beam can be irradiated to cover greater range. Accordingly, the inspection and the measurement may be performed with higher throughput. Further, the signal strengths of respective beams may be made almost equal to one another.

Figure 38:
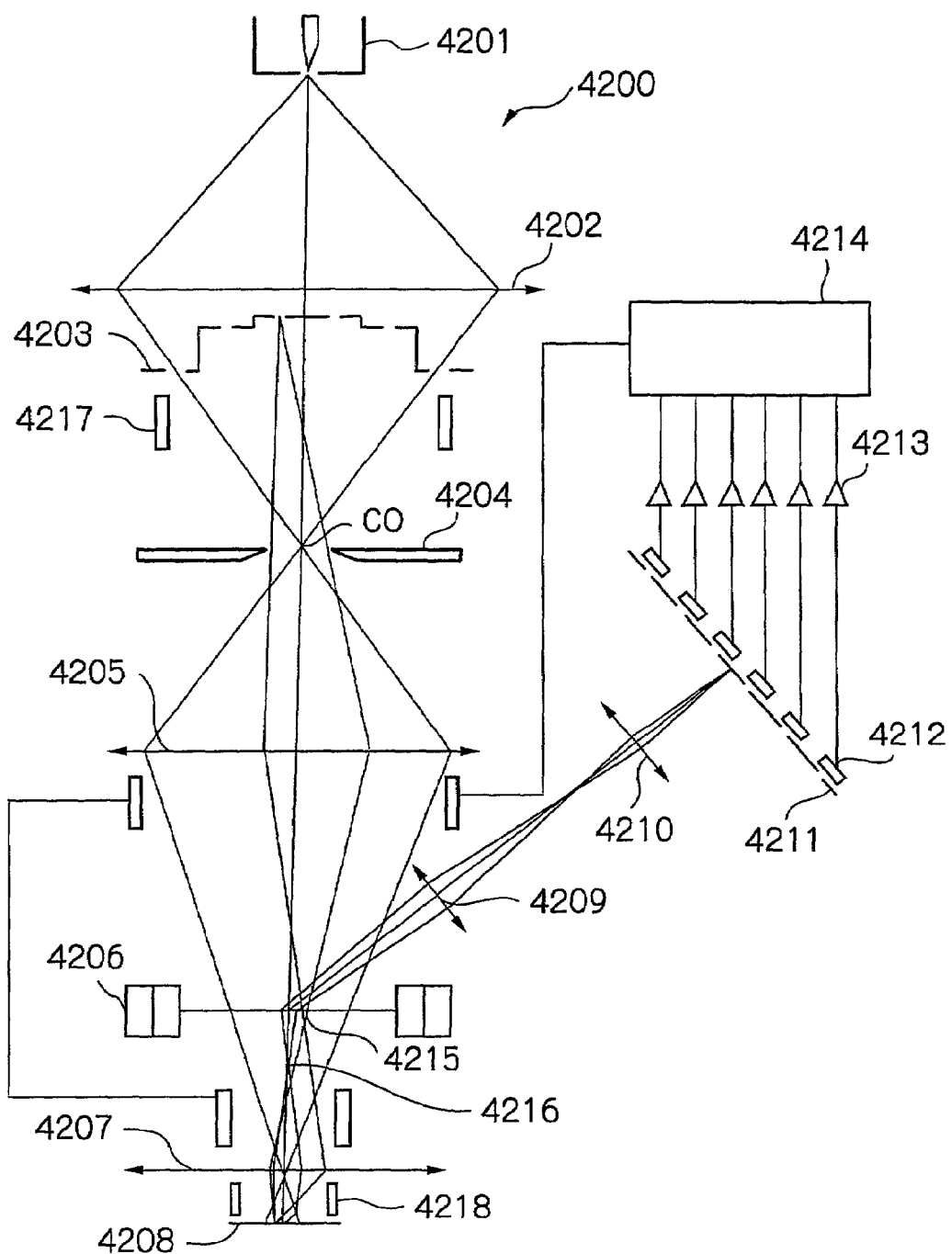
FIG. 38 is a schematic diagram illustrating an arrangement of an optical system of an electron beam apparatus of a 14th embodiment according to the present invention.

Referring to FIGS. 38 to 41, an electron beam apparatus 4200 of the fourteenth embodiment of the present invention will now be described below. FIG. 38 is a schematic diagram of an electron beam apparatus 4200 of one embodiment according to the present invention, in which the electron beam emitted from an electron gun 4201 is converged by a condenser lens 4202 to form a crossover at a point CO. At said crossover point CO is arranged the center of a diaphragm 4204 having an aperture for determining the NA.

Beneath the condenser lens 4202 is disposed a first multi-aperture plate 4203 having a plurality of apertures, thereby to form a plurality of primary electron beams. Each of those primary electron beams formed by the first multi-aperture plate 4203 is contracted by a demagnifying lens 4205 to be projected onto the deflection principal plane 4215 of an E×B separator 4206, and after having been focused once on the point 4125, the primary electron beams are further focused onto a sample 4208 by an objective lens 4207.

In order not to produce an image field curvature aberration possibly caused by the minifying lens 4205 and the objective lens 4207, as shown in FIG. 38, the multi-aperture plate 4203 has a stepped contour such that the smaller distance to the condenser lens 4202 at the central portion thereof is getting greater as toward the peripheral portion.

Secondary electrons emanated from said plurality of points on the sample 4208 to which the plurality of focused primary electrons is irradiated are attracted by an electric field of the objective lens 4207 to be converged narrower, and then focused on a point 4216 before the E×B separator 4206, that is, the point 4216 in the side closer to the sample with respect to the deflection principal plane of the E×B separator 4206. This is because each of the primary electron beams has the energy of 500 eV on the surface of the sample, while the secondary electron beam only has the energy of a few eV. The plurality of secondary electron beams emanated from the sample 4208 is deflected by the E×B separator 4206 to the outside of the axis extending from the electron gun 4201 to the sample 4208 to be separated from the primary electron beams and enters into a secondary optical system.

The secondary optical system has magnifying lenses 4209 and 4210, and the secondary electron beam passed through those magnifying lenses 4209 and 4210 further passes through a plurality of apertures in a second multi-aperture plate 4211 to be imaged on a plurality of detectors 4212. It is to be noted that the plurality of apertures formed through the second multi-aperture plate 4211 disposed in front of the detectors 4212 corresponds to the plurality of apertures formed through the first multi-aperture plate 4203 on one to one basis.

Each of the detectors 4212 converts the detected secondary electron beam into an electric signal representative of its intensity. The electric signals thus output from respective detectors are, after having been amplified respectively by an amplifier 4213, received by an image processing section 4214 and converted into image data. Said image data is utilized for the evaluation of a defect or line width of the sample.

That is, since the image processing section 4214 is further supplied with a scanning signal for deflecting the primary electron beam, the image processing section 4214 can display an image representing the surface of the sample 4208. Comparing this image with the reference image allows any defects in the sample 4208 to be detected, and further, the line width of the pattern on the sample 4208 can be measured in such a way that the sample 4208 is moved by a registration to the proximity of an optical axis of the primary optical system and then line-scanned to extract the line width evaluation signal, which is in turn appropriately calibrated.

In this regard, it is required to make special arrangements when the primary electrons passed through the apertures of the first multi-aperture plate 4203 is focused onto the surface of the sample 4208, and then the secondary electrons emanated from the sample 4208 are formed into an image on the detector 4212, in order to minimize the affection by the these aberrations, i.e., the distortion caused by the primary optical systems, the image field curvature, and the field astigmatism. Then the means employed in the fourteenth embodiment of the present invention in order to solve the above problem associated with the aberrations will be described with reference to FIGS. 39 to 41. It is to be noted that in those illustrations of FIGS. 39 to 41, the primary and secondary multi-aperture plates 4203 and 4211 have been illustrated with the size of the apertures, shapes and amounts of offset thereof being rather exaggerated for better understanding, which are all different from the actual ones.

Figure 39:
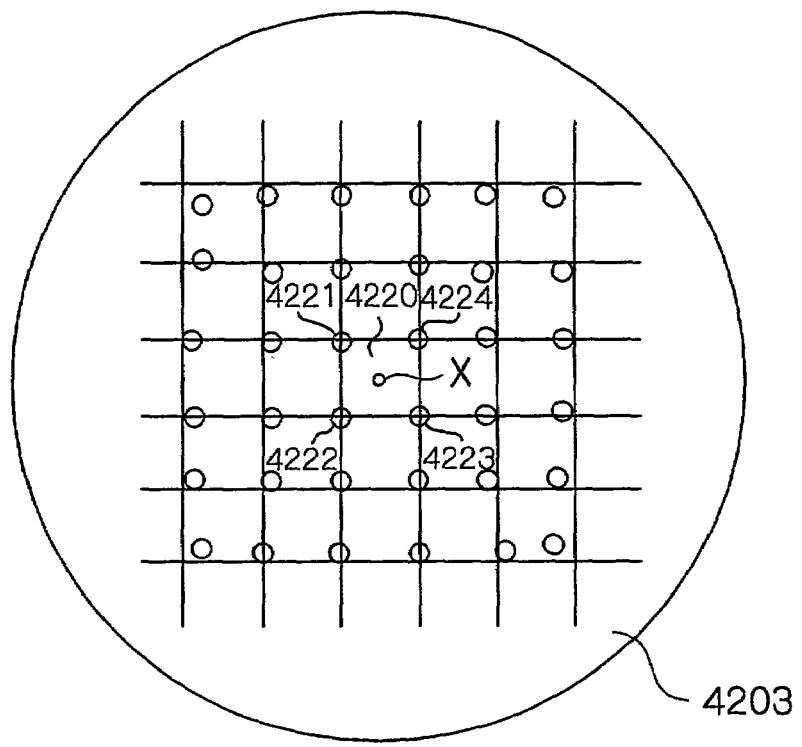
FIG. 39 illustrates an example of the multi-aperture plate to be used in the electron beam apparatus of FIG. 38.

FIG. 39 shows a first embodiment of a first multi-aperture plate 4203 used in an electron beam apparatus according to the present invention, and the multi-aperture plate 4203 of this embodiment is used when there is a distortion aberration of pin-cushion type appeared on a sample surface, and in order to compensate for the pincushion type distortion aberration, the first multi-aperture plate is provided with a plurality of apertures being displaced into a barrel shape. That is, each of the apertures 4221 to 4224 is formed at each of four corners of a square 4220 centered with the center X of the first multi-aperture plate 4203, i.e., the intersection point where the line extending from the electron gun 4201 to the sample 4208 is crossed with the first multi-aperture plate 4203.

The longitudinal and lateral solid lines illustrated in FIG. 39 are virtually drawn so as to be parallel with respective sides of said square, and the aperture should be located at each of those intersection points when a plurality of apertures is distributed evenly over the multi-aperture plate 4203. In practice, in order to minimize the distortion aberration in the primary optical system, each of the apertures will be designed to be located offset from the intersection point of the solid lines toward the center of the first multi-aperture plate 4203 by a certain amount depending on the distance from the center of the first multi-aperture plate 4203.

Figure 40:
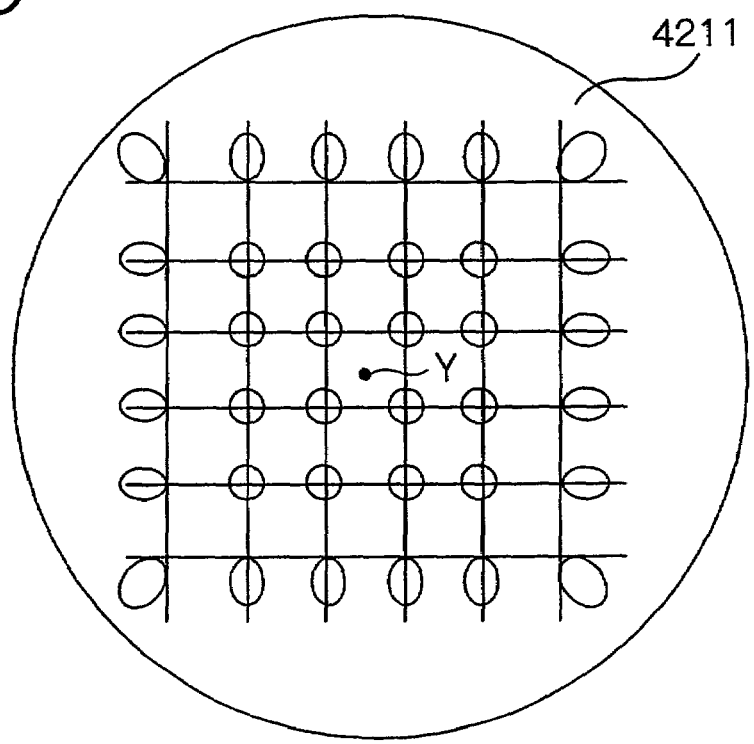
FIG. 40 illustrates an example of a detector aperture plate to be used in the electron beam apparatus of FIG. 38.

FIG. 40 shows an embodiment of a second multi-aperture plate 4211 used in the electron beam apparatus according to the present invention, and this multi-aperture plate 4211 is used to minimize the affection by the potential distortion of pin-cushion type that might be caused from the distortion existing in the secondary optical system. Also in FIG. 40, each of the apertures of the second multi-aperture plate 4211 is offset outwardly from the ideal location in case of uniform distribution thereof, by a certain amount depending on the distance from the center Y.

The amount of this offset has been calculated from the simulation for the system comprising the objective lens 4207, the magnifying lenses 4209 and 4210, and the E×B separator 4206. Since the outermost aperture never causes a cross talk even if it is made too large, it may be formed to be large enough. In addition, although each of the multi-aperture plates 4203 and 4211 respectively shown in FIGS. 39 and 40 is illustrated as an embodiment of a single plate which comprises a plurality of apertures formed therethrough, a plurality of multi-aperture plates, i.e., two or more pieces of plates may be employed in the viewpoint of designing the apparatus.

Concerning to the image field curvature, the first multi-aperture plate 4203 may be made into a shape of stepped contours in sectional view so as to compensate for the field curvature caused by the primary optical system, as described above. The field curvature may possibly be caused even by the secondary optical system, but because of the larger size of the aperture of the second multi-aperture plate 4211 disposed in front of the detectors 4212, the field curvature by the secondary optical system could be actually ignored.

The aberration of field astigmatism occurs because the refractive index of the lens in the radial direction is different from that in the circumferential direction. FIGS. 41A and 41B show respectively a second embodiment of the first multi-aperture plate 4203 used in the electron beam apparatus according to the present invention in order to correct this aberration of field astigmatism, and in the first multi-aperture plate 4203 shown in FIG. 41A, each of the apertures are elongated in the radial direction with respect to the center of the first multi-aperture plate 2403 by a certain amount depending on the distance from said center. Alternatively, in FIG. 41B, each of the apertures is designed to have a specified shape so that its size in the radial direction and that in the circumferential direction with respect to the vertical circle centered with the center of the first multi-aperture plate 4203 vary depending on the distance from the center.

Reference numeral 4217 in FIG. 38 designates a blanking deflector, and applying a pulse of narrow width to said blanking deflector 4217 may form an electron beam having a narrow pulse width. Using thus formed pulse with narrow width allows the potential of the pattern formed in the sample 4208 to be measured with high time-resolution, and this implies that the electron beam apparatus may be added with another function of, what is called, a strobe SEM (scanning electron microscope).

On the other hand, reference numeral 4218 in FIG. 38 designates an axis-symmetrical electrode, and applying to said axis-symmetrical electrode 4218 a certain level of potential lower by some 10V than that of the sample 4208 may drive the secondary electrons emanated from the sample 4208 to flow toward the objective lens 4207 or to return toward the sample, depending on the potential pertaining to the pattern of the sample 4208. Thereby, the potential contrast on the sample 4208 may be measured.

The electron beam apparatus 4200 according to the fourteenth embodiment of the present invention shown in FIGS. 38 to 40 is applicable to a defect inspection apparatus, a line width measuring apparatus, an alignment accuracy measuring apparatus, a potential contrast measuring apparatus, a defect review apparatus, and a strobe SEM apparatus. Further, the electron beam apparatus according to the present invention may be used to evaluate the wafer in the course of processing. Then, the evaluation of the wafer in the course of processing will be described. The manufacturing process of the semiconductor device has been illustrated in FIG. 12.

The lithography process, which is a core process in the wafer processing process of FIG. 12, comprises the resist coating process for coating with a resist the surface of the wafer having a circuit pattern formed therein in the previous process, the exposing process for exposing the resist, the developing process for developing the exposed resist to obtain the pattern of resist, and the annealing process for stabilizing the developed pattern of the resist.

The electron beam apparatus 4200 of the fourteenth embodiment according to the present invention may be further used in the wafer inspection process of FIG. 12 for inspecting the processed wafer.

The present invention is not limited to those embodiments. For example, in order to accomplish synchronous irradiation against different locations on the sample 4201, the apparatus may includes a plurality of electron beam irradiation and detection systems each comprising the electron gun 4201, the first multi-aperture plate 4203, the primary and the secondary optical systems, the second multi-aperture plate 4211, and the detector 4212, so that a plurality of primary electron beams emitted from a plurality of electron guns may be irradiated against the sample and a plurality of secondary electron beams emanated from the sample may be received by a plurality of detectors. Thereby, the time necessary for the inspection or measurement could be significantly shortened.

As will be understood from the above description, the electron beam apparatus of the fourteenth embodiment according to the present invention may provide the particular effects as follows:

1. Since the apparatus can compensate for the distortion aberration by the primary optical system and reduce the field astigmatism as well, therefore extended region may be irradiated with a plurality of beams thus to carry out the defect inspection or the like of the sample with higher throughput;

2. Since the apparatus can compensate for the distortion by the secondary optical system, as well, therefore there would be no cross talk even when a plurality of electron beams is used with narrow pitch therebetween for irradiating and scanning the sample, and further, since it can increase the transmittance of the secondary electrons thus to allow the signal having higher S/N ratio to be obtainable, a highly reliable line width measurement or the like may be provided; and 3. Since the primary optical system can form an image on the deflection principal plane of the E×B separator 4206, the chromatic aberration of the primary electron beam may be reduced, and when the primary electron beam is formed into a multi-beam, the multi-beam may be converged narrower.

Figure 42:
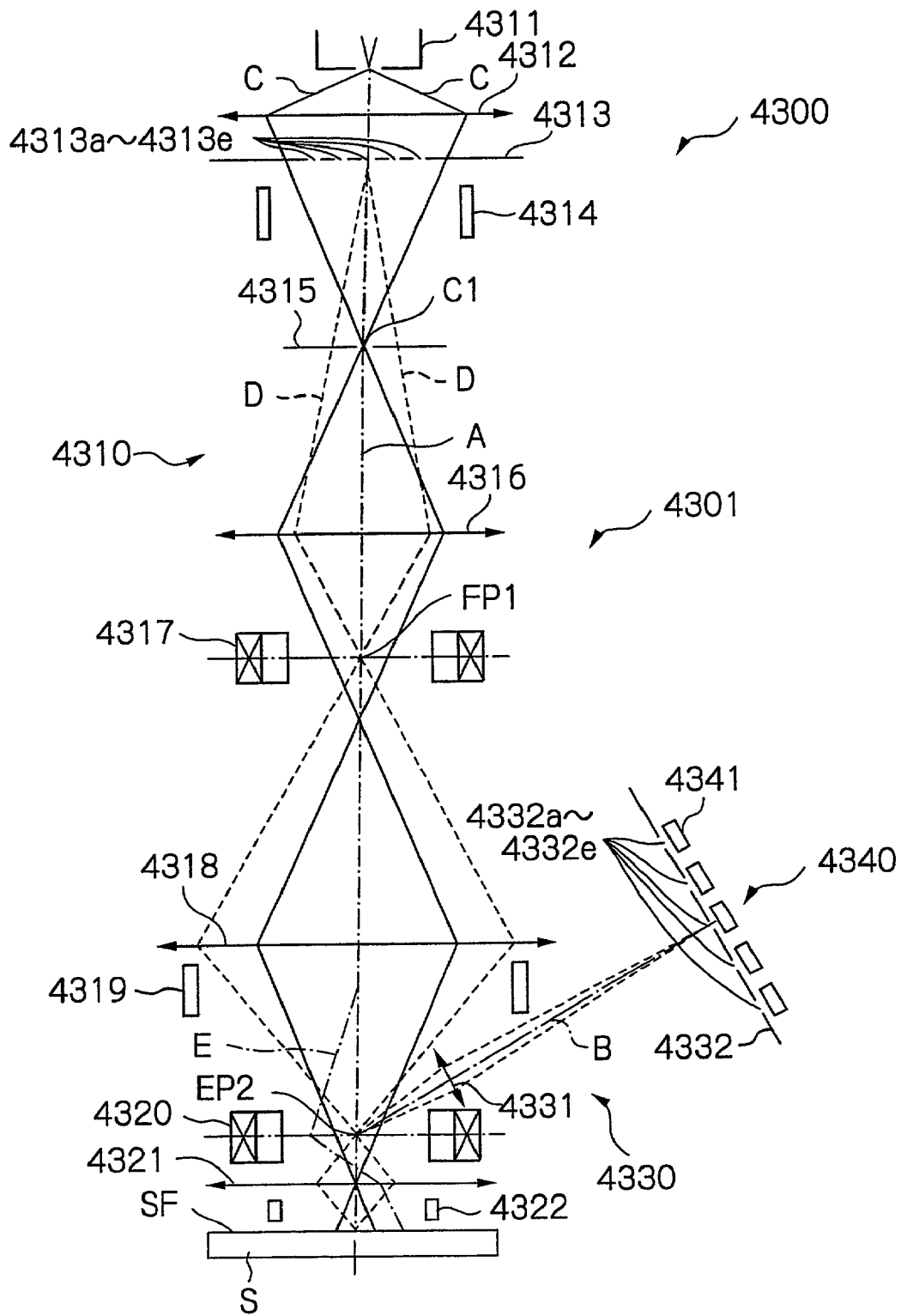
FIG. 42 is a schematic diagram illustrating an optical system in an electron beam apparatus of a 15th embodiment according to the present invention.

An electron beam apparatus 4300 of a fifteenth embodiment according to the present invention will now be described with reference to FIG. 42. FIG. 42 schematically shows an electron beam apparatus 4301 of the fifteenth embodiment of the present invention. This electron beam apparatus 4301 comprises a primary optical system 4310, a secondary optical system 4330 and an inspection apparatus 4340.

The primary optical system 4310, which is an optical system for irradiating an electron beam onto the surface of the sample S (sample surface), comprises: an electron gun 4311 for emitting the electron beam; an electrostatic lens 4312 for deflecting the electron beam emitted from the electron gun; a multi-aperture plate 4313 having a plurality of small apertures arranged two-dimensionally therethrough (FIG. 42 shows only 4313a to 4313e); an electrostatic deflector 4314; an aperture plate 4315; an electrostatic intermediate lens 4316 for converging the electron beam pass through the aperture plate; a first E×B separator 4317; an electrostatic intermediate lens 4318 for converging the electron beam; an electrostatic deflector 4319; a second E×B separator 4320; an electrostatic objective lens 4321; and an electrostatic deflector 4322, which are disposed, as shown in FIG. 42, in order with the electron gun 4311 placed in the top so that the optical axis of the electron beam emitted from the electron gun could be normal to the sample surface SF.

Therefore, the space between the electrostatic objective lens 4321 and the sample S is allowed to be of axial symmetrical configuration, so that the electron beam can be converged to be narrower.

The secondary optical system 4330 comprises an electrostatic magnifying lens 4331 disposed along an optical axis B, which is inclined to and separated from the optical axis A near the second E×B separator 4320 in the primary optical system 4310, and a multi-aperture plate 4332 with a plurality of small apertures arranged two-dimensionally therethrough (FIG. 42 shows only 4332a to 4332e).

The inspection apparatus 4340 comprises a plurality of detectors 4341 each corresponding to each aperture in the multi-aperture plate 4332. It is to be noted that the number and the arrangement of the apertures (4332a or 4332e) in the multi-aperture plate 4332 correspond respectively to the number and arrangement of the apertures (4313a to 4313e) formed in the multi-aperture plate 4313 of the primary optical system. Each component described above may be of well-known one, so the detailed descriptions about their structures will be omitted.

Then, an operation of the electron beam apparatus 4300 configured as above will be described.

An electron beam C emitted from the single electron gun 4311 is converged by the electrostatic lens 4312 to be irradiated onto the multi-aperture plate 4313. The electron beam C goes through a plurality of apertures formed in the multi-aperture plate 4313 to be separated into a plurality of electron beams. This plurality of electron beams forms crossover C1 at the aperture plate 4315 having an aperture. The electron beams, after forming the crossover, advance toward the sample S to be converged by the electrostatic intermediate lens 4316 and another electrostatic intermediate lens 4318 which are disposed on the way, and to be imaged onto a principal plane of the electrostatic objective lens 4321, thus to satisfy the Koehler illumination requirement.

On the other hand, an electron beam D, which forms the respective image of each aperture of the multi-aperture plate 4313, is converged by the electrostatic intermediate lens 4316 to form an image onto the deflection principal plane FP1 of the first E×B separator 4317, and further converged by the electrostatic intermediate lens 4318 to form an image onto the deflection principal plane FP2 of the second E×B separator 4320, and finally forms an image onto the sample surface SF.

The secondary electrons emanated from the sample surface SF are accelerated and converged by an accelerating electric field for the secondary electron applied between the electrostatic objective lens 4321 and the sample surface SF, pass through the electrostatic objective lens 4321, and then image the crossover just at a front side of the deflection principal plane FP2 of the second E×B separator 4320. This imaged secondary electron is deflected by the second separator 4320 to move along the optical axis B and to enter the electrostatic magnifying lens 4331. Then the secondary electron is magnified by the electrostatic magnifying lens 4331 and forms a magnified image at the apertures (4332*a* to 4332*e*) of the multi-aperture plate 4332.

The sample surface SF and the multi-aperture plate 4332 are in an optical conjugate relation for the value of 2 eV of the secondary electron intensity, so that the secondary electrons emanated from the sample surface by the electron beam pass through respective apertures of the aperture plate 4332 corresponding respectively to the respective apertures of the aperture plate 4313 and enter the detector 4341 such that the secondary electrons emanated from the sample surface SF by the electron beam having passed through the aperture 4313*a* of the aperture plate 4313 pass through the aperture 4332*a* of the aperture plate 4332, the secondary electrons emanated from the sample surface SF by the electron beam having passed through the aperture 4313*b* of the aperture plate 4313 pass through the aperture 4332*b* of the aperture plate 4332, and the secondary electrons emanated from the sample surface SF by the electron beam having passed through the aperture 4313*c* of the aperture plate 4313 pass through the aperture 4332*c* of the aperture plate 4332.

A space between each of said plurality of electron beams and the electron beam adjacent thereto can be scanned by controlling the electron beam so as to cause a deflecting scanning motion exhibiting a principal beam trajectory shown by symbol E in FIG. 42, using the electrostatic deflector 4319 and the second E×B separator 4320. To cause the deflecting scanning motion by the second E×B separator, such a voltage waveform may be applied thereto that satisfies a Wien filter requirements of the second E×B separator 4320 and is formed by superimposing the scanning voltage onto the dc voltage Vw as a center voltage, wherein the voltage to allow the electron beam to advance forward is defined as Vw and a magnetic field as Bw, and thereby the two-dimensional scanning could be performed when an eight poles type electrostatic deflector is employed as the electrodes used to generate the electric field of the second E×B separator 4320. Therefore it is unnecessary to install a new deflector on an upper side of the electrostatic object lens 4321, and in addition, both of the E×B separator and the electrostatic deflector can be disposed at their optimum positions respectively.

Then, a problem of so-called a beam blur due to a chromatic aberration which is possibly caused by using a single E×B separator in the prior art, and the solution thereof will be described.

Generally, in the electron beam apparatus using the E×B separator, the degree of aberration is the lowest when the position of an image of the aperture coincides with the deflection principal plane of the E×B separator for the electron beam. Furthermore, the deflection principal plane of the E×B separator and the sample surface are in a conjugate relationship. Accordingly, when an electron beam with a certain energy width enters into the E×B separator, the quantity of deflection of the electron beam with low energy caused by an electric field increases inversely proportional to the energy, but the quantity of deflection caused by the magnetic field increases inversely proportional only to the ½th power of the energy.

On the other hand, in case of the electron beam with high energy, a quantity of deflection of the electron beam along the direction caused by the magnetic field is more than that along the direction caused by the electric field. In this case, if the electrostatic lens is disposed under the E×B separator and said lens had no aberration, there would occur no beam blur, but actually the beam blur occurs because the lens has its aberration. Therefore, with only a single E×B separator being used, it is impossible to avoid causing the beam blur due to the chromatic aberration when the electron beam has a certain energy width.

The present invention comprises both of the first and the second E×B separators 4317 and 4320, and coordinates the electric fields of said two E×B separators so that the directions of the deflection caused by the electric fields of the first E×B separator 4317 and second E×B separator 4320 would be reversed each other on the sample surface, and their absolute values of the magnitude of deflections would be equal. Accordingly, even when the electron beam has a certain energy width, the chromatic aberration due to the E×B separator can be compensated for between the first and the second E×B separators 4317 and 4320.

When the electron beam apparatus 4301 configured as above is used to inspect the sample surface for defects, to measure the line width of the pattern formed on the sample surface and so on, a sample to be inspected is to be set therein and the electron beam apparatus 4301 is to be operated as described above. In this case, the inspection for defects can be performed by producing an image data with a scan signal waveform provided for the electrostatic deflector 4319 and the second E×B separator 4320 and also with an output signal from the detector 4341 for the secondary electron, and by comparing said image data with the other image data produced from another pattern data. Also, the line widths of the pattern can be measured by the use of signal waveform of the secondary electron obtained by scanning the measured pattern at the right angle with the electrostatic deflector 4319 and the second E×B separator 4320.

Furthermore, the alignment accuracy can be evaluated, by forming a pattern produced with a second layer of lithography in the vicinity of a pattern produced with a first layer of lithography so as for these two patterns to have the same distance therebetween as that of the electron beams in a plurality of electron beams of the electron beam apparatus 4301, by measuring the distance between these two patterns, and finally by comparing the measured value with the design value.

In addition, the image obtained by a scanning type electron microscope (SEM) can be displayed on the CRT monitor by connecting the CRT monitor to a part or all of the detector 4341 for the secondary electrons and by inputting the data therefrom together with the scanning signal waveform. This makes it possible for the checker to watch this SEM image to observe defects for determining the types thereof and the like.

Referring to FIG. 42, since the electrostatic deflector 4322 is disposed co-axially between the electrostatic objective lens 4321 and the sample surface SF, a potential contrast can be measured by applying negative voltage to this electrostatic deflector 4322.

Again referring to FIG. 42, the short pulse electron beam can be obtained by providing the electrostatic deflector 4314 with the voltage so as not to deflect the electron beam only for a short period and to deflect the electron beam for the rest period in order to make a blanking of the electron beam so that the deflected electron beam is removed by the aperture 4315. When this short pulse electron beam is entered onto the sample surface SF, so the device on the sample surface is made to be in an operating state, then the potential of the pattern is measured with good time-resolution, the operation analysis of the device on the sample surface can be performed.

Figure 43:
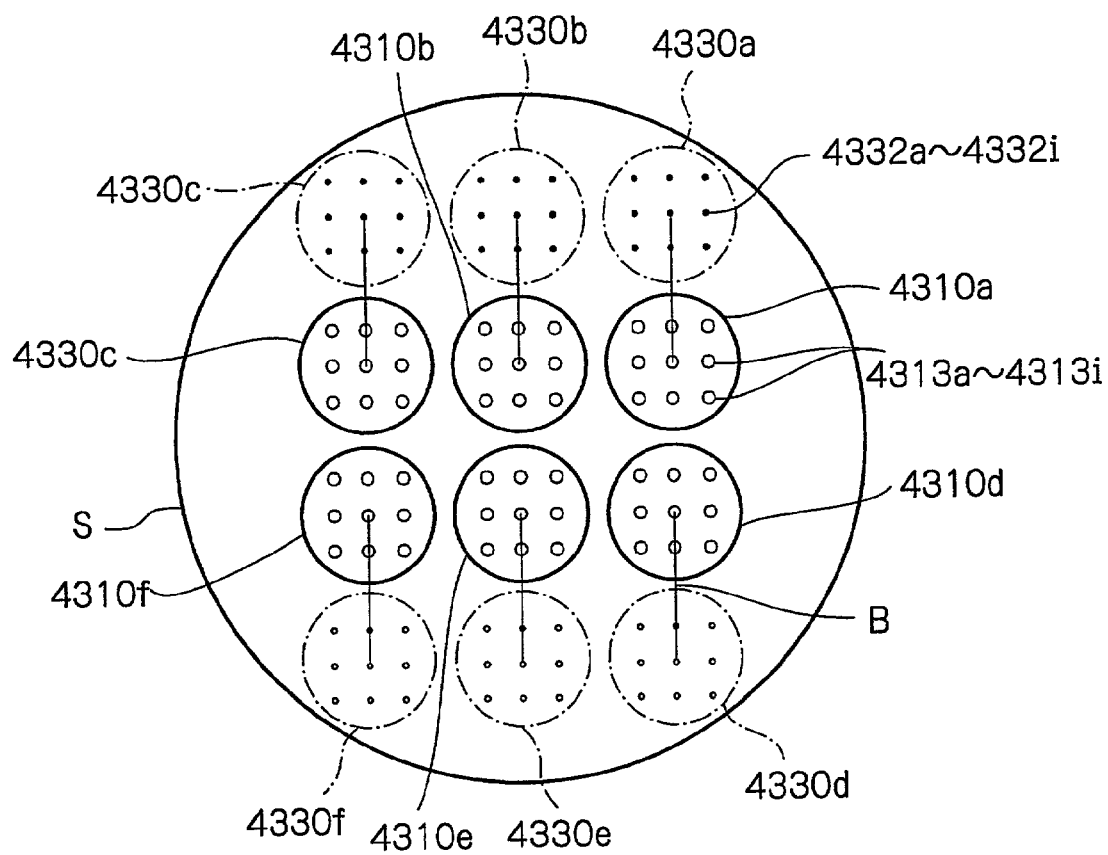
FIG. 43 illustrates a condition where a plurality of optical systems in the electron beam apparatus of FIG. 42 is arranged so as for each of them to be disposed in parallel on a wafer in the array of 2 rows×multiple columns.

FIG. 43 is a plan view illustrating a condition where a plurality of pairs of the primary and the secondary optical systems in the electron beam apparatus configured as described above is arranged on the sample S, in which six pairs of the primary and the secondary optical systems 4310 and 4330 are arranged in an array of 2 rows×3 columns in this embodiment. The circles 4310*a* to 4310*f* shown with solid line represent the maximum outer diameter of the primary optical systems, while the circles 4330*a* to 4330*f* shown with chain line represent the maximum outer diameter of the secondary optical systems respectively. In the present embodiment, the apertures of the multi-aperture plate 4313 in the primary optical system 4310 are arranged in an array of 3 rows×3 columns, and similarly the apertures of the multi-aperture plate 4332 in the secondary optical system 4330 are arranged also in an array of 3 rows×3 columns.

A plurality of pairs of respective optical systems is disposed such that the optical axis B of each secondary optical system 4330 heads toward the outside of the sample along the alignment direction of the column in order not to interfere with each other. The number of the column is preferably three or four, but it may be less than these values, for example, two, or may be four or more.

The electron beam apparatus 4300 of the fifteenth embodiment according to the present invention also can be used in the wafer inspection process of FIG. 12 for inspecting the processed wafers. When the defect inspection method and apparatus of the fifteenth embodiment of the present invention is used in the inspection process, even a semiconductor device having a fine pattern can be inspected with higher throughput, so that a hundred percent inspection may be carried out while allowing the yield of the products to be improved and preventing any faulty products from being delivered.

According to the fifteenth embodiment of the present invention, the following effects may be expected to obtain.

(1) Since a plurality of electron beams is employed, the throughput can be improved.

(2) Since a plurality of E×B separators is employed and arranged such that the positions of the image of the apertures in the aperture plate coincide with respective positions of the E×B separators and the directions of the electron beams deflected by the electric fields of respective E×B separators are reversed each other on the sample surface, the chromatic aberration possibly caused by the E×B separators can be compensated for and the electron beam can be converged narrower, so that higher inspection accuracy can be provided.

(3) Since the electron beam is controlled to make a scanning motion by superimposing the scanning voltage on the electric field of the second E×B separator, the second E×B separator is allowed to work also as an electrostatic deflector, which means that there is no necessity to install a new electrostatic deflector above the electrostatic objective lens 4321 and both of the E×B separator and the electrostatic deflector can be disposed in their optimum positions respectively. This makes it possible both to improve the inspection efficiency for the secondary electron and to reduce the deflection aberration, and further to greatly shorten the paths of the secondary optical system.

(4) Since a plurality of pairs of the primary and the secondary optical systems in the electron beam apparatus is arranged on the sample, a plurality of samples can be inspected at one time, and thereby the throughput can be improved more.

(5) since the electrostatic deflector 4322 is disposed co-axially between the electrostatic objective lens 4321 and the sample surface SF, a potential contrast can be measured by applying negative voltage to this electrostatic deflector 4332.

(6) When a function for blanking the electron beam is provided to control the voltage of the electrostatic deflector 4314, to generate a short pulse electron beam, to make the device on the sample surface in an operating state, and to measure the potential of the pattern with good time-resolution, thereby the operation analysis of the device on the sample surface can be performed.

FIG. 44A is a schematic diagram illustrating an electron beam apparatus 4400 according to a sixteenth embodiment of the present invention, wherein an electron beam emitted from an electron gun 4401 is focused by a condenser lens 4402 to form a cross-over at a point 4404. A first multi-aperture plate 4403 having a plurality of small apertures is disposed beneath the condenser lens 4402, and thereby a plurality of primary electron beams is formed. Each of the plurality of primary electron beams formed by the first multi-aperture plate 4403 is contracted by a demagnification lens 4405 to be projected onto a point 4415. After having been focused onto the point 4415, the primary electron beam is focused by an objective lens 4407 onto a sample 4408. The plurality of primary electron beams emitted through the first multi-aperture plate 4403 is deflected by a deflector 4419 disposed between the demagnification lens 4405 and the objective lens 4407 so as to simultaneously scan a surface of the sample 4408 loaded on an x-y stage 4420.

In order to eliminate an effect of field curvature aberration possibly caused by the reduction lens 4405 and the objective lens 4407, the first multi-aperture plate 4403 is provided with a plurality of small apertures 4433 disposed therein along a circle such that projected points thereof onto x-axis may be equally spaced by Lx, as shown in FIG. 44B.

A plurality of spots on the sample 4408 is irradiated by the plurality of focused primary electron beams, and secondary electron beams emanated from the plurality of irradiated spots are attracted by an electric field of the objective lens 4407 to be focused narrower, deflected by an E×B separator 4406, and then introduced into a secondary optical system. A secondary electron image is focused on a point 4416 which is closer to the objective lens 4407 than the point 4415. This is because the secondary electron beam has only a few eV of energy while each of the primary electron beams has 500 eV of energy on the sample surface.

The secondary optical system includes magnifying lenses 4409 and 4410, and the secondary electron beam, after having passed through these magnifying lenses, passes through a plurality of apertures 4443 formed on a second multi-aperture plate 4411, and is focused on a plurality of electron detectors 4412. As shown in FIG. 44B, each of the plurality of apertures 4443 formed on the second multi-aperture plate 4411 disposed in front of the detectors 4412 corresponds to each of the plurality of apertures 4433 formed on the first multi-aperture plate 4403 in a manner of one-by-one basis. Each of the plurality of detectors 4412 is disposed so as to face to each of the plurality of apertures of the second multi-aperture plate 4411.

The detector 4412 converts a detected secondary electron beam into an electric signal representative of intensity thereof. The electric signal output from each of the detectors 4412, after having been amplified respectively by an amplifier 4413, is converted into an image data by an image processing section 4414. Since the image processing section 4414 is further supplied with a scanning signal SS for deflecting the primary electron beam, the image processing section 4414 can generate an image representative of the surface of the sample 4408. Comparing this image with a reference pattern allows any defects of the sample 4408 to be detected. Although being separated during process, a build-up width detecting section 4430 operates in a stage for determining an excitation voltage for initial focusing. The operation thereof will be described later.

Further, a line width of a pattern on the sample 4408 can be measured in such a way that the pattern to be measured of the sample 4408 is moved by a registration to a proximity of an optical axis of the primary optical system, and the pattern is line-scanned to extract a line width evaluation signal, which is in turn appropriately calibrated.

In this regard, when the primary electron beams passed through the apertures 4433 of the first multi-aperture plate 4403 are focused on the surface of the sample 4408, and the secondary electron beams emanated from the sample 4408 are formed into an image on the detectors 4412, much attention should be paid in order to minimize the affection by the three aberrations, i.e., a distortion caused by the primary optical system, an on-axis chromatic aberration and an astigmatism in the field of view. As for a relation between the spacing among the plurality of primary electron beams and the secondary optical system, if the space between respective primary electron beams is determined to be greater than the aberration of the secondary optical system, then the crosstalk among a plurality of beams can be eliminated.

The objective lens 4407 is, as shown in FIG. 44C, a uni-potential lens, wherein a positive high voltage $V_0$ volt is applied to a center electrode of the objective lens 4407 from a power supply 4428 and an excitation voltage $\pm\Delta V_0$, which is low voltage near to earth potential, is applied to an upper and an under electrodes of the objective lens 4407 from a power supply 4429 in order to focus the primary electron beam onto the surface of the sample 4408.

Each of the electron gun 4401, the deflector 4417 for aligning the axes, the first aperture plate 4403, the condenser lens 4402, the deflector 4419, the Wien filter or the E×B separator 4406, the objective lens 4407, an axisymmetric electrode 4423, and the secondary electron detector 4412 is accommodated in an optical column 4426 of appropriate size to configure a complete electron beam scanning/detecting system. It is to be noted that the initial focusing of the electron beam scanning/detecting system may be executed by fixing the excitation voltage $\Delta V_0$ to be ×10 Volts while varying the positive voltage $V_0$.

AS described above, the electron beam scanning/detecting system in the optical column 4426 scans a chip pattern on the sample, detects the secondary electron beam emanated from the sample as a result of scanning, and outputs the electric signal representative of the intensity thereof. In practice, since a plurality of chip patterns is formed on the sample surface, a plurality of electron beam scanning/detecting systems (though not shown) each having the same configuration as that shown in FIG. 44A is arranged in parallel so as for the respective systems to be spaced by integer times of a chip size on the sample.

To further describe the electron beam scanning/detecting system, the electric signal output from the electron detector 4412 is converted in the image processing section 4414 into a binary information, which is then converted into the image data. As a result, the image data of a circuit pattern formed on the sample surface is obtained, and the obtained image data is stored in an appropriate storage means and compared with a reference circuit pattern. Thereby the defect of the pattern formed on the sample or the like can be detected.

As the reference circuit pattern used to be compared with the image data representative of the circuit pattern on the sample surface, various kinds of data may be employed. For example, an image data obtained from a CAD data used to fabricate the circuit patter to which the scanning has been applied to generate said image data.

In the electron beam apparatus shown in FIG. 44A, a value of the excitation voltage $\pm\Delta V_0$ to be applied to the upper or the under electrode of the objective lens 4407 is determined under control of a control device such as CPU (though not shown) as follows:

At first, a location where a pattern edge parallel with a first direction and another pattern edge parallel with a second direction orthogonal to said first direction exist on a single arbitrary circuit pattern formed on the surface of the sample 4408 is read out, for example, from the pattern data and is identified.

Then, the primary electron beam is used by the deflector 4419 and the E×B separator 4406 to scan the pattern edge parallel with the first direction in the second direction; the electric signal representative of the intensity of the secondary electron beam emanated as a result of the scanning operation is obtained from the electron detector 4412; and then a build-up width p(μm) of said electric signal is measured in the build-up width detection section 4430. Similarly, the primary electron beam is used by the deflector 4419 and the E×B separator 4406 to scan the pattern edge parallel with the second direction in the first direction; the electric signal representative of the intensity of the secondary electron beam emanated as a result of the scanning operation is obtained from the electron detector 4412; and then the build-up width p of said electric signal is measured in the build-up width detection section 4430. This operation is repeated at least three times for different voltage values by varying the voltage $\pm\Delta V_0$.

A control device (not shown) produces curves A and B of FIG. 45A based on the data from the build-up width detection section 4430. The curve A shows a relation between the build-up width pμm and each of $\pm\Delta V$ for the pattern edge parallel with the first direction. The curve B shows a relation between the build-up width pμm and each of $\pm\Delta V_0$ for the pattern edge parallel with the second direction.

As shown in the graph of FIG. 45B, the "build-up width R" of the electric signal is represented as a distance of scanning R(μm) during which the electric signal varies from 12% to 88% of its maximum value when said electric signal is measured by scanning the pattern edge parallel with the first (or second) direction in the second (or first) direction under the condition where the excitation voltage $\pm\Delta V_0$ is fixed.

The curve A of FIG. 45A shows that the build-up width p is minimum, that is, the build-up is the sharpest when the excitation voltage $\pm\Delta V_0$ is $-\Delta V_0(x)$. Similarly, the curve B shows that the build-up width is minimum, that is, the build-up is the sharpest when the excitation voltage $\pm\Delta V_0$ is $\pm\Delta V_0(x)$. Accordingly, the focusing condition of the objective lens 7, that is, the value of the voltage $\pm\Delta V_0$ to be applied to the upper and the under electrodes is preferably set to be equal to $\{-\Delta V_0(x)+\Delta V_0(y)\}/2$.

Since the excitation voltage $\pm\Delta V_0$ varies only within a range of 0 to $\pm 20$ Volts, the setting operation of the objective lens 4407 was actually tried in a manner described above and could be finished in high speed within 10 micro-seconds, and it took only 150 micro-seconds to obtain the curves A and B of FIG. 45A.

It is to be apprehended that there is no need to make a measurement for a number of $\pm\Delta V_0$ values, but only $-\Delta V(1)$, $+\Delta V(1)$ and $+\Delta V(3)$ should be set as the three voltage values of $\pm\Delta V_0$ to measure the build-up width p so as to determine the curves A and B by hyperbolic approximation, and thereby to determine the minimum values of the build-up width, i.e., $-\Delta V_0(x)$ and $+\Delta V_0(y)$. In this case, the measurement may be completed within about 45 microseconds.

As described above, the curves A and B of FIG. 45A approximate to quadratic curve or hyperbola. Assuming that the build-up width is p(μm), and the objective lens's voltage $\pm\Delta V_0$ is q(volts), the graphs A and B can be represented as:

$$(p^2/a^2)-(q-c)^2/B^2=1$$

where, a, b and c are constants. When three q (voltage $\pm\Delta V_0$) values, $q_1$, $q_2$ and $q_3$, and p (build-up width) values corresponding thereto, $p_1$, $p_2$ and $p_3$ are substituted for the corresponding terms in the above equation, three equations (1) to (3) can be obtained as below:

$$(p_1^2/a^2)-(q_1-c)^2/b^2=1 \quad (1)$$

$$(p_2^2/a^2)-(q_2-c)^2/b^2=1 \quad (2)$$

$$(p_3^2/a^2)-(q_3-c)^2/b^2=1 \quad (3)$$

From these equations, the values of a, b and c can be calculated and when q=c, the minimum value may be obtained.

As described above, the excitation voltage $\Delta V_0(x)$ to be applied to the objective lens for the pattern edge parallel with the first direction, which provides the smallest build-up width p, can be determined by three lens conditions. Quite similarly, the excitation voltage $\Delta V_0(y)$ to be applied to the objective lens for the pattern edge parallel with the second direction can be determined.

As is shown in FIG. 45A by the curves A and B, the build-up width obtained when the pattern edge extending along the first direction is scanned in the second direction is typically different from that obtained when the pattern edge extending along the second direction is scanned in the first direction. In this case, it is necessary to perform an astigmatic correction by further installing an eight-pole astigmatic correcting lens 4421 (see FIG. 44) and adjusting the voltage to be applied to said lens 4421 so that the build-up of the electric signal from the electron detector 4415 generated by scanning the pattern edges in the first and the second directions may be made further smaller. When there are little astigmatism, since either of $\Delta V_0(x)$ or $\Delta V_0(y)$ is required to be determined, only either of curve A or B may be determined.

As described above, after the focusing operation of the electron beam scanning/detecting system having been finished, the process for evaluating the sample 4408 will be set about. In the present method, since the focusing condition is determined by using not an optical Z sensor but the electronic optical system, it is advantageous in that the correct focusing condition may be determined even if the sample is charged with electricity.

When other optical column (not shown) each having the similar configuration to that of the optical column 4426 including the electron beam scanning/detecting system are arranged parallel with the optical column 4426 so as for each of them to be spaced from each other by a distance of integer times of the chip size on the sample 4408, it is necessary to perform the focusing operation in each optical column so as for the primary electron beam to be focused on the sample. Such a focusing operation, however, can be performed almost simultaneously, so the throughput budget does not take much.

Then a semiconductor device manufacturing method according to the present invention will now be described. The semiconductor device manufacturing method according to the present invention is performed by using the electron beam apparatus described above in the semiconductor device manufacturing method shown in FIGS. 12 and 13 described above.

Figure 44:
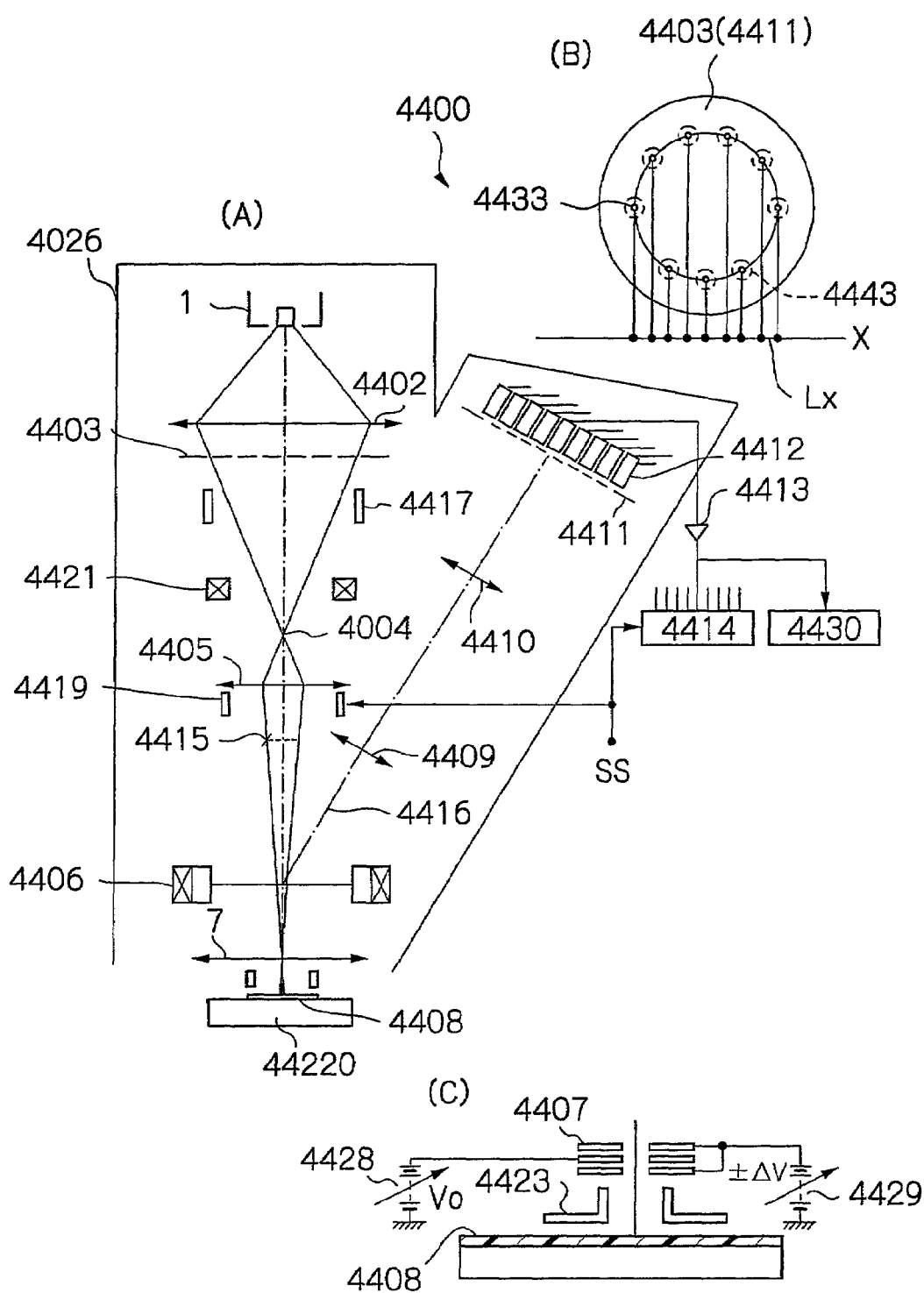
FIG. 44A is a view showing a brief configuration of an electron beam apparatus according to a 16th embodiment of the present invention.
FIG. 44B is a plan view showing apertures of a multi-aperture plate, FIG. 44C a diagram showing structure for applying voltage to an objective lens.

In the semiconductor device manufacturing method according to the present invention, any defects on the wafer can be surely detected since an image with reduced distortion and blur may be obtained even for the semiconductor device with finer pattern by using the electron beam apparatus having described with reference to FIG. 44 not only in a process in the course of processing (wafer inspection process) but also in a chip inspection process for inspecting the finished chip.

Using the electron beam apparatus according to the present invention in the wafer inspection process and the chip inspection process of FIG. 12 allows even the semiconductor device with finer pattern to be inspected with high throughput, which allows a hundred percent inspection and an improvement in yield of the products, and also allows to prevent the defective product from being delivered.

The electron beam apparatus 4400 according to the sixteenth embodiment of the present invention provides such operational effects as below:

(1) Since no optical sensor is necessary for measuring a height of the sample surface, spacing between the objective lens and the sample can be designed under optimum conditions with only electronic optical system;

(2) Since the focusing operation of the electron beam scanning/detecting system can be performed only with the adjustment in low voltage, the setting time may be made shorter, that is, the focusing operation can be performed in short time;

(3) If desired, the astigmatic correction may be performed in short time during focusing operation; and (4) Since the sample in the course of process can be evaluated in short time, the yield of the device manufacturing may be improved.

Figure 46:
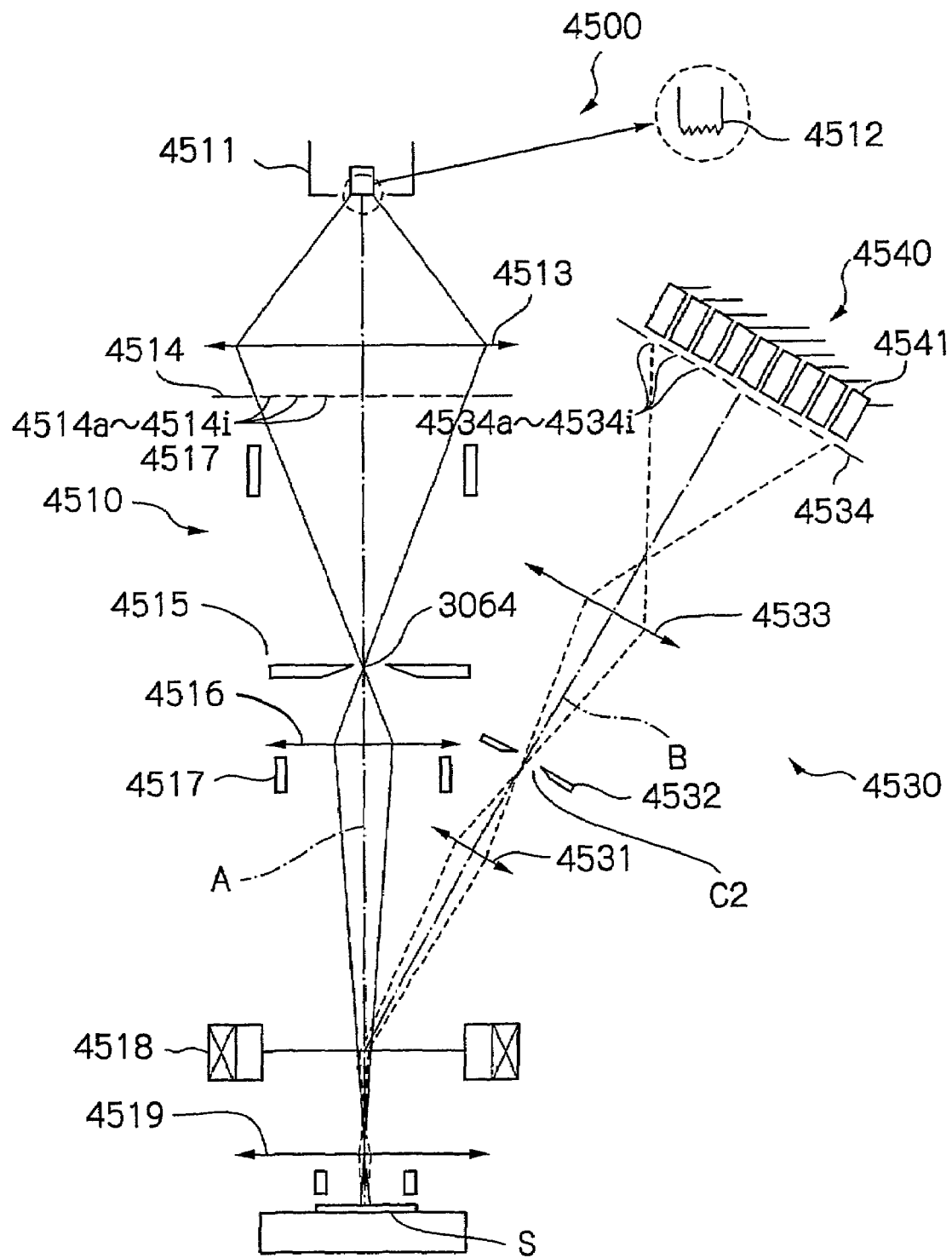
FIG. 46 is a diagram illustrating a schematic configuration of an optical system of an electron beam apparatus according to a 17th embodiment of the present invention.

Now, a description will be given regarding an electron beam apparatus 4500 of Embodiment 18 with reference to FIGS. 46 and 47. FIG. 46 schematically illustrates an electron beam apparatus 4501 of Embodiment 18. The electron beam apparatus 4501 comprises a primary optical system 4510, a secondary optical system 4530, and a detection device 4540. The primary optical system 4510 is composed of an optical system for irradiating the surface of a sample S with an electron beam.

This optical system comprises an electron gun 4511 for emitting electron beams, an electrostatic lens 4513 for demagnifying the electron beams emitted from the electron gun, a first aperture plate 4514 with a plurality of small apertures formed in a two-dimensional arrangement (only small apertures 4514a to 4514i, inclusive, being illustrated in FIG. 46), an open aperture 4515, an electrostatic lens 4516 for demagnifying the electron beams passed through the first aperture plate, an electrostatic deflector 4517, an ExB separator 4518, and an electrostatic objective lens 4519. As shown in FIG. 46, these components are arranged in such a manner that the electron gun 4511 is disposed on top of all the other components in the order as shown in FIG. 46 and that the optical axis A of the electron beams emitted from the electron gun is disposed so as to extend in the direction perpendicularly to the sample S. Inside the electron gun 4511, there is formed a projection portion 4512 that is made of a single crystal, LaB$_6$ cathode, polished into a form having a number of projections.

Figure 47:
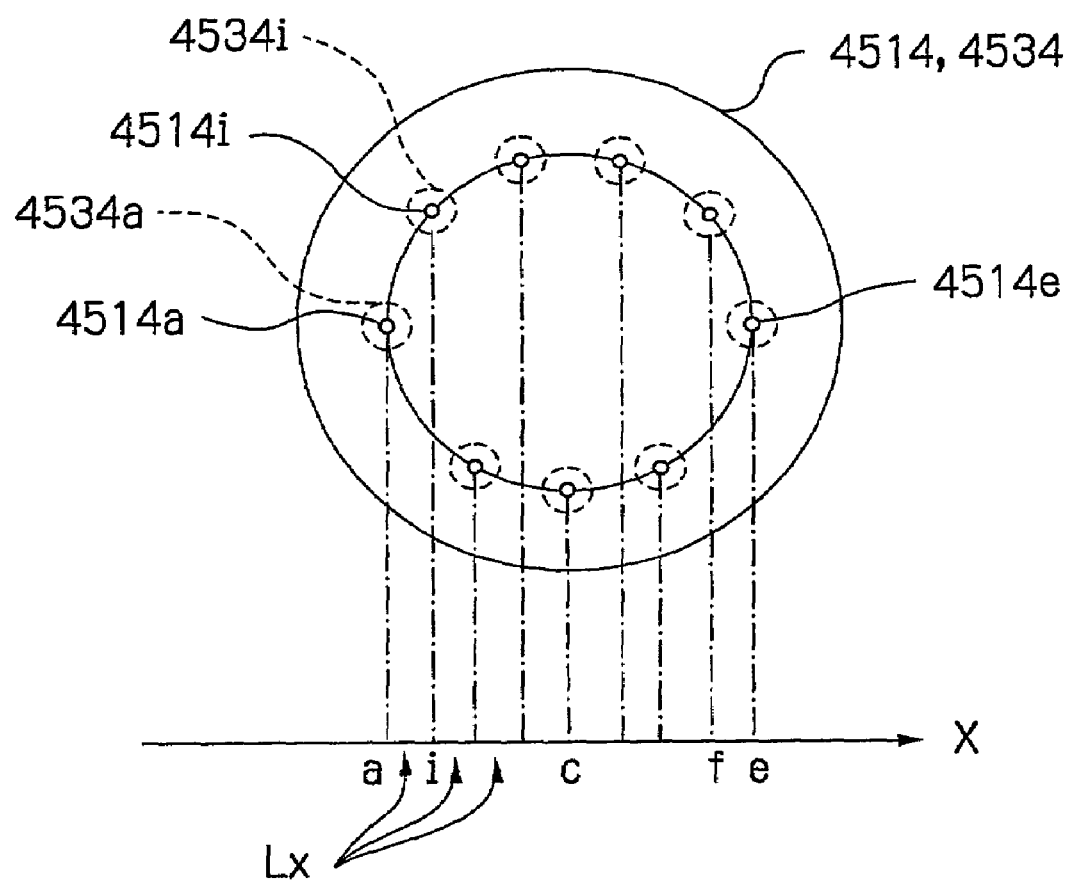
FIG. 47 is a plan view illustrating respective arrangements of apertures formed in a first aperture plate and a second aperture plate of the electron beam apparatus of FIG. 46.

The first aperture plate 4514 is provided with a plurality of the small apertures on its circumference, as shown in FIG. 47, so as for the images projected in the X-direction to be disposed at an equal interval Lx, in order to undergo no influence of an aberration caused by a curvature of the image plane of the electrostatic lenses 4513 and 4516 as well as the electrostatic objective lens 4519.

The secondary optical system 4530 includes a first electrostatic magnifying lens 4531, an open aperture 4532, a second electrostatic magnifying lens 4533, and a second aperture plate 4534 with a plurality of small apertures (only small apertures 4534a–4534i, inclusive, being illustrated in FIG. 46) disposed in a two-dimensional arrangement. These components are arranged in the above order along the optical axis B inclined with respect to the optical axis A in the vicinity of the E×B separator 4518.

The detection device 4540 is provided with a detector 4541 for each aperture of the second aperture plate 4534. The number and arrangement of the small apertures (as indicated by broken line in FIG. 47), e.g., 4534a to 4534e, of the second aperture plate 4534 are adjusted so as to agree with the number and arrangement of the small apertures (as indicated by solid line in FIG. 47), e.g., 4514a to 4514e, of the first aperture plate 4514. Each of the structuring elements may be known and its detailed description will be omitted herein.

Then, a description will be given regarding a standard mode in the electron beam apparatus 4500 having the configuration as described above. In this electron beam apparatus, electron beams C emitted from the number of the projection portions 4512 of the single electron gun 4511 are converged with the electrostatic lens 4513 and then irradiated on the first aperture plate 4514. The electron beams C are formed into multi-beams by allowing the electron beams C to pass through the small apertures (e.g., 4514a to 4514e) formed in the first aperture plate 4514. The multi-beams form each a crossover image C1 by means of the open aperture 4515. The crossover multi-beams travel toward the sample S and converged with the electrostatic intermediate lens 4516 disposed on the way, followed by forming an image on the main plane of the electrostatic objective lens 4519 so as to meet with Keller's illumination conditions. The multi-beams with the image formed then produce a reduced image on the sample and the surface of the sample is then scanned with the electrostatic deflector and a deflector of the E×B separator 4518.

The secondary electron beams emitted from the sample S are accelerated and converged by the accelerating electric field for the secondary electrons, applied between the electrostatic objective lens 4519 and the sample S, followed by passing through the electrostatic objective lens 4519 and entering into the first electrostatic magnifying lens 4531 after being deflected with the E×B separator 4518 so as to travel along the optical axis B. The secondary electron beams are then magnified with the first electrostatic magnifying lens 4531 and form a crossover image C2 on the open aperture 4532. The secondary electron beams that formed the image are then magnified with the electrostatic magnifying lens 4533 and form an image at each of the small apertures (e.g., 4534a to 4534e) of the second aperture plate 4534. The magnification factor of the secondary optical system can be decided by the two electrostatic magnifying lenses 4531 and 4533.

As shown in FIG. 47, the secondary electron beams emitted at the surface of the sample by means of the electron beams scanning are delivered to the detector 4541 after passage through each of the small apertures of the second aperture plate 4534 corresponding to the respective small apertures of the first aperture plate 4514. More specifically, for example, the secondary electron beams emitted from the sample S by means of the electron beams passed through the small aperture 4514a of the first aperture plate 4514 is delivered to the detector 4541 through the corresponding small aperture 4534a of the second aperture plate 4534.

Likewise, the secondary electron beams emitted from the sample S by means of the electron beams passed through the small aperture 4514b of the first aperture plate 4514 is then delivered on the detector 4541 through the corresponding small aperture 4534b of the second aperture plate 4534. The electron beam emitted from the sample S by means of the electron beams passed through the small aperture 4514c of the first aperture plate 4514 is likewise delivered to the detector 4541 in substantially the same manner as the secondary electron beams emitted from the sample S by means of the electron beams passed through the corresponding small aperture 4514a or 4514b of the first aperture plate 4514. The remaining secondary electron beams can be said true.

In order to allow changes from the standard mode to the high resolution mode, it is required to alter a scanning width and a magnification of an image. The scanning width can be altered by adjusting a degree of sensitivity to deflection per bit of the electrostatic deflector 4517 and the deflector of the E×B separator 4518. If the scanning width would become narrower than that of the standard mode, however, a gap of scanning may be caused to happen between each of the beams of the multi-beams. Further, in the secondary optical system, the intervals of the beam images result in disagreement with the intervals of the detectors.

The problem with the formation of the scanning gap between the beams can be solved by varying the rate of reduction from the first aperture plate 4514 to the sample S so as to correspond with a variation in a dimension of a pixel by subjecting the electrostatic lens 4516 and the electrostatic objective lens 4519 to zoom operation. The Keller's illumination conditions to form the crossover image C1 on the principal plane of the electrostatic objective lens 4519 are adjusted so as to be satisfied in the standard mode only, but not in the high-resolution mode.

As the measure against the problem that the interval of the beam images fails to agree with the dimension of the interval between the detectors in the secondary optical system, the principal ray of the secondary electrons emitted from each of the multiple beams from the sample is delivered to the corresponding small aperture of the secondary aperture plate by fixing the position and dimension of the aperture 4532 of the secondary optical system and varying an excitation voltage of the electrostatic magnifying lens 4533. In other words, the magnification factor is adjusted by the electrostatic magnifying lens 4533 of the secondary optical system so as to comply with the conditions for focusing the crossover image on the aperture 4532. Further, the sample can be evaluated on the basis of two kinds of dimensions of the image by subjecting the rate of reduction of the multi-beams to zoom operations of the electrostatic lens 4516 and the electrostatic objective lens 4519 as well as by altering the rate of magnification of the electrostatic magnifying lenses 4531 and 4533 of the secondary optical system in association with the zoom operations.

As to the relation between a demagnification ratio of the multi-beam in the primary optical system and a magnification ratio in the electrostatic lens of the secondary optical system, in specific, assuming that in FIG. 46, a dimension between the apertures (for example, the distance between 4514a and 4514b) is 1 mm and the demagnification ratio of the multi-beam in the primary optical system is 1/100, the distance between the beam going out of the aperture 4514a and that out of the aperture 4514b is 10 µm. When the magnification ratio of the secondary optical system is 500, the distance between the apertures 4534a and 4534b is 5 mm.

When the demagnification ratio of the multi-beam in the primary optical system is changed to be 1/200, the distance between the apertures 4534a and 4534b may be kept to be 5 mm by setting the magnification ratio of the secondary optical system to be 500×2=1000, and thereby the secondary electron can be detected without changing the distance between the apertures 4534a and 4534b. This feature is advantageous in that the beam dimensions, the beam current or the scanning width can be changed by varying the demagnification ratio of the multi-beam in the primary optical system. This allows to perform the evaluation with high resolution at the sacrifice of low throughput, or the evaluation with high throughput at the sacrifice of low resolution.

Further, the cross-over image is formed on the principal plane of the objective lens in a mode with high throughput and low resolution. In specific, for example, in the apparatus having a mode with the resolution of 50 nm and the throughput of 8.8 min/cm$^2$ and another mode with the resolution of 100 nm and the throughput of 33 sec/cm$^2$, the cross-over image is set on the principal plane of the objective lens in the former mode.

The electron beam apparatus 4500 according to the seventeenth embodiment of the present invention (FIG. 46) may be preferably applied to the semiconductor device manufacturing method shown in FIGS. 12 and 13. That is, using the defect inspection method and apparatus according to the eighteenth embodiment of the present invention in the inspection process of the present manufacturing method allows even the semiconductor device with finer pattern to be inspected with high throughput, which allows a hundred percent inspection and an improvement in yield of the products, and also allows to prevent the defective product from being delivered.

The electron beam apparatus 4500 of the embodiment 17 according to the present invention can demonstrate the effects as follows:

(1) As an image of an optional magnification can be formed without causing any scanning gap, both of the standard mode and the high-resolution mode can be used.

(2) Even if the rate of magnification would be changed, the image dimension can be adjusted so as to substantially correspond to the beam dimension.

(3) In the standard mode, the Keller illumination conditions of the primary optical system can be met. On the other hand, even in the high-resolution mode, a deviation from the Keller's illumination conditions of the primary optical system can be rendered small and an increase in aberration is not caused so much.

(4) As the aperture is disposed in the position in which the secondary electrons emitted from the sample in the direction perpendicular to the sample plane crosses the optical axis of the secondary optical system, the secondary electrons having no difference in strength between the multi-beams can be detected even if the mode would be changed.

Figure 48:
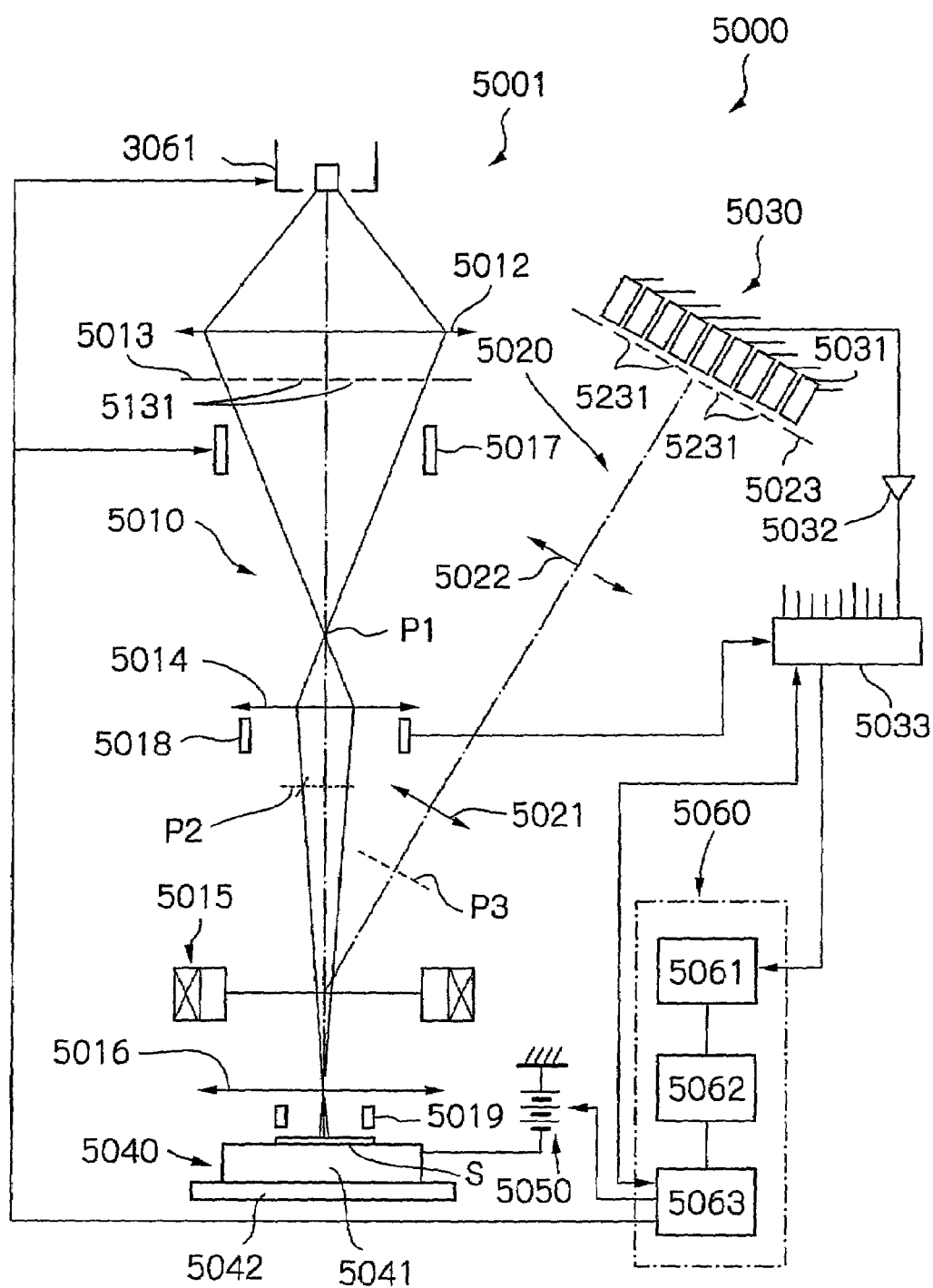
FIG. 48 is a diagram illustrating a schematic configuration of an electron beam apparatus according to an 18th embodiment of the present invention.

Then, a description will be given regarding the electron beam apparatus 5000 according to Embodiment 19 of the present invention with reference to FIGS. 48 and 49, which schematically illustrate an electron beam apparatus 5001 of Embodiment 19. The electron beam apparatus 5000 comprises a primary electron-optical system (hereinafter referred to as "the primary optical system") 5010, a secondary electron-optical system (hereinafter referred to as "the secondary optical system") 5020, and a detection system 5030.

The primary optical system 5010 is an optical system that irradiates the surface of an object of evaluation (hereinafter referred to as "the sample") S such as a wafer or the like with an electron beam, which comprises an electron gun 5011 for emitting electron beams, or electron beams, a condenser lens 5012 for converging the primary electron beams emitted from the electron gun 5011, a first multi-aperture plate 5013 with a plurality of apertures formed therein, a reducing lens 5014, an E×B separator 5015, and an objective lens 5016. These elements are disposed in this order, as shown in FIG. 48, with the electron gun 5011 disposed on top. Reference numerals 5017 and 5018 designate each a deflector for scanning the primary electron beams and reference numeral 5019 designates an axially symmetrical electrode.

The secondary optical system 5020 comprises magnifying lenses 5021 and 5022 and a second multi-aperture plate 5023, which are disposed along the optical axis inclined with respect to the optical axis of the primary optical system. The detection system 5030 includes a detector 5031 disposed for each of the apertures 5231 of the second multi-aperture plate 5023 and an image forming portion 5033 connected to each of the detectors through an amplifier 5032. For the primary optical system 5010, the secondary optical system 5020 and the detection system 5030, there can be used those having the structure and function of each of the structuring elements known to the art, so that a more detailed description of those structuring elements is omitted herefrom. Moreover, the apertures 5131 of the first multi-aperture plate 5013 are formed so as to correspond to the apertures 5231 of the second multi-aperture plate 5023. In FIG. 49, the apertures 5131 as indicated by solid line are illustrated to be smaller in size than the apertures 5231 as indicated by broken line.

The sample S is detachably held on a stage device 5040 through a holder 5041 by means of a conventional technique, and the holder 5041 is held with a XY-stage 5042 so as to be movable in the orthogonal direction.

The electron beam apparatus 5001 is further provided with a retarding voltage applying device (hereinafter referred to as "the applying device") 5050 electrically connected to the holder 5041, and a charging state investigating and retarding voltage determining system (hereinafter referred to as "the investigating and determining system") 5060. The investigating and determining system 5060 comprises a monitor 5061 electrically connected to the image forming portion 5033, an operator 5062 connected to the monitor 5061, and a CPU 5063 connected to the operator 5062. Further, the CPU 5063 is arranged to supply a signal to the applying device 5050 and the deflector 5017.

Then, a description will be given regarding the operations of the electron beam apparatus of embodiment 20. The primary electron beam emitted from the electron gun 5011 is converged with the condenser lens 5012 forming a cross-over image at a point P1. The electron beam passed through the aperture 5131 of the first multi-aperture plate 5013 is converted into plural primary electron beams by means of the plural apertures 5131. The primary electron beams formed by the first multi-aperture plate 5013 are reduced with the reducing lens 5014 and projected on a point P2. After focused on the point P2, the primary electron beams are then focused on the surface of the sample S with the objective lens 5016. The plural primary electron beams are then deflected with the deflector 5018 disposed between the reducing lens 5014 and the objective lens 5016 so as to concurrently scan the top surface of the sample.

Figure 49:
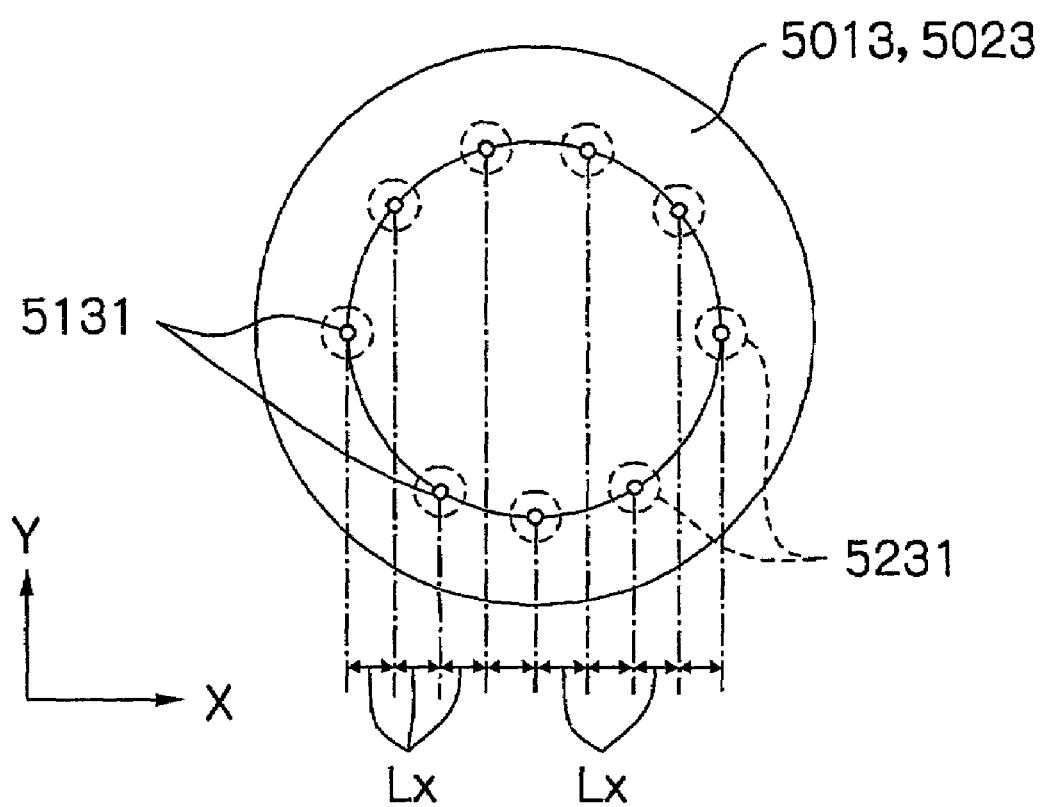
FIG. 49 a plan view illustrating a positioning relation among apertures formed in a multi-aperture plate used in a primary optical system of the electron beam apparatus of FIG. 48.

In order to eliminate the influences from the aberration caused by the field curvature of each of the reducing lens 5014 and the objective lens 5016, the plural apertures 5131 and 5231 of the first and second multi-aperture plates 5013 and 5016 are disposed on the circumference around the optical axis of the optical system, respectively, and the distance Lx of each of the adjacent apertures is arranged so as to become equal to each other, as shown in FIG. 49, when projected in the X-direction.

The plural primary electron beams focused are irradiated on the points on the sample S, and the secondary electrons emitted from the points thereof are converged slenderly by the attraction of the electric field of the objective lens 5016 and then deflected with the E×B separator 5015, followed by entering into the secondary optical system 5020. The images of the secondary electrons are focused on a point P3 closer to the objective lens than the point P2. This is because the secondary electron beam has only the energy of several eV, compared with each of the primary electron beams having an energy as high as 500 eV.

The image of the secondary electron is allowed to form an image on the detector 5031 disposed for each of the apertures 5231 of the second multi-aperture plate 5023 by means of the magnifying lenses 5021 and 5022. Therefore, the secondary electron image is detected with the respective detectors 5031. Each of the detectors 5031 converts the secondary electron image detected into an electric signal representative of its intensity. The electric signal generated from each of the detectors is amplified with the corresponding amplifier 5032 and delivered to the image forming portion 5033 where the electric signal is converted into an image data. To the image forming portion 5033 is fed a scanning signal for deflecting the primary electron beams, and an image forming portion displays an image representing the plane of the sample S. This image is compared with the reference pattern to detect a defect of the sample S.

Further, the sample S is transferred to the position close to the optical axis of the primary optical system 5010 by means of registration and the line scanning, or scanning, is performed on the surface of the sample to extract a signal for use in evaluating the line width of the pattern formed on the surface thereof. By calibrating the signals in an appropriate way, the line width of the pattern can be measured.

It is to be noted herein that it is necessary to draw a special attention to minimize the influences caused by three aberrations including distortion caused by the primary optical system, axial chromatic aberration, and field astigmatism, when the primary electron beams passed through the apertures of the first multi-aperture plate 5013 are focused on the top surface of the sample S and the secondary electron beams emitted from the sample S are focused to form an image on the detector 5031.

Moreover, a crosstalk among the plural beams can be eliminated by bringing the distance between the primary electron beams to be irradiated on the sample into a relationship with the secondary optical system in such a manner that each the distances among the primary electron beams to be irradiated on the sample is apart by the distance larger than the aberration of the secondary optical system.

The image data converted with the image forming portion 5033 is displayed as an image with a display unit 5061 of the investigating and determining device 5060. The image displayed can be evaluated by the operator 5062. The operator 5062 constitutes a charging state investigating unit in this embodiment adapted to investigate a charging state on the basis of the image. The result of investigation is inputted into the CPU 5063 to set the retarding voltage to an optimal value. The CPU constitutes a retarding voltage determining unit in this embodiment.

FIG. 50A is a diagram for explaining an evaluation location and an evaluation method of charging. A peripheral portion of a memory cell boundary 5102 of a chip 5100 is a peripheral circuit section of low density region. An inside thereof is a memory cell section of high density region. Accordingly, A1 and A2 provide an image of the boundary region, and A3 and A4 provide an image of the memory cell section. A two dot chain line and a dashed line show the boundary on which the density changed greatly.

More specifically, the evaluation is performed on a location of the sample to be evaluated, which is likely to undergo an influence from the charging, that is, a corner portion of a memory cell 5101 of a chip 5100 formed on the surface of a wafer as the sample, as shown in FIG. 50A. In other words, (1) distortion amounts 5103 and 5104 of a pattern of a memory cell boundary 5102 at the corner portion may be measured or (2) a contrast of the signal intensity obtained upon scanning the pattern at the corner portion of the memory cell in a way of crossing the pattern (as indicated by arrows A1 and A2) may be compared with contrasts 5106 and 5108 (as indicated by broken lines in FIG. 50B) of the strength of the signals obtained by displaying solid lines 5105 and 5107, respectively, as shown in FIG. 50B, and scanning the pattern at the central portion of the chip in the directions as indicated by arrows A3 and A4.

Voltage of plural values is applied to the retarding voltage applying device 5050 while measuring the distortion amounts 5103 and 5104 or the contrasts 5105, 5107 and 5106, 5108 whenever the voltage is applied, thereby conducting evaluations to the effect that the distortion amount 5103 or 504, whichever smaller, has a smaller influence from the charging state. Likewise, it is evaluated that the contrast value 5105 or 5107 at the corner portion, whichever closer to the contrast value at the central portion, has a smaller influence of the charging state.

If the retarding voltage having a good charging state could be found, the value is applied to the applying device 5050 through the CPU 5063 and the sample, i.e., the wafer, is evaluated on the basis of this value. Moreover, a beam current may be made small when using a sample that can reduce its charging state at a small beam current.

Thus, an image-forming around the boundary where the pattern density on the sample greatly changes emphasizes an effect of charging, which facilitates an evaluation of charging, and makes it easy to find the landing voltage for hardly causing the charging.

The electron beam apparatus 5000 of Embodiment 19 (FIG. 48) of the present invention can be preferably used for the method for the manufacturing of the semiconductor device as shown in FIGS. 12 and 13. When the defect inspection method and the defect inspection apparatus according to Embodiment 19 of the present invention are used for the inspection step of the manufacturing method, the semiconductor device having a fine pattern can also be inspected at a high throughput so that all the number of products can be inspected. Further, a yield of products can be improved and a shipment of defective products can be prevented.

The Embodiment 19 (FIG. 48) of the present invention can demonstrate the effects as follows:

(a) A high throughput can be achieved at a value close to the multiple proportional to the number of electron beams, and the value of the throughput may be improved by several times.

(b) An evaluation at a higher reliability can be achieved because the evaluation of the wafer can be performed in a state in which the charging state is smallest.

(c) A more accurate result of evaluation can be obtained because the charging performance can be evaluated on the basis of an actual image, without measurements of various currents.

Figure 51:
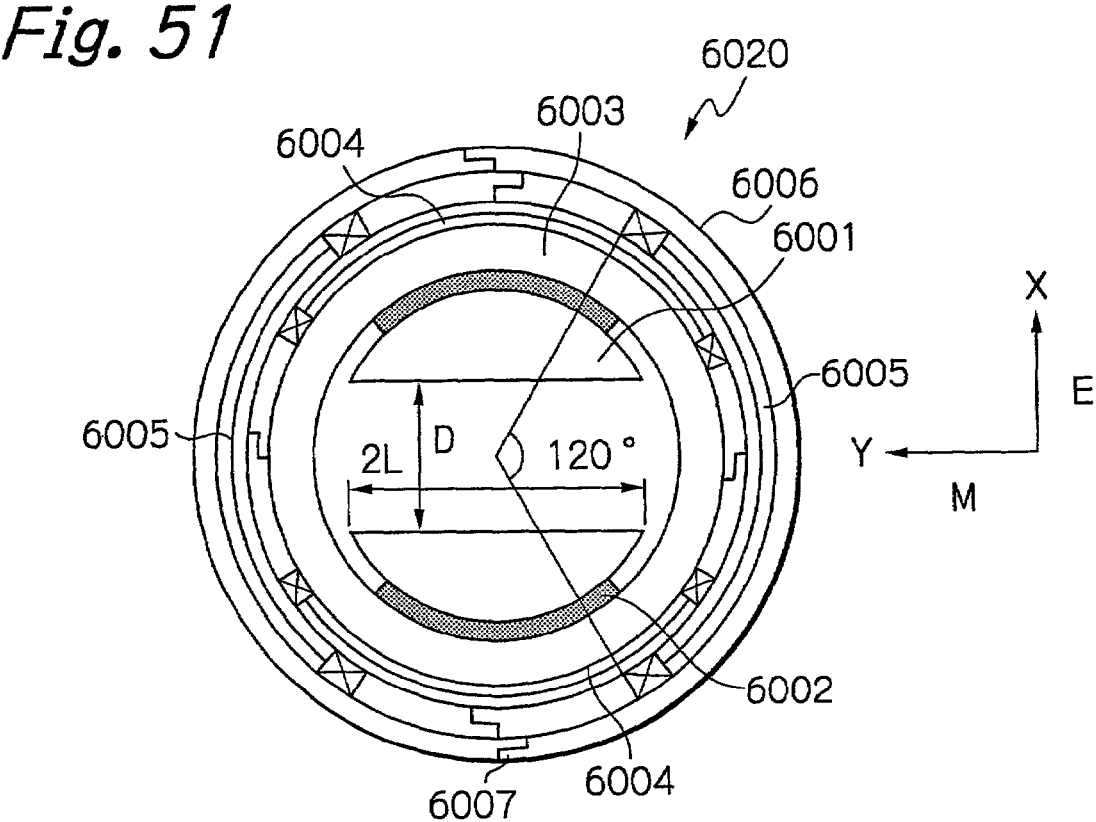
FIG. 51 is a cross sectional view of an E×B separator according to a 19th embodiment of the present invention, taken on a plane orthogonal to an optical axis thereof.

FIG. 51 shows an E×B separator 6020 of Embodiment 20 according to an embodiment of the present invention. The E×B separator 6020 comprises the electrostatic deflector and the electromagnetic deflector. FIG. 51 is a view in section, as taken along an x-y plane crossing the optical axis (the axis perpendicular to the plane of this drawing: z-axis) at a right angle. Further, the x-axial direction intersects with the y-axial direction at a right angle.

The electrostatic deflector is provided with a pair of electrodes (electrostatically deflecting electrodes) 6001 in a vacuum container to create the electric field in the x-axial direction. The electrostatically deflecting electrodes 6001 are mounted on a vacuum wall 6003 of the vacuum container through an insulating spacer 6002. The distance D between these electrodes is set to become smaller than the y-axial length 2L of the electrostatically deflecting electrode 6001. This setting can make the range of the uniform strength of the electric field formed around the z-axis relatively large. Ideally, the range where the strength of the electric field is uniform can be made larger if the distance D is smaller than L, i.e., D<L.

In other words, as the electric field strength is irregular in the range of D/2 from the edge of the electrode, the range where the electric field strength is nearly uniform is located in the range of 2L–D at the central portion, excluding the irregular edge region. Therefore, in order to allow the range of the uniform electric field strength to exist, it is necessary to make 2L larger than D, i.e., 2L>D. Moreover, by setting to be L>D, the range of the uniform electric field strength can be rendered larger.

Outside the vacuum wall 6003 is disposed the electromagnetically deflecting device for forming a magnetic field in the y-axial direction. The electromagnetically deflecting device is provided with electromagnetic coils 6004 and 6005, which can form the magnetic field in the x-axial and y-axial directions, respectively. Although only the magnetic coil 6005 can create the y-axial magnetic field, the magnetic coil 6004 for forming the x-axial magnetic field may be additionally disposed in order to improve the orthogonality between the electric field and the magnetic field. In other words, the orthogonality between the electric field and the magnetic field can be made better by offsetting the magnetic field component in the +x-axial direction formed by the magnetic coil 6005 for the magnetic field component in the −x-axial direction formed by the magnetic coil 6004.

As the magnetic coils 6004 and 6005 for forming the magnetic fields are mounted outside the vacuum container, each of them may be divided into two sections which may be mounted on the vacuum wall 6003 from the both sides and integrally fastened at portions 6007 with screws or other fastening tools.

The outermost layer 6006 of the E×B separator may be composed of a permalloy or ferrite yoke. The outermost layer may be divided into two sections, like the magnetic coils 6004 and 6005, and the two sections may be mounted on the outer periphery of the magnetic coil 6005 from the both sides and integrally fastened at portions 6007 with screws or the like.

Figure 52:
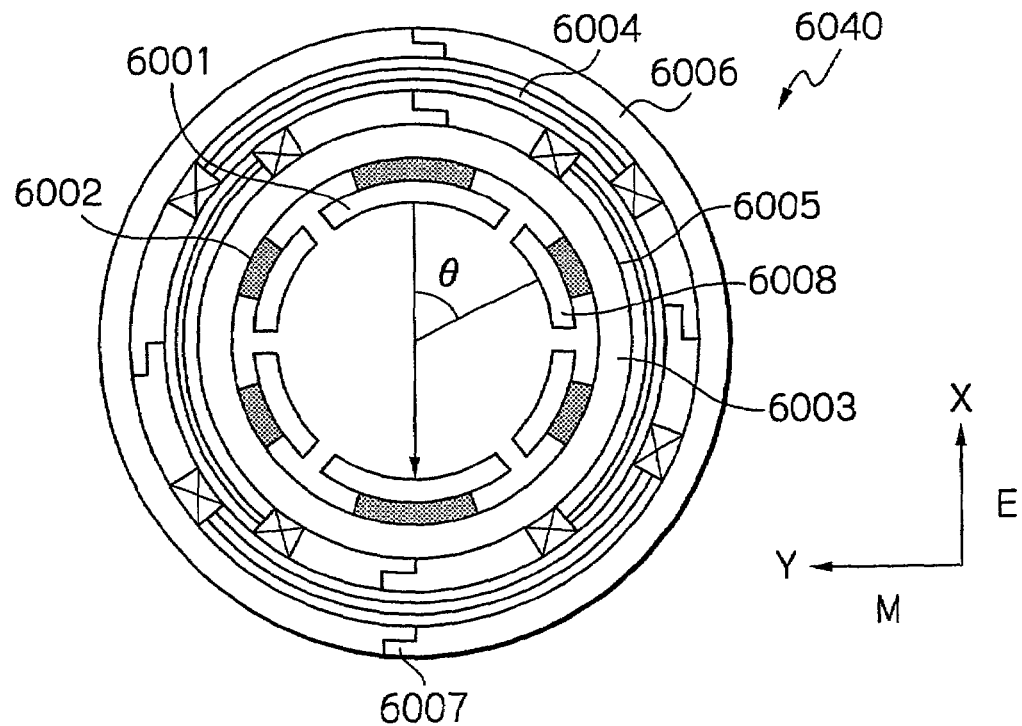
FIG. 52 is a cross sectional view of an E×B separator according to a 20th embodiment of the present invention, taken on a plane orthogonal to an optical axis thereof.

FIG. 52 shows a section of an E×B separator of Embodiment 21 according to the present invention, the section extending in the direction orthogonal to the optical axis (z-axis) thereof. The E×B separator of Embodiment 21 differs from that of Embodiment 20, as shown in FIG. 51, that six electrostatically deflecting electrodes 6001 are disposed. To the electrostatically deflecting electrodes 6001 are fed voltage, k×cos θi (where k is constant and θi is an optional angle) proportional to cos θi, when the angle of the line connecting the center of each of the electrodes and the optical axis (z-axis) with respect to the direction of the electric field (x-axial direction) is set to θi (where i=0, 1, 2, 3, 4, 5).

In Embodiment 21 as shown in FIG. 52, too, the electric field can be formed in the x-axial direction only, so that the coils 6004 and 6005 for forming the magnetic fields in the respective x-axial and y-axial directions are disposed to correct the orthogonality.

Embodiment 21 can make the range of the uniform electric field strength larger than Embodiment 20 as shown in FIG. 51.

In Embodiments 20 and 21 as shown in FIGS. 51 and 52, respectively, a coil of a saddle type may be used for forming the magnetic field. It is also possible to use a coil of a toroidal type as a coil for forming the magnetic field.

Figure 53:
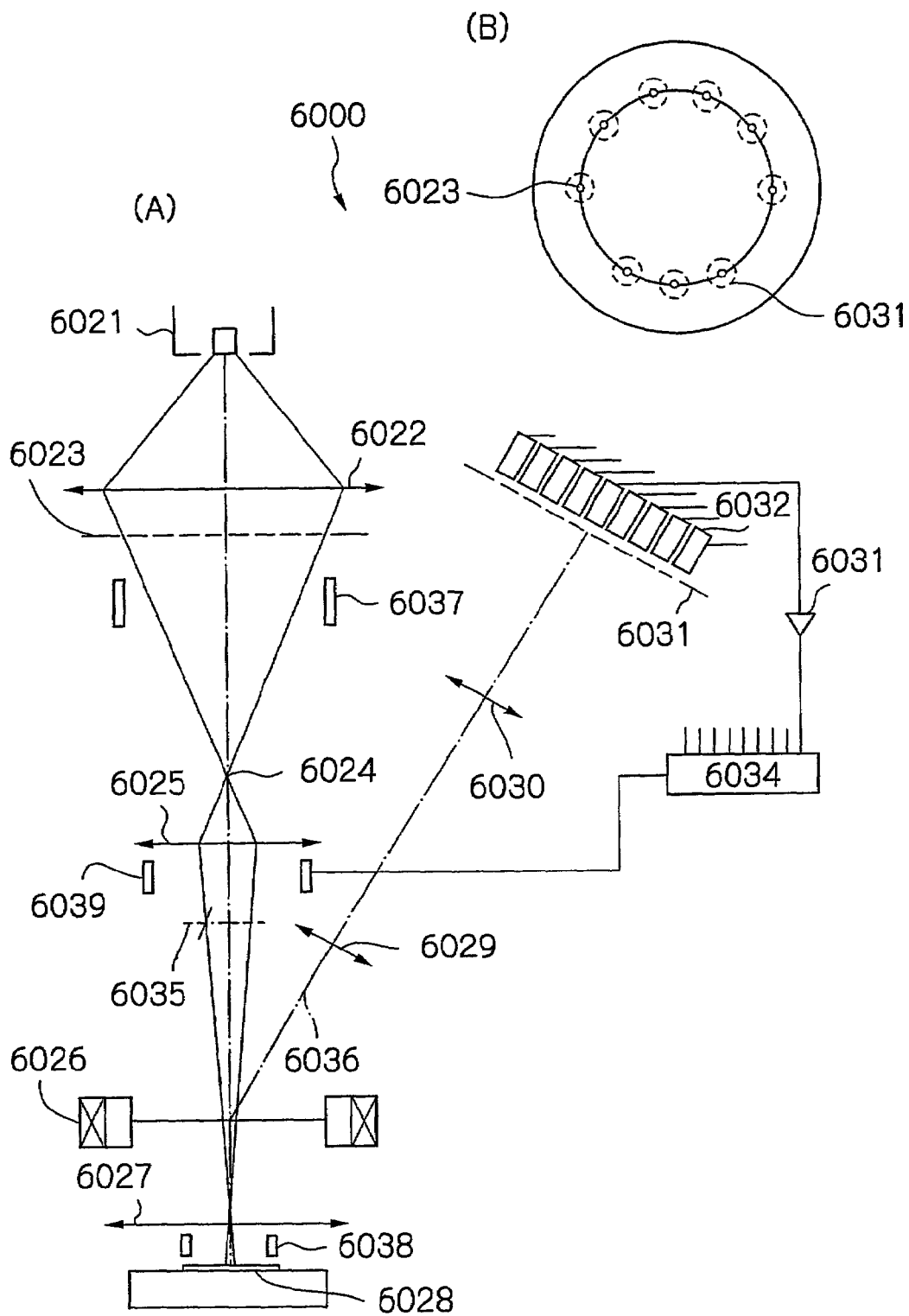
FIG. 53A is a diagram illustrating a schematic configuration of a defect inspection apparatus for wafer according to a 21st embodiment of the present invention, capable of employing the E×B separator of FIG. 51 or 52.
FIG. 53B is a diagram illustrating a positioning relation among apertures formed in a multi-aperture plate.
Figure 54:
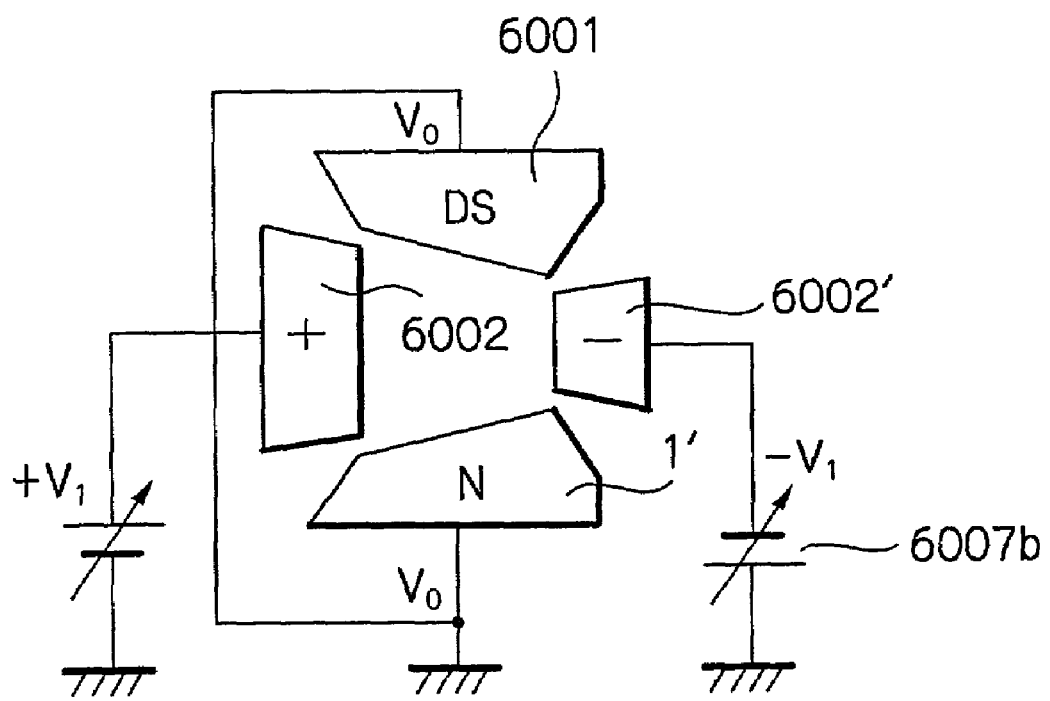
FIG. 54 is a diagram illustrating a schematic configuration of an E×B energy filter according to a prior art.

FIG. 53A is a schematic view of an electron apparatus 6000 (a defect inspection apparatus) for which the E×B separator of Embodiments 20 and 21 can be adopted to separate the secondary electron beams from the primary electron beams. In FIG. 53A, the electron beams emitted from an electron gun 6021 are converged with a condenser lens 6022 to form a crossover image at a point 6024.

Beneath the condenser lens 6022 is disposed a first multi-aperture plate 6023 having a plurality of apertures to form a plurality of primary electron beams. The plural electron beams formed are each reduced with a reducing lens 6025 and projected on a point 6035. After focused on the point 6035, the primary electron beams are then focused with an objective lens 6027 on a wafer 6028 as a sample. The primary electron beams from the first multi-aperture plate 6023 are then deflected with a deflector disposed between the reducing lens 6025 and the objective lens 6027 so as to simultaneously scan the surface of the wafer 6028.

In order to cause no aberration due to the curvature on an image plane of the reducing lens 6025 and the objective lens 6027, the first multi-aperture plate 6023 may be provided with a plurality of small apertures on the circumference, as shown in FIG. 53B, thereby arranging the points projected on the x-axis so as to assume an equally spaced relationship.

The plural primary electron beams focused are irradiated at plural points of the wafer 6028, and the secondary electron beams emitted from the plural points irradiated are then converged by means of attraction of the electric field of the objective lens 6027 and deflected with the E×B separator 6026 to deliver them to the secondary optical system. The image formed by the secondary electron beams is focused on a point 6036 closer to the objective lens 6027 than the point 6035. This is because the secondary electron beam has energy of several eV only, while each of the primary electron beams has energy of approximately 500 eV on the surface of the wafer 6028.

The secondary optical system has magnifying lenses 6029 and 6030. The secondary electron beams passed through the magnifying lenses form images on the plural apertures of the second multi-aperture plate 6031. The secondary electron beams are detected with a plurality of detectors 6032 after passage through the apertures thereof. Each of the plural apertures of the second multi-aperture plate 6031 are arranged so as to correspond to each of the plural apertures of the first multi-aperture plate 6023, as shown in FIG. 53B.

Each of the detectors 6032 converts the secondary electron beams into an electric signal representing its intensity. The electric signal is then amplified with an amplifier 6033 and converted into an image data with an image processing unit 6034. To the image processing unit 6034 is fed a scanning signal for deflecting the primary electron beams from a deflector 6039, and the image processing unit 6034 obtains an image data for displaying an image on the surface of the wafer 6028. The image data obtained is then compared with the reference pattern to detect a defect of the wafer 6028. Further, a pattern for evaluation on the wafer 6028 is transferred to a position in the vicinity of the optical axis of the primary optical system by means of registration, and a signal for use in the evaluation of a line width is extracted by line scanning. The appropriate calibration of the signal permits a measurement for a line width of the pattern on the wafer 6028.

Upon focusing the primary electron beams passed through the apertures of the first multi-aperture plate 6023 on the surface of the wafer 6028 and then forming an image on the second multi-aperture plate 6031 for use in detecting the secondary electron beams emitted from the wafer 6028, it is preferred to take necessary measures to minimize the influences due to three aberrations, that is, distortion caused by the primary optical system and the secondary optical system, curvature of an image plane, and field astigmatism.

Further, a crosstalk among the plural beams can be eliminated if the minimal value of the interval of the positions of irradiation with the plural primary electron beams is arranged so as to be separated apart by the distance longer than the aberration of the secondary optical system.

For the E×B separator 6020 of Embodiment 19 of the present invention, there may be used an electrode of a parallel plate type as a pair of electrodes for the electrostatic deflector for forming an electric field, the electrode of the parallel plate type being configured such that the magnitude of the direction perpendicular to the optical axis is set to be longer than the distance between the electrodes. Therefore, the use of the electrode of the parallel plate type can make the range larger, in which the electric field having a uniform and parallel strength around the optical axis is formed.

Further, in the E×B separators of Embodiments 19 and 20, there is used the coil of the saddle type for the electromagnetic deflector, and a calculated angle of the coil from the optical axis on one side is set to be $2\pi/3$, so that no $3\theta$ component is caused to be formed. Therefore, this configuration can make the range larger, in which the magnetic field having a uniform and parallel strength is formed around the optical axis.

Moreover, the electromagnetic coil forms the magnetic field, so that a deflecting current can be superimposed on the coil, thereby providing a scanning function.

The E×B separator of Embodiments 19 and 20 is composed of a combination of the electrostatic deflector with the electromagnetic deflector, so that the aberration of the optical system can be obtained by computing the aberration of the electrostatic deflector and the lens system, computing the aberration of the electromagnetic deflector and the lens system separately, and totaling the computed aberrations.

A charged beam apparatus 7000 according to a twenty-second embodiment of the present invention will now be described with reference to FIGS. 55 and 56. In the present embodiment, a term "vacuum" means a vacuum as referred to in this field of art.

Figure 55:
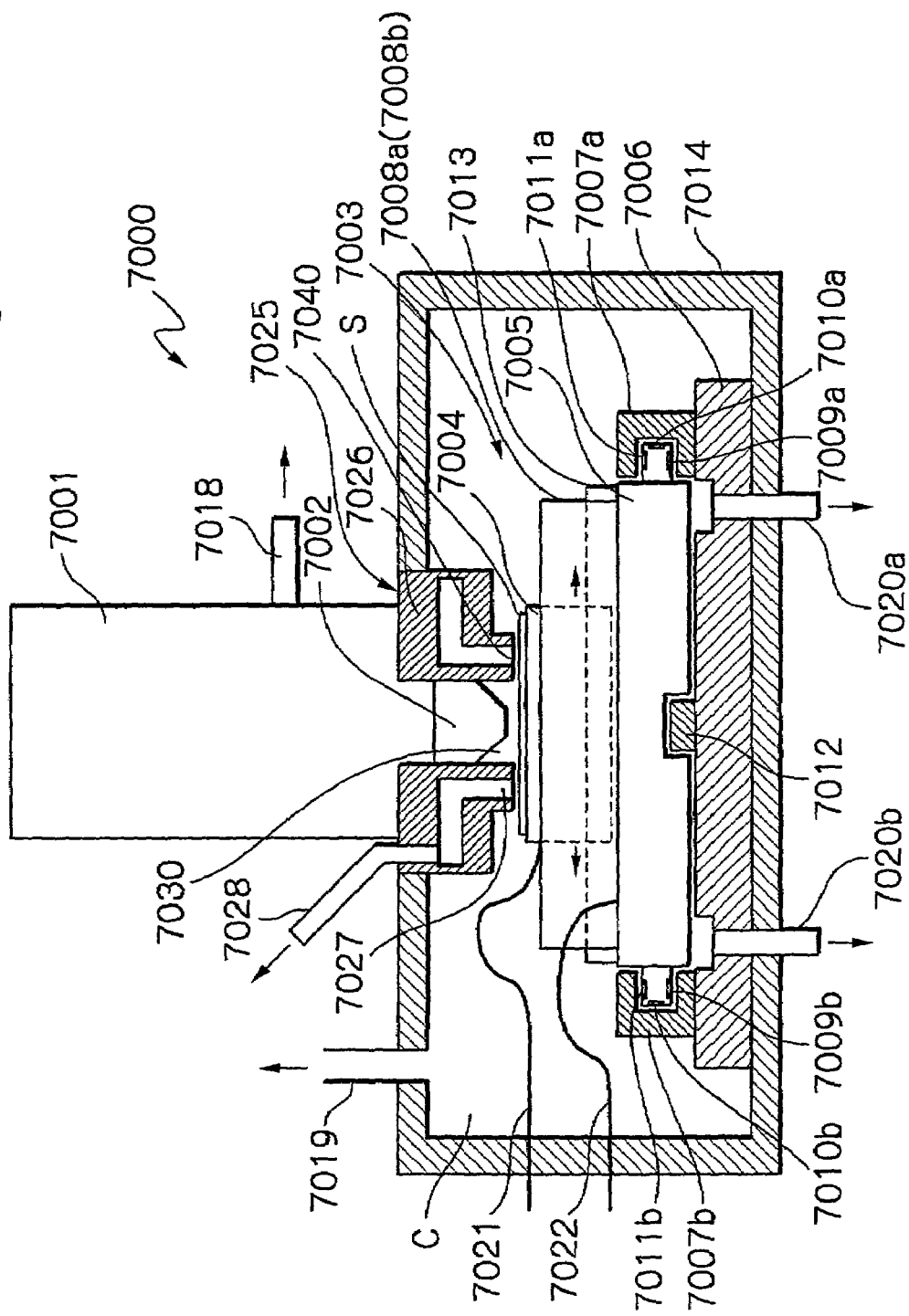
FIG. 55 is a cross sectional view illustrating a vacuum chamber and an XY stage of a charged beam apparatus according to a 22nd embodiment of the present invention.

In the charged beam apparatus 7000 shown in FIG. 55, a tip portion of a optical column 7001 or a charged beam irradiating section 7002, which functions to irradiate a charged beam against a sample, is mounted to a housing 7014 defining a vacuum chamber C. The sample "S" loaded on a table of an XY stage 7003 movable in the X direction (the lateral direction in FIG. 55) is positioned immediately below the optical column 7001. The XY stage 7003 of high precision allows the charged beam to be irradiated onto this sample S accurately in any arbitrary location of the sample surface.

A pedestal 7006 of the XY stage 7003 is fixedly mounted on a bottom wall of the housing 7014, and a Y table 7005 movable in the Y direction (the vertical direction on paper in FIG. 55) is loaded on the pedestal 7006. Convex portions are formed on both of opposite sidewall faces (the left and the right side faces in FIG. 55) of the Y table 7005 respectively, each of which projects into a concave groove formed on a side surface facing to the Y table in either of a pair of Y-directional guides 7007a and 7007b mounted on the pedestal 7006. The concave groove extends approximately along the full length of the Y directional guide in the Y direction.

A top, a bottom and a side faces of respective convex portions protruding into the grooves are provided with known hydrostatic bearings 7011a, 7009a, 7010a, 7011b, 7009b and 7010b respectively, through which a high-pressure gas is blown out and thereby the Y table 7005 is supported by the Y directional guides 7007a and 7007b in non-contact manner so as to be movable smoothly reciprocating in the Y direction. Further, a linear motor 7012 of known structure is arranged between the pedestal 7006 and the Y table 7005 for driving the Y table 7005 in the Y direction. The Y table is supplied with the high-pressure gas through a flexible pipe 7022 for supplying a high-pressure gas, and the high-pressure gas is further supplied to the above-described hydrostatic bearings 7009a to 7011a and 7009b to 7011b though a gas passage (not shown) formed within the Y table. The high-pressure gas supplied to the hydrostatic bearings blows out into a gap of some microns to some ten microns formed respectively between the bearings and the opposing guide planes of the Y directional guide so as to position the Y table accurately with respect to the guide planes in the X and Z directions (up and down directions in FIG. 55).

The X table 7004 is loaded on the Y table so as to be movable in the X direction (the lateral direction in FIG. 55). A pair of X directional guides 7008a and 7008b (only 7008a is illustrated) with the same configuration as of the Y directional guides 7007a and 7007b is arranged on the Y table 7005 with the X table 7004 sandwiched therebetween. Concave grooves are also formed in the X directional guides on the sides facing to the X table and convex portions are formed on the side portions of the X table (side portions facing to the X directional guides). The concave groove extends approximately along the full length of the X directional guide. A top, a bottom and a side faces of respective convex portions of the X table 7004 protruding into the concave grooves are provided with hydrostatic bearings (not shown) similar to those hydrostatic bearings 7011a, 7009a, 7010a, 7011b, 7009b and 7010b in the similar arrangements. A linear motor 7013 of known configuration is disposed between the Y table 7005 and the X table 7004 so as to drive the X table in the X direction.

Further, the X table 7004 is supplied with a high-pressure gas through a flexible pipe 7021, and thus the high-pressure gas is supplied to the hydrostatic bearings. The X table 7004 is supported highly precisely with respect to the Y directional guide in a non-contact manner by way of said high-pressure gas blowing out from the hydrostatic bearings to the guide planes of the X-directional guides. The vacuum chamber C is evacuated through vacuum pipes 7019, 7020a and 7020b coupled to a vacuum pump of known structure. Those pipes 7020a and 7020b penetrate through the pedestal 7006 to the top surface thereof to open their inlet sides (inner side of the vacuum chamber) in the proximity of the locations to which the high-pressure gas is ejected from the XY stage 7003, so that the pressure in the vacuum chamber may be prevented to the utmost from rising up by the blown-out gas from the hydrostatic bearings.

A differential exhausting mechanism 7025 is arranged so as to surround the tip portion of the optical column 7001 or the charged particles beam irradiating section 7002, so that the pressure in a charged particles beam irradiation space 7030 can be controlled to be sufficiently low even if there exists high pressure in the vacuum chamber C. That is, an annular member 7026 of the differential exhausting mechanism 7025 mounted so as to surround the charged beam irradiating section 7002 is positioned with respect to the housing 7014 so that a micro gap (in a range of some microns to some-hundred microns) 7040 can be formed between the lower face thereof (the surface facing to the sample S) and the sample, and an annular groove 7027 is formed in the lower face thereof.

That annular groove 7027 is coupled to a vacuum pump or the like, though not shown, through an exhausting pipe 7028. Accordingly, the micro gap 7040 can be exhausted through the annular groove 7027 and the exhausting pipe 7028, and if any gaseous molecules from the chamber C attempt to enter the space 7030 circumscribed by the annular member 7026, they may be exhausted. Thereby, the pressure within the charged beam irradiation space 7030 can be maintained to be low and thus the charged beam can be irradiated without any troubles. That annular groove may be made doubled or tripled, depending on the pressure in the chamber and the pressure within the charged beam irradiation space 7030.

Typically, dry nitrogen is used as the high-pressure gas to be supplied to the hydrostatic bearings. If available, however, a much higher-purity inert gas should be preferably used instead. This is because any impurities, such as water contents or oil and fat contents, included in the gas could stick on the inner surface of the housing defining the vacuum chamber or on the surfaces of the stage components leading to the deterioration in vacuum level, or could stick on the sample surface leading to the deterioration in vacuum level in the charged beam irradiation space.

It should be appreciated that though typically the sample S is not placed directly on the X table, but may be placed on a sample table having a function to detachably carry the sample and/or a function to make a fine tuning of the position of the sample relative to the XY stage 7003, an explanation therefor is omitted in the above description for simplicity due to the reason that the presence and structure of the sample table has no concern with the principal concept of the present invention.

Since a stage mechanism of a hydrostatic bearing used in the atmospheric pressure can be used in the above-described charged beam apparatus 7000 mostly as it is, a high precision stage having an equivalent level of precision to those of the stage of high-precision adapted to be used in the atmospheric pressure, which is typically used in an exposing apparatus or the likes, may be accomplished for an XY stage to be used in a charged beam apparatus with equivalent cost and size. It should be also appreciated that in the above description, the configuration and arrangement of the hydrostatic guide and the actuator (the linear motor) have been explained only as an example, and any hydrostatic guides and actuators usable in the atmospheric pressure may be applicable.

Figure 56:
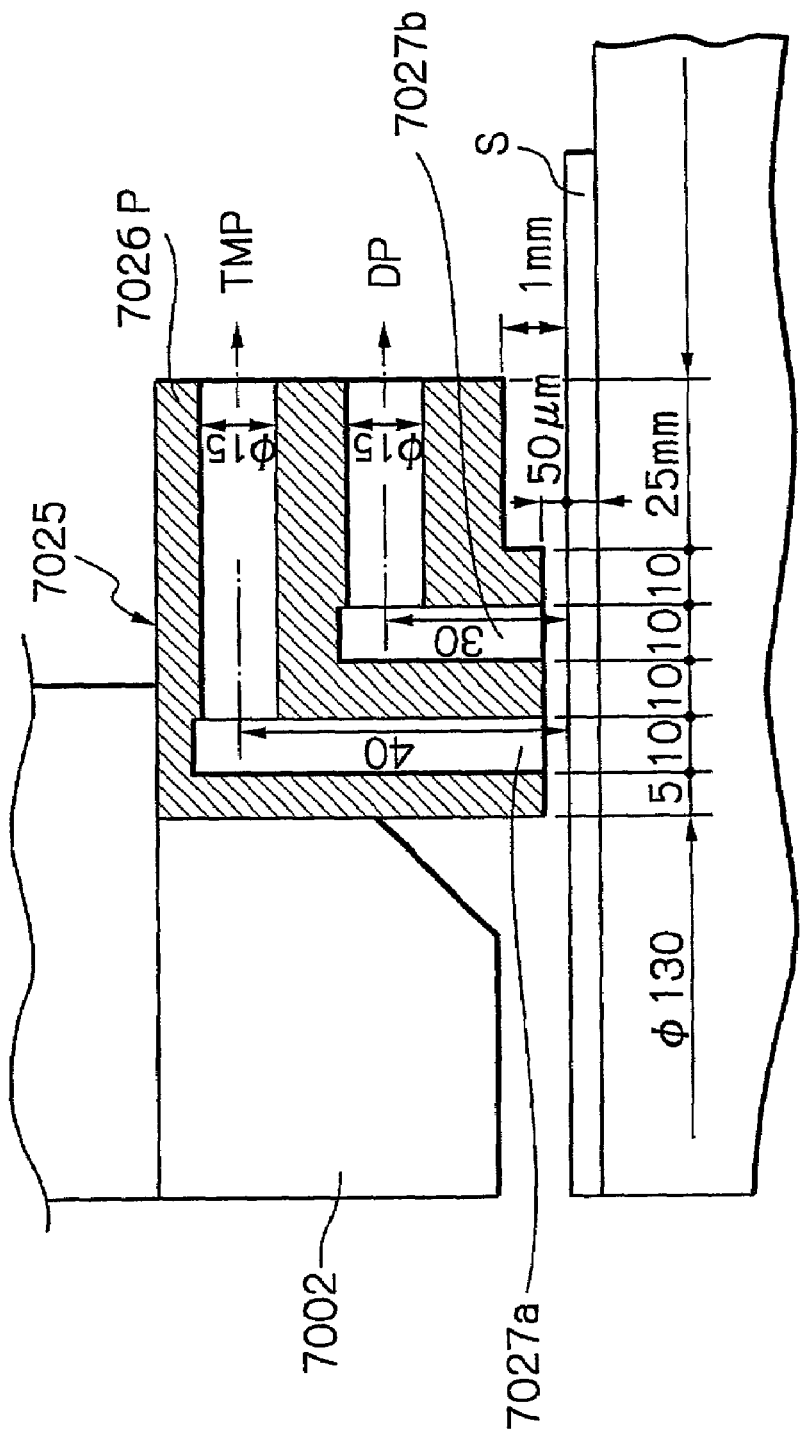
FIG. 56 shows an example of a differential exhausting mechanism provided in the charged beam apparatus of FIG. 55.

FIG. 56 shows an example of numeric values representative of the dimensions of the annular grooves formed in the annular member 7026 of the differential pumping mechanism 7025. The annular member 7026 of FIG. 56 has a doubled structure of annular grooves 7027a and 7027b, which are separated from each other in the radial direction and evacuated by TMP and DP respectively.

The flow rate of the high-pressure gas supplied to the hydrostatic bearing is typically in the order of about 20 L/min (in the conversion into the atmospheric pressure). Assuming that the vacuum chamber C is evacuated by a dry pump having a function of pumping speed of 20000 L/min through a vacuum pipe with an inner diameter of 50 mm and a length of 2 m, the pressure in the vacuum chamber will be about 160 Pa (about 1.2 Torr). At that time, with the applied size of the annular member 7026, the annular groove and others of the differential pumping mechanism as illustrated in FIG. 56, the pressure within the charged particles beam irradiation space 7030 can be controlled to be $10^{-4}$ Pa ($10^{-6}$ Torr).

Figure 57:
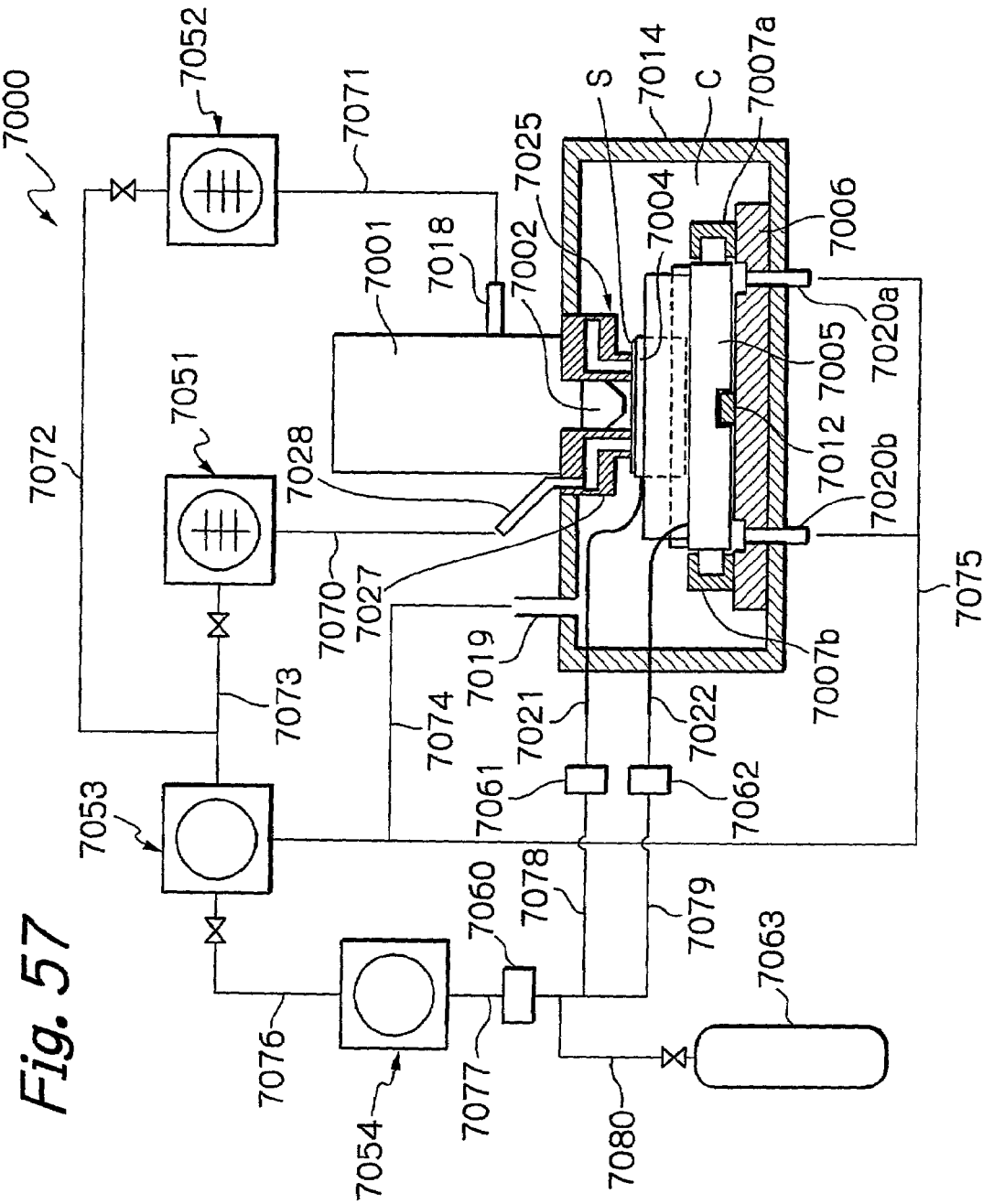
FIG. 57 is a block diagram illustrating a circulation piping system for gas of the charged beam apparatus of FIG. 55.

FIG. 57 shows a charged particles beam apparatus 7000 according to a twenty-third embodiment of the present invention. A vacuum chamber C defined by a housing 7014 is connected with a dry vacuum pump 7053 via vacuum pipes 7074 and 7075. An annular groove 7027 of a differential pumping mechanism 7025 is connected with an ultra-high vacuum pump or a turbo molecular pump 7051 via a vacuum pipe 7070 connected to an exhaust port 7028. Further, the interior of a optical column 7001 is connected with a turbo molecular pump 7052 via a vacuum pipe 7071 connected to an exhaust port 7018. Those turbo molecular pumps 7051 and 7052 are connected to the dry vacuum pump 7053 through vacuum pipes 7072 and 7073.

In the charged particles beam apparatus 7000 shown in FIG. 57, the single dry vacuum pump has been used to serve both as a roughing vacuum pump of the turbo molecular pump and as a pump for vacuum pumping of the vacuum chamber, but alternatively multiple dry vacuum pumps of separate systems may be employed for pumping, depending on the flow rate of the high-pressure gas supplied to the hydrostatic bearings of the XY stage, the volume and inner surface area of the vacuum chamber and the inner diameter and length of the vacuum pipes.

A high-purity inert gas ($N_2$ gas, Ar gas or the like) is supplied to a hydrostatic bearing of an XY stage 7003 through flexible pipes 7021 and 7022. Those gaseous molecules blown out of the hydrostatic bearing are diffused into the vacuum chamber and evacuated by the dry vacuum pump 7053 through exhaust ports 7019, 7020a and 7020b. Further, those gaseous molecules having invaded into the differential pumping mechanism and/or the charged particles beam irradiation space are sucked from the annular groove 7027 or the tip portion of the optical column 7001 through the exhaust ports 7028 and 7018 to be exhausted by the turbo molecular pumps 7051 and 7052, and then those gaseous molecules, after having been exhausted by the turbo molecular pumps, are further exhausted by the dry vacuum pump 7053.

In this way, the high-purity inert gas supplied to the hydrostatic bearing is collected into the dry vacuum pump and then exhausted away.

On the other hand, the exhaust port of the dry vacuum pump 7053 is connected to a compressor 7054 via a pipe 7076, and an exhaust port of the compressor 7054 is connected to flexible pipes 7021 and 7022 via pipes 7077, 7078 and 7079 and regulators 7061 and 7062. Owing to this configuration, the high-purity inert gas exhausted from the dry vacuum pump 7053 is compressed again by the compressor 7054 and then the gas, after being regulated to an appropriate pressure by regulators 7061 and 7062, is supplied again to the hydrostatic bearings of the XY stage.

In this regard, since the gas to be supplied to the hydrostatic bearings is required to be as highly purified as possible in order not to have any water contents or oil and fat contents included therein, as described above, the turbo molecular pump, the dry pump and the compressor are all required to have such structures that prevent any water contents or oil and fat contents from entering the gas flow path. It is also considered effective that a cold trap, a filter 7060 or the like is provided in the course of the outlet side piping 7077 of the compressor so as to trap the impurities such as water contents or oil and fat contents, if any, included in the circulating gas and to prevent them from being supplied to the hydrostatic bearings.

This may allow the high purity inert gas to be circulated and reused, and thus allows the high-purity inert gas to be saved, while the inert gas would not remain desorbed into a room where the present apparatus is installed, thereby eliminating a fear that any accidents such as suffocation or the like would be caused by the inert gas.

A circulation piping system is connected with a high-purity inert gas supply source 7063, which serves both to fill up with the high-purity inert gas all of the circulation systems including the vacuum chamber C, the vacuum pipes 7070 to 7075, and the pipes in compression side 7076 to 7080, prior to the starting of the gas circulation, and to supply a deficiency of gas if the flow rate of the circulation gas decreases by some reason. Further, if the dry vacuum pump 7053 is further provided with a function for compressing up to the atmospheric pressure or more, it may be employed as a single pump so as to serve both as the dry vacuum pump 7053 and the compressor 7054. As the ultra-high vacuum pump to be used for evacuating the optical column, other pumps including an ion pump and a getter pump may be used instead of the turbo molecular pump. Further, instead of the dry vacuum pump, a dry pump of other type, for example, a dry pump of diaphragm type may be used.

Figure 58:
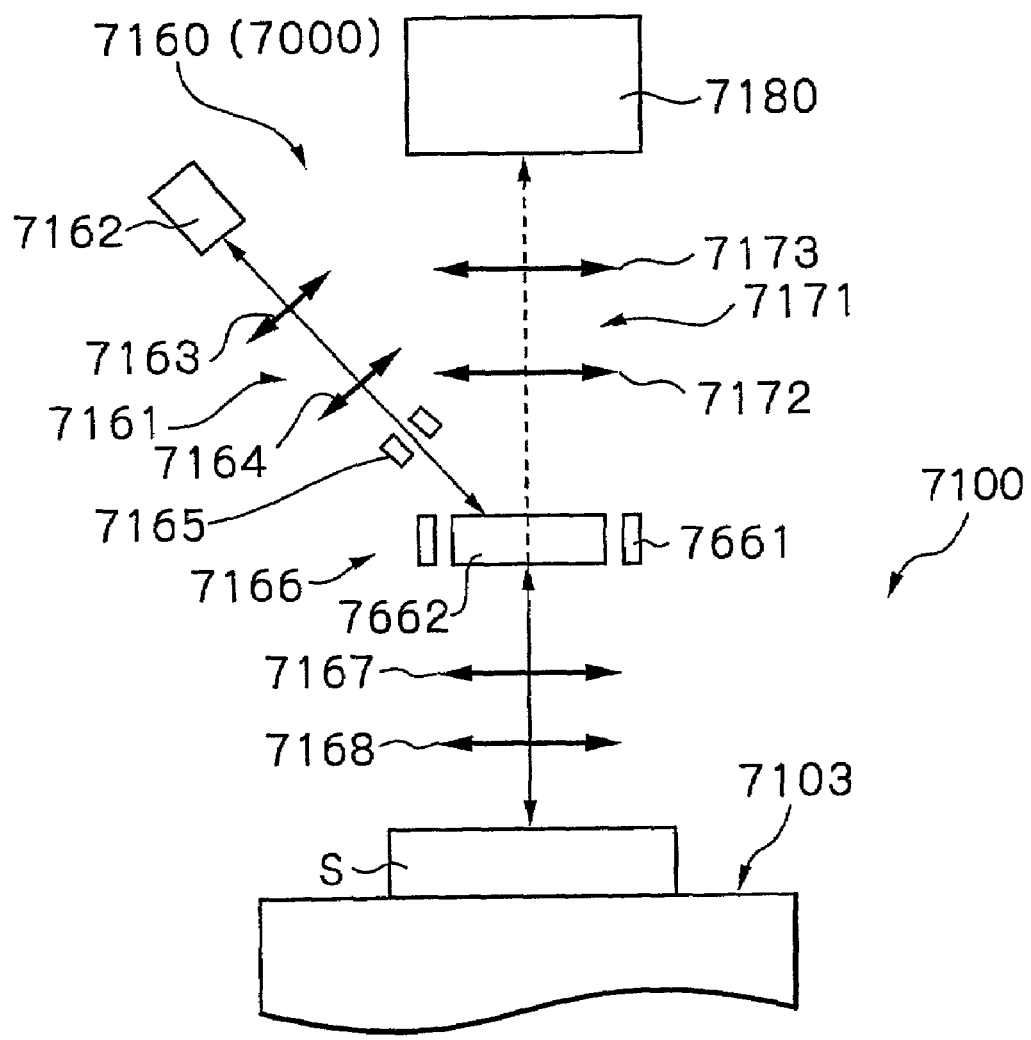
FIG. 58 is a diagram illustrating a schematic configuration of an optical system and a detecting system of a charged beam apparatus according to a 23rd embodiment of the present invention.

FIG. 58 shows a charged particles beam apparatus 7100 according to the twenty-third embodiment of the present invention. The charged beam apparatus 7100 includes an optical system 7160 and a detector 7180, each applicable to the charged particles beam apparatus 7000 of FIG. 57. The optical system 7160 comprises a primary optical system 7161 for irradiating the charged particles beam against the sample S loaded on the stage 7003 and a secondary optical system 7171 into which the secondary electrons emanated from the sample are to be introduced.

The primary optical system 7161 comprises an electron gun 7162 for emitting the charged particles beam, a lens systems composed of two stages of electrostatic lenses 7163 and 7164 for converging the charged particles beam emitted from the electron gun 7162, a deflector 7165, a Wien filter or an E×B separator 7166 for deflecting the charged beam so as for an optical axis thereof to be directed to perpendicular to a surface of an object, and a lens system composed of two stages of electrostatic lenses 7167 and 7168, wherein those components described above are arranged in the order with the electron gun 7162 at the topmost location so that the optical axis of the charged beam is inclined to the line normal to a surface of the sample S (a sample surface) as illustrated in FIG. 58. The E×B separating system 7166 comprises an electrode 7661 and a magnet 7662.

The secondary optical system 7171 is another optical system to which the secondary electrons emanated from the sample S are introduced, which comprises a lens system composed of two stages of electrostatic lenses 7172 and 7173 disposed in an upper side of the E×B type separating system of the primary optical system. The detector 7180 detects the secondary electrons sent through the secondary optical system 7171. Since the structures and functions of respective components of said optical systems 7160 and said detector 7180 are similar to those in the prior art, a detailed description thereof should be omitted.

The charged particles beam emitted from the electron gun 7162 is appropriately shaped in a square aperture of the electron gun, contracted by the lens system of two stages of lenses 7163 and 7164, and then, after the optical axis thereof being adjusted by the deflector 7165, the charged beam is formed into an image of 1.25 mms square on a deflection principal plane of the E×B separating system 7166. The E×B separating system 7166 is designed such that an electric field and a magnetic field are crossed at a right angle within a plane orthogonal to a normal line of the sample, wherein when the relationship among the electric field, the magnetic field and the energy of electrons satisfies a certain condition, the electrons are advanced straight forward, and for the case other than the above, the electrons are deflected into a predetermined direction depending on said mutual relationship among the electric field, the magnetic field and the energy of electrons.

The relationship has been set such that the charged beam from the electron gun is deflected to enter the sample S at a right angle and the secondary electrons emanated from the sample can be advanced straight ahead toward the detector 7180. The shaped beam, after having been deflected by the E×B deflecting system, is contracted to $\frac{1}{5}$ in size with the lens system composed of the lenses 7167 and 7168 to be projected onto the sample S.

The secondary electrons emanated from the sample S, which have the information of a pattern image, are magnified by the lens systems composed of the lenses 7167 and 7168 and the lenses 7172 and 7173 so as to form the secondary electron image on the detector 7180. These four stages of magnifying lenses, which are composed of the lens system of the lenses 7167 and 7168 forming a symmetrical tablet lens and the lens system of the lenses 7172 and 7173 also forming another symmetrical tablet lens, make up the lenses of no distortion.

The charged particles beam apparatus 7000 shown in FIGS. 55 to 58 may be applied to the semiconductor device manufacturing method shown in FIGS. 12 and 13. That is, using the charged beam apparatus 7000 in the wafer inspection process of FIG. 12 or the exposing process of FIG. 13 allows the finer pattern to be inspected or exposed with high precision and certain stableness, which allows to improve the yield of the products and to prevent the defective product from being delivered.

The charged particles beam apparatus 7000 shown in FIGS. 55 to 58 provides such effects as below:

(A) A processing by the charged beam can be stably applied to a sample on the stage by use of the stage having a structure similar to that of a stage of hydrostatic bearing type which is typically used in the atmospheric pressure (a stage supported by the hydrostatic bearing having no differential exhausting mechanism);

(B) An affection on the vacuum level in the charged particles beam irradiation region can be minimized, and thereby the processing by the charged particles beam applied to the sample can be stabilized;

(C) An inspection apparatus which accomplishes the positioning performance of the stage with high precision and provides a stable vacuum level in the irradiation region of the charged particles beam can be provided in low cost;

(D) An exposing apparatus which accomplishes the positioning performance of the stage with high precision and provides a stable vacuum level in the irradiation region of the charged particles beam can be provided in low cost; and (E) A fine semiconductor circuit can be formed by manufacturing the semiconductor using an apparatus which accomplishes the positioning performance of the stage with high precision and provides a stable vacuum level in the irradiation region of the charged particles beam.

Figure 59:
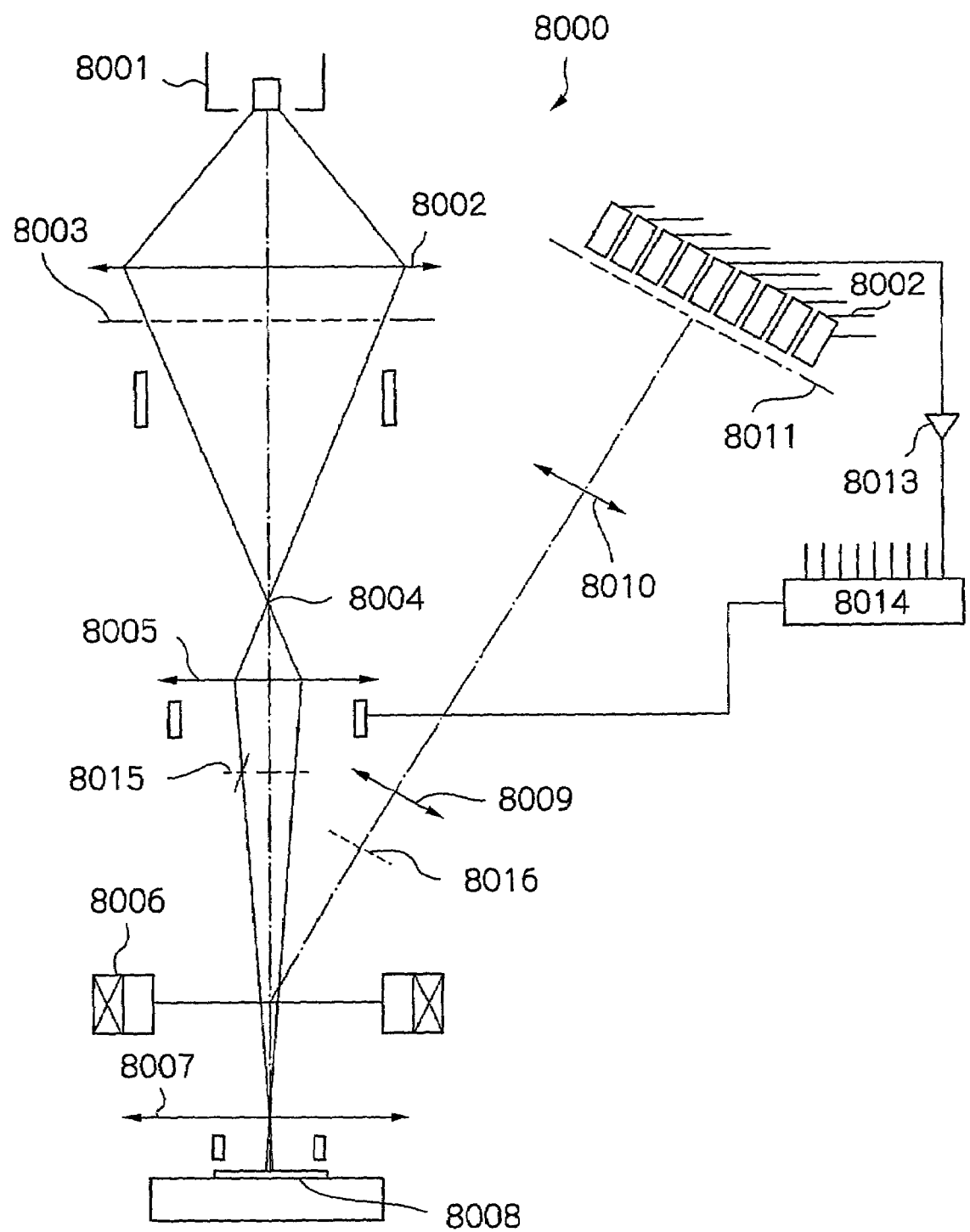
FIG. 59 is a diagram illustrating a schematic configuration of an electron beam apparatus according to the present invention.

FIG. 59 is a schematic diagram illustrating an electron beam apparatus 8000 according to a twenty-fifth embodiment of the present invention, wherein an electron beam emitted from an electron gun 8001 is focused by a condenser lens 8002 to form a cross-over at a point 8004.

A first multi-aperture plate 8003 having a plurality of apertures 8003' is disposed beneath the condenser lens 8002, and thereby a plurality of primary electron beams is formed. Each of the plurality of primary electron beams formed by the first multi-aperture plate, after having been contracted by a demagnification lens 8005 to be focused onto a point 8015, is focused by an objective lens 8007 onto a sample 8008. The plurality of primary electron beams emitted through the first multi-aperture plate 8003 is deflected by a deflector disposed between the reduction lens 8005 and the objective lens 8007 so as to simultaneously scan different locations on a surface of the sample 8008.

Figure 60:
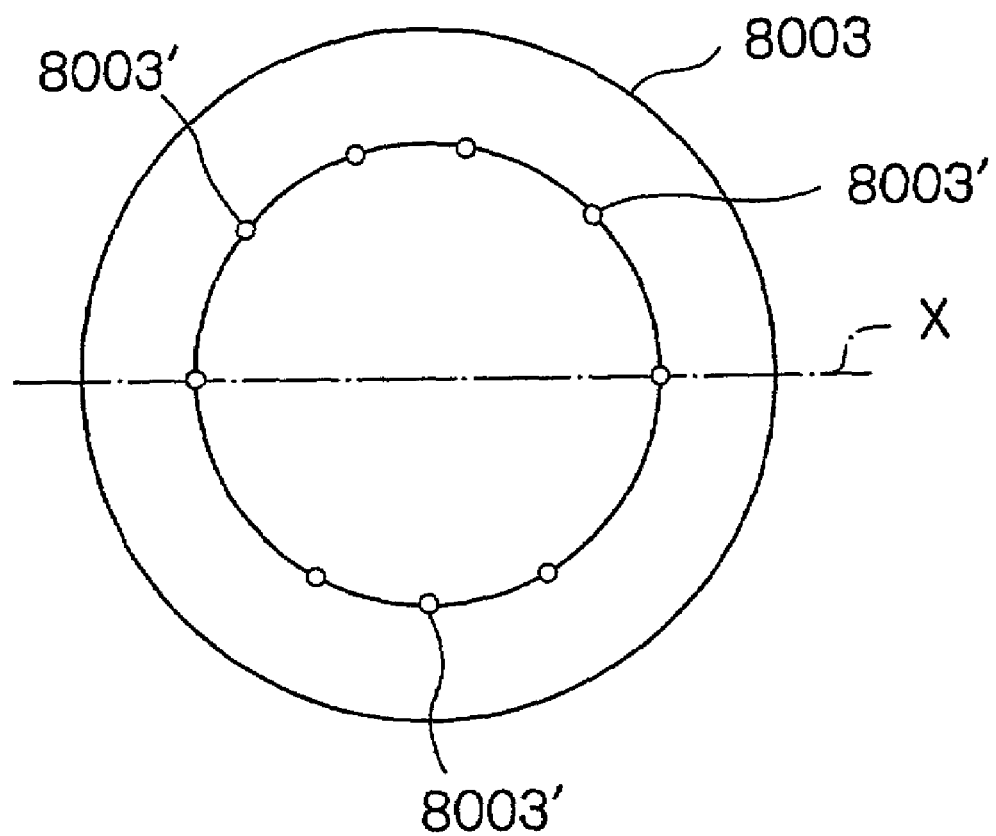
FIG. 60 is a plan view of an aperture plate used in the electron beam apparatus of FIG. 58.

In order to eliminate an effect of field curvature aberration possibly caused by the reduction lens 8005 and the objective lens 8007, the multi-aperture plate 8003 is provided with a plurality of apertures 8003' arranged along a circle on said multi-aperture plate 8003 such that projected points of centers of said apertures 8003' onto x-axis may be equally spaced, as shown in FIG. 60.

In the electron beam apparatus 8000 of the twenty-fifth embodiment shown in FIG. 59, from a plurality of spots on the sample 8008 irradiated by the plurality of primary electron beams, a plurality of secondary electron beams is emanated, attracted by an electric field of the objective lens 8007 to be focused narrower, deflected by an E×B separator 8006, and then introduced into a secondary optical system. A secondary electron image is focused on a point 8016 which is closer to the objective lens 8007 than the point 8015. This is because the secondary electron beam has only a few eV of energy while each of the primary electron beams has 500 eV of energy on the sample surface.

The secondary optical system includes magnifying lenses 8009 and 8010, and the secondary electron beam, after having passed through these magnifying lenses 8009 and 8010, passes through a plurality of apertures formed on a second multi-aperture plate 8011, and is focused on a plurality of electron detectors 8012. It is to be noted that each of the plurality of apertures formed on the second multi-aperture plate 8011 disposed in front of the detectors 8012 corresponds to each of the plurality of apertures 8003' formed on the first multi-aperture plate 8003 in a geometric relationship therebetween in a manner of one-by-one basis.

Each of the detectors 8012 converts a detected secondary electron beam into an electric signal representative of intensity thereof. The electric signal output from each of the detectors, after having been amplified respectively by an amplifier 8013, is received by an image processing section 8014 to be converted into an image data. Since the image processing section 8014 is further supplied with a scanning signal for deflecting the primary electron beam, the image processing section 8014 can display an image representative of the surface of the sample 8008.

Comparing this image with a reference pattern allows any defects of the sample 8008 to be detected, and also a line width of a pattern on the sample 8008 can be measured in such a way that the pattern to be measured of the sample 8008 is moved by a registration to a proximity of an optical axis of the primary optical system, and the pattern is line-scanned to extract a line width evaluation signal, which is in turn appropriately calibrated.

In this regard, when the primary electron beams passed through the apertures of the first multi-aperture plate 8003 are focused on the surface of the sample 8008, and the secondary electron beams emanated from the sample are formed into an image on the detectors 8012, much attention should be paid in order to minimize the affection by the three aberrations, i.e., a distortion caused by the primary optical system, a field curvature and a astigmatism field.

As for a relation between the spacing among the plurality of primary electron beams and the secondary optical system, if the space between respective primary electron beams is determined to be greater than the aberration of the secondary optical system, then the crosstalk among a plurality of beams can be eliminated.

Although in the above-described optical system, the electron beam emitted from the single electron gun is passed through the multi-apertures to be formed into multi-beams, a plurality of electron guns may be provided or a single electron gun having a plurality of emission areas of cathode may be employed.

Figure 61:
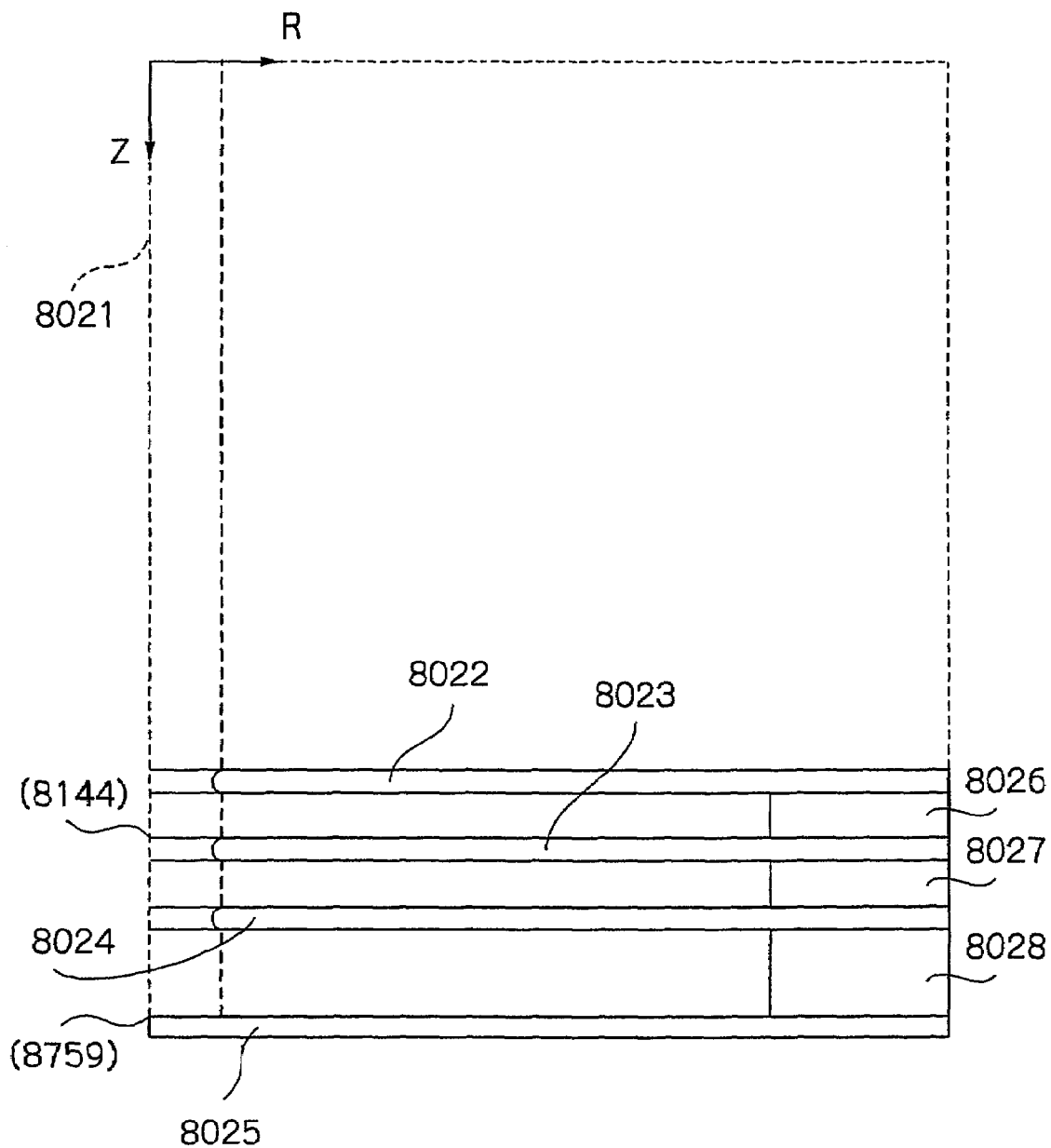
FIG. 61 is a diagram illustrating a simulation of an objective lens of a charged beam apparatus according to a present invention.

FIG. 61 shows a simulation model for the objective lens 8007 of FIG. 59. Reference numeral 8021 is an optical axis, 8022 is an upper electrode of the objective lens 8007, which is set to 0 volt, 8023 is a center electrode of the objective lens, to which high voltage is to be applied, 8024 is an under electrode of the objective lens, which is set to earth voltage, and a sample surface 8025 is set to 4000 volts. Reference numerals 8026, 8027 and 8028 are insulator spacers for supporting the electrodes. An image of the multi-beam in a position of z=0 mm was focused on the sample surface 8025 by varying a position of the crossover produced by the demagnification lens 8005 and also by varying the voltage of center electrode in the objective lens, and the aberration generated thereby was calculated.

Figure 62:
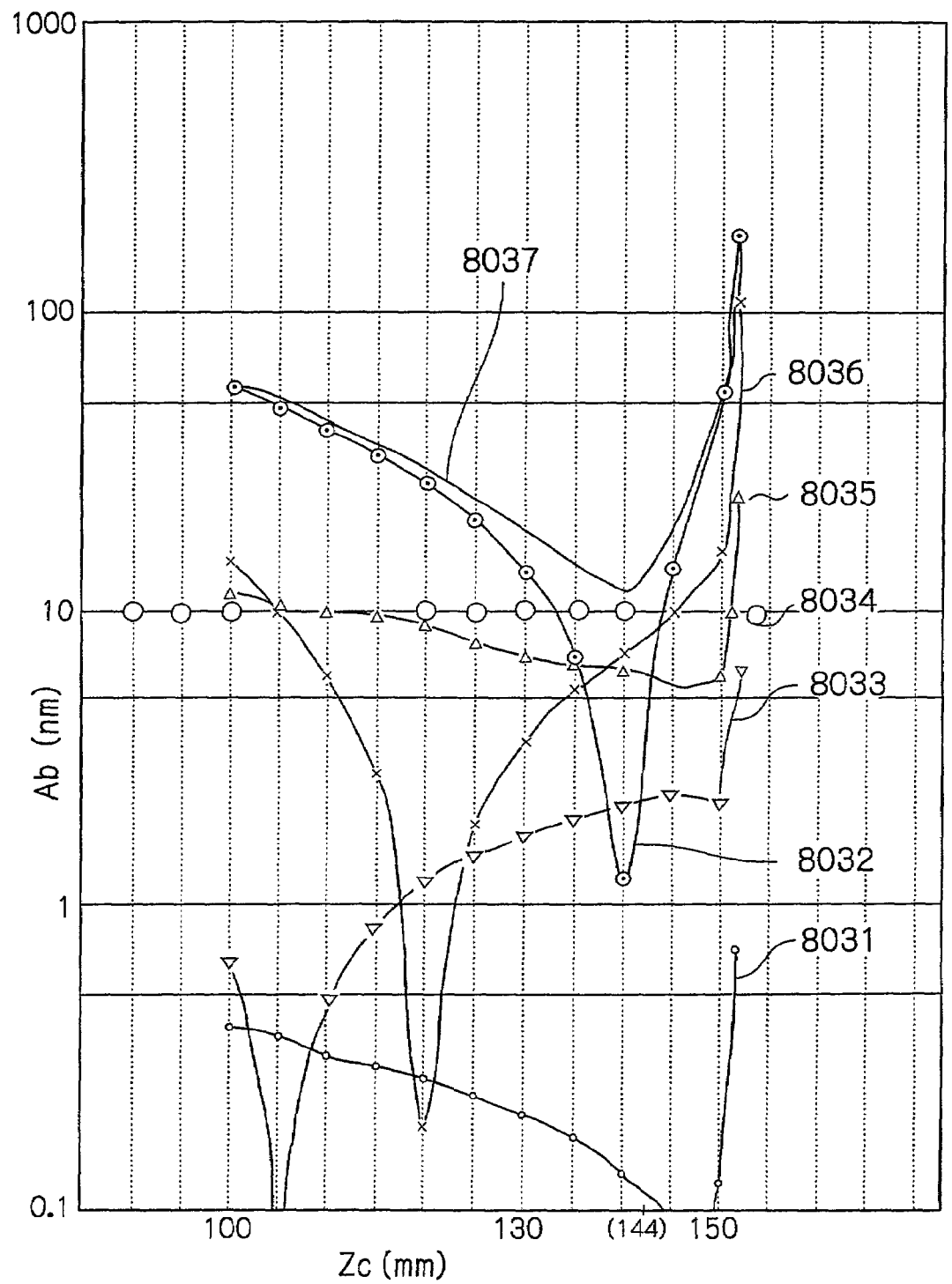
FIG. 62 is a graph illustrating a result of the simulation of FIG. 61.
Figure 63:
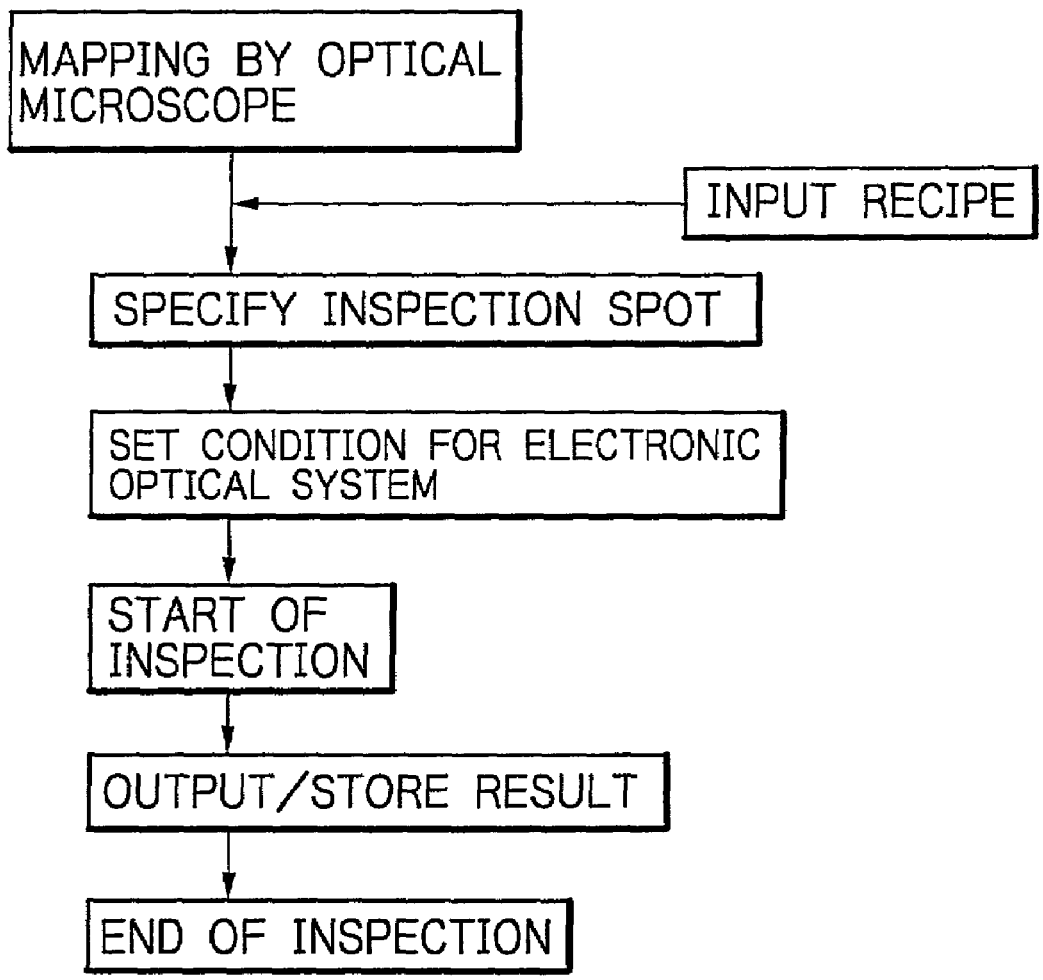
FIG. 63 is an inspection flow diagram illustrating a procedure of inspection.

FIG. 62 is a graph illustrating a result of the above simulation. In FIG. 62, the values of aberration (nm, y-axis) are shown as a function of varied cross-over positions (mm, x-axis). An upper surface of the center electrode 8023 (FIG.

61) was located at z=144 mm. An r position of the multi-beam and a half angular aperture were set to 50 μm and 5 mrad respectively.

In the graph of FIG. 62, a curve 8031 indicates a coma-aberration, 8032 a magnification chromatic aberration, 8033 an astigmatism, 8034 an on-axis chromatic aberration, 8035 an field curvature, 8036 a distortion, and 8037 indicates a blur.

When the multi-beams are arranged along a circle centering around the optical axis, the blur 8037 is determined substantially by the magnification chromatic aberration 8032 and the on-axis chromatic aberration 8034 since the field curvature is zero. Hereupon, the energy spread of the electron beam is set to 5 eV. When the cross-over position is set to 140 mm, the magnification chromatic aberration is reduced to almost non-problematic level. That is, according to this simulation, it is found that the cross-over position produced by the front stage lens should be formed in the electron gun side of the position of the center electrode of the objective lens (144 mm).

The electron beam apparatus 8000 of the twenty-fifth embodiment shown in FIG. 59 can be used for evaluating the wafer in the semiconductor device manufacturing process shown in FIGS. 12 and 13. Using the electron beam apparatus of FIGS. 59 to 62 in the wafer inspection process of FIG. 12 allows even the semiconductor device with finer pattern to be inspected with high throughput, which allows a hundred percent inspection and an improvement in yield of the products, and also allows to prevent the defective product from being delivered. The electron beam apparatus 8000 of the twenty-fifth embodiment shown in FIG. 59 provides such operational effects as below:

(1) Using the multi-beams allows an evaluation of the wafer or the like by the electron beam to be performed with high throughput; and (2) The magnification chromatic aberration which is problematic when large radius is employed for arranging the multi-beams can be reduced down to non-problematic level.

Figure 64:
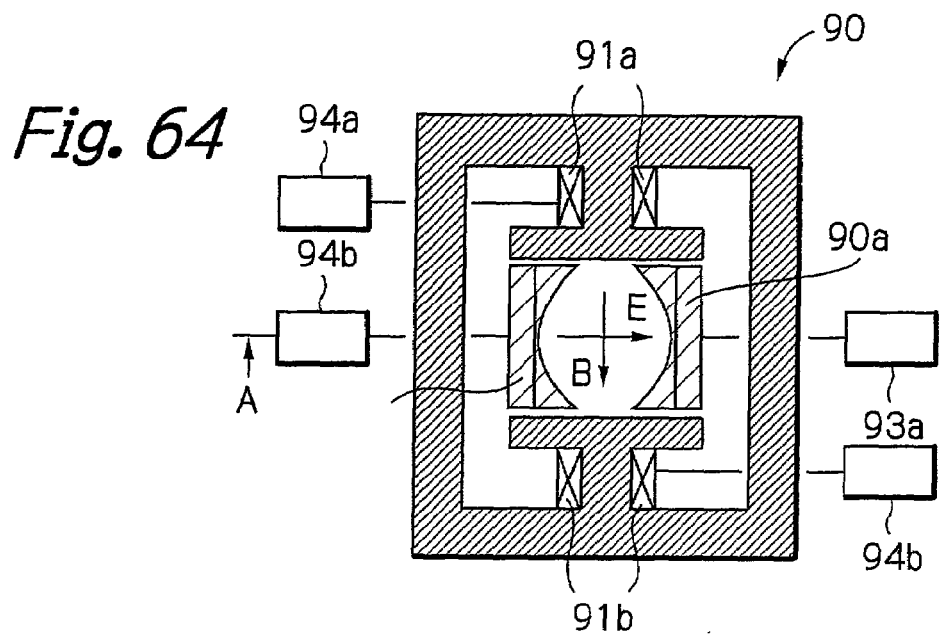
FIG. 64 is a horizontal cross sectional view illustrating an electron beam deflecting system.
Figure 65:
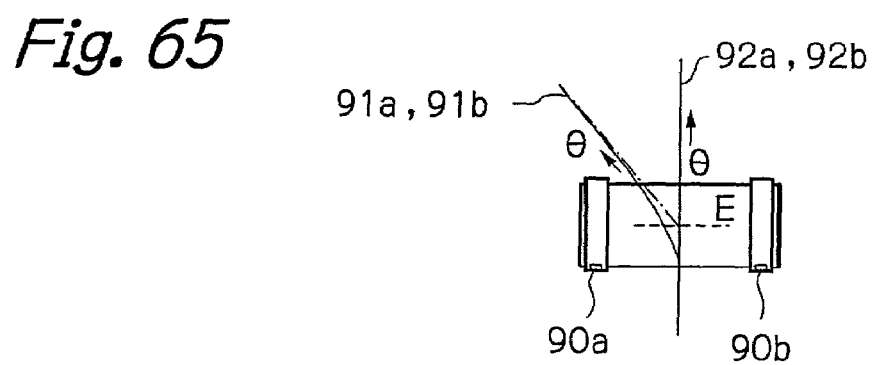
FIG. 65 is a side elevational view illustrating a deflecting condition of beam in the beam deflecting system.

FIG. 64 is a horizontal cross sectional view illustrating a detailed structure of the electron beam deflector 90 applicable to the electron beam apparatus according to the present invention. FIG. 65 is a side elevational view taken along a line A—A of FIG. 64. As shown in FIG. 64, the electron beam deflector 90 has a configuration in which an electric field and a magnetic field are crossed at a right angle within a plane orthogonal to an optical axis of a image projecting optical section, that is, an E×B configuration. Hereupon, the electric field E is generated by a pair of electrodes 90a and 90b each having concaved curved surface. The electric field generated by the electrodes 90a and 90b are controlled by control sections 93a and 93b respectively. On the other hand, a pair of electromagnetic coils 91a and 91b is arranged so as to cross at a right angle with the electrodes 90a and 90b for generating the electric field, to generate the magnetic field. The electrodes 90a and 90b for generating the electric field is designed to be point-symmetry (concentric circle type).

To improve a uniformity level of the magnetic field, a magnetic path is formed by providing a pole piece of plane parallel plate shape. A behavior of the electron beam in a longitudinal cross-section along a line A—A is shown in FIG. 65. Irradiated electron beams 91a and 91b, after having been deflected by the electric field generated by the electrodes 90a and 90b and the magnetic field generated by the electromagnetic coils 91a and 91b, enter the sample surface at a right angle.

Incident location and angle of the electron beams 91a and 91b to the electron beam deflecting section 90 are univocally defined when the energy of the electron is given. The secondary electrons advance straight ahead through the electron beam deflecting section 27 to enter the image projecting optical section when respective control section 93a and 93b, and 94a and 94b control the electric field generated by the electrodes 90a and 90b, and the magnetic field generated by the electromagnetic coil 91a and 91b such that the condition of the electric and the magnetic fields for allowing the secondary electrons to advance straight forward, that is, evB=eE, may be satisfied. Where, v is a velocity of electron (m/s), B is a magnetic field (T), e is a charge amount (C), and E is the electric field (V/m).

Figure 66:
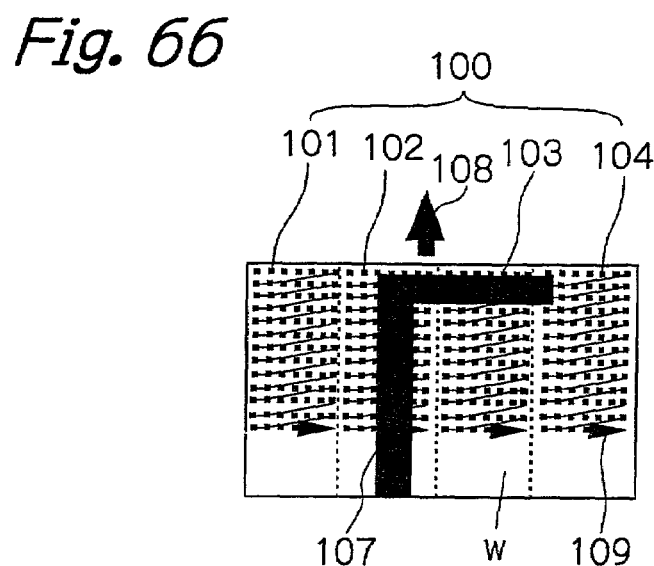
FIG. 66 is a plan view for explaining a method for irradiating a primary electron beam according to the present invention.
Figure 67:
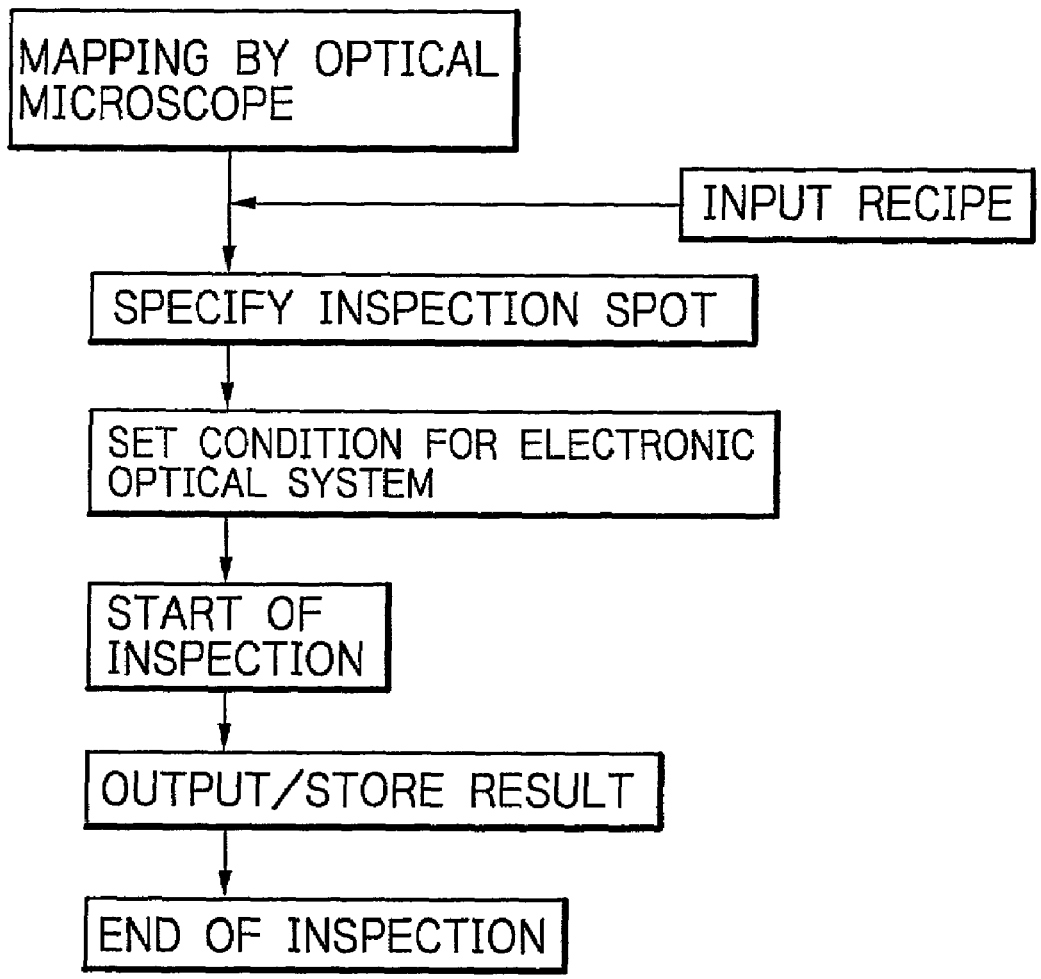
FIG. 67 is an inspection flow diagram illustrating a procedure of inspection.

FIG. 66 is a plan view for explaining an irradiating method of the primary electron beam according to the present invention. In FIG. 66, the primary electron beam 100 is composed of four electron beams 101, 102, 103 and 104. Each of the electron beams scan the width of 50 μm. For example, the primary electron beam 101 is initially in the left end, then scan a substrate W (sample) with a pattern 107 to the right end, and after having reached to the right end, immediately returns to the left end, and then scans again in the right direction. Moving direction of the stage on which the substrate W is loaded is perpendicular to the scanning direction of the primary electron beam.

The invention claimed is:

1. An inspection apparatus (4000) comprising:
   a primary electronic optical system with an optical axis for irradiating a surface of a sample by a plurality of primary charged particles; and
   a secondary electronic optical system for leading secondary charged particles emitted from each point of irradiation by the plurality of the primary charged particles formed on the surface of the sample to a secondary electron detector after separation from the primary electronic optical system by accelerating the secondary charged particles by an electric field applied between an objective lens and the surface of the sample, converging the secondary charged particles accelerated, and separating the secondary charged particles from the first optical system by a separator, wherein said separator is disposed between the objective lens and a neighbor lens of said objective lens at the side of a beam source.

2. A method for manufacturing devices comprising the steps of:
   a. providing a wafer;
   b. processing the wafer;
   c. detecting a defect on the wafer using the inspection apparatus of claim 1;
   d. repeating necessary times of the steps b and c;
   e. assembling the wafer into a device.

3. An inspection apparatus for inspecting a sample using a plurality of beams, comprising:
   a plurality of primary charged particle beam irradiation systems each having a beam source, a lens and a deflector and adapted to form a plurality of points of irradiation with primary charged particle beams on the surface of the sample using an aperture plate,
   a plurality of secondary charged particle optical systems each corresponding to each primary charged particle beam irradiation system, each of the secondary charged particle optical systems having a lens and a plurality of secondary charged particle detectors and
   an objective lens and a separator which are common to each of the primary charged particle beam irradiation systems and corresponding secondary charged particle optical system,
   wherein secondary charged particles are separated from the primary charged particle beams after they pass through the objective lens before they enter to the next lens.

4. An inspection apparatus (4100) comprising: a plurality of optical systems each having a beam source for irradiating output beam and focusing and irradiating beam passed through the optical system on a sample surface, wherein secondary charged particle generated from the sample is separated from the optical system and the separated secondary charged particle is delivered into a detector so as to be detected, wherein said plurality of optical systems are disposed in two row and multiple columns, and the detectors in the first row and the detectors in the second row are disposed oppositely each other in order not to interfere with each other.

5. An inspection apparatus for inspecting a sample using a plurality of beams, comprising:
 a plurality of primary charged particle beam irradiation systems each having a beam source, a lens and a deflector and adapted to form a plurality of points of irradiation with primary charged particle beams on the surface of the sample using an aperture plate,
 a plurality of secondary charged particle optical systems each corresponding to each primary charged particle beam irradiation system, each of the secondary charged particle optical systems having a lens and a plurality of secondary charged particle detectors and
 an objective lens and a separator which are common to each of the primary charged particle beam irradiation systems and corresponding secondary charged particle optical system,
 wherein secondary charged particles are separated from the primary charged particle beams after they pass through the objective lens before they enter to the next lens,
 wherein the primary charged particle beam irradiation system and the corresponding secondary charged particle optical systems are disposed in two rows and in plural columns so as to prevent a path of secondary charged particles deflected by one of the separators from interfering with other column of a path of the secondary charged particles deflected by the other separator, and wherein the secondary charged particle detectors in the first row and the secondary charged particle detectors in the second row are disposed oppositely each other in order not to interfere with each other.

6. An inspection apparatus (4300) having a primary optical system containing an optical axis, a beam source discharging a beam, an aperture plate with a plurality of apertures, a plurality of lenses, and a beam separator so as to irradiate a surface of a sample to be inspected with the beam emitted from the beam source, and a secondary optical system with an optical axis for separating secondary charged particles emitted from the sample from the primary optical system by the beam separator, and delivering and detecting the secondary charged particles in a secondary charged particle detector;
 wherein an image of each of the plurality of the apertures is formed by irradiating the aperture plate with the beam from the beam source, and a scanning voltage is applied on an electrostatic deflector so as to have the beam deflect.

7. The inspection apparatus of claim 6, wherein plural sets of the primary optical system and the secondary optical system are disposed in two rows and in plural columns so that paths of the secondary charged particles deflected by the beam separator do not interfere with each other, and wherein the secondary charged particle detectors in the first row and the secondary charged particle detectors in the second row are disposed oppositely each other in order not to interfere with each other.

8. A method for manufacturing devices comprising the steps of:
 a. providing a wafer;
 b. processing the wafer;
 c. detecting a defect on the wafer using the inspection apparatus of claim 6;
 d. repeating necessary times of the steps b and c;
 e. assembling the wafer into a device.

9. An inspection method for inspecting a sample using a plurality of beams, comprising:
 a. emitting charged particle beam from a beam generator;
 b. irradiating an aperture plate having a plurality of apertures with the charged particle beam;
 c. focusing and scanning the plurality of beams formed by the plurality of the apertures on a sample surface by primary optical systems each of which comprises an optical axis, a lens and a deflector;
 d. converging secondary electrons emitted from scanning points on the sample and separating them from the primary optical system by a plurality of separators;
 e. forming an enlarged image of the secondary electrons in detecting devices each of which comprises a plurality of detectors through secondary optical systems each of which comprises an optical axis and at least one stage lens;
 f. detecting through the plurality of detectors and forming an image;
 wherein the primary and the secondary optical columns are disposed in two rows and in plural columns.

10. The inspector method of claim 9, wherein directions of deflection of the separators are set so that the secondary electron detectors in the first row and the secondary electron detectors in the second row are disposed oppositely each other in order not to interfere with each other.

11. An inspection method (4100) comprising:
 delivering a plurality of images of apertures onto a sample, said plurality of images of apertures being produced by irradiating a beam emitted from a beam source to an aperture plate having a plurality of apertures; and
 separating secondary charged particles generated from the sample from a primary optical system to be delivered into a secondary optical system, and enlarging the secondary charged particles by the secondary optical system to be projected to a surface of a detector by a separator disposed between the objective lens and a neighbor lens of said objective lens at the side of the beam source.

12. An inspection method (4300) comprising:
 providing a primary optical system comprising a single beam source for discharging a beam, an aperture plate with a plurality of apertures, a plurality of lenses, and a beam separator, so as to irradiate a surface of a sample to be inspected with the beam emitted from the beam source; and
 separating secondary charged particles emitted from the sample from the primary optical system by the beam separator so as to introduce them into a secondary charged particle detector to be detected therein;
 wherein the beam from the beam source is irradiated onto the aperture plate to form an image of the plurality of apertures, and a scanning voltage is applied on an electrostatic deflector so as to cause a deflecting operation of the beam.

* * * * *